US008058390B2

(12) United States Patent
Schubert et al.

(10) Patent No.: US 8,058,390 B2
(45) Date of Patent: Nov. 15, 2011

(54) HDM2-INHIBITOR COMPLEXES AND USES THEREOF

(75) Inventors: Carsten Schubert, Exton, PA (US);
Bruce Grasberger, Trappe, PA (US);
Diane Maguire, Downington, PA (US);
Ingrid Deckman, Berwyn, PA (US);
John Spurlino, Downington, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 12/766,139

(22) Filed: Apr. 23, 2010

(65) Prior Publication Data

US 2010/0311945 A1     Dec. 9, 2010

(51) Int. Cl.
*C07K 14/00* (2006.01)
(52) U.S. Cl. .................. 530/300; 530/324; 530/344
(58) Field of Classification Search .................. None
See application file for complete search history.

(56) References Cited

U.S. PATENT DOCUMENTS

| | | | | |
|---|---|---|---|---|
| 5,702,908 | A * | 12/1997 | Picksley et al. .................. 506/9 |
| 6,407,062 | B1 | 6/2002 | Sherr et al. | |
| 2002/0045192 | A1 | 4/2002 | Kriwacki et al. | |
| 2003/0109518 | A1 | 6/2003 | Lu et al. | |
| 2003/0166240 | A1 | 9/2003 | Shrader et al. | |

OTHER PUBLICATIONS

Kussi et al. Structure of the MDM2 oncoprotein bound to the p53 tumor supressor transactivation domain. Science 1996, 274, 948-953.*
Weincek, J. M. New Stratigies for protein crystal growth. Ann. Rev. Biomed. Eng. 1999, 1, 505-534.*
Oliner et al., "Amplification of a Gene Encoding a p53-Associated Protein in Human Sarcomas", Nature, vol. 358, pp. 80-83 (1992).
Reinfenberger et al., "Amplificaton and Overexpressin of the MDM2 Gene in a Subset of Human Malignant Gliomas without p53 Mutations", Cancer Reserch, vol. 53, pp. 2736-2739, (1993).
Bueso-Ramos et al., "Abnormal expression of MDM-2 in breast carcinomas", Breast Cancer Research and Treatment, vol. 37, pp. 179-188 (1996).
Garcia-Echeverria et al., "Discovery of Potent Antagonists of the Interaction between Human Double Minute 2 and Tumor Suppressor p53", J. Med. Chem., vol. 43, pp. 3205-3208 (2000).
Lai et al., "Thermodynamics of p53 Binding to hdm2(10126):Effects of Phosphorylation and p53 Peptide Length", Archives of Biochemistry and Biophysics, vol. 381, pp. 278-284 (2000).

(Continued)

*Primary Examiner* — Nashaat Nashed
(74) *Attorney, Agent, or Firm* — Rajiv S. Shah

(57) ABSTRACT

The present invention includes crystallized HDM2 peptides as well as descriptions of the X-ray diffraction patterns of the crystals. The diffraction patterns allow the three dimensional structure of HDM2 to be determined at atomic resolution so that ligand binding sites on HDM2 can be identified and the interactions of ligands with HDM2 amino acid residues can be modeled. Models prepared using such maps permit the design of ligands which can function as active agents which include, but are not limited to, those that function as inhibitors of MDM2 and HDM2 oncoproteins.

5 Claims, 3 Drawing Sheets

OTHER PUBLICATIONS

Chene, et al., "A Small Synthetic Peptide, which Inhibits the p53-hdm2 Interaction, Stimulates the p53 Pathway in Tumour Cell Lines", J. Mol. Biol., vol. 299, pp. 245-253, (2000).

Kane et al., "Development of a Binding Assay for p53/HDM2 by Using Homogeneous Time-Resolved Fluorescence", Analytical Biochemistry, vol. 278, pp. 29-38 (2000).

Lai et al., "Metal and RNA Binding Properties of the hdm2 RING Finger Domain", Biochemistry, vol. 37, pp. 17005-17015 (1998).

Gilliland et al., "Crystallization of Biological Molecules for X-ray Diffraction Studies", Current Opinion in Structural Biology, 1996, 6, pp. 595-603.

Ke et al., "Crystallization of RNA and RNA-protein Complexes", Methods, 2004, 34, pp. 408-414.

* cited by examiner

HDM2-INHIBITOR COMPLEXES AND USES THEREOF

CROSS REFERENCE TO RELATED APPLICATIONS

This Application claims priority to U.S. application Ser. No. 10/685,838, filed Oct. 15, 2003 and Application No. 60/418,350, filed Oct. 16, 2002, both of which are incorporated herein by reference in their entirety.

STATEMENT REGARDING FEDERALLY SPONSORED RESEARCH DEVELOPMENT

Not applicable.

FIELD OF THE INVENTION

The present invention generally pertains to the fields of molecular biology, protein crystallization, X-ray diffraction analysis, three-dimensional structural determination, molecular modeling and structure based rational drug design. The present invention provides crystallized HDM2 peptides as well as descriptions of the X-ray diffraction patterns. The X-ray diffraction patterns of the crystals in question are of sufficient resolution so that the three-dimensional structure of HDM2 can be determined at atomic resolution, ligand binding sites on HDM2 can be identified, and the interactions of ligands with HDM2 amino acid residues can be modeled.

The high resolution maps provided by the present invention and the models prepared using such maps also permit the design of ligands which can function as active agents. Thus, the present invention has applications to the design of active agents which include, but are not limited to, those that find use as inhibitors of MDM2 and HDM2 oncoproteins.

BACKGROUND OF THE INVENTION

HDM2

Structure and Function

HDM2 (human double minute 2 protein) is the expression product of hdm2, an oncogene that is overexpressed in a subset of human tumors including soft tissue sarcomas, glioblastomas and mammary carcinomas (Oliner, J. D. et al., *Nature*, 358(6381):80-83 (1992); Reifenberger, G. et al., *Cancer Res.*, 53:2736-2739 (1993); Bueso-Ramos, C. E. et al., *Breast Canc. Res. Treat.*, 37(2):179-188 (1996)).

Functional characterization of this oncogene revealed an interaction between HDM2 and p53, a tumor suppressor central to cell growth arrest and apoptosis (Momand, G. P. et al., *Cell*, 69:1237 (1992)). HDM2 is a transcriptional target of p53, and as such, HDM2 and p53 form a precisely regulated loop (Wu, X. et al., *Genes and Dev.*, 7:1126-1132 (1992)). HDM2 is further regulated by ubiquitination and by complex formation with Arf, which sequesters HDM2 to the nucleolus (Tao, W. and Levine, A. J., *Proc. Natl. Acad. Sci. USA*, 96(12): 6937-6941 (1999); Weber, J. D. et al., *Nat. Cell Biol.*, 1(1): 20-26 (1999)).

There are several lines of evidence that suggest that HDM2 can also function independently of p53. Splice variants of HDM2 not containing the p53-binding domain have been found in human tumors and have been shown to possess transforming ability (Sigalas, I. et al. *Nat. Med.* 2(8):912-917 (1996)). In vivo studies have also demonstrated that the spectrum of tumors that develop in transgenic mice overexpressing HDM2 is different from the spectrum found in p53-null mice and that HDM2 can drive sarcomagenesis in p53-null animals (Jones, S, N. et al., *Proc. Natl. Acad. Sci. USA*, 95(26):15608-15612 (1998)). Lastly, other binding partners of HDM2 could assist HDM2 function along an oncogenic pathway, for example, HDM2 inhibition of MTBP-induced p53-independent G1 arrest (Boyd, M. T. et al., *J. Biol. Chem.* 275 (41):31883-31890 (2000)).

Reports of enhanced tumor cell death following hdm2 inhibition by antisense nucleotides (Chen, L. et al., *Proc. Natl. Acad. Sci. USA*, 95(1):195-200 (1998); Chen, L. et al., *Mol. Med.*, 5(1):21-34 (1999); Tortora, G. et al., *Int. J. Cancer*, 88(5):804-809 (2000)) and HDM2-binding mini-proteins (Bottger, A. et al., *Curr. Biol.*, 7(11):860-869 (1997)) substantiate a prediction that inhibition of HDM2 will activate p53 and in turn trigger apoptosis. Following on this idea, a small molecule inhibitor generated against the p53 binding groove of HDM2 would be expected to prevent the interaction of the two proteins and induce p53 activity. It has been further suggested that inhibiting the interaction between p53 and HDM2 will act additively or synergistically with standard chemotherapeutic agents in the treatment of neoplasm, and this too is supported by work utilizing antisense hdm2 constructs (Wang, H. et al., *Clin. Canc. Res.* 7(11):3613-3624 (2001)).

MDM2: Structure and Function mdm2, the murine homolog of HDM2 was originally found on mouse double minute chromosomes and was initially identified as one of three genes amplified in a tumorigenic cell line (Cahilly-Snyder., L. et al., *Somatic Cell Mol. Genet.* 13:235-244 (1987)). Its protein product was subsequently found to form a complex with p53, which was first observed in a rat fibroblast cell line (Clone 6) previously transfected with a temperature sensitive mouse p53 gene (Michalovitz, D. et al., *Cell* 62:671-680 (1990)). The rat cell line grew well at 37° C. but exhibited a G1 arrest when shifted down to 32° C., which was entirely consistent with an observed temperature dependent switch in p53 conformation and activity. However, the p53-MDM2 complex was only observed in abundance at 32° C., at which temperature p53 was predominantly in a functional or "wild-type" form (Barak, Y. et al., *EMBO J.* 11:2115-2121 (1992) and Momand, J. et al., *Cell* 69:1237-1245 (1992)). By shifting the rat cell line down to 32° C. and blocking de novo protein synthesis it was shown that only "wild-type" p53 induced expression of the mdm2 gene, thereby accounting for the differential abundance of the complex in terms of p53 transcriptional activity (Barak, Y. et al., *EMBO J.* 12:461-468 (1993)). The explanation was further developed by the identification of a DNA binding site for wild-type p53 within the first intron of the mdm2 gene (Wu, X. et al., *Genes Dev.* 7:1126-1132 (1993)). Reporter constructs employing this p53 DNA binding site revealed that they were inactivated when wild-type p53 was co-expressed with MDM2.

This inhibition of the transcriptional activity of p53 may be caused by MDM2 blocking the activation domain of p53 and/or the DNA binding site. Consequently, it was proposed that mdm2 expression is autoregulated, via the inhibitory effect of MDM2 protein on the transcriptional activity of wild-type p53. This p53-mdm2 autoregulatory feedback loop provided a novel insight as to how cell growth might be regulated by p53. Up to a third of human sarcomas are considered to overcome p53-regulated growth control by amplification of the mdm2 gene (Oliner, J. D. et al., *Nature* 358: 80-83 (1992)). Hence, the interaction between p53 and MDM2 represents a key potential therapeutic target.

p53: Interaction with HDM2 and MDM2 p53 is a transcription factor for a number of proteins that cause cell cycle arrest or cell death by apoptosis, such as p21, 14-3-3ρ, and bax. The level and transcriptional activity of p53 are increased by damage to cellular DNA. The MDM2 protein inhibits p53 function by binding to an amphipathic N-terminal helix of p53, abrogating the interaction of p53 with other proteins and its transactivation activity. The interaction with MDM2 also targets p53 for ubiquitin dependent protein degradation. MDM2 exhibits p53 independent effects on cell cycling as well, possibly by direct interaction with some of the downstream effectors such as pRB and EF2 (Reviewed in Zhang, R. and Wang, H., *Cur. Pharm. Des.* 6:393-416 (2000)).

Mutations of the p53 protein occur in 50% of all human cancers (reviewed in Agarwal, M. L. et al. *J. Biol. Chem.* 273:1-4 (1998); Levine, A. J., *Cell* 88:323-331 (1997); and, references cited in Oren, M., *J. Biol. Chem.* 274:36031-36034 (1999)). Under normal circumstances, p53 is latent and a very labile protein, which turns over with a very short half-life of a few minutes (Rogel, A. et al., *Mol. Cell. Biol.* 5:2851-2855 (1985)). DNA damage or stress induces a remarkable increase in the stability of p53 (Kastan, M. B. et al., *Cancer Res.* 51:6304-6311 (1991)). Furthermore, these signals also activate the function of p53 as a transcriptional activator of the apoptotic machinery, a function normally suppressed by autoregulatory inhibition of its transactivation domain. The amount of p53 present in the cell is tightly regulated by a negative feedback loop between p53 and the oncogene hdm2.

p53 is located in the cell nucleus and induces the expression of hdm2 through its transactivation domain. Expressed hdm2 subsequently binds to residues 19-26 of the p53 transactivation domain, inactivates it (Chen, J. et al., *Mol. Cell. Biol.* 16:2445-2452 (1996); Haupt, Y. et al., *EMBO J.* 15:1596-1606 (1996); Momand, J. et al., *Cell* 69:1237-1245 (1992)) and blocks recruitment of transcription factors necessary for gene expression (Lu, H. et al., *PNAS* 92:5154-5158 (1995); Thut, C. J. et al., *Science* 267:00-104 (1995)). Furthermore, the p53-hdm2-complex is shuttled to the cytoplasm where degradation occurs. This tight control through negative feedback is critical for the survival of the organism. Inactivation of hdm2 in hdm2-knockout mice leads to early embryonal lethality, but is completely prevented by simultaneous inactivation of p53 (Jones, S, N. et al., *Nature* 378:206-208 (1995); Montes de Oca Luna, R. et al., *Nature* 378:203-206 (1995)). On the other hand, excessive expression of hdm2 can lead to constitutive inhibition of p53 and promote cancer. Excess HDM2 also promotes cancer independently of p53 (Lundgren, K. et al., *Genes and Dev.* 11:714-725 (1997); Sun, P. et al., *Science* 282:2270-2272 (1998)).

As discussed above, inhibition of the interaction between HDM2 and p53 is an attractive target for cancer therapy (Lane, D. P., *TIBS* 22: 372-374 (1997)). It has been shown that inhibition of the complex formation between p53 and HDM2 raises the levels of p53 in the cell (Bottger, A. et al., *Current Biol.* 7:860-869 (1997)). Also, blocking HDM2 from binding p53 would be therapeutically useful in restoring cell cycle control to cells that overexpress HDM2 as a front line cancer treatment. More generally, inhibition of HDM2 may increase the effectiveness of chemotherapy and radiation in p53 normal cancers by enhancing apoptosis and growth arrest signaling pathways. This approach may render tumor cells containing functional p53 more susceptible to chemotherapeutic agents.

One method of identifying inhibitors of the p53/HDM2 protein complex is to determine the amino acid specificities of HDM2 binding pockets by crystallography in order to establish a model for the interaction. Using this method, Kussie et al. identified p53 based peptide antagonists (Kussie, P. H. et al., *Science* 274:948-953 (1996)). A crystal structure of a truncated form of HDM2 (residues 17-125) and a 15' mer peptide derived from the N-terminal transactivation domain of p53 was published by Kussie et al. (Kussie et al., (1996)). Kussie et al. also published a crystal structure of MDM2 (Kussie et al., (1996)) derived from *Xenopus laevis* (residues 13 to 118), having a 71% sequence identity towards HDM2. Based on molecular modeling, Garcia-Echeverria et al. published a model of an 8' mer peptidomimetic, derived from the 15' mer wild-type p53 peptide, bound to the N-terminal domain of hdm2 (Garcia-Echeverria, C. et al., *J. Med. Chem.* 43:3205-3208 (2000)). No crystal structure of HDM2 with inhibitory compounds, such as small molecule inhibitors, for example, or other peptides is believed to have been disclosed.

Therefore, a need continues to exist for the development of modeling systems to design and select potent, small molecules that inhibit the interactions between HDM2 (and homologs thereof) and natural binding ligands such as p53.

SUMMARY OF THE INVENTION

The present invention includes methods of producing and using three-dimensional structure information derived from human MDM2 protein (HDM2) and inhibitory compounds which form a complex with HDM2 and prevent HDM2 from interacting with the p53 protein. The present invention also includes specific crystallization conditions to obtain crystals of the inhibitor-HDM2 complex. The crystals are subsequently used to obtain a 3-dimensional structure of the complex using X-ray crystallography (or NMR) and the obtained data is used for rational drug discovery design with the aim to improve the complex formation between HDM2 and the inhibitor, and, also to improve the inhibition of the binding of HDM2 to p53.

The present invention includes a crystal comprising HDM2, or a fragment, or target structural motif or derivative thereof, and a ligand, wherein the ligand is a small molecule inhibitor. In another embodiment, the crystal has a spacegroup selected from the group consisting of a trigonal spacegroup of $P3_221$ and a tetragonal spacegroup $P4_32_12$. The present invention also includes a crystal comprising HDM2 which comprises a peptide having at least 95% sequence identity to SEQ ID NO. 2.

In another aspect of the invention, the invention includes a computer system comprising: (a) a database containing information on the three dimensional structure of a crystal comprising HDM2, or a fragment or a target structural motif or derivative thereof, and a ligand, wherein the ligand is a small molecule inhibitor, stored on a computer readable storage medium; and, (b) a user interface to view the information.

The present invention also includes a method of evaluating the potential of an agent to associate with HDM2 comprising: (a) exposing HDM2 to the agent; and (b) detecting the association of said agent to HDM2 amino acid residues $Ser^{17}$, $Ile^{19}$, $Leu^{82}$ and $Arg^{97}$ thereby evaluating the potential.

The invention further includes a method of evaluating the potential of an agent to associate with the peptide having $aa^{16}$-SEQ ID NO: 2, comprising: (a) exposing $aa^{16}$-SEQ ID NO: 2 to the agent; and (b) detecting the level of association of the agent to $aa^{16}$-SEQ ID NO: 2, thereby evaluating the potential.

Further included in the present invention is a method of identifying a potential agonist or antagonist against HDM2 comprising: (a) employing the three dimensional structure of HDM2 cocrystallized with a small molecule inhibitor to design or select said potential agonist or antagonist.

The instant invention comprises a method of locating the attachment site of an inhibitor to HDM2, comprising: (a) obtaining X-ray diffraction data for a crystal of HDM2; (b) obtaining X-ray diffraction data for a complex of HDM2 and an inhibitor; (c) subtracting the X-ray diffraction data obtained in step (a) from the X-ray diffraction data obtained in step (b) to obtain the difference in the X-ray diffraction data; (d) obtaining phases that correspond to X-ray diffraction data obtained in step (a); (e) utilizing the phases obtained in step (d) and the difference in the X-ray diffraction data obtained in step (c) to compute a difference Fourier image of the inhibitor; and, (f) locating the attachment site of the inhibitor to HDM2 based on the computations obtained in step (e).

The present invention further comprises a method of obtaining a modified inhibitor comprising: (a) obtaining a crystal comprising HDM2 and an inhibitor; (b) obtaining the atomic coordinates of the crystal; (c) using the atomic coordinates and one or more molecular modeling techniques to determine how to modify the interaction of the inhibitor with HDM2; and, (d) modifying the inhibitor based on the determinations obtained in step (c) to produce a modified inhibitor.

In another aspect of the invention, the invention includes an isolated protein fragment comprising a binding pocket or active site defined by structure coordinates of HDM2 amino acid residues $Ser^{17}$, $Ile^{19}$, $Leu^{82}$ and $Arg^{97}$.

In another aspect of the invention, the invention includes an isolated nucleic acid molecule encoding the fragment which comprises a binding pocket or active site defined by structure coordinates of HDM2 amino acid residues $Ser^{17}$, $Ile^{19}$, $Leu^{82}$ and $Arg^{97}$. In another aspect of the invention, the invention includes a method of screening for an agent that associates with HDM2, comprising: (a) exposing a protein molecule fragment to the agent; and (b) detecting the level of association of the agent to the fragment. In another aspect of the invention, the invention includes a kit comprising a protein molecule fragment.

The invention additionally comprises a method for the production of a crystal complex comprising an HDM2 polypeptide-ligand comprising: (a) contacting the HDM2 polypeptide with said ligand in a suitable solution comprising PEG and NaSCN; and, b) crystallizing said resulting complex of HDM2 polypeptide-ligand from said solution.

The invention further includes a method for the production of a crystal comprising HDM2 and a ligand wherein the ligand is a small molecule inhibitor comprising crystallizing a peptide comprising a sequence selected from the group consisting of SEQ ID NO: 1, SEQ ID NO: 2, SEQ ID NO: 3 and SEQ ID NO:4 with a potential inhibitor.

The instant invention includes a method for identifying a potential inhibitor of HDM2 comprising: a) using a three dimensional structure of HDM2 as defined by atomic coordinates according to table 1 or table 2; b) replacing one or more HDM2 amino acids selected from $Ser^{17}$, $Ile^{19}$, $Leu^{82}$ and $Arg^{97}$ in said three-dimensional structure with a different amino acid to produce a modified HDM2; c) using said three-dimensional structure to design or select said potential inhibitor; d) synthesizing said potential inhibitor; and, e) contacting said potential inhibitor with said modified HDM2 in the presence of a substrate to test the ability of said potential inhibitor to inhibit HDM2 or said modified HDM2. Also included in the invention is an inhibitor identified by the method.

DETAILED DESCRIPTION OF THE INVENTION

Definitions

Figure 1:
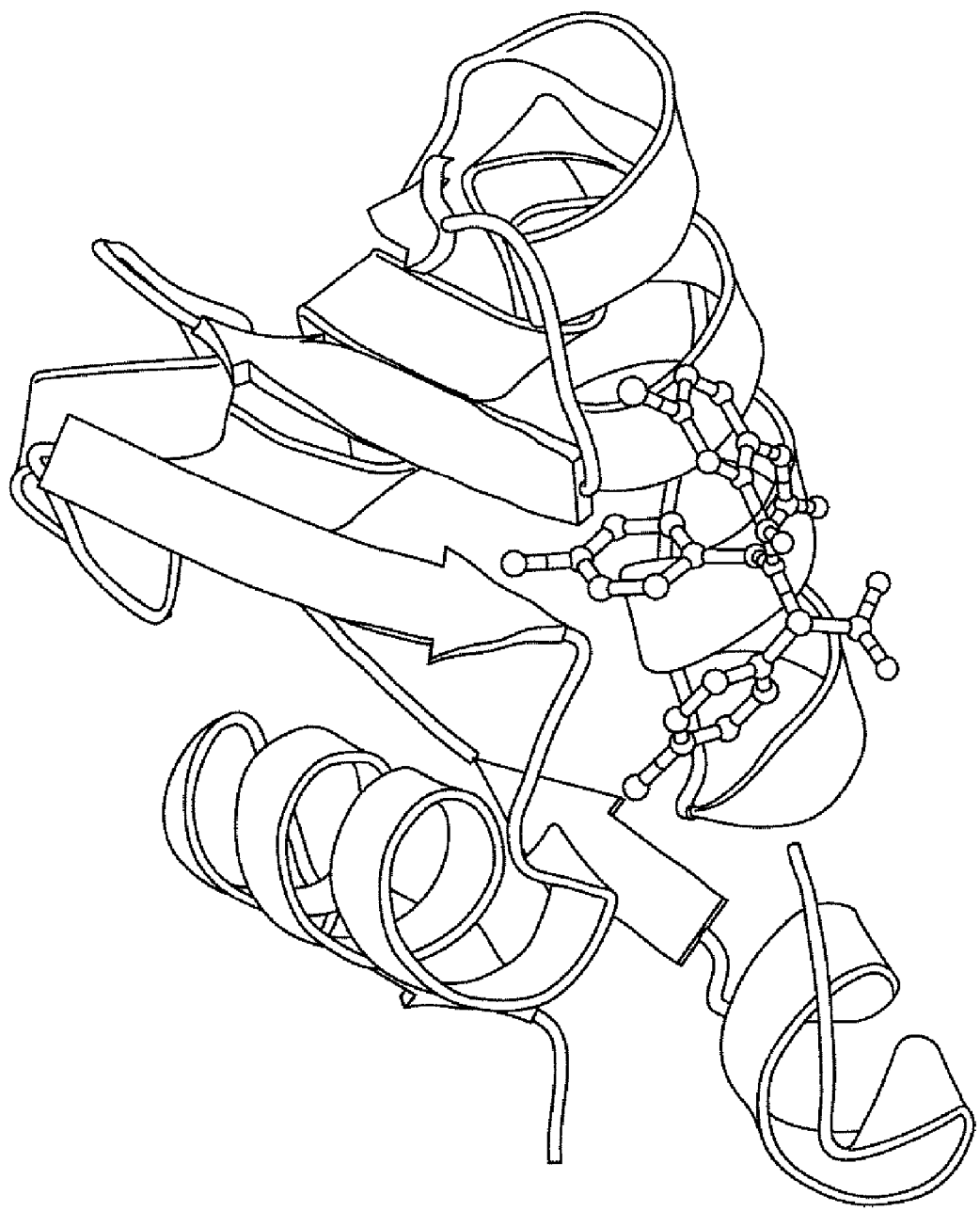
FIG. 1 Ribbon representation of HDM2 (SEQ ID NO: 2) bound to compound 338437.

As is generally the case in biotechnology and chemistry, the description of the present invention has required the use of a number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which this invention belongs. Definitions for other terms also appear elsewhere herein. However, the definitions provided here and elsewhere herein should always be considered in determining the intended scope and meaning of the defined terms. Although any methods and materials similar or equivalent to those described herein can be used in the practice of the present invention, the preferred methods and materials are described.

As used herein, the term "atomic coordinates" or "structure coordinates" refers to mathematical coordinates that describe the positions of atoms in crystals of HDM2 in Protein Data Bank (PDB) format, including X, Y, Z and B, for each atom. The diffraction data obtained from the crystals are used to calculate an electron density map of the repeating unit of the crystal. The electron density maps may be used to establish the positions (i.e. coordinates X, Y and Z) of the individual atoms within the crystal. Those of skill in the art understand that a set of structure coordinates determined by X-ray crystallography is not without standard error. For the purpose of this invention, any set of structure coordinates for HDM2 from any source having a root mean square deviation of non-hydrogen atoms of less than about 1.5 Å when superimposed on the non-hydrogen atom positions of the corresponding atomic coordinates of Table 1 or Table 2 are considered substantially identical or homologous. In a more preferred embodiment, any set of structure coordinates for HDM2 from any source having a root mean square deviation of non-hydrogen atoms of less than about 0.75 Å when superimposed on the non-hydrogen atom positions of the corresponding atomic coordinates of Table 1 or Table 2 are considered substantially identical or homologous.

The term "atom type" refers to the chemical element whose coordinates are measured. The first letter in a column in Table 1 identifies the element.

The terms "X," "Y" and "Z" refer to the crystallographically-defined atomic position of the element measured with respect to the chosen crystallographic origin. The term "B" refers to a thermal factor that measures the mean variation of an atom's position with respect to its average position.

As used herein, the term "crystal" refers to any three-dimensional ordered array of molecules that diffracts X-rays.

As used herein, the term "carrier" in a composition refers to a diluent, adjuvant, excipient, or vehicle with which the product is mixed.

As used herein, the term "composition" refers to the combining of distinct elements or ingredients to form a whole. A composition comprises more than one element or ingredient. For the purposes of this invention, a composition will often, but not always, comprise a carrier.

As used herein, "mdm2" is used to mean the murine double minute 2 gene, and homologous genes found in other animals.

As used herein, "MDM2" is used to mean a protein obtained as a result of expression of the mdm2 oncogene. Within the meaning of this term, it will be understood that MDM2 encompasses all proteins encoded by mdm2, mutants thereof, conservative amino acid substitutions, alternative splice proteins thereof, and phosphorylated proteins thereof. Additionally, as used herein, it will be understood that the term "MDM2" includes MDM2 homologues of other animals.

As used herein, "hdm2" is used to mean the human gene, which is homologous to the mouse mdm2 gene.

As used herein, "HDM2" is used to mean a protein obtained as a result of expression of the hdm2 oncogene. Within the meaning of this term, it will be understood that HDM2 encompasses all proteins encoded by hdm2, mutants thereof, conservative amino acid substitutions, alternative splice proteins thereof, and phosphorylated proteins thereof. As an example, HDM2 includes the protein comprising SEQ ID NO: 2 and variants thereof comprising at least about 70% amino acid sequence identity to SEQ ID NO: 2, or preferably 80%, 85%, 90% and 95% sequence identity to SEQ ID NO: 2, or more preferably, at least about 95% or more sequence identity to SEQ ID NO: 2.

As used herein, the term "SAR," an abbreviation for Structure-Activity Relationships, collectively refers to the structure-activity/structure property relationships pertaining to the relationship(s) between a compound's activity/properties and its chemical structure.

As used herein, the term "molecular structure" refers to the three dimensional arrangement of molecules of a particular compound or complex of molecules (e.g., the three dimensional structure of HDM2 and ligands that interact with HDM2).

As used herein, the term "molecular modeling" refers to the use of computational methods, preferably computer assisted methods, to draw realistic models of what molecules look like and to make predictions about structure activity relationships of ligands. The methods used in molecular modeling range from molecular graphics to computational chemistry.

As used herein, the term "molecular model" refers to the three dimensional arrangement of the atoms of a molecule connected by covalent bonds or the three dimensional arrangement of the atoms of a complex comprising more than one molecule, e.g., a protein-ligand complex.

As used herein, the term "molecular graphics" refers to 3D representations of the molecules, for instance, a 3D representation produced using computer assisted computational methods.

As used herein, the term "computational chemistry" refers to calculations of the physical and chemical properties of the molecules.

As used herein, the term "molecular replacement" refers to a method that involves generating a preliminary model of a crystal of HDM2 whose coordinates are unknown, by orienting and positioning the said atomic coordinates described in the present invention so as best to account for the observed diffraction pattern of the unknown crystal. Phases can then be calculated from this model and combined with the observed amplitudes to give an approximate Fourier synthesis of the structure whose coordinates are unknown. (Rossmann, M. G., ed., "The Molecular Replacement Method", Gordon & Breach, New York, 1972).

As used herein, the term "homolog" refers to the HDM2 protein molecule or the nucleic acid molecule which encodes the protein, or a functional domain from said protein from a first source having at least about 30%, 40% or 50% sequence identity, or at least about 60%, 70% or 75% sequence identity, or at least about 80% sequence identity, or more preferably at least about 85% sequence identity, or even more preferably at least about 90% sequence identity, and most preferably at least about 95%, 97% or 99% amino acid or nucleotide sequence identity, with the protein, encoding nucleic acid molecule or any functional domain thereof, from a second source. The second source may be a version of the molecule from the first source that has been genetically altered by any available means to change the primary amino acid or nucleotide sequence or may be from the same or a different species than that of the first source.

As used herein, the term "active site" refers to regions on HDM2 or a structural motif of HDM2 that are directly involved in the function or activity of HDM2.

As used herein, the terms "binding site" or "binding pocket" refer to a region of HDM2 or a molecular complex comprising HDM2 that, as a result of the primary amino acid sequence of HDM2 and/or its three-dimensional shape, favorably associates with another chemical entity or compound including ligands or inhibitors.

For the purpose of this invention, any active site, binding site or binding pocket defined by a set of structure coordinates for HDM2 or for a homolog of HDM2 from any source having a root mean square deviation of non-hydrogen atoms of less than about 1.5 Å when superimposed on the non-hydrogen atom positions of the corresponding atomic coordinates of Table 1 or Table 2 are considered substantially identical or homologous. In a more preferred embodiment, any set of structure coordinates for HDM2 or a homolog of HDM2 from any source having a root mean square deviation of non-hydrogen atoms of less than about 0.75 Å when superimposed on the non-hydrogen atom positions of the corresponding atomic coordinates of Table 1 or Table 2 are considered substantially identical or homologous.

The term "root mean square deviation" means the square root of the arithmetic mean of the squares of the deviations from the mean.

As used herein, the term "amino acids" refers to the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine, and lysine. Unless specifically indicated, all amino acids are referred to in this application are in the L-form.

As used herein, the term "nonnatural amino acids" refers to amino acids that are not naturally found in proteins. For example, selenomethionine.

As used herein, the term "positively charged amino acid" includes any amino acids having a positively charged side chain under normal physiological conditions. Examples of positively charged naturally occurring amino acids are arginine, lysine, and histidine.

As used herein, the term "negatively charged amino acid" includes any amino acids having a negatively charged side chains under normal physiological conditions. Examples of negatively charged naturally occurring amino acids are aspartic acid and glutamic acid.

As used herein, the term "hydrophobic amino acid" includes any amino acids having an uncharged, nonpolar side chain that is relatively insoluble in water. Examples of naturally occurring hydrophobic amino acids are alanine, leucine, isoleucine, valine, proline, phenylalanine, tryptophan, and methionine.

As used herein, the term "hydrophilic amino acid" refers to any amino acids having an uncharged, polar side chain that is relatively soluble in water. Examples of naturally occurring hydrophilic amino acids are serine, threonine, tyrosine, asparagine, glutamine and cysteine.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as C).

As used herein, the term "conjugated system" refers to more than two double bonds are adjacent to each other, in which electrons are completely delocalized with the entire system. This also includes and aromatic residues.

As used herein, the term "aromatic residue" refers to amino acids with side chains having a delocalized conjugated system. Examples of aromatic residues are phenylalanine, tryptophan, and tyrosine.

As used herein, the phrase "inhibiting the binding" refers to preventing or reducing the direct or indirect association of one or more molecules, peptides, proteins, enzymes, or receptors, or preventing or reducing the normal activity of one or more molecules, peptides, proteins, enzymes or receptors, e.g., preventing or reducing the direct or indirect association of HDM2 and p53.

As used herein, the term "competitive inhibitor" refers to inhibitors that bind to HDM2 at the same sites as its binding partner(s) (e.g., p53), thus directly competing with them. Competitive inhibition may, in some instances, be reversed completely by increasing the substrate concentration.

As used herein, the term "uncompetitive inhibitor" refers to one that inhibits the functional activity of HDM2 by binding to a different site than does its substrate(s) e.g. (p53).

As used herein, the term "non-competitive inhibitor" refers to one that can bind to either the free or p53 bound form of HDM2.

Those of skill in the art may identify inhibitors as competitive, uncompetitive, or non-competitive by computer fitting enzyme kinetic data using standard methods. See, for example, Segel, I. H., Enzyme Kinetics, J. Wiley & Sons, (1975).

As used herein, the term "R or S-isomer" refers to two possible stereoisomers of a chiral carbon according to the Cahn-Ingold-Prelog system adopted by International Union of Pure and Applied Chemistry (IUPAC). Each group attached to the chiral carbon is first assigned to a preference or priority a, b, c, or d on the basis of the atomic number of the atom that is directly attached to the chiral carbon. The group with the highest atomic number is given the highest preference a, the group with next highest atomic number is given the next highest preference b; and so on. The group with the lowest preference (d) is then directed away from the viewer. If the trace of a path from a to b to c is counter clockwise, the isomer is designated (S); in the opposite direction, clockwise, the isomer is designated (R).

As used herein, the term "ligand" refers to any molecule, or chemical entity which binds with or to HDM2, a subunit of HDM2, a domain of HDM2, a target structural motif of HDM2 or a fragment of HDM2. Thus, ligands include, but are not limited to, small molecule inhibitors, for example.

As used herein, the term "small molecule inhibitor" refers to compounds useful in the present invention having measurable MDM2 or HDM2 inhibiting activity. In addition to small organic molecules, peptides, antibodies, cyclic peptides and peptidomimetics are contemplated as being useful in the disclosed methods. Excluded from the invention are the p53 peptides disclosed in Kussie et al., Garcia-Echeverria et al., and the peptides derived from phage display which inhibit the binding of mdm2 to p53 (Böttger, V. A., et al., *Oncogene* 13(10): 2141-2147 (1996)). Preferred inhibitors are small molecules, preferably less than 700 Daltons, and more preferably less than 450 Daltons. Examples of classes of compounds having this property include compounds disclosed in U.S. Provisional Application No. 60/275,629; in U.S. Provisional Application No. 60/331,235; in U.S. Provisional Application No. 60/379,617; and, in U.S. application Ser. No. 10/097,249, incorporated herein in their entirety.

As used herein the terms "bind," "binding," "bond," or "bonded" when used in reference to the association of atoms, molecules, or chemical groups, refer to any physical contact or association of two or more atoms, molecules, or chemical groups.

As used herein, the terms "covalent bond" or "valence bond" refer to a chemical bond between two atoms in a molecule created by the sharing of electrons, usually in pairs, by the bonded atoms.

As used herein, "noncovalent bond" refers to an interaction between atoms and/or molecules that does not involve the formation of a covalent bond between them.

As used herein, the term "native protein" refers to a protein comprising an amino acid sequence identical to that of a protein isolated from its natural source or organism.

Specific Embodiments

Detailed Embodiments

The present invention includes a crystal comprising HDM2, or a fragment, or target structural motif or derivative thereof, and a ligand, wherein the ligand is a small molecule inhibitor. In one embodiment, the fragment or derivative thereof is a peptide selected from the group consisting of SEQ ID NO: 1 (amino acid sequence of full length HDM2), SEQ ID NO: 2 (amino acid residues 17-111 of SEQ ID NO: 1), SEQ ID NO. 3 (amino acid residues 23-114 of SEQ ID NO: 1) and SEQ ID NO. 4 (Gly$^{16}$-SEQ ID NO: 2).

In another embodiment, the crystal has a spacegroup selected from the group consisting of a trigonal spacegroup of P3$_2$21 and a tetragonal spacegroup of P4$_3$2$_1$2. In a different embodiment, the crystal effectively diffracts X-rays for determination of atomic coordinates to a resolution of at least about 3.0 Å. In a preferred embodiment, the ligand is in crystalline form. In a highly preferred embodiment, the ligand is selected from the group consisting of (4-Chloro-phenyl)-[3-(4-chloro-phenyl)-7-iodo-2,5-dioxo-1,2,3,5-tetrahydro-benzo[e][1,4]diazepin-4-yl]-acetic acid; [8-Chloro-3-(4-chloro-phenyl)-7-iodo-2,5-dioxo-1,2,3,5-tetrahydro-benzo[e][1,4]diazepin-4-yl]-(4-chloro-phenyl)-acetic acid, and, derivatives thereof.

The present invention also includes a crystal comprising HDM2 which comprises a peptide having at least 95% sequence identity to SEQ ID NO. 2. In a preferred embodiment, the crystal comprising SEQ ID NO: 2 comprises an atomic structure characterized by the coordinates of Table 1 or Table 2. In another preferred embodiment, the crystal comprises a unit cell selected from the group consisting of: a cell having dimensions of about 98.6 Å, 98.6 Å and 74.7 Å, and about alpha=90°, beta=90° and gamma=120°; and, a cell having dimensions of about 54.3 Å, 54.3 Å, 83.3 Å and about alpha=90°, beta=90° and gamma=90°.

In another aspect of the invention, the invention includes a computer system comprising: (a) a database containing information on the three dimensional structure of a crystal comprising HDM2, or a fragment or a target structural motif or derivative thereof, and a ligand, wherein the ligand is a small molecule inhibitor, stored on a computer readable storage medium; and, (b) a user interface to view the information. In one embodiment, the information comprises diffraction data obtained from a crystal comprising SEQ ID NO:2. In another embodiment, the information comprises an electron density map of a crystal form comprising SEQ ID NO:2. In a different embodiment, the information comprises the structure coordinates of Table 1 or Table 2 or homologous structure coordinates comprising a root mean square deviation of non-hydrogen atoms of less than about 1.5 Å when superimposed on the non-hydrogen atom positions of the corresponding atomic coordinates of Table 1 or Table 2. In a preferred embodiment, the information comprises structure coordinates comprising a root mean square deviation of non-hydrogen atoms of less than about 0.75 Å when superimposed on the non-hydrogen atom positions of the corresponding atomic coordinates of Table 1 or Table 2. In a highly preferred embodiment, the information comprises the structure coordinates for amino acids $Ser^{17}$, $Ile^{19}$, $Leu^{82}$ and $Arg^{97}$ according to Table 1 or Table 2 or similar structure coordinates for said amino acids comprising a root mean square deviation of non-hydrogen atoms of less than about 1.5 Å when superimposed on the non-hydrogen atom positions of the corresponding atomic coordinates of Table 1 or Table 2. In another embodiment, the information further comprises the structure coordinates for amino acids $Val^{53}$, $Leu^{54}$, $Phe^{55}$, $Leu^{57}$, $Gly^{58}$, $Gln^{59}$, $Ile^{61}$, $Met^{62}$, $Tyr^{67}$, $Gln^{72}$, $His^{73}$, $Ile^{74}$, $Val^{75}$, $Phe^{86}$, $Phe^{91}$, $Val^{93}$, $Lys^{94}$, $Glu^{95}$, $His^{96}$, $Ile^{99}$, $Tyr^{100}$, $Ile^{103}$ according to Table 1 or Table 2 or similar structure coordinates for said amino acids comprising a root mean square deviation of non-hydrogen atoms of less than about 1.5 Å when superimposed on the non-hydrogen atom positions of the corresponding atomic coordinates of Table 1 or Table 2.

The present invention also includes a method of evaluating the potential of an agent to associate with HDM2 comprising: (a) exposing HDM2 to the agent; and (b) detecting the association of said agent to HDM2 amino acid residues $Ser^{17}$, $Ile^{19}$, $Leu^{82}$ and $Arg^{97}$ thereby evaluating the potential. In one embodiment of the invention, the agent is a virtual compound. In another embodiment of the invention, step (a) comprises comparing the atomic structure of the compound to the three dimensional structure of HDM2. In a different embodiment, the comparing comprises employing a computational means to perform a fitting operation between the compound and at least one binding site of HDM2. In a preferred embodiment, the binding site is defined by structure coordinates for amino acids $Ser^{17}$, $Ile^{19}$, $Leu^{82}$ and $Arg^{97}$ according to Table 1 or Table 2 similar structure coordinates for said amino acids comprising a root mean square deviation of non-hydrogen atoms of less than about 1.5 Å when superimposed on the non-hydrogen atom positions of the corresponding atomic coordinates of Table 1 or Table 2. In another different embodiment, the binding site is further defined by structure coordinates for amino acids $Val^{53}$, $Leu^{54}$, $Phe^{55}$, $Leu^{57}$, $Gly^{58}$, $Gln^{59}$, $Ile^{61}$, $Met^{62}$, $Tyr^{67}$, $Gln^{72}$, $His^{73}$, $Ile^{74}$, $Val^{75}$, $Phe^{86}$, $Phe^{91}$, $Val^{93}$, $Lys^{94}$, $Glu^{95}$, $His^{96}$, $Ile^{99}$, $Tyr^{100}$, $Ile^{103}$ according to Table 1 or Table 2 or similar structure coordinates for said amino acids comprising a root mean square deviation of non-hydrogen atoms of less than about 1.5 Å when superimposed on the non-hydrogen atom positions of the corresponding atomic coordinates of Table 1 or Table 2. In a highly preferred embodiment, the agent is exposed to crystalline SEQ ID NO:2 and the detecting of step (b) comprises determining the three dimensional structure of the agent-SEQ ID NO: 2 complex.

The invention further includes a method of evaluating the potential of an agent to associate with the peptide having $aa^{16}$-SEQ ID NO: 2, comprising: (a) exposing $aa^{16}$-SEQ ID NO: 2 to the agent; and (b) detecting the level of association of the agent to $aa^{16}$-SEQ ID NO: 2, thereby evaluating the potential. In one embodiment, the agent is a virtual compound.

The present invention includes a method of identifying a potential agonist or antagonist against HDM2 comprising: (a) employing the three dimensional structure of HDM2 cocrystallized with a small molecule inhibitor to design or select said potential agonist or antagonist. In one embodiment, the three dimensional structure corresponds to the atomic structure characterized by the coordinates of Table 1 or similar structure coordinates comprising a root mean square deviation of non-hydrogen atoms of less than about 1.5 Å when superimposed on the non-hydrogen atom positions of the corresponding atomic coordinates of Table 1 or Table 2. In a different embodiment, the method further comprises the steps of: (b) synthesizing the potential agonist or antagonist; and (c) contacting the potential agonist or antagonist with HDM2.

The instant invention comprises a method of locating the attachment site of an inhibitor to HDM2, comprising: (a) obtaining X-ray diffraction data for a crystal of HDM2; (b) obtaining X-ray diffraction data for a complex of HDM2 and an inhibitor; (c) subtracting the X-ray diffraction data obtained in step (a) from the X-ray diffraction data obtained in step (b) to obtain the difference in the X-ray diffraction data; (d) obtaining phases that correspond to X-ray diffraction data obtained in step (a); (e) utilizing the phases obtained in step (d) and the difference in the X-ray diffraction data obtained in step (c) to compute a difference Fourier image of the inhibitor; and, (f) locating the attachment site of the inhibitor to HDM2 based on the computations obtained in step (e).

The present invention further comprises a method of obtaining a modified inhibitor comprising: (a) obtaining a crystal comprising HDM2 and an inhibitor; (b) obtaining the atomic coordinates of the crystal; (c) using the atomic coordinates and one or more molecular modeling techniques to determine how to modify the interaction of the inhibitor with HDM2; and, (d) modifying the inhibitor based on the determinations obtained in step (c) to produce a modified inhibitor. In one embodiment, the crystal comprises a peptide selected from the group consisting of: a peptide having SEQ ID NO: 2; a peptide having SEQ ID NO: 3 and a peptide having SEQ ID NO:4. In a different embodiment, the one or more molecular modeling techniques are selected from the group consisting of graphic molecular modeling and computational chemistry. In a preferred embodiment, step (a) comprises detecting the interaction of the inhibitor to HDM2 amino acid residues $Ser^{17}$, $Ile^{19}$, $Leu^{82}$ and $Arg^{97}$. In another embodiment of the invention, the invention includes an HDM2 inhibitor identified by this method.

In another aspect of the invention, the invention includes an isolated protein fragment comprising a binding pocket or active site defined by structure coordinates of HDM2 amino acid residues $Ser^{17}$, $Ile^{19}$, $Leu^{82}$ and $Arg^{97}$. In one embodiment, the isolated fragment is linked to a solid support.

In another aspect of the invention, the invention includes an isolated nucleic acid molecule encoding the fragment which comprises a binding pocket or active site defined by structure coordinates of HDM2 amino acid residues $Ser^{17}$, $Ile^{19}$, $Leu^{82}$ and $Arg^{97}$. In one embodiment, a vector comprises the nucleic acid molecule. In another embodiment, a host cell comprises the vector. In yet another aspect of the invention, the invention includes a method of producing a protein fragment, comprising culturing the host cell under conditions in which the fragment is expressed. In another aspect of the invention, the invention includes a method of screening for an agent that associates with HDM2, comprising: (a) exposing a protein molecule fragment to the agent; and (b) detecting the level of association of the agent to the fragment. In another aspect of the invention, the invention includes a kit comprising a protein molecule fragment.

In another aspect of the invention, the invention includes a method for the production of a crystal complex comprising an HDM2 polypeptide-ligand comprising: (a) contacting the HDM2 polypeptide with said ligand in a suitable solution comprising PEG and NaSCN; and, b) crystallizing said resulting complex of HDM2 polypeptide-ligand from said solution. In one embodiment, the HDM2 polypeptide is a polypeptide having SEQ ID NO: 2. In another embodiment, PEG has an average molecular weight range from 100 to 1000, wherein said PEG is present in solution at a range from about 0.5% w/v to about 10% w/v and said NaSCN is present in solution at a range of from about 50 mM to about 150 mM. In a preferred embodiment, PEG has an average molecular weight of about 400 and is present in solution at about 2% w/v and said NaSCN is present in solution at about 100 mM. In a highly preferred embodiment, the solution further comprises about 1.8-2.4 M $(NH_4)_2SO_4$ and about 100 mM buffer.

The invention further includes a method for the production of a crystal comprising HDM2 and a ligand wherein the ligand is a small molecule inhibitor comprising crystallizing a peptide comprising a sequence selected from the group consisting of SEQ ID NO: 1, SEQ ID NO: 2, SEQ ID NO: 3 and SEQ ID NO:4 with a potential inhibitor.

The invention includes a method for identifying a potential inhibitor of HDM2 comprising: a) using a three dimensional structure of HDM2 as defined by atomic coordinates according to table 1; b) replacing one or more HDM2 amino acids selected from $Ser^{17}$, $Ile^{19}$, $Leu^{82}$ and $Arg^{97}$ in said three-dimensional structure with a different amino acid to produce a modified HDM2; c) using said three-dimensional structure to design or select said potential inhibitor; d) synthesizing said potential inhibitor; and, e) contacting said potential inhibitor with said modified HDM2 in the presence of a substrate to test the ability of said potential inhibitor to inhibit HDM2 or said modified HDM2. In one embodiment, replacing one or more amino acid residues further comprises replacing SEQ ID NO: 2 amino acids selected from the group consisting of $Val^{53}$, $Leu^{54}$, $Phe^{55}$, $Leu^{57}$, $Gly^{58}$, $Gln^{59}$, $Ile^{61}$, $Met^{62}$, $Tyr^{67}$, $Gln^{72}$, $His^{73}$, $Ile^{74}$, $Val^{75}$, $Phe^{86}$, $Phe^{91}$, $Val^{93}$, $Lys^{94}$, $Glu^{95}$, $His^{96}$, $Ile^{99}$, $Tyr^{100}$, and $Ile^{103}$. In another embodiment, the potential inhibitor is selected from a database. In a preferred embodiment, the potential inhibitor is designed de novo. In another preferred embodiment, the potential inhibitor is designed from a known inhibitor. In a highly preferred embodiment, the step of employing said three-dimensional structure to design or select said potential inhibitor comprises the steps of: a) identifying chemical entities or fragments capable of associating with modified HDM2; and b) assembling the identified chemical entities or fragments into a single molecule to provide the structure of said potential inhibitor. In one embodiment, the potential inhibitor is a competitive inhibitor of SEQ ID NO:4 ($Gly^{16}$-SEQ ID NO: 2). In a different embodiment, the potential inhibitor is a non-competitive or uncompetitive inhibitor of SEQ ID NO:4 ($Gly^{16}$-SEQ ID NO: 2). In yet another embodiment, an inhibitor is identified by the method.

A. Modeling the Three-Dimensional Structure of HDM2

The atomic coordinate data provided in Table 1, Table 2 or the coordinate data derived from homologous proteins may be used to build a three-dimensional model of HDM2. Any available computational methods may be used to build the three dimensional model. As a starting point, the X-ray diffraction pattern obtained from the assemblage of the molecules or atoms in a crystalline version of HDM2 or an HDM2 homolog can be used to build an electron density map using tools well known to those skilled in the art of crystallography and X-ray diffraction techniques. Additional phase information extracted either from the diffraction data and available in the published literature and/or from supplementing experiments may then used to complete the reconstruction.

For basic concepts and procedures of collecting, analyzing, and utilizing X-ray diffraction data for the construction of electron densities see, for example, Campbell et al., 1984, Biological Spectroscopy, The Benjamin/Cummings Publishing Co., Inc., Menlo Park, Calif.; Cantor et al., 1980, Biophysical Chemistry, Part II: Techniques for the study of biological structure and function, W.H. Freeman and Co., San Francisco, Calif.; A. T. Brunger, 1993, X-Flor Version 3.1: A system for X-ray crystallography and NMR, Yale Univ. Pr., New Haven, Conn.; M. M. Woolfson, 1997, An Introduction to X-ray Crystallography, Cambridge Univ. Pr., Cambridge, UK; J. Drenth, 1999, Principles of Protein X-ray Crystallography (Springer Advanced Texts in Chemistry), Springer Verlag; Berlin; Tsirelson et al., 1996, Electron Density and Bonding in Crystals: Principles, Theory and X-ray Diffraction Experiments in Solid State Physics and Chemistry, Inst. of Physics Pub.; U.S. Pat. No. 5,942,428; U.S. Pat. No. 6,037,117; U.S. Pat. No. 5,200,910 and U.S. Pat. No. 5,365,456 ("Method for Modeling the Electron Density of a Crystal"), each of which is herein specifically incorporated by reference in their entirety.

For basic information on molecular modeling, see, for example, M. Schlecht, Molecular Modeling on the PC, 1998, John Wiley & Sons; Gans et al., Fundamental Principals of Molecular Modeling, 1996, Plenum Pub. Corp.; N. C. Cohen (editor), Guidebook on Molecular Modeling in Drug Design, 1996, Academic Press; and W. B. Smith, Introduction to Theoretical Organic Chemistry and Molecular Modeling, 1996. U.S. patents which provide detailed information on molecular modeling include U.S. Pat. Nos. 6,093,573; 6,080,576; 6,075,014; 6,075,123; 6,071,700; 5,994,503; 5,612,894; 5,583,973; 5,030,103; 4,906,122; and 4,812,12, each of which are incorporated by reference herein in their entirety.

B. Methods of Using the Atomic Coordinates to Identify and Design Ligands of Interest The atomic coordinates of the invention, such as those described in Table 1, Table 2, Table 3 or coordinates substantially identical to or homologous to those of Table 1, Table 2, or Table 3 may be used with any available methods to prepare three dimensional models of HDM2 as well as to identify and design HDM2 ligands, inhibitors or antagonists or agonist molecules.

For instance, three-dimensional modeling may be performed using the experimentally determined coordinates derived from X-ray diffraction patterns, such as those in Table 1 or Table 2, for example, wherein such modeling includes, but is not limited to, drawing pictures of the actual structures, building physical models of the actual structures, and determining the structures of related subunits and HDM2/ligand and HDM2 subunit/ligand complexes using the coordinates. Such molecular modeling can utilize known X-ray diffraction molecular modeling algorithms or molecular modeling software to generate atomic coordinates corresponding to the three-dimensional structure of HDM2.

As described above, molecular modeling involves the use of computational methods, preferably computer assisted methods, to build realistic models of molecules that are identifiably related in sequence to the known crystal structure. It also involves modeling new small molecule inhibitors bound to HDM2 starting with the structures of HDM2 and or HDM2 complexed with known ligands or inhibitors. The methods utilized in ligand modeling range from molecular graphics (i.e., 3D representations) to computational chemistry (i.e., calculations of the physical and chemical properties) to make predictions about the binding of ligands or activities of ligands; to design new ligands; and to predict novel molecules, including ligands such as drugs, for chemical synthesis, collectively referred to as rational drug design.

One approach to rational drug design is to search for known molecular structures that might bind to an active site. Using molecular modeling, rational drug design programs can look at a range of different molecular structures of drugs that may fit into the active site of an enzyme, and by moving them in a three-dimensional environment it can be decided which structures actually fit the site well. See, for example, U.S. Appl. Nos. 60/275,629; 60/331,235; 60/379,617; and, 10/097,249. See, also, for example, data in Tables 1, 2 and 3.

An alternative but related rational drug design approach starts with the known structure of a complex with a small molecule ligand and models modifications of that small molecule in an effort to make additional favorable interactions with HDM2.

The present invention include the use of molecular and computer modeling techniques to design and select and design ligands, such as small molecule agonists or antagonists or other therapeutic agents that interact with HDM2. Such agents include, but are not limited to 1,4 benzodiazepines and derivatives thereof. For example, the invention as herein described includes the design of ligands that act as competitive inhibitors of at least one HDM2 function by binding to all, or a portion of, the active sites or other regions of HDM2.

This invention also includes the design of compounds that act as uncompetitive inhibitors of at least one function of HDM2. These inhibitors may bind to all, or a portion of, the active sites or other regions of HDM2 already bound to its substrate and may be more potent and less non-specific than competitive inhibitors that compete for HDM2 active sites. Similarly, non-competitive inhibitors that bind to and inhibit at least one function of HDM2 whether or not it is bound to another chemical entity may be designed using the atomic coordinates of HDM2 or complexes comprising HDM2 of this invention.

The atomic coordinates of the present invention also provide the needed information to probe a crystal of HDM2 with molecules composed of a variety of different chemical features to determine optimal sites for interaction between candidate inhibitors and/or activators and HDM2. For example, high resolution X-ray diffraction data collected from crystals saturated with solvent allows the determination of where each type of solvent molecule sticks. Small molecules that bind to those sites can then be designed and synthesized and tested for their inhibitory activity (Travis, J., Science 262:1374 (1993)).

The present invention also includes methods for computationally screening small molecule databases and libraries for chemical entities, agents, ligands, or compounds that can bind in whole, or in part, to HDM2. In this screening, the quality of fit of such entities or compounds to the binding site or sites may be judged either by shape complementarity or by estimated interaction energy (Meng, E. C. et al., J. Coma. Chem. 13:505-524 (1992)).

The design of compounds that bind to promote or inhibit the functional activity of HDM2 according to this invention generally involves consideration of two factors. First, the compound must be capable of physically and structurally associating with HDM2. Non-covalent molecular interactions important in the association of HDM2 with the compound, include hydrogen bonding, van der Waals and hydrophobic interactions. Second, the compound must be able to assume a conformation that allows it to associate with HDM2. Although certain portions of the compound may not directly participate in the association with HDM2, those portions may still influence the overall conformation of the molecule. This, in turn, may have a significant impact on binding affinities, therapeutic efficacy, drug-like qualities and potency. Such conformational requirements include the overall three-dimensional structure and orientation of the chemical entity or compound in relation to all or a portion of the active site or other region of HDM2, or the spacing between functional groups of a compound comprising several chemical entities that directly interact with HDM2.

The potential, predicted, inhibitory agonist, antagonist or binding effect of a ligand or other compound on HDM2 may be analyzed prior to its actual synthesis and testing by the use of computer modeling techniques. If the theoretical structure of the given compound suggests insufficient interaction and association between it and HDM2, synthesis and testing of the compound may be obviated. However, if computer modeling indicates a strong interaction, the molecule may then be synthesized and tested for its ability to interact with HDM2. In this manner, synthesis of inoperative compounds may be avoided. In some cases, inactive compounds are synthesized predicted on modeling and then tested to develop a SAR (structure-activity relationship) for compounds interacting with a specific region of HDM2.

One skilled in the art may use one of several methods to screen chemical entities fragments, compounds, or agents for their ability to associate with HDM2 and more particularly with the individual binding pockets or active sites of HDM2. This process may begin by visual inspection of, for example, the active site on the computer screen based on the atomic coordinates of HDM2 or HDM2 complexed with a ligand. Selected chemical entities, compounds, or agents may then be positioned in a variety of orientations, or docked within an individual binding pocket of HDM2. Docking may be accomplished using software such as Quanta and Sybyl, followed by energy minimization and molecular dynamics with standard molecular mechanics forcefields, such as CHARMM and AMBER.

Specialized computer programs may also assist in the process of selecting chemical entities. These include but are not limited to: GRID (Goodford, P. J., "A Computational Procedure for Determining Energetically Favorable Binding Sites on Biologically Important Macromolecules," J. Med. Chem. 28:849-857 (1985), available from Oxford University, Oxford, UK); MCSS (Miranker, A. and M. Karplus, "Functionality Maps of Binding Sites: A Multiple Copy Simultaneous Search Method." Proteins: Structure, Function and Genetics 11: 29-34 (1991), available from Molecular Simulations, Burlington, Mass.); AUTODOCK (Goodsell, D. S. and A. J. Olsen, "Automated Docking of Substrates to Proteins by Simulated Annealing" Proteins: Structure. Function, and Genetics 8:195-202 (1990), available from Scripps Research Institute, La Jolla, Calif.); and DOCK (Kuntz, I. D.

et al., "A Geometric Approach to Macromolecule-Ligand Interactions," *J. Mol. Biol.* 161:269-288 (1982), available from University of California, San Francisco, Calif.).

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand binding site and suggest ligands with complementary steric properties.

Once suitable chemical entities, compounds, or agents have been selected, they can be assembled into a single ligand or compound or inhibitor or activator. Assembly may proceed by visual inspection of the relationship of the fragments to each other on the three-dimensional image. This may be followed by manual model building using software such as Quanta or Sybyl.

Useful programs to aid in connecting the individual chemical entities, compounds, or agents include but are not limited to: CAVEAT (Bartlett, P. A. et al., "CAVEAT: A Program to Facilitate the Structure-Derived Design of Biologically Active Molecules." In Molecular Recognition in Chemical and Biological Problems, Special Pub., Royal Chem. Soc., 78, pp. 82-196 (1989)); 3D Database systems such as MACCS-3D (MDL Information Systems, San Leandro, Calif. and Martin, Y. C., "3D Database Searching in Drug Design", *J. Med. Chem.* 35: 2145-2154 (1992); and HOOK (available from Molecular Simulations, Burlington, Mass.).

Several methodologies for searching three-dimensional databases to test pharmacophore hypotheses and select compounds for screening are available. These include the program CAVEAT (Bacon et al., *J. Mol. Biol.* 225:849-858 (1992)). For instance, CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding.

Instead of proceeding to build an inhibitor activator, agonist or antagonist of HDM2 in a step-wise fashion one chemical entity at a time as described above, such compounds may be designed as a whole or "de novo" using either an empty active site or optionally including some portion(s) of a known molecules. These methods include: LUDI (Bohm, H.-J., "The Computer Program LUDI: A New Method for the De Novo Design of Enzyme Inhibitors", J. ComR. Aid. Molec. Design, 6, pp. 61-78 (1992), available from Biosym Technologies, San Diego, Calif.); LEGEND (Nishibata, Y. and A. Itai, *Tetrahedron* 47:8985 (1991), available from Molecular Simulations, Burlington, Mass.); and LeapFrog (available from Tripos Associates, St. Louis, Mo.).

For instance, the program LUDI can determine a list of interaction sites into which to place both hydrogen bonding and hydrophobic fragments. LUDI then uses a library of linkers to connect up to four different interaction sites into fragments. Then smaller "bridging" groups such as —CH2— and —COO— are used to connect these fragments. For example, for the enzyme DHFR, the placements of key functional groups in the well-known inhibitor methotrexate were reproduced by LUDI. See also, Rotstein and Murcko, *J. Med. Chem.* 36: 1700-1710 (1992).

Other molecular modeling techniques may also be employed in accordance with this invention. See, e.g., Cohen, N. C. et al., "Molecular Modeling Software and Methods for Medicinal Chemistry, *J. Med. Chem.* 33:883-894 (1990). See also, Navia, M. A. and M. A. Murcko, "The Use of Structural Information in Drug Design," Current Opinions in Structural Biology, 2, pp. 202-210 (1992).

Once a compound has been designed or selected by the above methods, the affinity with which that compound may bind or associate with HDM2 may be tested and optimized by computational evaluation and/or by testing biological activity after synthesizing the compound. Inhibitors or compounds may interact with the HDM2 in more than one conformation that is similar in overall binding energy. In those cases, the deformation energy of binding is taken to be the difference between the energy of the free compound and the average energy of the conformations observed when the compound binds to HDM2.

A compound designed or selected as binding or associating with HDM2 may be further computationally optimized so that in its bound state it would preferably lack repulsive electrostatic interaction with HDM2. Such non-complementary (e.g., electrostatic) interactions include repulsive charge-charge, dipole-dipole and charge-dipole interactions. Specifically, the sum of all electrostatic interactions between the inhibitor and HDM2 when the inhibitor is bound, preferably make a neutral or favorable contribution to the enthalpy of binding. Weak binding compounds will also be designed by these methods so as to determine SAR. See, for example, U.S. Appl. Nos. 60/275,629; 60/331,235; 60/379,617; and, Ser. No. 10/097,249.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., COPYRGT 1992); AMBER, version 4.0 (P. A. Kollman, University of California at San Francisco, COPYRGT 1994); QUANTA/CHARMM (Molecular Simulations, Inc., Burlington, Mass. COPYRGT 1994); and Insight II/Discover (Biosysm Technologies Inc., San Diego, Calif. COPYRGT 1994). Other hardware systems and software packages will be known to those skilled in the art.

Once a compound that associates with HDM2 has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted chemical compounds may then be analyzed for efficiency of fit to HDM2 by the same computer methods described in detail, above.

C. Use of Homology Structure Modeling to Design Ligands with Modulated Binding or Activity to HDM2

The present invention includes the use of the atomic coordinates and structures of HDM2 and/or HDM2 complexed with an inhibitor to design modifications to starting compounds, such as (4-Choloro-phenyl)-[3-(4-chloro-phenyl)-7-iodo-2,5-dioxo-1,2,3,5-tetrahydro-benzo[e][1,4]diazepin-4-yl]-acetic acid; [8-Chloro-3-(4-chloro-phenyl)-7-iodo-2,5-dioxo-1,2,3,5-tetrahydro-benzo[e][1,4]diazepin-4-yl]-(4-chloro-phenyl)-acetic acid; and derivatives thereof that will bind more tightly or interact more specifically to the target enzyme. See, U.S. Appl. Nos. 60/275,629; 60/331,235;

60/379,617; and, Ser. No. 10/097,249, disclosing compounds 1 and 2 and derivatives thereof, all of which are incorporated herein in their entirety.

Compound 1 (338437): (4-Chloro-phenyl)-[3-(4-chloro-phenyl)-7-iodo-2,5-dioxo-1,2,3,5-tetrahydro-benzo[e][1,4]diazepin-4-yl]-acetic acid

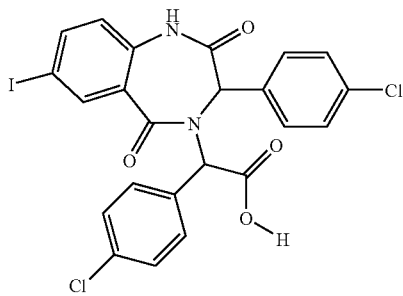

Compound 2 (876273): [8-Chloro-3-(4-chloro-phenyl)-7-iodo-2,5-dioxo-1,2,3,5-tetrahydro-benzo[e][1,4]diazepin-4-yl]-(4-chloro-phenyl)-acetic acid

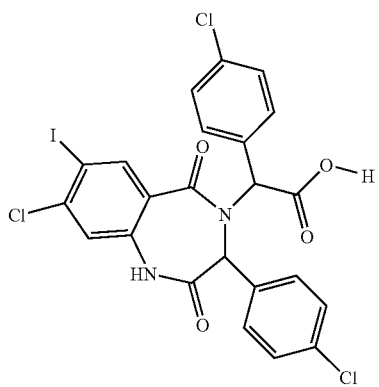

The structure of a complex between the HDM2 and the starting compound can be used to guide the modification of that compound to produce new compounds that have other desirable properties for applicable industrial and other uses (e.g., as pharmaceuticals), such as chemical stability, solubility or membrane permeability. (Lipinski et al., Adv. Drug Deliv. Rev. 23:3 (1997)).

Binding compounds, agonists, antagonists and such that are known in the art include but are not limited to p53 peptides and small molecule antagonists. See, for example, U.S. Appl. Nos. 60/275,629; 60/331,235; 60/379,617; and, Ser. No. 10/097,249 incorporated by reference herein in their entirety. Such compounds can be diffused into or soaked with the stabilized crystals of HDM2 to form a complex for collecting X-ray diffraction data. Alternatively, the compounds, known and unknown in the art, can be cocrystallized with HDM2 by mixing the compound with HDM2 before precipitation.

To produce custom high affinity and very specific compounds, the structure of HDM2 can be compared to the structure of a selected non-targeted molecule and a hybrid constructed by changing the structure of residues at the binding site for a ligand for the residues at the same positions of the non-target molecule. The process whereby this modeling is achieved is referred to as homology structure modeling. This is done computationally by removing the side chains from the molecule or target of known structure and replacing them with the side chains of the unknown structure put in sterically plausible positions. In this way it can be understood how the shapes of the active site cavities of the targeted and non-targeted molecules differ. This process, therefore, provides information concerning how a bound ligand can be chemically altered in order to produce compounds that will bind tightly and specifically to the desired target but will simultaneously be sterically prevented from binding to the non-targeted molecule. Likewise, knowledge of portions of the bound ligands that are facing to the solvent would allow introduction of other functional groups for additional pharmaceutical purposes. The use of homology structure modeling to design molecules (ligands) that bind more tightly to the target enzyme than to the non-target enzyme has wide spread applicability.

D. High Throughput Assays

Any high throughput screening may be utilized to test new compounds which are identified or designed for their ability to interact with HDM2. For general information on high-throughput screening see, for example, Devlin, 1998, High Throughput Screening, Marcel Dekker; and U.S. Pat. No. 5,763,263. High throughput assays utilize one or more different assay techniques including, but not limited to, those described below.

Immunodiagnostics and Immunoassays. These are a group of techniques used for the measurement of specific biochemical substances, commonly at low concentrations in complex mixtures such as biological fluids, that depend upon the specificity and high affinity shown by suitably prepared and selected antibodies for their complementary antigens. A substance to be measured must, of necessity, be antigenic—either an immunogenic macromolecule or a haptenic small molecule. To each sample a known, limited amount of specific antibody is added and the fraction of the antigen combining with it, often expressed as the bound:free ratio, is estimated, using as indicator a form of the antigen labeled with radioisotope (radioimmunoassay), fluorescent molecule (fluoroimmunoassay), stable free radical (spin immunoassay), enzyme (enzyme immunoassay), or other readily distinguishable label.

Antibodies can be labeled in various ways, including: enzyme-linked immunosorbent assay (ELISA); radioimmuno assay (RIA); fluorescent immunoassay (FIA); chemiluminescent immunoassay (CLIA); and labeling the antibody with colloidal gold particles (immunogold).

Common assay formats include the sandwich assay, competitive or competition assay, latex agglutination assay, homogeneous assay, microtitre plate format and the microparticle-based assay.

Enzyme-linked immunosorbent assay (ELISA). ELISA is an immunochemical technique that avoids the hazards of radiochemicals and the expense of fluorescence detection systems. Instead, the assay uses enzymes as indicators. ELISA is a form of quantitative immunoassay based on the use of antibodies (or antigens) that are linked to an insoluble carrier surface, which is then used to "capture" the relevant antigen (or antibody) in the test solution. The antigen-antibody complex is then detected by measuring the activity of an appropriate enzyme that had previously been covalently attached to the antigen (or antibody).

For information on ELISA techniques, see, for example, Crowther, (1995) ELISA—Theory and Practice (Methods in Molecular Biology), Humana Press; Challacombe &

Kemeny, (1998) ELISA and Other Solid Phase Immunoassays—Theoretical and Practical Aspects, John Wiley; Kemeny, (1991) A Practical Guide to ELISA, Pergamon Press; Ishikawa, (1991) Ultrasensitive and Rapid Enzyme Immunoassay (Laboratory Techniques in Biochemistry and Molecular Biology) Elsevier.

Colorimetric Assays for Enzymes. Colorimetry is any method of quantitative chemical analysis in which the concentration or amount of a compound is determined by comparing the color produced by the reaction of a reagent with both standard and test amounts of the compound, often using a colorimeter. A colorimeter is a device for measuring color intensity or differences in color intensity, either visually or photoelectrically.

Standard colorimetric assays of beta-galactosidase enzymatic activity are well known to those skilled in the art (see, for example, Norton et al., *Mol. Cell. Biol.* 5:281-290 (1985). A colorimetric assay can be performed on whole cell lysates using O-nitrophenyl-beta-D-galactopyranoside (ONPG, Sigma) as the substrate in a standard colorimetric beta-galactosidase assay (Sambrook et al., (1989) Molecular Cloning—A Laboratory Manual, Cold Spring Harbor Laboratory Press). Automated colorimetric assays are also available for the detection of beta-galactosidase activity, as described in U.S. Pat. No. 5,733,720.

Immunofluorescence Assays Immunofluorescence or immunofluorescence microscopy is a technique in which an antigen or antibody is made fluorescent by conjugation to a fluorescent dye and then allowed to react with the complementary antibody or antigen in a tissue section or smear. The location of the antigen or antibody can then be determined by observing the fluorescence by microscopy under ultraviolet light.

For general information on immunofluorescent techniques, see, for example, Knapp et al., (1978) Immunofluorescence and Related Staining Techniques, Elsevier; Allan, (1999) Protein Localization by Fluorescent Microscopy—A Practical Approach (The Practical Approach Series) Oxford University Press; Caul, (1993) Immunofluorescence Antigen Detection Techniques in Diagnostic Microbiology, Cambridge University Press. For detailed explanations of immunofluorescent techniques applicable to the present invention, see U.S. Pat. No. 5,912,176; U.S. Pat. No. 5,869,264; U.S. Pat. No. 5,866,319; and U.S. Pat. No. 5,861,259.

E. Databases and Computer Systems

An amino acid sequence or nucleotide sequence of HDM2 and/or X-ray diffraction data, useful for computer molecular modeling of HDM2 or a portion thereof, can be "provided" in a variety of mediums to facilitate use thereof. As used herein, "provided" refers to a manufacture, which contains, for example, an amino acid sequence or nucleotide sequence and/or atomic coordinates derived from X-ray diffraction data of the present invention, e.g., an amino acid or nucleotide sequence of HDM2, a representative fragment thereof, or a homologue thereof. Such a method provides the amino acid sequence and/or X-ray diffraction data in a form which allows a skilled artisan to analyze and molecular model the three-dimensional structure of HDM2 or related molecules, including a subdomain thereof.

In one application of this embodiment, databases comprising data pertaining to HDM2, or at least one subdomain thereof, amino acid and nucleic acid sequence and/or X-ray diffraction data of the present invention is recorded on computer readable medium. As used herein, "computer readable medium" refers to any medium which can be read and accessed directly by a computer. Such media include, but are not limited to: magnetic storage media, such as floppy discs, hard disc storage media, and magnetic tape; optical storage media such as optical discs or CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon an amino acid sequence and/or X-ray diffraction data of the present invention.

As used herein, "recorded" refers to a process for storing information on computer readable media. A skilled artisan can readily adopt any of the presently known methods for recording information on computer readable media to generate manufactures comprising an amino acid sequence and/or atomic coordinate/X-ray diffraction data information of the present invention.

A variety of data storage structures are available to a skilled artisan for creating a computer readable medium having recorded thereon an amino acid sequence and/or atomic coordinate/X-ray diffraction data of the present invention. The choice of the data storage structure will generally be based on the means chosen to access the stored information. In addition, a variety of data processor programs and formats can be used to store the sequence and X-ray data information of the present invention on computer readable media. The sequence information can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable media having recorded thereon the information of the present invention.

By providing computer readable media having sequence and/or atomic coordinates based on X-ray diffraction data, a skilled artisan can routinely access the sequence and atomic coordinate or X-ray diffraction data to model a related molecule, a subdomain, mimetic, or a ligand thereof. Computer algorithms are publicly and commercially available which allow a skilled artisan to access this data provided in a computer readable medium and analyze it for molecular modeling and/or RDD (rational drug design). See, e.g., Biotechnology Software Directory, MaryAnn Liebert Publ., New York (1995).

The present invention further provides systems, particularly computer-based systems, which contain the sequence and/or diffraction data described herein. Such systems are designed to do structure determination and RDD for HDM2 or at least one subdomain thereof. Non-limiting examples are microcomputer workstations available from Silicon Graphics Incorporated and Sun Microsystems running UNIX based, Windows NT or IBM OS/2 operating systems.

As used herein, "a computer-based system" refers to the hardware means, software means, and data storage means used to analyze the sequence and/or X-ray diffraction data of the present invention. The minimum hardware means of the computer-based systems of the present invention comprises a central processing unit (CPU), input means, output means, and data storage means. A skilled artisan can readily appreciate which of the currently available computer-based systems are suitable for use in the present invention. A visualization device, such as a monitor, is optionally provided to visualize structure data.

As stated above, the computer-based systems of the present invention comprise a data storage means having stored therein sequence and/or atomic coordinate/X-ray diffraction data of the present invention and the necessary hardware means and software means for supporting and implementing an analysis means. As used herein, "data storage means" refers to memory which can store sequence or atomic coordinate/X-ray diffraction data of the present invention, or a memory access means which can access manufactures having recorded thereon the sequence or X-ray data of the present invention.

As used herein, "search means" or "analysis means" refers to one or more programs which are implemented on the computer-based system to compare a target sequence or target structural motif with the sequence or X-ray data stored within the data storage means. Search means are used to identify fragments or regions of a protein which match a particular target sequence or target motif. A variety of known algorithms are disclosed publicly and a variety of commercially available software for conducting search means are and can be used in the computer-based systems of the present invention. A skilled artisan can readily recognize that any one of the available algorithms or implementing software packages for conducting computer analyses can be adapted for use in the present computer-based systems.

As used herein, "a target structural motif," or "target motif," refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymatic active sites, inhibitor binding sites, structural subdomains, epitopes, functional domains and signal sequences. Similar motifs are known for RNA. A variety of structural formats for the input and output means can be used to input and output the information in the computer-based systems of the present invention.

A variety of comparing means can be used to compare a target sequence or target motif with the data storage means to identify structural motifs or electron density maps derived in part from the atomic coordinate/X-ray diffraction data. A skilled artisan can readily recognize that any one of the publicly available computer modeling programs can be used as the search means for the computer-based systems of the present invention.

F. Target Molecule Fragments and Portions

Fragments of HDM2, for instance fragments comprising active sites defined by two or more amino acids selected from the group consisting of: $Ser^{17}$, $Ile^{19}$, $Leu^{82}$ and $Arg^{97}$, may be prepared by any available means including synthetic or recombinant means. Such fragments may then be used in the assays as described above, for instance, high through-put assays to detect interactions between prospective agents and the active site within the fragment.

For recombinant expression or production of the fragments of the invention, nucleic acid molecules encoding the fragment may be prepared. As used herein, "nucleic acid" is defined as RNA or DNA that encodes a protein or peptide as defined above, or is complementary to nucleic acid sequence encoding such peptides, or hybridizes to such nucleic acid and remains stably bound to it under appropriate stringency conditions.

Nucleic acid molecules encoding fragments of the invention may differ in sequence because of the degeneracy in the genetic code or may differ in sequence as they encode proteins or protein fragments that differ in amino acid sequence. Homology or sequence identity between two or more such nucleic acid molecules is determined by BLAST (Basic Local Alignment Search Tool) analysis using the algorithm employed by the programs blastp, blastn, blastx, tblastn and tblastx (Karlin et al., *Proc. Natl. Acad. Sci. USA* 87:2264-2268 (1990) and Altschul, et al., *J. Mol. Evol.* 36:290-300 (1993), fully incorporated by reference) which are tailored for sequence similarity searching.

The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (*Nat. Genet.* 6, 119-129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., *Proc. Natl. Acad. Sci. USA* 89:10915-10919 (1992), fully incorporated by reference). Four blastn parameters were adjusted as follows: Q=10 (gap creation penalty); R=10 (gap extension penalty); wink=1 (generates word hits at every $wink^{th}$ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS at 50° C. or (2) employ during hybridization a denaturing agent such as formamide, for example, 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC, 50 mM sodium phosphate (pH 6.8), 0.1% sodium pyrophosphate, 5×Denhardt's solution, sonicated salmon sperm DNA (50 mg/ml), 0.1% SDS and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

As used herein, a nucleic acid molecule is said to be "isolated" when the nucleic acid molecule is substantially separated from contaminant nucleic acid encoding other polypeptides from the source of nucleic acid.

The encoding nucleic acid molecules of the present invention (i.e., synthetic oligonucleotides) and those that are used as probes or specific primers for polymerase chain reaction (PCR) or to synthesize gene sequences encoding proteins of the invention can easily be synthesized by chemical techniques, for example, the phosphotriester method of Matteucci et al. (*J. Am. Chem. Soc.* 103: 185-3191 (1981)) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art-known labels to obtain a labeled encoding nucleic acid molecule.

The present invention further provides recombinant DNA molecules (rDNA) that contain a coding sequence for a protein fragment as described above. As used herein, a rDNA molecule is a DNA molecule that has been subjected to molecular manipulation. Methods for generating rDNA molecules are well known in the art, for example, see Sambrook et al. Molecular Cloning—A Laboratory Manual, Cold Spring Harbor Laboratory Press (1989). In the preferred rDNA molecules, a coding DNA sequence is operably linked to expression control sequences and/or vector sequences.

The choice of vector and expression control sequences to which one of the protein encoding sequences of the present invention is operably linked depends directly, as is well known in the art, on the functional properties desired (e.g., protein expression, and the host cell to be transformed). A vector of the present invention may be capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

The present invention further provides host cells transformed with a nucleic acid molecule that encodes a protein fragment of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells NIH-3T3 available from the ATCC as CRL1658, baby hamster kidney cells (BHK), and the like eukaryotic tissue culture cell lines.

Transformed host cells of the invention may be cultured under conditions that allow the production of the recombinant protein. Optionally the recombinant protein is isolated from the medium or from the cells; recovery and purification of the protein may not be necessary in some instances where some impurities may be tolerated.

Kits may also be prepared with any of the above described nucleic acid molecules, protein fragments, vector and/or host cells optionally packaged with the reagents needed for a specific assay, such as those described above. In such kits, the protein fragments or other reagents may be attached to a solid support, such as glass or plastic beads.

G. Integrated Procedures which Utilize the Present Invention

Molecular modeling is provided by the present invention for rational drug design (RDD) of mimetics and ligands of HDM2. As described above, the drug design paradigm uses computer modeling programs to determine potential mimetics and ligands which are expected to interact with sites on the protein. The potential mimetics or ligands are then screened for activity and/or binding and/or interaction. For HDM2-related mimetics or ligands, screening methods can be selected from assays for at least one biological activity of HDM2, e.g., such as blocking p53 binding, according to known method steps. See, for example, Kussie et al., Science 274:948-953 (1996); Bottger et al., J. Mol. Biol. 269:744-756 (1997).

Thus, the tools and methodologies provided by the present invention may be used in procedures for identifying and designing ligands which bind in desirable ways with the target. Such procedures utilize an iterative process whereby ligands are synthesized, tested and characterized. New ligands can be designed based on the information gained in the testing and characterization of the initial ligands and then such newly identified ligands can themselves be tested and characterized. This series of processes may be repeated as many times as necessary to obtain ligands with the desirable binding properties.

The following steps serve as an example of the overall procedure:

1. A biological activity of a target is selected (e.g., binding to p53).

2. A ligand is identified that appears to be in some way associated with the chosen biological activity (e.g., the ligand may be an inhibitor of a known activity). The activity of the ligand may be tested by in vivo and/or in vitro methods.

A ligand of the present invention can be, but is not limited to, at least one selected from a lipid, a nucleic acid, a compound, a protein, an element, an antibody, a saccharide, an isotope, a carbohydrate, an imaging agent, a lipoprotein, a glycoprotein, an enzyme, a detectable probe, and antibody or fragment thereof, or any combination thereof, which can be detectably labeled as for labeling antibodies. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the invention. Suitable compounds are then tested for activities in relationship to the target.

Complexes between HDM2 and ligands are made either by co-crystallization or more commonly by diffusing the small molecule ligand into the crystal. X-ray diffraction data from the complex crystal are measured and a difference electron density map is calculated. This process provides the precise location of the bound ligand on the target molecule. The difference Fourier is calculated using measure diffraction amplitudes and the phases of these reflections calculated from the coordinates.

3. Using the methods of the present invention, X-ray crystallography is utilized to create electron density maps and/or molecular models of the interaction of the ligand with the target molecule.

The entry of the coordinates of the target into the computer programs discussed above results in the calculation of most probable structure of the macromolecule. These structures are combined and refined by additional calculations using such programs to determine the probable or actual three-dimensional structure of the target including potential or actual active or binding sites of ligands. Such molecular modeling (and related) programs useful for rational drug design of ligands or mimetics, are also provided by the present invention.

4. The electron density maps and/or molecular models obtained in Step 3 are compared to the electron density maps and/or molecular models of a non-ligand containing target and the observed/calculated differences are used to specifically locate the binding of the ligand on the target or subunit.

5. Modeling tools, such as computational chemistry and computer modeling, are used to adjust or modify the structure of the ligand so that it can make additional or different interactions with the target.

The ligand design uses computer modeling programs which calculate how different molecules interact with the various sites of a target. This procedure determines potential ligands or mimetics of the ligand(s).

The ligand design uses computer modeling programs which calculate how different molecules interact with the various sites of the target, subunit, or a fragment thereof. Thus, this procedure determines potential ligands or ligand mimetics.

6. The newly designed ligand from Step 5 can be tested for its biological activity using appropriate in vivo or in vitro tests, including the high throughput screening methods discussed above.

The potential ligands or mimetics are then screened for activity relating to HDM2, or at least a fragment thereof. Such screening methods are selected from assays for at least one biological activity of the native target.

The resulting ligands or mimetics, provided by methods of the present invention, are useful for treating, screening or preventing diseases in animals, such as mammals (including humans) and birds.

7. Of course, each of the above steps can be modified as desired by those of skill in the art so as to refine the procedure for the particular goal in mind. Also, additional X-ray diffraction data may be collected on HDM2, HDM2/ligand complexes, HDM2 structural target motifs and HDM2 subunit/ligand complexes at any step or phase of the procedure. Such additional diffraction data can be used to reconstruct electron density maps and molecular models which may further assist in the design and selection of ligands with the desirable binding attributes.

It is to be understood that the present invention is considered to include stereoisomers as well as optical isomers, e.g., mixtures of enantiomers as well as individual enantiomers and diastereomers, which arise as a consequence of structural asymmetry in selected compounds, ligands or mimetics of the present series.

Some of the compounds or agents disclosed or discovered by the methods herein may contain one or more asymmetric centers and thus give rise to enantiomers, diastereomers, and other stereoisomeric forms. The present invention is also meant to encompass all such possible forms as well as their racemic and resolved forms and mixtures thereof. When the compounds described or discovered herein contain olefinic double bonds or other centers of geometric asymmetry, and unless otherwise specified, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

As used herein, the term "chiral center" refers to a carbon atom to which four different groups are attached.

As used herein, the term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

As used herein, the term "racemic" refers to a mixture of equal parts of enantiomers and which is optically active.

As used herein, the term "resolution" refers to the separation or concentration or depletion of one of the two enantiomeric forms of a molecule. In the context of this application, the term "resolution" also refers to the amount of detail which can be resolved by the diffraction experiment. Or in other terms, since the inherent disorder of a protein crystal diffraction pattern fades away at some diffraction angle $\theta_{max}$, the corresponding distance $d_{min}$ of the reciprocal lattices is determined by Bragg's law.

$$d_{min} = \frac{\lambda}{2\sin\theta_{max}}$$

In practice in protein crystallography it is usual to quote the nominal resolution of a protein electron density in terms of $d_{min}$, the minimum lattice distance to which data is included in the calculation of the map.

The compounds of the present invention are also useful at inhibiting the interaction between p53 and MDMX. MDMX, also known as MDM4, is a cellular protein involved in the regulation of the cell cycle. For example, see Riemenschneider et al., *Cancer Res.* 59(24):6091-6096 (1999).

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

GST HDM2 Fusion Protein Construction and Expression cDNA encoding residues 17-111 of HDM2 (SEQ ID NO: 2) were cloned and expressed as follows: PCR was performed using ATCC item number 384988 containing partial human MDM2 sequence as template and the following primers:

```
Forward:
                                          (SEQ ID NO: 5)
5'-CTCTCTCGGATCCCAGATTCCAGCTTCGGAACAAGAG, Reverse:
                                          (SEQ ID NO: 6)
5'-TATATATCTCGAGTCAGTTCTCACTCACAGATGTACCTGAG.
```

The PCR product was then digested with BamHI and XhoI (sequence recognition sites underlined in primers), gel purified, and ligated into pGEX4t-3 which had also been digested with BamHI and XhoI. The purified plasmid was transformed into *E. coli* strain BL21. Protein was produced at 37° C. in 2 L shake flasks containing 800 ml LB (Laura Bertani medium)+100 µg/ml ampicillin and supplemented with 0.2% glycerol. Briefly media was inoculated with 16 ml of overnight culture and induced with 1 mM IPTG when the absorbance at 600 reached 0.6-0.8 OD. Cells were harvested 5 hr post induction.

For HDM2 23-114(SEQ ID NO: 3), the primers used were as follows:

(SEQ ID NO: 7)
5'-CGACGATTGGATCCGAACAAAGACCCTG, (SEQ ID NO: 8)
3'-GGCTACTACTCCGAGTCATTCCTGCTGATTGACTAC

For HDM2 17-111(SEQ ID NO: 1), the primers used were (SEQ ID NO: 9)
5'-CTCTCTCGGATCCCAGATTCAGCTTCCGGAACAAGAG, (SEQ ID NO: 10)
3'-TTCAGCAGCTCGAGTCAATTGACTACTACCAAGTTC.

The PCR fragments were cloned and expressed as above with a few exceptions. *E. coli* strain BL21 RIL was used for expression. Cells were grown at 37° C. until $A_{600}$ of 0.2, then transferred to room temperature and induced at $A_{600}$ of 0.6-0.8 with 0.1 mM IPTG. Cells were harvested 5 hours post induction, centrifuged, and resuspended in PBS to 10 ml/g cell paste.

Protein Production

Cells were lysed in an Avestin microfluidizer, centrifuged, and the supernatant bound to a glutathione sepharose 4B resin (Pharmacia). The resin was washed with PBS and the HDM2 construct of interest was cleaved from the GST-resin by the addition of 2 µg/ml thrombin (Enzyme Research Labs). The cleaved HDM2 was loaded onto a Sepharose SP Fast Flow resin (Pharmacia), and eluted with a 20 mM HEPES pH. 7.5, 150 mM NaCl. Glutathione was added to 5 mM, and the protein stored at −70° C. The resulting protein has an N-terminal Glycine before amino acid 17 (Serine).

Protein Preparation for Crystallography

HDM2 17-111 (SEQ ID NO: 2) was complexed with the compound of interest by dialysis at a concentration of 0.7 mg/ml, the buffer brought to 20 mM HEPES pH. 7.4, 100 mM NaCl, 5 mM DTT, filtered through a 0.02 µm filter, and concentrated to 10 mg/ml.

Example 2

Crystallization and Data Collection

In a typical crystallization experiment, 1-2 µl of HDM2 protein (SEQ ID NO: 2), complexed with a compound and concentrated to ca. 10 mg/ml, was mixed in a 1:1 ratio with well solution (1.8-2.4M $(NH_4)_2SO_4$, 100 mM buffer pH. 6.5-9.0, 2% PEG 400, 100 mM NaSCN) and placed on a glass cover slip. The cover slip was inverted and sealed over a reservoir of 500-1000 µl of well solution and incubated at 4° C. Crystals usually appeared over night and were ready to harvest after 3-7 days. Crystals were harvested with a nylon loop, placed for less than 30 seconds in cryo-solution (2.2M $(NH_4)_2SO_4$, 100 mM bis-tris-propane pH. 7.5, 2% PEG 400, 100 mM NaSCN, 15% glycerol) and frozen by immersion in liquid nitrogen or liquid propane. Data were collected at 120K on a Bruker AXS M06XCE rotating anode and a SMART 6000 CCD detector. The diffraction data was processed with the Proteum suite (Bruker AXS).

Example 3

Assay Methods

Peptide Binding Assay

The inhibition of MDM2 binding to p53 was measured using a p53 peptide analog binding to MDM2 residues 17-125 (SEQ ID NO: 2). The published crystal structure of this complex (Kussie, P. H., et al., *Science* 274:948-953 (1996)) validates this fragment as containing the p53 binding site, and we have solved the X-ray structure of the p53 peptide analog MPRFMDYWEGLN, described to be a peptide inhibitor of the MDM2 p53 interaction (Bottger, A., et al., *J Mol Biol* 269:744-756 (1997)). The assay uses N terminal fluorescein RFMDYWEGL peptide (Fl 9 mer). Compound was incubated for 15 minutes with 30 nM fluorescein peptide Fl 9 mer and 120 nM HDM2 17-125 in 50 mM HEPES pH. 7.5, 150 mM NaCl, 3 mM octyl glucoside. The polarization of the fluorescein label was measured by excitation at 485 nm and emission at 530 nm Polarization was expressed as a percent of a no compound control, using no MDM2 with Fl 9 mer as background.

Example 4

HDM2 Atomic Coordinates

Table 1 (Compound 1) Complexes with HDM2 Protein (SEQ ID NO: 2)

Table 1 describes the 3-dimensional atomic coordinates of HDM2 complexed with compound 1 (338437) ((4-Chloro-phenyl)-[3-(4-chloro-phenyl)-7-iodo-2,5-dioxo-1,2,3,5-tetrahydro-benzo[e][1,4]diazepin-4-yl]-acetic acid and bound waters in standard pdb-format. The relevant crystallographic data are contained in the REMARK section of Table 1. Two molecules of HDM2, related by non-crystallographic symmetry, are present in the asymmetric unit and are identified by the CHAINID of A for the first molecule and B for the second molecule. The compound (compound 1) is present under the residue name DCB. Compound 1 and HDM2 molecule sharing the same CHAINID are forming a complex.

Example 5

HDM2 Atomic Coordinates

Table 2 (Compound 2) Complexes with HDM2 Protein (SEQ ID NO: 2)

Compound 2 [8-Chloro-3-(4-chloro-phenyl)-7-iodo-2,5-dioxo-1,2,3,5-tetrahydro-benzo[e][1,4]diazepin-4-yl]-(4-chloro-phenyl)-acetic acid (876273) and HDM2 protein were cocrystallized as described above in Example 2. Table 2 describes the 3-dimensional atomic coordinates of HDM2 complexed with compound 2 (876273) ([8-Chloro-3-(4-chloro-phenyl)-7-iodo-2,5-dioxo-1,2,3,5-tetrahydro-benzo [e][1,4]diazepin-4-yl]-(4-chloro-phenyl)-acetic acid). The relevant crystallographic data are contained in the REMARK section of Table 2. Data were collected as described above. Different crystal forms can be observed under the same crystallization conditions used to obtain the trigonal crystal form.

Example 6

HDM2 Atomic Coordinates

Table 3

Table 3 describes the 3-dimensional atomic coordinates of HDM2 cocrystallized with compound 2 (compound 876273: [8-Chloro-3-(4-chloro-phenyl)-7-iodo-2,5-dioxo-1,2,3,5-tetrahydro-benzo[e][1,4]diazepin-4-yl]-(4-chloro-phenyl)-acetic acid) in tetragonal spacegroup aligned to the structure of HDM2 complexed with compound 1 (compound 338437 ((4-Chloro-phenyl)-[3-(4-chloro-phenyl)-7-iodo-2,5-dioxo-1,2,3,5-tetrahydro-benzo[e][1,4]diazepin-4-yl]-acetic acid). The relevant crystallographic data are contained in the REMARK section of Table 3. Data were collected as described above.

The pdb-format is described on various sites on the web. Depending on the program crystallographic application minor modifications to this format may be found. A good primer is provided at the website of The Collaborative Computational Project No. 4. A more extended description can be found at the RCSB home page.

Example 7

Phasing

Model Building and Refinement

Phases were obtained by molecular replacement using the published HDM2-structure as a search model in CNX (Brunger, A. T., et al., P. D. *Acta Cryst* D54:905-921 (1998); Accelrys Inc.). Alternating cycles of structure refinement and model building were carried out according to standard protocols using CNX and O (Jones, T. A., et al., *Acta Cryst* A47: 110-119 (1991)).

Example 8

Structural Features of HDM2

FIG. 1. Ribbon representation of HDM2 bound to compound 1 (compound 338437: ((4-Chloro-phenyl)-[3-(4-chloro-phenyl)-7-iodo-2,5-dioxo-1,2,3,5-tetrahydro-benzo[e][1,4]diazepin-4-yl]-acetic acid).

Figure 2:
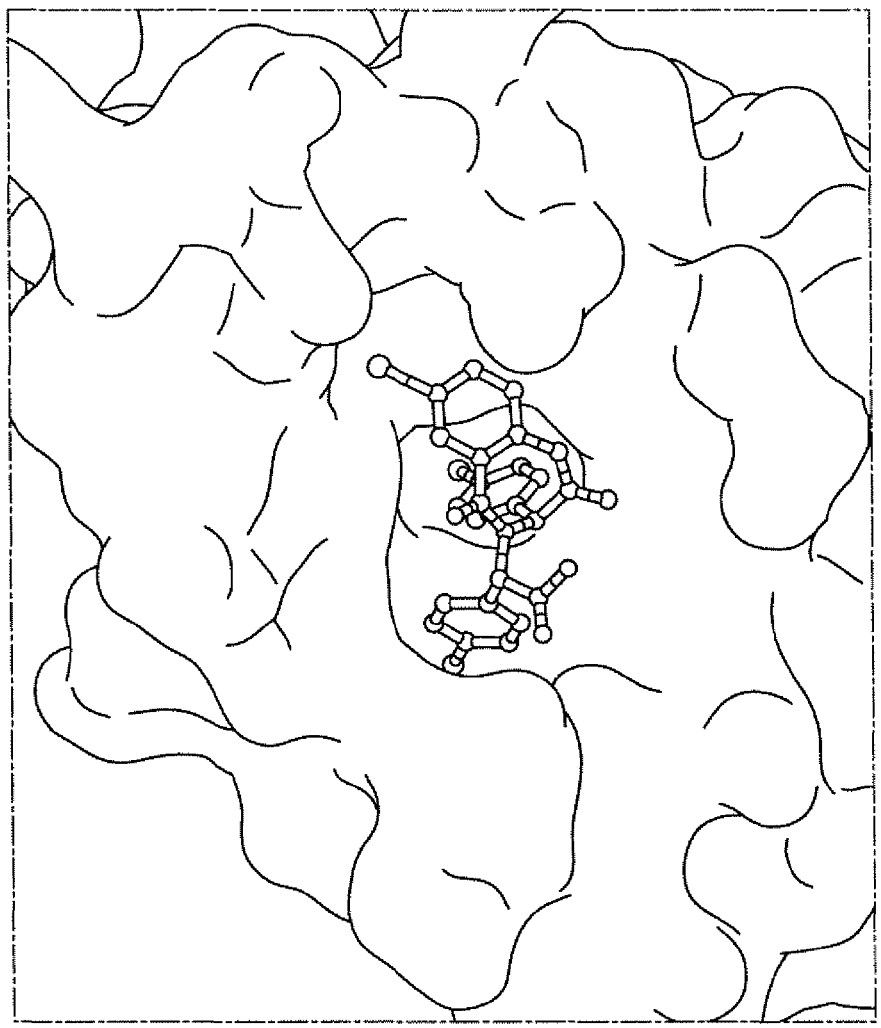
FIG. 2 Fit of compound 338437 into the active site of HDM2 (SEQ ID NO: 2) represented as a molecular surface.
Figure 3:
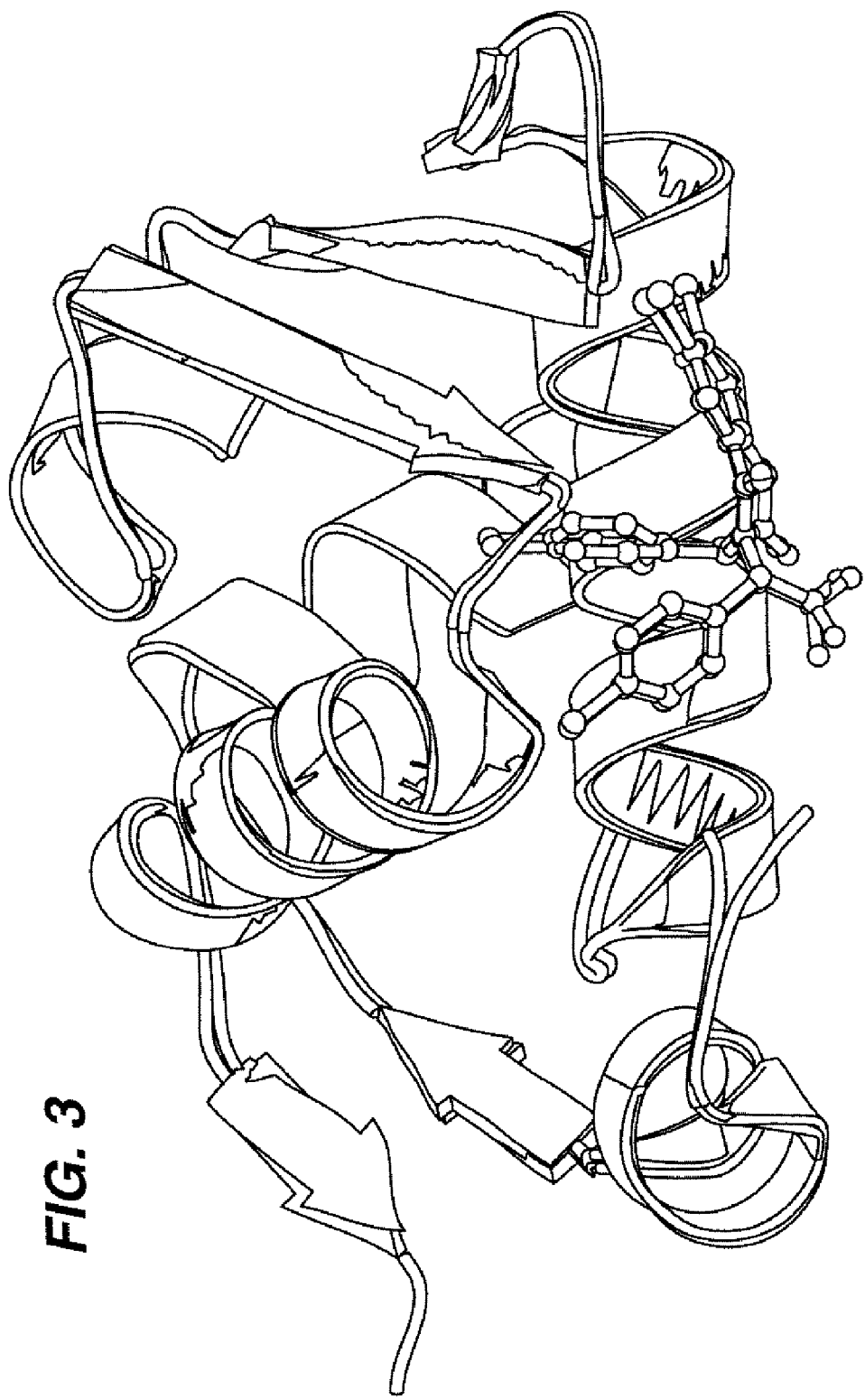
FIG. 3 Ribbon representation of a superposition between hdm2 (SEQ ID NO: 2) in the trigonal crystal form and in the tetragonal form. The RMS deviation between C-alpha atom positions is 0.25 Angstroms.

FIG. 2. Fit of compound 1 (compound 338437: ((4-Chloro-phenyl)-[3-(4-chloro-phenyl)-7-iodo-2,5-dioxo-1,2,3,5-tetrahydro-benzo[e][1,4]diazepin-4-yl]-acetic acid into the active site of HDM2 presented as a molecular surface.

Although the present invention has been described in detail with reference to examples above, it is understood that various modifications can be made without departing from the spirit of the invention. All cited patents, patent applications and publications and other documents cited in this application are herein incorporated by reference in their entirety.

TABLE 1

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | |
|---|---|---|---|---|---|---|---|---|---|---|
| REMARK | coordinates from restrained individual B-factor refinement | | | | | | | | | |
| REMARK | refinement resolution: 500.0-2.6 A | | | | | | | | | |
| REMARK | starting   r= 0.2398 free_r= 0.2763 | | | | | | | | | |
| REMARK | final       r= 0.2390 free_r= 0.2765 | | | | | | | | | |
| REMARK | B rmsd for bonded mainchain atoms= 1.358    target= 1.5 | | | | | | | | | |
| REMARK | B rmsd for bonded sidechain atoms= 1.887    target= 2.0 | | | | | | | | | |
| REMARK | B rmsd for angle mainchain atoms= 2.371    target= 2.0 | | | | | | | | | |
| REMARK | B rmsd for angle sidechain atoms= 2.965    target= 2.5 | | | | | | | | | |
| REMARK | rweight=   0.1000 (with wa= 2.71183) | | | | | | | | | |
| REMARK | target= mlf    steps= 30 | | | | | | | | | |
| REMARK | sg=P3(2)21 a=98.486 b=98.486 c=74.038 alpha=90 beta=90 gamma=120 | | | | | | | | | |
| REMARK | parameter file 1   : MSI_CNX_TOPPAR:protein_rep.param | | | | | | | | | |
| REMARK | parameter file 2   : dcb.par | | | | | | | | | |
| REMARK | parameter file 3   : MSI_CNX_TOPPAR:water_rep.param | | | | | | | | | |
| REMARK | molecular structure file: cycle8.psf | | | | | | | | | |
| REMARK | input coordinates: minimize.pdb | | | | | | | | | |
| REMARK | reflection file= ../M338437_P3221.cv | | | | | | | | | |
| REMARK | ncs= none | | | | | | | | | |
| REMARK | B-correction resolution: 6.0-2.6 | | | | | | | | | |
| REMARK | initial B-factor correction applied to fobs: | | | | | | | | | |
| REMARK |     B11=   5.509 B22=   5.509 B33=   −11.019 | | | | | | | | | |
| REMARK |     B12=   0.263 B13=   0.000 B23=    0.000 | | | | | | | | | |
| REMARK | B-factor correction applied to coordinate array B:     0.036 | | | | | | | | | |
| REMARK | bulk solvent: (Mask) density level= 0.372649 e/Â3, B-factor= 25.2844 Â2 | | | | | | | | | |
| REMARK | reflections with |Fobs|/sigma_F < 0.0 rejected | | | | | | | | | |
| REMARK | reflections with |Fobs| > 10000 * rms(Fobs) rejected | | | | | | | | | |
| REMARK | theoretical total number of refl. in resol. range:    13090 (100.0%) | | | | | | | | | |
| REMARK | number of unobserved reflections (no entry or |F|=0):   176 (1.3%) | | | | | | | | | |
| REMARK | number of reflections rejected:    0 (0.0%) | | | | | | | | | |
| REMARK | total number of reflections used:    12914 (98.7%) | | | | | | | | | |
| REMARK | number of reflections in working set:    11964 (91.4%) | | | | | | | | | |
| REMARK | number of reflections in test set:    950 (7.3%) | | | | | | | | | |
| CRYST1 | 98.486    98.486    74.038    90.00    90.00 120.00 P 32 2 1 | | | | | | | | | |
| REMARK | FILENAME="bindividual.pdb" | | | | | | | | | |
| REMARK | Written by CNX VERSION: 2000.12 | | | | | | | | | |
| ATOM | 1 | C | GLY | A | 16 | 47.235 | 17.293 | 23.953 | 1.00 | 68.07 A | C |
| ATOM | 2 | O | GLY | A | 16 | 48.284 | 16.646 | 23.907 | 1.00 | 68.13 A | O |
| ATOM | 3 | N | GLY | A | 16 | 44.698 | 17.056 | 23.726 | 1.00 | 66.75 A | N |
| ATOM | 4 | CA | GLY | A | 16 | 46.042 | 16.904 | 23.083 | 1.00 | 67.77 A | C |
| ATOM | 5 | N | SER | A | 17 | 47.083 | 18.352 | 24.744 | 1.00 | 67.81 A | N |
| ATOM | 6 | CA | SER | A | 17 | 48.154 | 18.831 | 25.618 | 1.00 | 66.82 A | C |
| ATOM | 7 | CB | SER | A | 17 | 48.407 | 17.831 | 26.743 | 1.00 | 67.50 A | C |
| ATOM | 8 | OG | SER | A | 17 | 47.247 | 17.658 | 27.540 | 1.00 | 67.94 A | O |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | | |
|---|---|---|---|---|---|---|---|---|---|---|---|
| ATOM | 9 | C | SER | A | 17 | 49.456 | 19.118 | 24.864 | 1.00 | 65.58 A | C |
| ATOM | 10 | O | SER | A | 17 | 49.699 | 20.265 | 24.476 | 1.00 | 66.26 A | O |
| ATOM | 11 | N | GLN | A | 18 | 50.304 | 18.108 | 24.657 | 1.00 | 63.21 A | N |
| ATOM | 12 | CA | GLN | A | 18 | 51.543 | 18.367 | 23.921 | 1.00 | 60.51 A | C |
| ATOM | 13 | CB | GLN | A | 18 | 52.778 | 17.995 | 24.735 | 1.00 | 60.31 A | C |
| ATOM | 14 | CG | GLN | A | 18 | 53.833 | 19.070 | 24.574 | 1.00 | 59.93 A | C |
| ATOM | 15 | CD | GLN | A | 18 | 53.200 | 20.457 | 24.506 | 1.00 | 59.70 A | C |
| ATOM | 16 | OE1 | GLN | A | 18 | 52.584 | 20.919 | 25.464 | 1.00 | 59.78 A | O |
| ATOM | 17 | NE2 | GLN | A | 18 | 53.333 | 21.112 | 23.362 | 1.00 | 59.29 A | N |
| ATOM | 18 | C | GLN | A | 18 | 51.619 | 17.752 | 22.529 | 1.00 | 58.18 A | C |
| ATOM | 19 | O | GLN | A | 18 | 52.569 | 17.049 | 22.158 | 1.00 | 57.08 A | O |
| ATOM | 20 | N | ILE | A | 19 | 50.573 | 18.064 | 21.776 | 1.00 | 54.61 A | N |
| ATOM | 21 | CA | ILE | A | 19 | 50.380 | 17.673 | 20.399 | 1.00 | 49.59 A | C |
| ATOM | 22 | CB | ILE | A | 19 | 49.130 | 16.771 | 20.256 | 1.00 | 47.27 A | C |
| ATOM | 23 | CG2 | ILE | A | 19 | 48.730 | 16.643 | 18.802 | 1.00 | 46.21 A | C |
| ATOM | 24 | CG1 | ILE | A | 19 | 49.407 | 15.403 | 20.880 | 1.00 | 44.27 A | C |
| ATOM | 25 | CD1 | ILE | A | 19 | 50.565 | 14.675 | 20.263 | 1.00 | 40.62 A | C |
| ATOM | 26 | C | ILE | A | 19 | 50.112 | 19.056 | 19.806 | 1.00 | 48.49 A | C |
| ATOM | 27 | O | ILE | A | 19 | 49.344 | 19.838 | 20.374 | 1.00 | 46.95 A | O |
| ATOM | 28 | N | PRO | A | 20 | 50.765 | 19.396 | 18.686 | 1.00 | 47.71 A | N |
| ATOM | 29 | CD | PRO | A | 20 | 51.681 | 18.610 | 17.840 | 1.00 | 46.47 A | C |
| ATOM | 30 | CA | PRO | A | 20 | 50.521 | 20.721 | 18.107 | 1.00 | 46.58 A | C |
| ATOM | 31 | CB | PRO | A | 20 | 51.072 | 20.574 | 16.695 | 1.00 | 46.92 A | C |
| ATOM | 32 | CG | PRO | A | 20 | 52.256 | 19.667 | 16.919 | 1.00 | 46.74 A | C |
| ATOM | 33 | C | PRO | A | 20 | 49.041 | 21.112 | 18.134 | 1.00 | 45.69 A | C |
| ATOM | 34 | O | PRO | A | 20 | 48.181 | 20.376 | 17.636 | 1.00 | 45.19 A | O |
| ATOM | 35 | N | ALA | A | 21 | 48.751 | 22.264 | 18.738 | 1.00 | 43.36 A | N |
| ATOM | 36 | CA | ALA | A | 21 | 47.379 | 22.755 | 18.832 | 1.00 | 40.68 A | C |
| ATOM | 37 | CB | ALA | A | 21 | 47.371 | 24.193 | 19.350 | 1.00 | 39.15 A | C |
| ATOM | 38 | C | ALA | A | 21 | 46.710 | 22.676 | 17.460 | 1.00 | 39.20 A | C |
| ATOM | 39 | O | ALA | A | 21 | 45.518 | 22.379 | 17.351 | 1.00 | 38.64 A | O |
| ATOM | 40 | N | SER | A | 22 | 47.490 | 22.937 | 16.414 | 1.00 | 37.13 A | N |
| ATOM | 41 | CA | SER | A | 22 | 46.996 | 22.881 | 15.042 | 1.00 | 34.91 A | C |
| ATOM | 42 | CB | SER | A | 22 | 48.140 | 23.167 | 14.077 | 1.00 | 36.91 A | C |
| ATOM | 43 | OG | SER | A | 22 | 49.177 | 22.202 | 14.208 | 1.00 | 39.98 A | O |
| ATOM | 44 | C | SER | A | 22 | 46.428 | 21.494 | 14.755 | 1.00 | 32.16 A | C |
| ATOM | 45 | O | SER | A | 22 | 45.349 | 21.356 | 14.179 | 1.00 | 32.41 A | O |
| ATOM | 46 | N | GLU | A | 23 | 47.179 | 20.474 | 15.159 | 1.00 | 28.39 A | N |
| ATOM | 47 | CA | GLU | A | 23 | 46.785 | 19.084 | 14.981 | 1.00 | 25.53 A | C |
| ATOM | 48 | CB | GLU | A | 23 | 47.986 | 18.167 | 15.280 | 1.00 | 24.74 A | C |
| ATOM | 49 | CG | GLU | A | 23 | 47.650 | 16.698 | 15.507 | 1.00 | 22.09 A | C |
| ATOM | 50 | CD | GLU | A | 23 | 48.881 | 15.805 | 15.524 | 1.00 | 21.23 A | C |
| ATOM | 51 | OE1 | GLU | A | 23 | 49.956 | 16.270 | 15.952 | 1.00 | 22.29 A | O |
| ATOM | 52 | OE2 | GLU | A | 23 | 48.775 | 14.631 | 15.120 | 1.00 | 19.31 A | O |
| ATOM | 53 | C | GLU | A | 23 | 45.597 | 18.733 | 15.879 | 1.00 | 23.76 A | C |
| ATOM | 54 | O | GLU | A | 23 | 44.756 | 17.928 | 15.501 | 1.00 | 21.78 A | O |
| ATOM | 55 | N | GLN | A | 24 | 45.524 | 19.345 | 17.059 | 1.00 | 22.33 A | N |
| ATOM | 56 | CA | GLN | A | 24 | 44.423 | 19.086 | 17.985 | 1.00 | 21.86 A | C |
| ATOM | 57 | CB | GLN | A | 24 | 44.628 | 19.838 | 19.294 | 1.00 | 22.56 A | C |
| ATOM | 58 | CG | GLN | A | 24 | 45.721 | 19.267 | 20.157 | 1.00 | 26.35 A | C |
| ATOM | 59 | CD | GLN | A | 24 | 45.896 | 20.017 | 21.458 | 1.00 | 27.27 A | C |
| ATOM | 60 | OE1 | GLN | A | 24 | 44.964 | 20.131 | 22.262 | 1.00 | 27.74 A | O |
| ATOM | 61 | NE2 | GLN | A | 24 | 47.101 | 20.533 | 21.676 | 1.00 | 29.00 A | N |
| ATOM | 62 | C | GLN | A | 24 | 43.063 | 19.464 | 17.423 | 1.00 | 21.99 A | C |
| ATOM | 63 | O | GLN | A | 24 | 42.047 | 18.871 | 17.786 | 1.00 | 21.50 A | O |
| ATOM | 64 | N | GLU | A | 25 | 43.045 | 20.456 | 16.542 | 1.00 | 22.95 A | N |
| ATOM | 65 | CA | GLU | A | 25 | 41.800 | 20.921 | 15.939 | 1.00 | 24.26 A | C |
| ATOM | 66 | CB | GLU | A | 25 | 41.874 | 22.432 | 15.665 | 1.00 | 25.71 A | C |
| ATOM | 67 | CG | GLU | A | 25 | 42.226 | 23.265 | 16.884 | 1.00 | 27.74 A | C |
| ATOM | 68 | CD | GLU | A | 25 | 41.218 | 23.107 | 18.006 | 1.00 | 30.63 A | C |
| ATOM | 69 | OE1 | GLU | A | 25 | 41.640 | 23.112 | 19.187 | 1.00 | 32.01 A | O |
| ATOM | 70 | OE2 | GLU | A | 25 | 40.005 | 22.987 | 17.705 | 1.00 | 30.20 A | O |
| ATOM | 71 | C | GLU | A | 25 | 41.479 | 20.179 | 14.644 | 1.00 | 23.62 A | C |
| ATOM | 72 | O | GLU | A | 25 | 40.472 | 20.461 | 13.995 | 1.00 | 24.16 A | O |
| ATOM | 73 | N | THR | A | 26 | 42.337 | 19.237 | 14.267 | 1.00 | 22.53 A | N |
| ATOM | 74 | CA | THR | A | 26 | 42.123 | 18.462 | 13.052 | 1.00 | 21.97 A | C |
| ATOM | 75 | CB | THR | A | 26 | 43.138 | 17.299 | 12.955 | 1.00 | 23.07 A | C |
| ATOM | 76 | OG1 | THR | A | 26 | 44.472 | 17.828 | 12.972 | 1.00 | 22.96 A | O |
| ATOM | 77 | CG2 | THR | A | 26 | 42.920 | 16.499 | 11.675 | 1.00 | 21.12 A | C |
| ATOM | 78 | C | THR | A | 26 | 40.705 | 17.894 | 13.031 | 1.00 | 21.66 A | C |
| ATOM | 79 | O | THR | A | 26 | 40.281 | 17.217 | 13.962 | 1.00 | 19.94 A | O |
| ATOM | 80 | N | LEU | A | 27 | 39.974 | 18.187 | 11.963 | 1.00 | 23.11 A | N |
| ATOM | 81 | CA | LEU | A | 27 | 38.602 | 17.713 | 11.805 | 1.00 | 25.25 A | C |
| ATOM | 82 | CB | LEU | A | 27 | 37.888 | 18.593 | 10.775 | 1.00 | 26.19 A | C |
| ATOM | 83 | CG | LEU | A | 27 | 36.362 | 18.646 | 10.828 | 1.00 | 28.80 A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 84 | CD1 | LEU | A | 27 | 35.918 | 19.212 | 12.183 | 1.00 | 26.94 | A | C |
|------|----|-----|-----|---|----|--------|--------|--------|------|-------|---|---|
| ATOM | 85 | CD2 | LEU | A | 27 | 35.840 | 19.512 | 9.677 | 1.00 | 28.47 | A | C |
| ATOM | 86 | C | LEU | A | 27 | 38.620 | 16.240 | 11.350 | 1.00 | 24.95 | A | C |
| ATOM | 87 | O | LEU | A | 27 | 39.275 | 15.901 | 10.359 | 1.00 | 26.23 | A | O |
| ATOM | 88 | N | VAL | A | 28 | 37.898 | 15.373 | 12.064 | 1.00 | 22.99 | A | N |
| ATOM | 89 | CA | VAL | A | 28 | 37.882 | 13.938 | 11.749 | 1.00 | 20.72 | A | C |
| ATOM | 90 | CB | VAL | A | 28 | 38.810 | 13.143 | 12.719 | 1.00 | 18.95 | A | C |
| ATOM | 91 | CG1 | VAL | A | 28 | 40.213 | 13.729 | 12.734 | 1.00 | 17.23 | A | C |
| ATOM | 92 | CG2 | VAL | A | 28 | 38.230 | 13.164 | 14.118 | 1.00 | 16.75 | A | C |
| ATOM | 93 | C | VAL | A | 28 | 36.500 | 13.284 | 11.833 | 1.00 | 21.21 | A | C |
| ATOM | 94 | O | VAL | A | 28 | 35.593 | 13.805 | 12.486 | 1.00 | 19.81 | A | O |
| ATOM | 95 | N | ARG | A | 29 | 36.365 | 12.131 | 11.174 | 1.00 | 22.25 | A | N |
| ATOM | 96 | CA | ARG | A | 29 | 35.126 | 11.340 | 11.159 | 1.00 | 23.75 | A | C |
| ATOM | 97 | CB | ARG | A | 29 | 34.559 | 11.229 | 9.742 | 1.00 | 25.97 | A | C |
| ATOM | 98 | CG | ARG | A | 29 | 33.678 | 12.388 | 9.308 | 1.00 | 32.69 | A | C |
| ATOM | 99 | CD | ARG | A | 29 | 33.206 | 12.199 | 7.866 | 1.00 | 38.68 | A | C |
| ATOM | 100 | NE | ARG | A | 29 | 32.256 | 13.231 | 7.455 | 1.00 | 45.71 | A | N |
| ATOM | 101 | CZ | ARG | A | 29 | 31.002 | 13.322 | 7.901 | 1.00 | 50.53 | A | C |
| ATOM | 102 | NH1 | ARG | A | 29 | 30.534 | 12.439 | 8.777 | 1.00 | 52.47 | A | N |
| ATOM | 103 | NH2 | ARG | A | 29 | 30.208 | 14.299 | 7.472 | 1.00 | 52.60 | A | N |
| ATOM | 104 | C | ARG | A | 29 | 35.402 | 9.931 | 11.680 | 1.00 | 22.61 | A | C |
| ATOM | 105 | O | ARG | A | 29 | 35.891 | 9.076 | 10.944 | 1.00 | 23.74 | A | O |
| ATOM | 106 | N | PRO | A | 30 | 35.094 | 9.669 | 12.959 | 1.00 | 20.77 | A | N |
| ATOM | 107 | CD | PRO | A | 30 | 34.654 | 10.607 | 14.006 | 1.00 | 19.85 | A | C |
| ATOM | 108 | CA | PRO | A | 30 | 35.334 | 8.340 | 13.523 | 1.00 | 19.49 | A | C |
| ATOM | 109 | CB | PRO | A | 30 | 34.798 | 8.471 | 14.951 | 1.00 | 18.27 | A | C |
| ATOM | 110 | CG | PRO | A | 30 | 35.081 | 9.895 | 15.276 | 1.00 | 18.94 | A | C |
| ATOM | 111 | C | PRO | A | 30 | 34.655 | 7.206 | 12.757 | 1.00 | 19.01 | A | C |
| ATOM | 112 | O | PRO | A | 30 | 33.552 | 7.367 | 12.236 | 1.00 | 18.19 | A | O |
| ATOM | 113 | N | LYS | A | 31 | 35.332 | 6.063 | 12.689 | 1.00 | 19.05 | A | N |
| ATOM | 114 | CA | LYS | A | 31 | 34.790 | 4.880 | 12.033 | 1.00 | 19.18 | A | C |
| ATOM | 115 | CB | LYS | A | 31 | 35.919 | 3.891 | 11.703 | 1.00 | 18.74 | A | C |
| ATOM | 116 | CG | LYS | A | 31 | 36.881 | 4.392 | 10.630 | 1.00 | 18.49 | A | C |
| ATOM | 117 | CD | LYS | A | 31 | 38.048 | 3.442 | 10.409 | 1.00 | 16.87 | A | C |
| ATOM | 118 | CE | LYS | A | 31 | 39.007 | 3.982 | 9.359 | 1.00 | 16.16 | A | C |
| ATOM | 119 | NZ | LYS | A | 31 | 40.238 | 3.161 | 9.254 | 1.00 | 17.03 | A | N |
| ATOM | 120 | C | LYS | A | 31 | 33.777 | 4.260 | 13.009 | 1.00 | 19.76 | A | C |
| ATOM | 121 | O | LYS | A | 31 | 33.862 | 4.465 | 14.221 | 1.00 | 19.24 | A | O |
| ATOM | 122 | N | PRO | A | 32 | 32.816 | 3.480 | 12.492 | 1.00 | 20.78 | A | N |
| ATOM | 123 | CD | PRO | A | 32 | 32.772 | 2.971 | 11.106 | 1.00 | 20.08 | A | C |
| ATOM | 124 | CA | PRO | A | 32 | 31.778 | 2.840 | 13.311 | 1.00 | 20.65 | A | C |
| ATOM | 125 | CB | PRO | A | 32 | 31.376 | 1.640 | 12.465 | 1.00 | 18.59 | A | C |
| ATOM | 126 | CG | PRO | A | 32 | 31.460 | 2.197 | 11.079 | 1.00 | 19.84 | A | C |
| ATOM | 127 | C | PRO | A | 32 | 32.108 | 2.460 | 14.761 | 1.00 | 21.61 | A | C |
| ATOM | 128 | O | PRO | A | 32 | 31.412 | 2.877 | 15.695 | 1.00 | 20.03 | A | O |
| ATOM | 129 | N | LEU | A | 33 | 33.164 | 1.679 | 14.955 | 1.00 | 22.55 | A | N |
| ATOM | 130 | CA | LEU | A | 33 | 33.522 | 1.237 | 16.296 | 1.00 | 23.06 | A | C |
| ATOM | 131 | CB | LEU | A | 33 | 34.677 | 0.236 | 16.223 | 1.00 | 23.79 | A | C |
| ATOM | 132 | CG | LEU | A | 33 | 34.537 | −0.992 | 17.135 | 1.00 | 24.29 | A | C |
| ATOM | 133 | CD1 | LEU | A | 33 | 33.136 | −1.597 | 17.020 | 1.00 | 22.52 | A | C |
| ATOM | 134 | CD2 | LEU | A | 33 | 35.597 | −2.015 | 16.747 | 1.00 | 23.61 | A | C |
| ATOM | 135 | C | LEU | A | 33 | 33.850 | 2.370 | 17.260 | 1.00 | 23.64 | A | C |
| ATOM | 136 | O | LEU | A | 33 | 33.348 | 2.385 | 18.382 | 1.00 | 25.22 | A | O |
| ATOM | 137 | N | LEU | A | 34 | 34.684 | 3.319 | 16.838 | 1.00 | 23.73 | A | N |
| ATOM | 138 | CA | LEU | A | 34 | 35.033 | 4.445 | 17.707 | 1.00 | 23.80 | A | C |
| ATOM | 139 | CB | LEU | A | 34 | 36.173 | 5.281 | 17.108 | 1.00 | 22.45 | A | C |
| ATOM | 140 | CG | LEU | A | 34 | 36.459 | 6.603 | 17.842 | 1.00 | 21.72 | A | C |
| ATOM | 141 | CD1 | LEU | A | 34 | 36.722 | 6.324 | 19.310 | 1.00 | 20.49 | A | C |
| ATOM | 142 | CD2 | LEU | A | 34 | 37.647 | 7.324 | 17.209 | 1.00 | 20.12 | A | C |
| ATOM | 143 | C | LEU | A | 34 | 33.829 | 5.351 | 17.949 | 1.00 | 24.92 | A | C |
| ATOM | 144 | O | LEU | A | 34 | 33.641 | 5.867 | 19.058 | 1.00 | 25.03 | A | O |
| ATOM | 145 | N | LEU | A | 35 | 33.019 | 5.549 | 16.911 | 1.00 | 24.02 | A | N |
| ATOM | 146 | CA | LEU | A | 35 | 31.841 | 6.394 | 17.027 | 1.00 | 24.15 | A | C |
| ATOM | 147 | CB | LEU | A | 35 | 31.113 | 6.470 | 15.690 | 1.00 | 21.76 | A | C |
| ATOM | 148 | CG | LEU | A | 35 | 30.415 | 7.787 | 15.341 | 1.00 | 20.69 | A | C |
| ATOM | 149 | CD1 | LEU | A | 35 | 29.176 | 7.489 | 14.522 | 1.00 | 17.66 | A | C |
| ATOM | 150 | CD2 | LEU | A | 35 | 30.026 | 8.526 | 16.589 | 1.00 | 20.82 | A | C |
| ATOM | 151 | C | LEU | A | 35 | 30.889 | 5.849 | 18.101 | 1.00 | 26.94 | A | C |
| ATOM | 152 | O | LEU | A | 35 | 30.302 | 6.617 | 18.870 | 1.00 | 27.88 | A | O |
| ATOM | 153 | N | LYS | A | 36 | 30.735 | 4.527 | 18.152 | 1.00 | 27.77 | A | N |
| ATOM | 154 | CA | LYS | A | 36 | 29.859 | 3.913 | 19.140 | 1.00 | 28.78 | A | C |
| ATOM | 155 | CB | LYS | A | 36 | 29.778 | 2.398 | 18.939 | 1.00 | 31.12 | A | C |
| ATOM | 156 | CG | LYS | A | 36 | 29.062 | 1.687 | 20.081 | 1.00 | 35.08 | A | C |
| ATOM | 157 | CD | LYS | A | 36 | 29.472 | 0.220 | 20.223 | 1.00 | 38.33 | A | C |
| ATOM | 158 | CE | LYS | A | 36 | 28.711 | −0.681 | 19.268 | 1.00 | 41.52 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 159 | NZ | LYS | A | 36 | 29.044 | −2.120 | 19.487 | 1.00 | 43.62 | A | N |
|---|---|---|---|---|---|---|---|---|---|---|---|---|
| ATOM | 160 | C | LYS | A | 36 | 30.397 | 4.200 | 20.530 | 1.00 | 28.98 | A | C |
| ATOM | 161 | O | LYS | A | 36 | 29.632 | 4.463 | 21.459 | 1.00 | 29.52 | A | O |
| ATOM | 162 | N | LEU | A | 37 | 31.719 | 4.137 | 20.664 | 1.00 | 28.82 | A | N |
| ATOM | 163 | CA | LEU | A | 37 | 32.396 | 4.395 | 21.936 | 1.00 | 28.09 | A | C |
| ATOM | 164 | CB | LEU | A | 37 | 33.908 | 4.244 | 21.751 | 1.00 | 28.11 | A | C |
| ATOM | 165 | CG | LEU | A | 37 | 34.888 | 4.330 | 22.929 | 1.00 | 27.55 | A | C |
| ATOM | 166 | CD1 | LEU | A | 37 | 34.655 | 5.592 | 23.736 | 1.00 | 27.78 | A | C |
| ATOM | 167 | CD2 | LEU | A | 37 | 34.730 | 3.109 | 23.788 | 1.00 | 27.77 | A | C |
| ATOM | 168 | C | LEU | A | 37 | 32.079 | 5.814 | 22.402 | 1.00 | 28.36 | A | C |
| ATOM | 169 | O | LEU | A | 37 | 31.730 | 6.034 | 23.559 | 1.00 | 27.57 | A | O |
| ATOM | 170 | N | LEU | A | 38 | 32.209 | 6.772 | 21.486 | 1.00 | 28.83 | A | N |
| ATOM | 171 | CA | LEU | A | 38 | 31.951 | 8.175 | 21.785 | 1.00 | 27.42 | A | C |
| ATOM | 172 | CB | LEU | A | 38 | 32.324 | 9.045 | 20.581 | 1.00 | 25.41 | A | C |
| ATOM | 173 | CG | LEU | A | 38 | 33.787 | 8.973 | 20.141 | 1.00 | 25.18 | A | C |
| ATOM | 174 | CD1 | LEU | A | 38 | 34.015 | 9.980 | 19.042 | 1.00 | 24.55 | A | C |
| ATOM | 175 | CD2 | LEU | A | 38 | 34.715 | 9.251 | 21.315 | 1.00 | 25.40 | A | C |
| ATOM | 176 | C | LEU | A | 38 | 30.504 | 8.449 | 22.186 | 1.00 | 27.27 | A | C |
| ATOM | 177 | O | LEU | A | 38 | 30.239 | 8.989 | 23.259 | 1.00 | 27.56 | A | O |
| ATOM | 178 | N | LYS | A | 39 | 29.562 | 8.083 | 21.327 | 1.00 | 26.08 | A | N |
| ATOM | 179 | CA | LYS | A | 39 | 28.163 | 8.325 | 21.638 | 1.00 | 24.78 | A | C |
| ATOM | 180 | CB | LYS | A | 39 | 27.294 | 7.885 | 20.461 | 1.00 | 23.77 | A | C |
| ATOM | 181 | CG | LYS | A | 39 | 27.593 | 8.696 | 19.215 | 1.00 | 25.97 | A | C |
| ATOM | 182 | CD | LYS | A | 39 | 26.657 | 8.409 | 18.051 | 1.00 | 26.72 | A | C |
| ATOM | 183 | CE | LYS | A | 39 | 26.943 | 9.401 | 16.916 | 1.00 | 29.24 | A | C |
| ATOM | 184 | NZ | LYS | A | 39 | 26.169 | 9.183 | 15.657 | 1.00 | 31.08 | A | N |
| ATOM | 185 | C | LYS | A | 39 | 27.708 | 7.655 | 22.940 | 1.00 | 23.69 | A | C |
| ATOM | 186 | O | LYS | A | 39 | 26.812 | 8.156 | 23.623 | 1.00 | 24.40 | A | O |
| ATOM | 187 | N | SER | A | 40 | 28.338 | 6.545 | 23.305 | 1.00 | 21.60 | A | N |
| ATOM | 188 | CA | SER | A | 40 | 27.946 | 5.850 | 24.522 | 1.00 | 18.78 | A | C |
| ATOM | 189 | CB | SER | A | 40 | 28.602 | 4.465 | 24.593 | 1.00 | 16.27 | A | C |
| ATOM | 190 | OG | SER | A | 40 | 29.947 | 4.538 | 25.020 | 1.00 | 13.26 | A | O |
| ATOM | 191 | C | SER | A | 40 | 28.299 | 6.663 | 25.766 | 1.00 | 18.97 | A | C |
| ATOM | 192 | O | SER | A | 40 | 27.808 | 6.376 | 26.854 | 1.00 | 18.43 | A | O |
| ATOM | 193 | N | VAL | A | 41 | 29.157 | 7.667 | 25.616 | 1.00 | 18.55 | A | N |
| ATOM | 194 | CA | VAL | A | 41 | 29.515 | 8.496 | 26.758 | 1.00 | 19.39 | A | C |
| ATOM | 195 | CB | VAL | A | 41 | 31.057 | 8.645 | 26.940 | 1.00 | 20.54 | A | C |
| ATOM | 196 | CG1 | VAL | A | 41 | 31.630 | 7.402 | 27.607 | 1.00 | 18.57 | A | C |
| ATOM | 197 | CG2 | VAL | A | 41 | 31.733 | 8.891 | 25.600 | 1.00 | 21.46 | A | C |
| ATOM | 198 | C | VAL | A | 41 | 28.887 | 9.881 | 26.662 | 1.00 | 20.20 | A | C |
| ATOM | 199 | O | VAL | A | 41 | 29.218 | 10.771 | 27.444 | 1.00 | 19.90 | A | O |
| ATOM | 200 | N | GLY | A | 42 | 27.975 | 10.062 | 25.707 | 1.00 | 20.98 | A | N |
| ATOM | 201 | CA | GLY | A | 42 | 27.306 | 11.345 | 25.571 | 1.00 | 21.00 | A | C |
| ATOM | 202 | C | GLY | A | 42 | 27.542 | 12.155 | 24.309 | 1.00 | 22.06 | A | C |
| ATOM | 203 | O | GLY | A | 42 | 26.809 | 13.107 | 24.060 | 1.00 | 23.06 | A | O |
| ATOM | 204 | N | ALA | A | 43 | 28.557 | 11.807 | 23.522 | 1.00 | 23.02 | A | N |
| ATOM | 205 | CA | ALA | A | 43 | 28.841 | 12.530 | 22.280 | 1.00 | 23.42 | A | C |
| ATOM | 206 | CB | ALA | A | 43 | 30.075 | 11.940 | 21.593 | 1.00 | 20.28 | A | C |
| ATOM | 207 | C | ALA | A | 43 | 27.632 | 12.427 | 21.354 | 1.00 | 23.40 | A | C |
| ATOM | 208 | O | ALA | A | 43 | 26.816 | 11.517 | 21.495 | 1.00 | 21.98 | A | O |
| ATOM | 209 | N | GLN | A | 44 | 27.505 | 13.352 | 20.407 | 1.00 | 25.42 | A | N |
| ATOM | 210 | CA | GLN | A | 44 | 26.369 | 13.279 | 19.502 | 1.00 | 27.06 | A | C |
| ATOM | 211 | CB | GLN | A | 44 | 25.130 | 13.872 | 20.165 | 1.00 | 27.82 | A | C |
| ATOM | 212 | CG | GLN | A | 44 | 25.315 | 15.232 | 20.763 | 1.00 | 28.96 | A | C |
| ATOM | 213 | CD | GLN | A | 44 | 24.576 | 15.357 | 22.085 | 1.00 | 32.56 | A | C |
| ATOM | 214 | OE1 | GLN | A | 44 | 24.357 | 16.462 | 22.585 | 1.00 | 34.47 | A | O |
| ATOM | 215 | NE2 | GLN | A | 44 | 24.200 | 14.215 | 22.668 | 1.00 | 31.28 | A | N |
| ATOM | 216 | C | GLN | A | 44 | 26.520 | 13.854 | 18.106 | 1.00 | 26.84 | A | C |
| ATOM | 217 | O | GLN | A | 44 | 25.532 | 14.268 | 17.500 | 1.00 | 26.83 | A | O |
| ATOM | 218 | N | LYS | A | 45 | 27.745 | 13.881 | 17.592 | 1.00 | 25.93 | A | N |
| ATOM | 219 | CA | LYS | A | 45 | 27.980 | 14.363 | 16.230 | 1.00 | 25.65 | A | C |
| ATOM | 220 | CB | LYS | A | 45 | 28.960 | 15.544 | 16.198 | 1.00 | 25.47 | A | C |
| ATOM | 221 | CG | LYS | A | 45 | 28.546 | 16.767 | 16.992 | 1.00 | 24.64 | A | C |
| ATOM | 222 | CD | LYS | A | 45 | 29.614 | 17.860 | 16.948 | 1.00 | 21.21 | A | C |
| ATOM | 223 | CE | LYS | A | 45 | 30.907 | 17.410 | 17.615 | 1.00 | 19.16 | A | C |
| ATOM | 224 | NZ | LYS | A | 45 | 31.849 | 18.543 | 17.785 | 1.00 | 16.01 | A | N |
| ATOM | 225 | C | LYS | A | 45 | 28.627 | 13.199 | 15.508 | 1.00 | 24.50 | A | C |
| ATOM | 226 | O | LYS | A | 45 | 28.904 | 12.162 | 16.112 | 1.00 | 24.58 | A | O |
| ATOM | 227 | N | ASP | A | 46 | 28.861 | 13.359 | 14.219 | 1.00 | 22.87 | A | N |
| ATOM | 228 | CA | ASP | A | 46 | 29.539 | 12.314 | 13.483 | 1.00 | 23.75 | A | C |
| ATOM | 229 | CB | ASP | A | 46 | 28.765 | 11.931 | 12.219 | 1.00 | 26.21 | A | C |
| ATOM | 230 | CG | ASP | A | 46 | 27.451 | 11.222 | 12.525 | 1.00 | 28.44 | A | C |
| ATOM | 231 | OD1 | ASP | A | 46 | 27.379 | 10.480 | 13.530 | 1.00 | 28.33 | A | O |
| ATOM | 232 | OD2 | ASP | A | 46 | 26.489 | 11.396 | 11.746 | 1.00 | 30.59 | A | O |
| ATOM | 233 | C | ASP | A | 46 | 30.913 | 12.872 | 13.125 | 1.00 | 23.42 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 234 | O   | ASP | A | 46 | 31.820 | 12.134 | 12.759 | 1.00 | 24.56 | A | O |
|------|-----|-----|-----|---|----|--------|--------|--------|------|-------|---|---|
| ATOM | 235 | N   | THR | A | 47 | 31.062 | 14.188 | 13.245 | 1.00 | 22.36 | A | N |
| ATOM | 236 | CA  | THR | A | 47 | 32.326 | 14.847 | 12.939 | 1.00 | 20.77 | A | C |
| ATOM | 237 | CB  | THR | A | 47 | 32.151 | 15.896 | 11.831 | 1.00 | 21.07 | A | C |
| ATOM | 238 | OG1 | THR | A | 47 | 31.573 | 15.276 | 10.676 | 1.00 | 22.41 | A | O |
| ATOM | 239 | CG2 | THR | A | 47 | 33.496 | 16.498 | 11.458 | 1.00 | 19.56 | A | C |
| ATOM | 240 | C   | THR | A | 47 | 32.859 | 15.536 | 14.187 | 1.00 | 19.61 | A | C |
| ATOM | 241 | O   | THR | A | 47 | 32.114 | 16.213 | 14.893 | 1.00 | 19.20 | A | O |
| ATOM | 242 | N   | TYR | A | 48 | 34.147 | 15.364 | 14.461 | 1.00 | 17.90 | A | N |
| ATOM | 243 | CA  | TYR | A | 48 | 34.744 | 15.966 | 15.646 | 1.00 | 17.29 | A | C |
| ATOM | 244 | CB  | TYR | A | 48 | 34.904 | 14.924 | 16.763 | 1.00 | 17.51 | A | C |
| ATOM | 245 | CG  | TYR | A | 48 | 33.645 | 14.195 | 17.178 | 1.00 | 18.47 | A | C |
| ATOM | 246 | CD1 | TYR | A | 48 | 33.094 | 13.199 | 16.376 | 1.00 | 17.60 | A | C |
| ATOM | 247 | CE1 | TYR | A | 48 | 31.926 | 12.549 | 16.743 | 1.00 | 19.18 | A | C |
| ATOM | 248 | CD2 | TYR | A | 48 | 32.993 | 14.518 | 18.368 | 1.00 | 18.07 | A | C |
| ATOM | 249 | CE2 | TYR | A | 48 | 31.826 | 13.877 | 18.746 | 1.00 | 18.21 | A | C |
| ATOM | 250 | CZ  | TYR | A | 48 | 31.291 | 12.893 | 17.930 | 1.00 | 19.97 | A | C |
| ATOM | 251 | OH  | TYR | A | 48 | 30.112 | 12.264 | 18.294 | 1.00 | 20.10 | A | O |
| ATOM | 252 | C   | TYR | A | 48 | 36.123 | 16.528 | 15.356 | 1.00 | 17.64 | A | C |
| ATOM | 253 | O   | TYR | A | 48 | 36.650 | 16.401 | 14.245 | 1.00 | 19.08 | A | O |
| ATOM | 254 | N   | THR | A | 49 | 36.695 | 17.172 | 16.364 | 1.00 | 16.11 | A | N |
| ATOM | 255 | CA  | THR | A | 49 | 38.057 | 17.677 | 16.267 | 1.00 | 16.21 | A | C |
| ATOM | 256 | CB  | THR | A | 49 | 38.219 | 19.061 | 16.891 | 1.00 | 15.01 | A | C |
| ATOM | 257 | OG1 | THR | A | 49 | 38.028 | 18.969 | 18.309 | 1.00 | 14.67 | A | O |
| ATOM | 258 | CG2 | THR | A | 49 | 37.212 | 20.006 | 16.316 | 1.00 | 14.41 | A | C |
| ATOM | 259 | C   | THR | A | 49 | 38.766 | 16.672 | 17.164 | 1.00 | 16.33 | A | C |
| ATOM | 260 | O   | THR | A | 49 | 38.142 | 16.091 | 18.057 | 1.00 | 16.33 | A | O |
| ATOM | 261 | N   | MET | A | 50 | 40.050 | 16.448 | 16.937 | 1.00 | 16.12 | A | N |
| ATOM | 262 | CA  | MET | A | 50 | 40.770 | 15.500 | 17.765 | 1.00 | 16.31 | A | C |
| ATOM | 263 | CB  | MET | A | 50 | 42.253 | 15.515 | 17.411 | 1.00 | 16.08 | A | C |
| ATOM | 264 | CG  | MET | A | 50 | 42.550 | 14.804 | 16.100 | 1.00 | 15.76 | A | C |
| ATOM | 265 | SD  | MET | A | 50 | 42.007 | 13.088 | 16.174 | 1.00 | 15.40 | A | S |
| ATOM | 266 | CE  | MET | A | 50 | 43.383 | 12.364 | 17.108 | 1.00 | 12.28 | A | C |
| ATOM | 267 | C   | MET | A | 50 | 40.570 | 15.820 | 19.236 | 1.00 | 17.20 | A | C |
| ATOM | 268 | O   | MET | A | 50 | 40.300 | 14.931 | 20.034 | 1.00 | 18.81 | A | O |
| ATOM | 269 | N   | LYS | A | 51 | 40.679 | 17.099 | 19.581 | 1.00 | 16.94 | A | N |
| ATOM | 270 | CA  | LYS | A | 51 | 40.515 | 17.551 | 20.952 | 1.00 | 16.59 | A | C |
| ATOM | 271 | CB  | LYS | A | 51 | 40.588 | 19.083 | 20.993 | 1.00 | 19.46 | A | C |
| ATOM | 272 | CG  | LYS | A | 51 | 40.773 | 19.662 | 22.382 | 1.00 | 24.41 | A | C |
| ATOM | 273 | CD  | LYS | A | 51 | 41.177 | 21.132 | 22.333 | 1.00 | 29.49 | A | C |
| ATOM | 274 | CE  | LYS | A | 51 | 41.633 | 21.623 | 23.711 | 1.00 | 30.87 | A | C |
| ATOM | 275 | NZ  | LYS | A | 51 | 42.111 | 23.039 | 23.693 | 1.00 | 32.84 | A | N |
| ATOM | 276 | C   | LYS | A | 51 | 39.195 | 17.059 | 21.555 | 1.00 | 15.64 | A | C |
| ATOM | 277 | O   | LYS | A | 51 | 39.133 | 16.677 | 22.729 | 1.00 | 14.01 | A | O |
| ATOM | 278 | N   | GLU | A | 52 | 38.139 | 17.062 | 20.750 | 1.00 | 15.07 | A | N |
| ATOM | 279 | CA  | GLU | A | 52 | 36.837 | 16.613 | 21.234 | 1.00 | 15.62 | A | C |
| ATOM | 280 | CB  | GLU | A | 52 | 35.738 | 17.017 | 20.254 | 1.00 | 16.29 | A | C |
| ATOM | 281 | CG  | GLU | A | 52 | 35.586 | 18.520 | 20.127 | 1.00 | 18.24 | A | C |
| ATOM | 282 | CD  | GLU | A | 52 | 34.649 | 18.921 | 19.018 | 1.00 | 19.03 | A | C |
| ATOM | 283 | OE1 | GLU | A | 52 | 34.764 | 18.341 | 17.918 | 1.00 | 22.90 | A | O |
| ATOM | 284 | OE2 | GLU | A | 52 | 33.812 | 19.821 | 19.236 | 1.00 | 19.46 | A | O |
| ATOM | 285 | C   | GLU | A | 52 | 36.808 | 15.110 | 21.454 | 1.00 | 15.03 | A | C |
| ATOM | 286 | O   | GLU | A | 52 | 36.232 | 14.638 | 22.435 | 1.00 | 16.38 | A | O |
| ATOM | 287 | N   | VAL | A | 53 | 37.432 | 14.361 | 20.546 | 1.00 | 14.02 | A | N |
| ATOM | 288 | CA  | VAL | A | 53 | 37.475 | 12.908 | 20.661 | 1.00 | 12.12 | A | C |
| ATOM | 289 | CB  | VAL | A | 53 | 38.216 | 12.274 | 19.478 | 1.00 | 11.38 | A | C |
| ATOM | 290 | CG1 | VAL | A | 53 | 38.129 | 10.769 | 19.566 | 1.00 | 10.68 | A | C |
| ATOM | 291 | CG2 | VAL | A | 53 | 37.612 | 12.750 | 18.171 | 1.00 | 12.22 | A | C |
| ATOM | 292 | C   | VAL | A | 53 | 38.191 | 12.540 | 21.955 | 1.00 | 12.50 | A | C |
| ATOM | 293 | O   | VAL | A | 53 | 37.691 | 11.744 | 22.761 | 1.00 | 12.84 | A | O |
| ATOM | 294 | N   | LEU | A | 54 | 39.362 | 13.129 | 22.158 | 1.00 | 9.57  | A | N |
| ATOM | 295 | CA  | LEU | A | 54 | 40.109 | 12.871 | 23.365 | 1.00 | 10.63 | A | C |
| ATOM | 296 | CB  | LEU | A | 54 | 41.365 | 13.726 | 23.405 | 1.00 | 11.63 | A | C |
| ATOM | 297 | CG  | LEU | A | 54 | 42.520 | 13.131 | 22.609 | 1.00 | 11.73 | A | C |
| ATOM | 298 | CD1 | LEU | A | 54 | 43.563 | 14.192 | 22.418 | 1.00 | 14.32 | A | C |
| ATOM | 299 | CD2 | LEU | A | 54 | 43.095 | 11.922 | 23.344 | 1.00 | 12.23 | A | C |
| ATOM | 300 | C   | LEU | A | 54 | 39.260 | 13.159 | 24.581 | 1.00 | 12.08 | A | C |
| ATOM | 301 | O   | LEU | A | 54 | 39.280 | 12.398 | 25.541 | 1.00 | 13.29 | A | O |
| ATOM | 302 | N   | PHE | A | 55 | 38.508 | 14.256 | 24.545 | 1.00 | 13.96 | A | N |
| ATOM | 303 | CA  | PHE | A | 55 | 37.653 | 14.612 | 25.675 | 1.00 | 14.56 | A | C |
| ATOM | 304 | CB  | PHE | A | 55 | 36.874 | 15.901 | 25.391 | 1.00 | 15.14 | A | C |
| ATOM | 305 | CG  | PHE | A | 55 | 35.984 | 16.330 | 26.530 | 1.00 | 12.59 | A | C |
| ATOM | 306 | CD1 | PHE | A | 55 | 36.478 | 17.135 | 27.551 | 1.00 | 12.50 | A | C |
| ATOM | 307 | CD2 | PHE | A | 55 | 34.674 | 15.870 | 26.614 | 1.00 | 11.59 | A | C |
| ATOM | 308 | CE1 | PHE | A | 55 | 35.679 | 17.473 | 28.643 | 1.00 | 12.57 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 309 | CE2 | PHE | A | 55 | 33.869 | 16.198 | 27.696 | 1.00 | 10.75 | A | C |
|---|---|---|---|---|---|---|---|---|---|---|---|---|
| ATOM | 310 | CZ | PHE | A | 55 | 34.373 | 17.001 | 28.714 | 1.00 | 12.37 | A | C |
| ATOM | 311 | C | PHE | A | 55 | 36.654 | 13.503 | 25.998 | 1.00 | 15.87 | A | C |
| ATOM | 312 | O | PHE | A | 55 | 36.537 | 13.073 | 27.149 | 1.00 | 14.84 | A | O |
| ATOM | 313 | N | TYR | A | 56 | 35.916 | 13.059 | 24.985 | 1.00 | 15.22 | A | N |
| ATOM | 314 | CA | TYR | A | 56 | 34.928 | 12.013 | 25.201 | 1.00 | 16.95 | A | C |
| ATOM | 315 | CB | TYR | A | 56 | 34.070 | 11.832 | 23.952 | 1.00 | 14.70 | A | C |
| ATOM | 316 | CG | TYR | A | 56 | 33.084 | 12.953 | 23.737 | 1.00 | 14.95 | A | C |
| ATOM | 317 | CD1 | TYR | A | 56 | 32.015 | 13.148 | 24.615 | 1.00 | 15.85 | A | C |
| ATOM | 318 | CE1 | TYR | A | 56 | 31.086 | 14.169 | 24.406 | 1.00 | 17.59 | A | C |
| ATOM | 319 | CD2 | TYR | A | 56 | 33.205 | 13.810 | 22.645 | 1.00 | 15.37 | A | C |
| ATOM | 320 | CE2 | TYR | A | 56 | 32.290 | 14.833 | 22.423 | 1.00 | 16.46 | A | C |
| ATOM | 321 | CZ | TYR | A | 56 | 31.231 | 15.007 | 23.303 | 1.00 | 18.11 | A | C |
| ATOM | 322 | OH | TYR | A | 56 | 30.311 | 16.001 | 23.059 | 1.00 | 18.28 | A | O |
| ATOM | 323 | C | TYR | A | 56 | 35.598 | 10.698 | 25.580 | 1.00 | 17.45 | A | C |
| ATOM | 324 | O | TYR | A | 56 | 35.117 | 9.958 | 26.440 | 1.00 | 16.40 | A | O |
| ATOM | 325 | N | LEU | A | 57 | 36.717 | 10.411 | 24.931 | 1.00 | 18.36 | A | N |
| ATOM | 326 | CA | LEU | A | 57 | 37.449 | 9.194 | 25.217 | 1.00 | 17.30 | A | C |
| ATOM | 327 | CB | LEU | A | 57 | 38.621 | 9.081 | 24.245 | 1.00 | 15.20 | A | C |
| ATOM | 328 | CG | LEU | A | 57 | 38.903 | 7.706 | 23.644 | 1.00 | 16.42 | A | C |
| ATOM | 329 | CD1 | LEU | A | 57 | 37.637 | 7.037 | 23.166 | 1.00 | 16.54 | A | C |
| ATOM | 330 | CD2 | LEU | A | 57 | 39.860 | 7.885 | 22.499 | 1.00 | 18.63 | A | C |
| ATOM | 331 | C | LEU | A | 57 | 37.915 | 9.332 | 26.675 | 1.00 | 17.78 | A | C |
| ATOM | 332 | O | LEU | A | 57 | 38.074 | 8.350 | 27.398 | 1.00 | 17.21 | A | O |
| ATOM | 333 | N | GLY | A | 58 | 38.099 | 10.576 | 27.103 | 1.00 | 17.15 | A | N |
| ATOM | 334 | CA | GLY | A | 58 | 38.515 | 10.832 | 28.464 | 1.00 | 16.26 | A | C |
| ATOM | 335 | C | GLY | A | 58 | 37.406 | 10.511 | 29.438 | 1.00 | 17.52 | A | C |
| ATOM | 336 | O | GLY | A | 58 | 37.656 | 9.909 | 30.482 | 1.00 | 18.49 | A | O |
| ATOM | 337 | N | GLN | A | 59 | 36.179 | 10.906 | 29.114 | 1.00 | 15.94 | A | N |
| ATOM | 338 | CA | GLN | A | 59 | 35.071 | 10.617 | 30.010 | 1.00 | 17.18 | A | C |
| ATOM | 339 | CB | GLN | A | 59 | 33.761 | 11.199 | 29.481 | 1.00 | 17.70 | A | C |
| ATOM | 340 | CG | GLN | A | 59 | 33.713 | 12.720 | 29.500 | 1.00 | 18.77 | A | C |
| ATOM | 341 | CD | GLN | A | 59 | 34.064 | 13.281 | 30.859 | 1.00 | 19.30 | A | C |
| ATOM | 342 | OE1 | GLN | A | 59 | 33.435 | 12.939 | 31.856 | 1.00 | 20.86 | A | O |
| ATOM | 343 | NE2 | GLN | A | 59 | 35.078 | 14.145 | 30.909 | 1.00 | 18.39 | A | N |
| ATOM | 344 | C | GLN | A | 59 | 34.966 | 9.115 | 30.109 | 1.00 | 17.93 | A | C |
| ATOM | 345 | O | GLN | A | 59 | 34.903 | 8.552 | 31.199 | 1.00 | 17.50 | A | O |
| ATOM | 346 | N | TYR | A | 60 | 34.984 | 8.473 | 28.949 | 1.00 | 19.35 | A | N |
| ATOM | 347 | CA | TYR | A | 60 | 34.906 | 7.023 | 28.854 | 1.00 | 19.97 | A | C |
| ATOM | 348 | CB | TYR | A | 60 | 35.270 | 6.580 | 27.450 | 1.00 | 18.67 | A | C |
| ATOM | 349 | CG | TYR | A | 60 | 35.061 | 5.121 | 27.258 | 1.00 | 18.93 | A | C |
| ATOM | 350 | CD1 | TYR | A | 60 | 33.783 | 4.608 | 27.114 | 1.00 | 19.95 | A | C |
| ATOM | 351 | CE1 | TYR | A | 60 | 33.573 | 3.256 | 26.945 | 1.00 | 22.90 | A | C |
| ATOM | 352 | CD2 | TYR | A | 60 | 36.139 | 4.243 | 27.235 | 1.00 | 21.13 | A | C |
| ATOM | 353 | CE2 | TYR | A | 60 | 35.946 | 2.880 | 27.068 | 1.00 | 22.87 | A | C |
| ATOM | 354 | CZ | TYR | A | 60 | 34.656 | 2.393 | 26.920 | 1.00 | 24.39 | A | C |
| ATOM | 355 | OH | TYR | A | 60 | 34.439 | 1.051 | 26.722 | 1.00 | 26.24 | A | O |
| ATOM | 356 | C | TYR | A | 60 | 35.833 | 6.309 | 29.837 | 1.00 | 20.15 | A | C |
| ATOM | 357 | O | TYR | A | 60 | 35.384 | 5.527 | 30.682 | 1.00 | 19.42 | A | O |
| ATOM | 358 | N | ILE | A | 61 | 37.130 | 6.564 | 29.701 | 1.00 | 20.01 | A | N |
| ATOM | 359 | CA | ILE | A | 61 | 38.116 | 5.949 | 30.574 | 1.00 | 21.24 | A | C |
| ATOM | 360 | CB | ILE | A | 61 | 39.508 | 6.556 | 30.346 | 1.00 | 19.34 | A | C |
| ATOM | 361 | CG2 | ILE | A | 61 | 40.449 | 6.169 | 31.481 | 1.00 | 17.74 | A | C |
| ATOM | 362 | CG1 | ILE | A | 61 | 40.050 | 6.096 | 28.993 | 1.00 | 18.22 | A | C |
| ATOM | 363 | CD1 | ILE | A | 61 | 41.343 | 6.774 | 28.602 | 1.00 | 17.99 | A | C |
| ATOM | 364 | C | ILE | A | 61 | 37.717 | 6.175 | 32.020 | 1.00 | 22.76 | A | C |
| ATOM | 365 | O | ILE | A | 61 | 37.731 | 5.261 | 32.837 | 1.00 | 19.91 | A | O |
| ATOM | 366 | N | MET | A | 62 | 37.342 | 7.414 | 32.309 | 1.00 | 26.52 | A | N |
| ATOM | 367 | CA | MET | A | 62 | 36.951 | 7.827 | 33.645 | 1.00 | 28.53 | A | C |
| ATOM | 368 | CB | MET | A | 62 | 36.735 | 9.338 | 33.661 | 1.00 | 28.55 | A | C |
| ATOM | 369 | CG | MET | A | 62 | 37.153 | 9.971 | 34.948 | 1.00 | 29.96 | A | C |
| ATOM | 370 | SD | MET | A | 62 | 38.843 | 9.527 | 35.301 | 1.00 | 32.30 | A | S |
| ATOM | 371 | CE | MET | A | 62 | 39.644 | 11.112 | 35.168 | 1.00 | 34.41 | A | C |
| ATOM | 372 | C | MET | A | 62 | 35.709 | 7.120 | 34.180 | 1.00 | 29.87 | A | C |
| ATOM | 373 | O | MET | A | 62 | 35.689 | 6.691 | 35.336 | 1.00 | 31.34 | A | O |
| ATOM | 374 | N | THR | A | 63 | 34.677 | 6.992 | 33.350 | 1.00 | 30.81 | A | N |
| ATOM | 375 | CA | THR | A | 63 | 33.450 | 6.342 | 33.792 | 1.00 | 31.38 | A | C |
| ATOM | 376 | CB | THR | A | 63 | 32.265 | 6.625 | 32.834 | 1.00 | 31.49 | A | C |
| ATOM | 377 | OG1 | THR | A | 63 | 31.505 | 5.427 | 32.649 | 1.00 | 33.06 | A | O |
| ATOM | 378 | CG2 | THR | A | 63 | 32.747 | 7.120 | 31.501 | 1.00 | 32.85 | A | C |
| ATOM | 379 | C | THR | A | 63 | 33.588 | 4.836 | 34.002 | 1.00 | 31.82 | A | C |
| ATOM | 380 | O | THR | A | 63 | 33.045 | 4.301 | 34.975 | 1.00 | 32.68 | A | O |
| ATOM | 381 | N | LYS | A | 64 | 34.305 | 4.149 | 33.115 | 1.00 | 31.19 | A | N |
| ATOM | 382 | CA | LYS | A | 64 | 34.491 | 2.706 | 33.279 | 1.00 | 30.89 | A | C |
| ATOM | 383 | CB | LYS | A | 64 | 34.719 | 2.032 | 31.922 | 1.00 | 29.02 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 384 | CG | LYS | A | 64 | 33.600 | 2.295 | 30.931 | 1.00 | 29.54 | A | C |
|---|---|---|---|---|---|---|---|---|---|---|---|---|
| ATOM | 385 | CD | LYS | A | 64 | 33.657 | 1.380 | 29.723 | 1.00 | 28.26 | A | C |
| ATOM | 386 | CE | LYS | A | 64 | 33.117 | 0.005 | 30.046 | 1.00 | 29.17 | A | C |
| ATOM | 387 | NZ | LYS | A | 64 | 32.990 | −0.829 | 28.825 | 1.00 | 27.96 | A | N |
| ATOM | 388 | C | LYS | A | 64 | 35.661 | 2.408 | 34.221 | 1.00 | 31.59 | A | C |
| ATOM | 389 | O | LYS | A | 64 | 35.926 | 1.256 | 34.559 | 1.00 | 31.45 | A | O |
| ATOM | 390 | N | ARG | A | 65 | 36.345 | 3.463 | 34.653 | 1.00 | 33.27 | A | N |
| ATOM | 391 | CA | ARG | A | 65 | 37.493 | 3.352 | 35.551 | 1.00 | 34.34 | A | C |
| ATOM | 392 | CB | ARG | A | 65 | 37.043 | 2.891 | 36.935 | 1.00 | 37.67 | A | C |
| ATOM | 393 | CG | ARG | A | 65 | 36.016 | 3.800 | 37.560 | 1.00 | 43.08 | A | C |
| ATOM | 394 | CD | ARG | A | 65 | 35.585 | 3.283 | 38.909 | 1.00 | 46.77 | A | C |
| ATOM | 395 | NE | ARG | A | 65 | 34.434 | 4.025 | 39.407 | 1.00 | 51.51 | A | N |
| ATOM | 396 | CZ | ARG | A | 65 | 33.927 | 3.888 | 40.628 | 1.00 | 53.49 | A | C |
| ATOM | 397 | NH1 | ARG | A | 65 | 34.474 | 3.032 | 41.484 | 1.00 | 54.10 | A | N |
| ATOM | 398 | NH2 | ARG | A | 65 | 32.872 | 4.608 | 40.993 | 1.00 | 54.47 | A | N |
| ATOM | 399 | C | ARG | A | 65 | 38.557 | 2.398 | 35.021 | 1.00 | 33.22 | A | C |
| ATOM | 400 | O | ARG | A | 65 | 39.086 | 1.576 | 35.770 | 1.00 | 32.38 | A | O |
| ATOM | 401 | N | LEU | A | 66 | 38.863 | 2.518 | 33.731 | 1.00 | 31.04 | A | N |
| ATOM | 402 | CA | LEU | A | 66 | 39.868 | 1.687 | 33.089 | 1.00 | 29.81 | A | C |
| ATOM | 403 | CB | LEU | A | 66 | 39.821 | 1.870 | 31.564 | 1.00 | 28.29 | A | C |
| ATOM | 404 | CG | LEU | A | 66 | 38.557 | 1.471 | 30.795 | 1.00 | 27.60 | A | C |
| ATOM | 405 | CD1 | LEU | A | 66 | 38.809 | 1.611 | 29.301 | 1.00 | 25.14 | A | C |
| ATOM | 406 | CD2 | LEU | A | 66 | 38.170 | 0.035 | 31.121 | 1.00 | 26.60 | A | C |
| ATOM | 407 | C | LEU | A | 66 | 41.272 | 2.020 | 33.597 | 1.00 | 30.22 | A | C |
| ATOM | 408 | O | LEU | A | 66 | 42.251 | 1.416 | 33.162 | 1.00 | 30.64 | A | O |
| ATOM | 409 | N | TYR | A | 67 | 41.375 | 2.980 | 34.514 | 1.00 | 30.84 | A | N |
| ATOM | 410 | CA | TYR | A | 67 | 42.677 | 3.365 | 35.055 | 1.00 | 32.60 | A | C |
| ATOM | 411 | CB | TYR | A | 67 | 42.688 | 4.846 | 35.438 | 1.00 | 33.43 | A | C |
| ATOM | 412 | CG | TYR | A | 67 | 41.642 | 5.226 | 36.463 | 1.00 | 36.96 | A | C |
| ATOM | 413 | CD1 | TYR | A | 67 | 41.809 | 4.922 | 37.810 | 1.00 | 37.60 | A | C |
| ATOM | 414 | CE1 | TYR | A | 67 | 40.833 | 5.254 | 38.745 | 1.00 | 39.51 | A | C |
| ATOM | 415 | CD2 | TYR | A | 67 | 40.468 | 5.875 | 36.077 | 1.00 | 38.20 | A | C |
| ATOM | 416 | CE2 | TYR | A | 67 | 39.488 | 6.211 | 37.004 | 1.00 | 38.78 | A | C |
| ATOM | 417 | CZ | TYR | A | 67 | 39.675 | 5.898 | 38.334 | 1.00 | 39.55 | A | C |
| ATOM | 418 | OH | TYR | A | 67 | 38.703 | 6.227 | 39.254 | 1.00 | 42.02 | A | O |
| ATOM | 419 | C | TYR | A | 67 | 43.037 | 2.534 | 36.270 | 1.00 | 33.52 | A | C |
| ATOM | 420 | O | TYR | A | 67 | 42.167 | 1.968 | 36.929 | 1.00 | 33.03 | A | O |
| ATOM | 421 | N | ASP | A | 68 | 44.327 | 2.459 | 36.567 | 1.00 | 35.06 | A | N |
| ATOM | 422 | CA | ASP | A | 68 | 44.765 | 1.699 | 37.721 | 1.00 | 36.88 | A | C |
| ATOM | 423 | CB | ASP | A | 68 | 46.146 | 1.100 | 37.476 | 1.00 | 37.88 | A | C |
| ATOM | 424 | CG | ASP | A | 68 | 46.658 | 0.340 | 38.674 | 1.00 | 38.95 | A | C |
| ATOM | 425 | OD1 | ASP | A | 68 | 45.863 | −0.408 | 39.281 | 1.00 | 39.74 | A | O |
| ATOM | 426 | OD2 | ASP | A | 68 | 47.850 | 0.486 | 39.006 | 1.00 | 39.12 | A | O |
| ATOM | 427 | C | ASP | A | 68 | 44.795 | 2.593 | 38.952 | 1.00 | 38.61 | A | C |
| ATOM | 428 | O | ASP | A | 68 | 45.391 | 3.671 | 38.939 | 1.00 | 36.17 | A | O |
| ATOM | 429 | N | GLU | A | 69 | 44.138 | 2.138 | 40.013 | 1.00 | 41.45 | A | N |
| ATOM | 430 | CA | GLU | A | 69 | 44.068 | 2.889 | 41.261 | 1.00 | 44.18 | A | C |
| ATOM | 431 | CB | GLU | A | 69 | 43.392 | 2.042 | 42.345 | 1.00 | 47.21 | A | C |
| ATOM | 432 | CG | GLU | A | 69 | 41.883 | 1.953 | 42.222 | 1.00 | 50.20 | A | C |
| ATOM | 433 | CD | GLU | A | 69 | 41.238 | 3.322 | 42.249 | 1.00 | 52.69 | A | C |
| ATOM | 434 | OE1 | GLU | A | 69 | 41.619 | 4.132 | 43.126 | 1.00 | 53.29 | A | O |
| ATOM | 435 | OE2 | GLU | A | 69 | 40.352 | 3.586 | 41.403 | 1.00 | 54.11 | A | O |
| ATOM | 436 | C | GLU | A | 69 | 45.421 | 3.366 | 41.774 | 1.00 | 44.17 | A | C |
| ATOM | 437 | O | GLU | A | 69 | 45.615 | 4.553 | 42.023 | 1.00 | 43.71 | A | O |
| ATOM | 438 | N | LYS | A | 70 | 46.349 | 2.430 | 41.933 | 1.00 | 44.88 | A | N |
| ATOM | 439 | CA | LYS | A | 70 | 47.679 | 2.733 | 42.441 | 1.00 | 45.87 | A | C |
| ATOM | 440 | CB | LYS | A | 70 | 48.260 | 1.482 | 43.113 | 1.00 | 47.39 | A | C |
| ATOM | 441 | CG | LYS | A | 70 | 48.001 | 0.194 | 42.326 | 1.00 | 50.82 | A | C |
| ATOM | 442 | CD | LYS | A | 70 | 48.491 | −1.060 | 43.052 | 1.00 | 52.70 | A | C |
| ATOM | 443 | CE | LYS | A | 70 | 48.068 | −2.333 | 42.307 | 1.00 | 53.19 | A | C |
| ATOM | 444 | NZ | LYS | A | 70 | 48.468 | −3.586 | 43.022 | 1.00 | 53.35 | A | N |
| ATOM | 445 | C | LYS | A | 70 | 48.639 | 3.255 | 41.376 | 1.00 | 45.61 | A | C |
| ATOM | 446 | O | LYS | A | 70 | 49.687 | 3.803 | 41.703 | 1.00 | 46.82 | A | O |
| ATOM | 447 | N | GLN | A | 71 | 48.284 | 3.079 | 40.107 | 1.00 | 45.07 | A | N |
| ATOM | 448 | CA | GLN | A | 71 | 49.123 | 3.539 | 38.995 | 1.00 | 44.59 | A | C |
| ATOM | 449 | CB | GLN | A | 71 | 49.852 | 2.352 | 38.357 | 1.00 | 45.81 | A | C |
| ATOM | 450 | CG | GLN | A | 71 | 51.048 | 2.754 | 37.525 | 1.00 | 48.21 | A | C |
| ATOM | 451 | CD | GLN | A | 71 | 52.085 | 3.500 | 38.343 | 1.00 | 49.07 | A | C |
| ATOM | 452 | OE1 | GLN | A | 71 | 53.008 | 4.103 | 37.795 | 1.00 | 49.90 | A | O |
| ATOM | 453 | NE2 | GLN | A | 71 | 51.940 | 3.458 | 39.665 | 1.00 | 49.28 | A | N |
| ATOM | 454 | C | GLN | A | 71 | 48.199 | 4.207 | 37.977 | 1.00 | 42.82 | A | C |
| ATOM | 455 | O | GLN | A | 71 | 48.023 | 3.733 | 36.851 | 1.00 | 41.55 | A | O |
| ATOM | 456 | N | GLN | A | 72 | 47.628 | 5.327 | 38.406 | 1.00 | 40.92 | A | N |
| ATOM | 457 | CA | GLN | A | 72 | 46.658 | 6.096 | 37.639 | 1.00 | 38.61 | A | C |
| ATOM | 458 | CB | GLN | A | 72 | 46.144 | 7.232 | 38.519 | 1.00 | 39.65 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | | |
|---|---|---|---|---|---|---|---|---|---|---|---|
| ATOM | 459 | CG   | GLN | A | 72 | 45.172 | 6.741  | 39.576 | 1.00 | 41.28 A | C |
| ATOM | 460 | CD   | GLN | A | 72 | 44.819 | 7.799  | 40.590 | 1.00 | 41.51 A | C |
| ATOM | 461 | OE1  | GLN | A | 72 | 44.671 | 8.976  | 40.253 | 1.00 | 42.50 A | O |
| ATOM | 462 | NE2  | GLN | A | 72 | 44.666 | 7.385  | 41.842 | 1.00 | 41.01 A | N |
| ATOM | 463 | C    | GLN | A | 72 | 46.948 | 6.631  | 36.247 | 1.00 | 35.53 A | C |
| ATOM | 464 | O    | GLN | A | 72 | 46.015 | 6.973  | 35.532 | 1.00 | 34.95 A | O |
| ATOM | 465 | N    | HIS | A | 73 | 48.210 | 6.712  | 35.847 | 1.00 | 33.43 A | N |
| ATOM | 466 | CA   | HIS | A | 73 | 48.508 | 7.216  | 34.512 | 1.00 | 31.21 A | C |
| ATOM | 467 | CB   | HIS | A | 73 | 49.841 | 7.975  | 34.514 | 1.00 | 32.43 A | C |
| ATOM | 468 | CG   | HIS | A | 73 | 51.039 | 7.111  | 34.753 | 1.00 | 35.52 A | C |
| ATOM | 469 | CD2  | HIS | A | 73 | 51.615 | 6.683  | 35.901 | 1.00 | 36.10 A | C |
| ATOM | 470 | ND1  | HIS | A | 73 | 51.796 | 6.588  | 33.725 | 1.00 | 36.24 A | N |
| ATOM | 471 | CE1  | HIS | A | 73 | 52.788 | 5.876  | 34.230 | 1.00 | 36.90 A | C |
| ATOM | 472 | NE2  | HIS | A | 73 | 52.701 | 5.918  | 35.548 | 1.00 | 37.46 A | N |
| ATOM | 473 | C    | HIS | A | 73 | 48.518 | 6.076  | 33.487 | 1.00 | 29.68 A | C |
| ATOM | 474 | O    | HIS | A | 73 | 48.681 | 6.297  | 32.278 | 1.00 | 28.72 A | O |
| ATOM | 475 | N    | ILE | A | 74 | 48.315 | 4.859  | 33.987 | 1.00 | 26.57 A | N |
| ATOM | 476 | CA   | ILE | A | 74 | 48.281 | 3.663  | 33.152 | 1.00 | 25.03 A | C |
| ATOM | 477 | CB   | ILE | A | 74 | 49.167 | 2.538  | 33.745 | 1.00 | 23.93 A | C |
| ATOM | 478 | CG2  | ILE | A | 74 | 48.928 | 1.244  | 33.010 | 1.00 | 23.04 A | C |
| ATOM | 479 | CG1  | ILE | A | 74 | 50.643 | 2.933  | 33.669 | 1.00 | 22.73 A | C |
| ATOM | 480 | CD1  | ILE | A | 74 | 51.140 | 3.210  | 32.279 | 1.00 | 21.40 A | C |
| ATOM | 481 | C    | ILE | A | 74 | 46.856 | 3.135  | 33.017 | 1.00 | 24.39 A | C |
| ATOM | 482 | O    | ILE | A | 74 | 46.199 | 2.833  | 34.010 | 1.00 | 25.39 A | O |
| ATOM | 483 | N    | VAL | A | 75 | 46.387 | 3.025  | 31.782 | 1.00 | 23.12 A | N |
| ATOM | 484 | CA   | VAL | A | 75 | 45.048 | 2.527  | 31.506 | 1.00 | 22.39 A | C |
| ATOM | 485 | CB   | VAL | A | 75 | 44.413 | 3.306  | 30.319 | 1.00 | 21.87 A | C |
| ATOM | 486 | CG1  | VAL | A | 75 | 43.016 | 2.784  | 30.024 | 1.00 | 19.40 A | C |
| ATOM | 487 | CG2  | VAL | A | 75 | 44.376 | 4.777  | 30.629 | 1.00 | 21.46 A | C |
| ATOM | 488 | C    | VAL | A | 75 | 45.121 | 1.044  | 31.120 | 1.00 | 23.43 A | C |
| ATOM | 489 | O    | VAL | A | 75 | 46.031 | 0.631  | 30.396 | 1.00 | 24.66 A | O |
| ATOM | 490 | N    | TYR | A | 76 | 44.174 | 0.246  | 31.604 | 1.00 | 22.50 A | N |
| ATOM | 491 | CA   | TYR | A | 76 | 44.115 | -1.173 | 31.256 | 1.00 | 22.83 A | C |
| ATOM | 492 | CB   | TYR | A | 76 | 44.106 | -2.063 | 32.508 | 1.00 | 22.60 A | C |
| ATOM | 493 | CG   | TYR | A | 76 | 45.435 | -2.130 | 33.237 | 1.00 | 23.26 A | C |
| ATOM | 494 | CD1  | TYR | A | 76 | 45.728 | -1.257 | 34.284 | 1.00 | 23.34 A | C |
| ATOM | 495 | CE1  | TYR | A | 76 | 46.964 | -1.291 | 34.928 | 1.00 | 24.06 A | C |
| ATOM | 496 | CD2  | TYR | A | 76 | 46.414 | -3.041 | 32.855 | 1.00 | 22.74 A | C |
| ATOM | 497 | CE2  | TYR | A | 76 | 47.654 | -3.083 | 33.493 | 1.00 | 23.63 A | C |
| ATOM | 498 | CZ   | TYR | A | 76 | 47.926 | -2.207 | 34.526 | 1.00 | 23.89 A | C |
| ATOM | 499 | OH   | TYR | A | 76 | 49.159 | -2.234 | 35.150 | 1.00 | 23.35 A | O |
| ATOM | 500 | C    | TYR | A | 76 | 42.825 | -1.367 | 30.465 | 1.00 | 23.68 A | C |
| ATOM | 501 | O    | TYR | A | 76 | 41.727 | -1.245 | 31.003 | 1.00 | 24.33 A | O |
| ATOM | 502 | N    | CYS | A | 77 | 42.953 | -1.663 | 29.181 | 1.00 | 24.40 A | N |
| ATOM | 503 | CA   | CYS | A | 77 | 41.780 | -1.826 | 28.342 | 1.00 | 26.23 A | C |
| ATOM | 504 | CB   | CYS | A | 77 | 41.778 | -0.744 | 27.258 | 1.00 | 24.90 A | C |
| ATOM | 505 | SG   | CYS | A | 77 | 43.313 | -0.601 | 26.325 | 1.00 | 17.76 A | S |
| ATOM | 506 | C    | CYS | A | 77 | 41.681 | -3.193 | 27.692 | 1.00 | 29.22 A | C |
| ATOM | 507 | O    | CYS | A | 77 | 41.001 | -3.354 | 26.676 | 1.00 | 29.98 A | O |
| ATOM | 508 | N    | SER | A | 78 | 42.337 | -4.176 | 28.300 | 1.00 | 32.27 A | N |
| ATOM | 509 | CA   | SER | A | 78 | 42.366 | -5.538 | 27.775 | 1.00 | 35.19 A | C |
| ATOM | 510 | CB   | SER | A | 78 | 43.016 | -6.469 | 28.798 | 1.00 | 36.60 A | C |
| ATOM | 511 | OG   | SER | A | 78 | 43.133 | -7.782 | 28.279 | 1.00 | 38.65 A | O |
| ATOM | 512 | C    | SER | A | 78 | 41.020 | -6.119 | 27.340 | 1.00 | 36.61 A | C |
| ATOM | 513 | O    | SER | A | 78 | 40.777 | -6.309 | 26.144 | 1.00 | 38.66 A | O |
| ATOM | 514 | N    | ASN | A | 79 | 40.145 | -6.402 | 28.297 | 1.00 | 36.16 A | N |
| ATOM | 515 | CA   | ASN | A | 79 | 38.849 | -6.982 | 27.961 | 1.00 | 37.19 A | C |
| ATOM | 516 | CB   | ASN | A | 79 | 38.340 | -7.871 | 29.109 | 1.00 | 40.14 A | C |
| ATOM | 517 | CG   | ASN | A | 79 | 39.448 | -8.682 | 29.769 | 1.00 | 42.98 A | C |
| ATOM | 518 | OD1  | ASN | A | 79 | 40.255 | -8.146 | 30.538 | 1.00 | 44.77 A | O |
| ATOM | 519 | ND2  | ASN | A | 79 | 39.495 | -9.978 | 29.471 | 1.00 | 42.57 A | N |
| ATOM | 520 | C    | ASN | A | 79 | 37.805 | -5.909 | 27.669 | 1.00 | 36.10 A | C |
| ATOM | 521 | O    | ASN | A | 79 | 36.619 | -6.105 | 27.936 | 1.00 | 36.61 A | O |
| ATOM | 522 | N    | ASP | A | 80 | 38.227 | -4.787 | 27.101 | 1.00 | 33.75 A | N |
| ATOM | 523 | CA   | ASP | A | 80 | 37.283 | -3.716 | 26.836 | 1.00 | 31.35 A | C |
| ATOM | 524 | CB   | ASP | A | 80 | 37.630 | -2.513 | 27.708 | 1.00 | 33.87 A | C |
| ATOM | 525 | CG   | ASP | A | 80 | 36.563 | -1.448 | 27.672 | 1.00 | 34.54 A | C |
| ATOM | 526 | OD1  | ASP | A | 80 | 35.832 | -1.315 | 28.679 | 1.00 | 35.54 A | O |
| ATOM | 527 | OD2  | ASP | A | 80 | 36.453 | -0.758 | 26.631 | 1.00 | 33.13 A | O |
| ATOM | 528 | C    | ASP | A | 80 | 37.229 | -3.280 | 25.383 | 1.00 | 29.65 A | C |
| ATOM | 529 | O    | ASP | A | 80 | 38.182 | -3.474 | 24.634 | 1.00 | 30.16 A | O |
| ATOM | 530 | N    | LEU | A | 81 | 36.109 | -2.675 | 24.995 | 1.00 | 27.43 A | N |
| ATOM | 531 | CA   | LEU | A | 81 | 35.932 | -2.200 | 23.629 | 1.00 | 26.30 A | C |
| ATOM | 532 | CB   | LEU | A | 81 | 34.605 | -1.461 | 23.475 | 1.00 | 25.12 A | C |
| ATOM | 533 | CG   | LEU | A | 81 | 34.437 | -0.778 | 22.111 | 1.00 | 23.81 A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 534 | CD1 | LEU | A | 81 | 34.714 | −1.778 | 21.013 | 1.00 | 23.42 | A | C |
|------|-----|-----|-----|---|----|--------|--------|--------|------|-------|---|---|
| ATOM | 535 | CD2 | LEU | A | 81 | 33.040 | −0.213 | 21.971 | 1.00 | 23.74 | A | C |
| ATOM | 536 | C   | LEU | A | 81 | 37.064 | −1.278 | 23.194 | 1.00 | 26.69 | A | C |
| ATOM | 537 | O   | LEU | A | 81 | 37.416 | −1.235 | 22.010 | 1.00 | 27.34 | A | O |
| ATOM | 538 | N   | LEU | A | 82 | 37.621 | −0.529 | 24.144 | 1.00 | 25.53 | A | N |
| ATOM | 539 | CA  | LEU | A | 82 | 38.717 | 0.375  | 23.827 | 1.00 | 24.07 | A | C |
| ATOM | 540 | CB  | LEU | A | 82 | 39.087 | 1.217  | 25.047 | 1.00 | 20.46 | A | C |
| ATOM | 541 | CG  | LEU | A | 82 | 40.236 | 2.202  | 24.829 | 1.00 | 18.75 | A | C |
| ATOM | 542 | CD1 | LEU | A | 82 | 39.913 | 3.166  | 23.689 | 1.00 | 17.60 | A | C |
| ATOM | 543 | CD2 | LEU | A | 82 | 40.488 | 2.955  | 26.112 | 1.00 | 18.82 | A | C |
| ATOM | 544 | C   | LEU | A | 82 | 39.908 | −0.468 | 23.376 | 1.00 | 25.11 | A | C |
| ATOM | 545 | O   | LEU | A | 82 | 40.569 | −0.149 | 22.381 | 1.00 | 26.18 | A | O |
| ATOM | 546 | N   | GLY | A | 83 | 40.162 | −1.553 | 24.105 | 1.00 | 24.69 | A | N |
| ATOM | 547 | CA  | GLY | A | 83 | 41.249 | −2.451 | 23.760 | 1.00 | 24.41 | A | C |
| ATOM | 548 | C   | GLY | A | 83 | 41.170 | −2.920 | 22.318 | 1.00 | 24.29 | A | C |
| ATOM | 549 | O   | GLY | A | 83 | 42.196 | −3.139 | 21.681 | 1.00 | 23.83 | A | O |
| ATOM | 550 | N   | ASP | A | 84 | 39.958 | −3.076 | 21.796 | 1.00 | 24.91 | A | N |
| ATOM | 551 | CA  | ASP | A | 84 | 39.803 | −3.503 | 20.410 | 1.00 | 27.77 | A | C |
| ATOM | 552 | CB  | ASP | A | 84 | 38.386 | −3.996 | 20.149 | 1.00 | 28.89 | A | C |
| ATOM | 553 | CG  | ASP | A | 84 | 38.093 | −5.295 | 20.837 | 1.00 | 31.01 | A | C |
| ATOM | 554 | OD1 | ASP | A | 84 | 39.042 | −6.085 | 21.039 | 1.00 | 32.12 | A | O |
| ATOM | 555 | OD2 | ASP | A | 84 | 36.913 | −5.532 | 21.160 | 1.00 | 31.66 | A | O |
| ATOM | 556 | C   | ASP | A | 84 | 40.119 | −2.392 | 19.410 | 1.00 | 28.99 | A | C |
| ATOM | 557 | O   | ASP | A | 84 | 40.587 | −2.664 | 18.297 | 1.00 | 29.29 | A | O |
| ATOM | 558 | N   | LEU | A | 85 | 39.849 | −1.146 | 19.799 | 1.00 | 28.12 | A | N |
| ATOM | 559 | CA  | LEU | A | 85 | 40.104 | −0.009 | 18.926 | 1.00 | 26.68 | A | C |
| ATOM | 560 | CB  | LEU | A | 85 | 39.385 | 1.241  | 19.441 | 1.00 | 27.62 | A | C |
| ATOM | 561 | CG  | LEU | A | 85 | 37.866 | 1.155  | 19.582 | 1.00 | 29.80 | A | C |
| ATOM | 562 | CD1 | LEU | A | 85 | 37.325 | 2.478  | 20.104 | 1.00 | 28.93 | A | C |
| ATOM | 563 | CD2 | LEU | A | 85 | 37.245 | 0.807  | 18.234 | 1.00 | 30.79 | A | C |
| ATOM | 564 | C   | LEU | A | 85 | 41.592 | 0.268  | 18.866 | 1.00 | 25.94 | A | C |
| ATOM | 565 | O   | LEU | A | 85 | 42.169 | 0.400  | 17.783 | 1.00 | 25.60 | A | O |
| ATOM | 566 | N   | PHE | A | 86 | 42.208 | 0.354  | 20.042 | 1.00 | 24.28 | A | N |
| ATOM | 567 | CA  | PHE | A | 86 | 43.636 | 0.633  | 20.143 | 1.00 | 23.89 | A | C |
| ATOM | 568 | CB  | PHE | A | 86 | 43.980 | 1.113  | 21.563 | 1.00 | 23.07 | A | C |
| ATOM | 569 | CG  | PHE | A | 86 | 43.601 | 2.548  | 21.837 | 1.00 | 21.05 | A | C |
| ATOM | 570 | CD1 | PHE | A | 86 | 42.858 | 3.284  | 20.914 | 1.00 | 19.37 | A | C |
| ATOM | 571 | CD2 | PHE | A | 86 | 43.992 | 3.165  | 23.021 | 1.00 | 20.29 | A | C |
| ATOM | 572 | CE1 | PHE | A | 86 | 42.509 | 4.612  | 21.167 | 1.00 | 18.94 | A | C |
| ATOM | 573 | CE2 | PHE | A | 86 | 43.649 | 4.496  | 23.285 | 1.00 | 20.32 | A | C |
| ATOM | 574 | CZ  | PHE | A | 86 | 42.903 | 5.220  | 22.352 | 1.00 | 19.94 | A | C |
| ATOM | 575 | C   | PHE | A | 86 | 44.498 | −0.575 | 19.781 | 1.00 | 22.94 | A | C |
| ATOM | 576 | O   | PHE | A | 86 | 45.550 | −0.430 | 19.156 | 1.00 | 22.42 | A | O |
| ATOM | 577 | N   | GLY | A | 87 | 44.049 | −1.762 | 20.178 | 1.00 | 21.80 | A | N |
| ATOM | 578 | CA  | GLY | A | 87 | 44.800 | −2.969 | 19.881 | 1.00 | 20.71 | A | C |
| ATOM | 579 | C   | GLY | A | 87 | 45.882 | −3.270 | 20.904 | 1.00 | 18.88 | A | C |
| ATOM | 580 | O   | GLY | A | 87 | 46.874 | −3.940 | 20.604 | 1.00 | 17.62 | A | O |
| ATOM | 581 | N   | VAL | A | 88 | 45.703 | −2.769 | 22.119 | 1.00 | 17.60 | A | N |
| ATOM | 582 | CA  | VAL | A | 88 | 46.685 | −3.014 | 23.158 | 1.00 | 17.15 | A | C |
| ATOM | 583 | CB  | VAL | A | 88 | 47.642 | −1.815 | 23.356 | 1.00 | 16.00 | A | C |
| ATOM | 584 | CG1 | VAL | A | 88 | 48.277 | −1.430 | 22.032 | 1.00 | 13.25 | A | C |
| ATOM | 585 | CG2 | VAL | A | 88 | 46.901 | −0.652 | 23.975 | 1.00 | 15.16 | A | C |
| ATOM | 586 | C   | VAL | A | 88 | 45.997 | −3.290 | 24.472 | 1.00 | 17.59 | A | C |
| ATOM | 587 | O   | VAL | A | 88 | 44.841 | −2.922 | 24.667 | 1.00 | 18.43 | A | O |
| ATOM | 588 | N   | PRO | A | 89 | 46.699 | −3.966 | 25.390 | 1.00 | 18.50 | A | N |
| ATOM | 589 | CD  | PRO | A | 89 | 47.976 | −4.673 | 25.177 | 1.00 | 17.26 | A | C |
| ATOM | 590 | CA  | PRO | A | 89 | 46.138 | −4.287 | 26.705 | 1.00 | 17.37 | A | C |
| ATOM | 591 | CB  | PRO | A | 89 | 46.958 | −5.496 | 27.137 | 1.00 | 16.69 | A | C |
| ATOM | 592 | CG  | PRO | A | 89 | 48.310 | −5.170 | 26.575 | 1.00 | 17.70 | A | C |
| ATOM | 593 | C   | PRO | A | 89 | 46.271 | −3.115 | 27.677 | 1.00 | 17.13 | A | C |
| ATOM | 594 | O   | PRO | A | 89 | 45.549 | −3.042 | 28.669 | 1.00 | 18.98 | A | O |
| ATOM | 595 | N   | SER | A | 90 | 47.196 | −2.200 | 27.397 | 1.00 | 16.91 | A | N |
| ATOM | 596 | CA  | SER | A | 90 | 47.394 | −1.044 | 28.273 | 1.00 | 16.57 | A | C |
| ATOM | 597 | CB  | SER | A | 90 | 48.002 | −1.485 | 29.612 | 1.00 | 15.12 | A | C |
| ATOM | 598 | OG  | SER | A | 90 | 49.329 | −1.956 | 29.439 | 1.00 | 13.05 | A | O |
| ATOM | 599 | C   | SER | A | 90 | 48.291 | 0.023  | 27.653 | 1.00 | 16.15 | A | C |
| ATOM | 600 | O   | SER | A | 90 | 49.090 | −0.261 | 26.764 | 1.00 | 17.41 | A | O |
| ATOM | 601 | N   | PHE | A | 91 | 48.138 | 1.256  | 28.116 | 1.00 | 15.54 | A | N |
| ATOM | 602 | CA  | PHE | A | 91 | 48.958 | 2.358  | 27.636 | 1.00 | 14.57 | A | C |
| ATOM | 603 | CB  | PHE | A | 91 | 48.411 | 2.928  | 26.306 | 1.00 | 13.00 | A | C |
| ATOM | 604 | CG  | PHE | A | 91 | 47.020 | 3.493  | 26.400 | 1.00 | 12.08 | A | C |
| ATOM | 605 | CD1 | PHE | A | 91 | 46.812 | 4.809  | 26.808 | 1.00 | 11.68 | A | C |
| ATOM | 606 | CD2 | PHE | A | 91 | 45.912 | 2.696  | 26.121 | 1.00 | 11.99 | A | C |
| ATOM | 607 | CE1 | PHE | A | 91 | 45.523 | 5.319  | 26.942 | 1.00 | 13.06 | A | C |
| ATOM | 608 | CE2 | PHE | A | 91 | 44.619 | 3.192  | 26.252 | 1.00 | 11.29 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 609 | CZ | PHE | A | 91 | 44.421 | 4.509 | 26.666 | 1.00 | 12.95 | A | C |
|---|---|---|---|---|---|---|---|---|---|---|---|---|
| ATOM | 610 | C | PHE | A | 91 | 49.023 | 3.428 | 28.725 | 1.00 | 15.66 | A | C |
| ATOM | 611 | O | PHE | A | 91 | 48.287 | 3.370 | 29.720 | 1.00 | 15.88 | A | O |
| ATOM | 612 | N | SER | A | 92 | 49.938 | 4.375 | 28.548 | 1.00 | 16.43 | A | N |
| ATOM | 613 | CA | SER | A | 92 | 50.131 | 5.468 | 29.490 | 1.00 | 16.90 | A | C |
| ATOM | 614 | CB | SER | A | 92 | 51.619 | 5.639 | 29.781 | 1.00 | 15.41 | A | C |
| ATOM | 615 | OG | SER | A | 92 | 51.844 | 6.761 | 30.611 | 1.00 | 17.40 | A | O |
| ATOM | 616 | C | SER | A | 92 | 49.567 | 6.760 | 28.902 | 1.00 | 18.57 | A | C |
| ATOM | 617 | O | SER | A | 92 | 49.840 | 7.096 | 27.743 | 1.00 | 18.49 | A | O |
| ATOM | 618 | N | VAL | A | 93 | 48.783 | 7.480 | 29.702 | 1.00 | 20.07 | A | N |
| ATOM | 619 | CA | VAL | A | 93 | 48.183 | 8.734 | 29.257 | 1.00 | 20.40 | A | C |
| ATOM | 620 | CB | VAL | A | 93 | 47.061 | 9.195 | 30.207 | 1.00 | 20.59 | A | C |
| ATOM | 621 | CG1 | VAL | A | 93 | 45.998 | 8.112 | 30.324 | 1.00 | 18.90 | A | C |
| ATOM | 622 | CG2 | VAL | A | 93 | 47.645 | 9.543 | 31.572 | 1.00 | 19.55 | A | C |
| ATOM | 623 | C | VAL | A | 93 | 49.231 | 9.842 | 29.187 | 1.00 | 21.59 | A | C |
| ATOM | 624 | O | VAL | A | 93 | 48.921 | 10.980 | 28.851 | 1.00 | 21.46 | A | O |
| ATOM | 625 | N | LYS | A | 94 | 50.471 | 9.511 | 29.523 | 1.00 | 22.56 | A | N |
| ATOM | 626 | CA | LYS | A | 94 | 51.540 | 10.493 | 29.467 | 1.00 | 24.25 | A | C |
| ATOM | 627 | CB | LYS | A | 94 | 52.631 | 10.173 | 30.489 | 1.00 | 25.19 | A | C |
| ATOM | 628 | CG | LYS | A | 94 | 52.207 | 10.232 | 31.945 | 1.00 | 26.24 | A | C |
| ATOM | 629 | CD | LYS | A | 94 | 53.412 | 9.981 | 32.837 | 1.00 | 27.27 | A | C |
| ATOM | 630 | CE | LYS | A | 94 | 53.043 | 9.944 | 34.308 | 1.00 | 30.80 | A | C |
| ATOM | 631 | NZ | LYS | A | 94 | 54.257 | 9.744 | 35.158 | 1.00 | 32.53 | A | N |
| ATOM | 632 | C | LYS | A | 94 | 52.165 | 10.522 | 28.073 | 1.00 | 24.60 | A | C |
| ATOM | 633 | O | LYS | A | 94 | 52.767 | 11.521 | 27.683 | 1.00 | 26.90 | A | O |
| ATOM | 634 | N | GLU | A | 95 | 52.025 | 9.433 | 27.322 | 1.00 | 23.48 | A | N |
| ATOM | 635 | CA | GLU | A | 95 | 52.600 | 9.360 | 25.982 | 1.00 | 23.51 | A | C |
| ATOM | 636 | CB | GLU | A | 95 | 53.112 | 7.943 | 25.728 | 1.00 | 26.58 | A | C |
| ATOM | 637 | CG | GLU | A | 95 | 54.100 | 7.483 | 26.793 | 1.00 | 30.58 | A | C |
| ATOM | 638 | CD | GLU | A | 95 | 54.664 | 6.106 | 26.527 | 1.00 | 32.79 | A | C |
| ATOM | 639 | OE1 | GLU | A | 95 | 55.285 | 5.926 | 25.458 | 1.00 | 36.40 | A | O |
| ATOM | 640 | OE2 | GLU | A | 95 | 54.494 | 5.209 | 27.384 | 1.00 | 33.54 | A | O |
| ATOM | 641 | C | GLU | A | 95 | 51.583 | 9.770 | 24.929 | 1.00 | 21.33 | A | C |
| ATOM | 642 | O | GLU | A | 95 | 50.998 | 8.938 | 24.246 | 1.00 | 21.30 | A | O |
| ATOM | 643 | N | HIS | A | 96 | 51.404 | 11.076 | 24.795 | 1.00 | 19.78 | A | N |
| ATOM | 644 | CA | HIS | A | 96 | 50.435 | 11.643 | 23.877 | 1.00 | 19.53 | A | C |
| ATOM | 645 | CB | HIS | A | 96 | 50.438 | 13.163 | 24.018 | 1.00 | 22.57 | A | C |
| ATOM | 646 | CG | HIS | A | 96 | 50.141 | 13.631 | 25.410 | 1.00 | 26.45 | A | C |
| ATOM | 647 | CD2 | HIS | A | 96 | 50.220 | 12.988 | 26.600 | 1.00 | 27.85 | A | C |
| ATOM | 648 | ND1 | HIS | A | 96 | 49.701 | 14.906 | 25.694 | 1.00 | 27.37 | A | N |
| ATOM | 649 | CE1 | HIS | A | 96 | 49.517 | 15.026 | 26.997 | 1.00 | 26.91 | A | C |
| ATOM | 650 | NE2 | HIS | A | 96 | 49.824 | 13.878 | 27.569 | 1.00 | 28.84 | A | N |
| ATOM | 651 | C | HIS | A | 96 | 50.543 | 11.259 | 22.412 | 1.00 | 17.69 | A | C |
| ATOM | 652 | O | HIS | A | 96 | 49.536 | 10.931 | 21.792 | 1.00 | 16.79 | A | O |
| ATOM | 653 | N | ARG | A | 97 | 51.747 | 11.293 | 21.855 | 1.00 | 16.65 | A | N |
| ATOM | 654 | CA | ARG | A | 97 | 51.921 | 10.946 | 20.451 | 1.00 | 17.02 | A | C |
| ATOM | 655 | CB | ARG | A | 97 | 53.386 | 11.043 | 20.031 | 1.00 | 15.18 | A | C |
| ATOM | 656 | CG | ARG | A | 97 | 53.625 | 10.528 | 18.619 | 1.00 | 12.29 | A | C |
| ATOM | 657 | CD | ARG | A | 97 | 52.608 | 11.108 | 17.651 | 1.00 | 10.86 | A | C |
| ATOM | 658 | NE | ARG | A | 97 | 52.705 | 12.561 | 17.563 | 1.00 | 11.13 | A | N |
| ATOM | 659 | CZ | ARG | A | 97 | 51.782 | 13.343 | 17.005 | 1.00 | 12.71 | A | C |
| ATOM | 660 | NH1 | ARG | A | 97 | 50.678 | 12.817 | 16.480 | 1.00 | 7.43 | A | N |
| ATOM | 661 | NH2 | ARG | A | 97 | 51.968 | 14.659 | 16.966 | 1.00 | 11.79 | A | N |
| ATOM | 662 | C | ARG | A | 97 | 51.414 | 9.554 | 20.120 | 1.00 | 19.08 | A | C |
| ATOM | 663 | O | ARG | A | 97 | 50.768 | 9.357 | 19.086 | 1.00 | 20.69 | A | O |
| ATOM | 664 | N | LYS | A | 98 | 51.710 | 8.589 | 20.985 | 1.00 | 18.63 | A | N |
| ATOM | 665 | CA | LYS | A | 98 | 51.264 | 7.228 | 20.749 | 1.00 | 18.59 | A | C |
| ATOM | 666 | CB | LYS | A | 98 | 51.935 | 6.280 | 21.734 | 1.00 | 18.48 | A | C |
| ATOM | 667 | CG | LYS | A | 98 | 53.447 | 6.253 | 21.566 | 1.00 | 19.06 | A | C |
| ATOM | 668 | CD | LYS | A | 98 | 54.096 | 5.206 | 22.447 | 1.00 | 19.89 | A | C |
| ATOM | 669 | CE | LYS | A | 98 | 55.607 | 5.329 | 22.415 | 1.00 | 19.38 | A | C |
| ATOM | 670 | NZ | LYS | A | 98 | 56.239 | 4.302 | 23.281 | 1.00 | 20.88 | A | N |
| ATOM | 671 | C | LYS | A | 98 | 49.746 | 7.089 | 20.807 | 1.00 | 19.21 | A | C |
| ATOM | 672 | O | LYS | A | 98 | 49.150 | 6.420 | 19.955 | 1.00 | 20.63 | A | O |
| ATOM | 673 | N | ILE | A | 99 | 49.108 | 7.714 | 21.791 | 1.00 | 18.36 | A | N |
| ATOM | 674 | CA | ILE | A | 99 | 47.651 | 7.634 | 21.883 | 1.00 | 17.63 | A | C |
| ATOM | 675 | CB | ILE | A | 99 | 47.124 | 8.421 | 23.082 | 1.00 | 16.98 | A | C |
| ATOM | 676 | CG2 | ILE | A | 99 | 45.647 | 8.750 | 22.882 | 1.00 | 16.18 | A | C |
| ATOM | 677 | CG1 | ILE | A | 99 | 47.363 | 7.617 | 24.358 | 1.00 | 15.24 | A | C |
| ATOM | 678 | CD1 | ILE | A | 99 | 46.946 | 8.332 | 25.608 | 1.00 | 14.96 | A | C |
| ATOM | 679 | C | ILE | A | 99 | 47.019 | 8.189 | 20.609 | 1.00 | 17.52 | A | C |
| ATOM | 680 | O | ILE | A | 99 | 46.097 | 7.608 | 20.051 | 1.00 | 17.08 | A | O |
| ATOM | 681 | N | TYR | A | 100 | 47.527 | 9.324 | 20.154 | 1.00 | 17.72 | A | N |
| ATOM | 682 | CA | TYR | A | 100 | 47.029 | 9.945 | 18.945 | 1.00 | 17.07 | A | C |
| ATOM | 683 | CB | TYR | A | 100 | 47.857 | 11.194 | 18.626 | 1.00 | 17.38 | A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | | |
|---|---|---|---|---|---|---|---|---|---|---|---|
| ATOM | 684 | CG | TYR | A | 100 | 47.175 | 12.490 | 18.997 | 1.00 | 18.41 A | C |
| ATOM | 685 | CD1 | TYR | A | 100 | 46.833 | 12.765 | 20.323 | 1.00 | 18.50 A | C |
| ATOM | 686 | CE1 | TYR | A | 100 | 46.137 | 13.921 | 20.661 | 1.00 | 18.48 A | C |
| ATOM | 687 | CD2 | TYR | A | 100 | 46.808 | 13.414 | 18.014 | 1.00 | 17.87 A | C |
| ATOM | 688 | CE2 | TYR | A | 100 | 46.107 | 14.577 | 18.339 | 1.00 | 19.07 A | C |
| ATOM | 689 | CZ | TYR | A | 100 | 45.771 | 14.822 | 19.667 | 1.00 | 19.64 A | C |
| ATOM | 690 | OH | TYR | A | 100 | 45.059 | 15.953 | 20.002 | 1.00 | 18.84 A | O |
| ATOM | 691 | C | TYR | A | 100 | 47.064 | 8.990 | 17.752 | 1.00 | 17.45 A | C |
| ATOM | 692 | O | TYR | A | 100 | 46.050 | 8.760 | 17.093 | 1.00 | 17.05 A | O |
| ATOM | 693 | N | THR | A | 101 | 48.228 | 8.419 | 17.471 | 1.00 | 17.36 A | N |
| ATOM | 694 | CA | THR | A | 101 | 48.323 | 7.536 | 16.323 | 1.00 | 18.06 A | C |
| ATOM | 695 | CB | THR | A | 101 | 49.786 | 7.081 | 16.069 | 1.00 | 18.65 A | C |
| ATOM | 696 | OG1 | THR | A | 101 | 50.051 | 5.875 | 16.783 | 1.00 | 21.69 A | O |
| ATOM | 697 | CG2 | THR | A | 101 | 50.760 | 8.147 | 16.522 | 1.00 | 16.26 A | C |
| ATOM | 698 | C | THR | A | 101 | 47.412 | 6.329 | 16.504 | 1.00 | 16.52 A | C |
| ATOM | 699 | O | THR | A | 101 | 46.894 | 5.768 | 15.534 | 1.00 | 16.44 A | O |
| ATOM | 700 | N | MET | A | 102 | 47.199 | 5.954 | 17.758 | 1.00 | 15.80 A | N |
| ATOM | 701 | CA | MET | A | 102 | 46.344 | 4.819 | 18.089 | 1.00 | 14.43 A | C |
| ATOM | 702 | CB | MET | A | 102 | 46.515 | 4.484 | 19.572 | 1.00 | 13.64 A | C |
| ATOM | 703 | CG | MET | A | 102 | 46.355 | 3.027 | 19.941 | 1.00 | 13.28 A | C |
| ATOM | 704 | SD | MET | A | 102 | 47.540 | 2.468 | 21.221 | 1.00 | 10.86 A | S |
| ATOM | 705 | CE | MET | A | 102 | 47.349 | 3.728 | 22.494 | 1.00 | 6.45 A | C |
| ATOM | 706 | C | MET | A | 102 | 44.907 | 5.235 | 17.772 | 1.00 | 13.90 A | C |
| ATOM | 707 | O | MET | A | 102 | 44.106 | 4.432 | 17.301 | 1.00 | 14.80 A | O |
| ATOM | 708 | N | ILE | A | 103 | 44.590 | 6.503 | 18.017 | 1.00 | 13.28 A | N |
| ATOM | 709 | CA | ILE | A | 103 | 43.256 | 7.028 | 17.725 | 1.00 | 13.02 A | C |
| ATOM | 710 | CB | ILE | A | 103 | 43.004 | 8.396 | 18.428 | 1.00 | 10.40 A | C |
| ATOM | 711 | CG2 | ILE | A | 103 | 41.697 | 9.007 | 17.940 | 1.00 | 7.72 A | C |
| ATOM | 712 | CG1 | ILE | A | 103 | 42.974 | 8.215 | 19.942 | 1.00 | 11.39 A | C |
| ATOM | 713 | CD1 | ILE | A | 103 | 42.806 | 9.524 | 20.725 | 1.00 | 11.61 A | C |
| ATOM | 714 | C | ILE | A | 103 | 43.082 | 7.232 | 16.210 | 1.00 | 13.88 A | C |
| ATOM | 715 | O | ILE | A | 103 | 42.009 | 6.975 | 15.664 | 1.00 | 13.40 A | O |
| ATOM | 716 | N | TYR | A | 104 | 44.138 | 7.685 | 15.538 | 1.00 | 13.99 A | N |
| ATOM | 717 | CA | TYR | A | 104 | 44.071 | 7.933 | 14.097 | 1.00 | 17.99 A | C |
| ATOM | 718 | CB | TYR | A | 104 | 45.422 | 8.430 | 13.578 | 1.00 | 16.14 A | C |
| ATOM | 719 | CG | TYR | A | 104 | 45.621 | 9.917 | 13.746 | 1.00 | 15.96 A | C |
| ATOM | 720 | CD1 | TYR | A | 104 | 46.759 | 10.425 | 14.378 | 1.00 | 15.68 A | C |
| ATOM | 721 | CE1 | TYR | A | 104 | 46.943 | 11.795 | 14.524 | 1.00 | 14.23 A | C |
| ATOM | 722 | CD2 | TYR | A | 104 | 44.673 | 10.819 | 13.267 | 1.00 | 15.02 A | C |
| ATOM | 723 | CE2 | TYR | A | 104 | 44.846 | 12.182 | 13.405 | 1.00 | 14.75 A | C |
| ATOM | 724 | CZ | TYR | A | 104 | 45.981 | 12.667 | 14.031 | 1.00 | 15.94 A | C |
| ATOM | 725 | OH | TYR | A | 104 | 46.155 | 14.028 | 14.143 | 1.00 | 17.64 A | O |
| ATOM | 726 | C | TYR | A | 104 | 43.602 | 6.760 | 13.234 | 1.00 | 20.21 A | C |
| ATOM | 727 | O | TYR | A | 104 | 42.964 | 6.962 | 12.199 | 1.00 | 21.85 A | O |
| ATOM | 728 | N | ARG | A | 105 | 43.907 | 5.538 | 13.655 | 1.00 | 21.85 A | N |
| ATOM | 729 | CA | ARG | A | 105 | 43.506 | 4.371 | 12.885 | 1.00 | 21.76 A | C |
| ATOM | 730 | CB | ARG | A | 105 | 44.272 | 3.138 | 13.361 | 1.00 | 22.75 A | C |
| ATOM | 731 | CG | ARG | A | 105 | 45.731 | 3.143 | 12.953 | 1.00 | 23.10 A | C |
| ATOM | 732 | CD | ARG | A | 105 | 46.356 | 1.779 | 13.162 | 1.00 | 23.66 A | C |
| ATOM | 733 | NE | ARG | A | 105 | 46.518 | 1.474 | 14.573 | 1.00 | 22.31 A | N |
| ATOM | 734 | CZ | ARG | A | 105 | 47.674 | 1.540 | 15.217 | 1.00 | 22.19 A | C |
| ATOM | 735 | NH1 | ARG | A | 105 | 48.770 | 1.897 | 14.565 | 1.00 | 18.18 A | N |
| ATOM | 736 | NH2 | ARG | A | 105 | 47.726 | 1.255 | 16.517 | 1.00 | 24.90 A | N |
| ATOM | 737 | C | ARG | A | 105 | 42.010 | 4.099 | 12.949 | 1.00 | 22.18 A | C |
| ATOM | 738 | O | ARG | A | 105 | 41.471 | 3.381 | 12.106 | 1.00 | 23.20 A | O |
| ATOM | 739 | N | ASN | A | 106 | 41.333 | 4.677 | 13.936 | 1.00 | 20.61 A | N |
| ATOM | 740 | CA | ASN | A | 106 | 39.903 | 4.452 | 14.074 | 1.00 | 18.60 A | C |
| ATOM | 741 | CB | ASN | A | 106 | 39.547 | 4.250 | 15.538 | 1.00 | 16.23 A | C |
| ATOM | 742 | CG | ASN | A | 106 | 40.187 | 3.023 | 16.107 | 1.00 | 15.21 A | C |
| ATOM | 743 | OD1 | ASN | A | 106 | 41.382 | 3.005 | 16.389 | 1.00 | 14.14 A | O |
| ATOM | 744 | ND2 | ASN | A | 106 | 39.400 | 1.973 | 16.261 | 1.00 | 16.32 A | N |
| ATOM | 745 | C | ASN | A | 106 | 39.060 | 5.565 | 13.501 | 1.00 | 18.34 A | C |
| ATOM | 746 | O | ASN | A | 106 | 37.908 | 5.746 | 13.895 | 1.00 | 18.15 A | O |
| ATOM | 747 | N | LEU | A | 107 | 39.620 | 6.306 | 12.558 | 1.00 | 17.64 A | N |
| ATOM | 748 | CA | LEU | A | 107 | 38.875 | 7.401 | 11.973 | 1.00 | 18.35 A | C |
| ATOM | 749 | CB | LEU | A | 107 | 38.888 | 8.604 | 12.929 | 1.00 | 16.91 A | C |
| ATOM | 750 | CG | LEU | A | 107 | 40.265 | 9.202 | 13.273 | 1.00 | 18.09 A | C |
| ATOM | 751 | CD1 | LEU | A | 107 | 40.853 | 9.969 | 12.077 | 1.00 | 14.35 A | C |
| ATOM | 752 | CD2 | LEU | A | 107 | 40.114 | 10.138 | 14.470 | 1.00 | 17.65 A | C |
| ATOM | 753 | C | LEU | A | 107 | 39.449 | 7.816 | 10.639 | 1.00 | 18.05 A | C |
| ATOM | 754 | O | LEU | A | 107 | 40.510 | 7.355 | 10.239 | 1.00 | 17.80 A | O |
| ATOM | 755 | N | VAL | A | 108 | 38.733 | 8.708 | 9.968 | 1.00 | 18.61 A | N |
| ATOM | 756 | CA | VAL | A | 108 | 39.161 | 9.247 | 8.694 | 1.00 | 19.37 A | C |
| ATOM | 757 | CB | VAL | A | 108 | 38.118 | 8.985 | 7.596 | 1.00 | 17.78 A | C |
| ATOM | 758 | CG1 | VAL | A | 108 | 38.562 | 9.636 | 6.300 | 1.00 | 16.53 A | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | | |
|---|---|---|---|---|---|---|---|---|---|---|---|
| ATOM | 759 | CG2 | VAL | A | 108 | 37.939 | 7.495 | 7.401 | 1.00 | 18.03 A | C |
| ATOM | 760 | C | VAL | A | 108 | 39.322 | 10.755 | 8.867 | 1.00 | 20.94 A | C |
| ATOM | 761 | O | VAL | A | 108 | 38.406 | 11.433 | 9.324 | 1.00 | 20.81 A | O |
| ATOM | 762 | N | VAL | A | 109 | 40.495 | 11.275 | 8.517 | 1.00 | 23.78 A | N |
| ATOM | 763 | CA | VAL | A | 109 | 40.761 | 12.710 | 8.611 | 1.00 | 26.16 A | C |
| ATOM | 764 | CB | VAL | A | 109 | 42.278 | 13.011 | 8.516 | 1.00 | 22.72 A | C |
| ATOM | 765 | CG1 | VAL | A | 109 | 42.504 | 14.496 | 8.395 | 1.00 | 22.45 A | C |
| ATOM | 766 | CG2 | VAL | A | 109 | 42.997 | 12.480 | 9.737 | 1.00 | 21.93 A | C |
| ATOM | 767 | C | VAL | A | 109 | 40.043 | 13.448 | 7.470 | 1.00 | 30.24 A | C |
| ATOM | 768 | O | VAL | A | 109 | 40.298 | 13.187 | 6.287 | 1.00 | 30.49 A | O |
| ATOM | 769 | N | VAL | A | 110 | 39.138 | 14.355 | 7.832 | 1.00 | 33.46 A | N |
| ATOM | 770 | CA | VAL | A | 110 | 38.397 | 15.138 | 6.850 | 1.00 | 36.26 A | C |
| ATOM | 771 | CB | VAL | A | 110 | 37.210 | 15.872 | 7.489 | 1.00 | 34.68 A | C |
| ATOM | 772 | CG1 | VAL | A | 110 | 36.511 | 16.703 | 6.448 | 1.00 | 32.97 A | C |
| ATOM | 773 | CG2 | VAL | A | 110 | 36.252 | 14.882 | 8.103 | 1.00 | 33.70 A | C |
| ATOM | 774 | C | VAL | A | 110 | 39.314 | 16.191 | 6.246 | 1.00 | 40.32 A | C |
| ATOM | 775 | O | VAL | A | 110 | 39.808 | 17.071 | 6.952 | 1.00 | 40.87 A | O |
| ATOM | 776 | N | ASN | A | 111 | 39.543 | 16.091 | 4.940 | 1.00 | 45.40 A | N |
| ATOM | 777 | CA | ASN | A | 111 | 40.398 | 17.040 | 4.226 | 1.00 | 49.94 A | C |
| ATOM | 778 | CB | ASN | A | 111 | 41.073 | 16.364 | 3.019 | 1.00 | 50.86 A | C |
| ATOM | 779 | CG | ASN | A | 111 | 42.382 | 15.675 | 3.386 | 1.00 | 52.48 A | C |
| ATOM | 780 | OD1 | ASN | A | 111 | 43.283 | 16.296 | 3.956 | 1.00 | 53.64 A | O |
| ATOM | 781 | ND2 | ASN | A | 111 | 42.495 | 14.393 | 3.052 | 1.00 | 51.26 A | N |
| ATOM | 782 | C | ASN | A | 111 | 39.604 | 18.262 | 3.753 | 1.00 | 51.80 A | C |
| ATOM | 783 | O | ASN | A | 111 | 39.362 | 18.363 | 2.526 | 1.00 | 53.21 A | O |
| ATOM | 784 | OXT | ASN | A | 111 | 39.228 | 19.098 | 4.615 | 1.00 | 52.33 A | O |
| ATOM | 785 | C | GLY | B | 16 | 53.854 | −21.456 | 19.940 | 1.00 | 68.34 B | C |
| ATOM | 786 | O | GLY | B | 16 | 54.218 | −22.369 | 20.690 | 1.00 | 69.67 B | O |
| ATOM | 787 | N | GLY | B | 16 | 56.279 | −20.814 | 19.623 | 1.00 | 65.62 B | N |
| ATOM | 788 | CA | GLY | B | 16 | 54.867 | −20.597 | 19.196 | 1.00 | 67.24 B | C |
| ATOM | 789 | N | SER | B | 17 | 52.576 | −21.151 | 19.730 | 1.00 | 67.70 B | N |
| ATOM | 790 | CA | SER | B | 17 | 51.454 | −21.865 | 20.345 | 1.00 | 67.10 B | C |
| ATOM | 791 | CB | SER | B | 17 | 51.431 | −21.641 | 21.858 | 1.00 | 67.49 B | C |
| ATOM | 792 | OG | SER | B | 17 | 52.590 | −22.178 | 22.475 | 1.00 | 68.01 B | O |
| ATOM | 793 | C | SER | B | 17 | 50.200 | −21.284 | 19.691 | 1.00 | 66.62 B | C |
| ATOM | 794 | O | SER | B | 17 | 50.268 | −20.198 | 19.108 | 1.00 | 67.53 B | O |
| ATOM | 795 | N | GLN | B | 18 | 49.064 | −21.984 | 19.777 | 1.00 | 65.03 B | N |
| ATOM | 796 | CA | GLN | B | 18 | 47.833 | −21.519 | 19.117 | 1.00 | 62.52 B | C |
| ATOM | 797 | CB | GLN | B | 18 | 47.417 | −20.132 | 19.614 | 1.00 | 63.01 B | C |
| ATOM | 798 | CG | GLN | B | 18 | 46.783 | −20.084 | 20.983 | 1.00 | 63.28 B | C |
| ATOM | 799 | CD | GLN | B | 18 | 46.536 | −18.655 | 21.437 | 1.00 | 64.15 B | C |
| ATOM | 800 | OE1 | GLN | B | 18 | 45.964 | −17.847 | 20.702 | 1.00 | 64.39 B | O |
| ATOM | 801 | NE2 | GLN | B | 18 | 46.967 | −18.337 | 22.652 | 1.00 | 64.33 B | N |
| ATOM | 802 | C | GLN | B | 18 | 48.190 | −21.421 | 17.633 | 1.00 | 60.63 B | C |
| ATOM | 803 | O | GLN | B | 18 | 47.364 | −21.081 | 16.784 | 1.00 | 59.42 B | O |
| ATOM | 804 | N | ILE | B | 19 | 49.455 | −21.721 | 17.360 | 1.00 | 58.87 B | N |
| ATOM | 805 | CA | ILE | B | 19 | 50.046 | −21.693 | 16.039 | 1.00 | 57.04 B | C |
| ATOM | 806 | CB | ILE | B | 19 | 51.187 | −20.647 | 15.978 | 1.00 | 57.12 B | C |
| ATOM | 807 | CG2 | ILE | B | 19 | 51.857 | −20.675 | 14.620 | 1.00 | 57.22 B | C |
| ATOM | 808 | CG1 | ILE | B | 19 | 50.635 | −19.253 | 16.284 | 1.00 | 56.68 B | C |
| ATOM | 809 | CD1 | ILE | B | 19 | 49.517 | −18.819 | 15.365 | 1.00 | 55.99 B | C |
| ATOM | 810 | C | ILE | B | 19 | 50.625 | −23.085 | 15.792 | 1.00 | 55.95 B | C |
| ATOM | 811 | O | ILE | B | 19 | 51.432 | −23.583 | 16.578 | 1.00 | 55.35 B | O |
| ATOM | 812 | N | PRO | B | 20 | 50.202 | −23.736 | 14.700 | 1.00 | 54.93 B | N |
| ATOM | 813 | CD | PRO | B | 20 | 49.131 | −23.312 | 13.782 | 1.00 | 54.65 B | C |
| ATOM | 814 | CA | PRO | B | 20 | 50.676 | −25.074 | 14.344 | 1.00 | 53.57 B | C |
| ATOM | 815 | CB | PRO | B | 20 | 50.014 | −25.310 | 12.995 | 1.00 | 53.84 B | C |
| ATOM | 816 | CG | PRO | B | 20 | 48.702 | −24.629 | 13.181 | 1.00 | 54.58 B | C |
| ATOM | 817 | C | PRO | B | 20 | 52.196 | −25.214 | 14.286 | 1.00 | 52.28 B | C |
| ATOM | 818 | O | PRO | B | 20 | 52.910 | −24.281 | 13.911 | 1.00 | 51.94 B | O |
| ATOM | 819 | N | ALA | B | 21 | 52.677 | −26.395 | 14.662 | 1.00 | 50.58 B | N |
| ATOM | 820 | CA | ALA | B | 21 | 54.103 | −26.685 | 14.663 | 1.00 | 48.29 B | C |
| ATOM | 821 | CB | ALA | B | 21 | 54.338 | −28.144 | 15.065 | 1.00 | 47.65 B | C |
| ATOM | 822 | C | ALA | B | 21 | 54.706 | −26.412 | 13.287 | 1.00 | 46.77 B | C |
| ATOM | 823 | O | ALA | B | 21 | 55.853 | −25.967 | 13.181 | 1.00 | 46.51 B | O |
| ATOM | 824 | N | SER | B | 22 | 53.933 | −26.680 | 12.236 | 1.00 | 44.16 B | N |
| ATOM | 825 | CA | SER | B | 22 | 54.407 | −26.458 | 10.878 | 1.00 | 41.95 B | C |
| ATOM | 826 | CB | SER | B | 22 | 53.314 | −26.804 | 9.868 | 1.00 | 42.69 B | C |
| ATOM | 827 | OG | SER | B | 22 | 53.760 | −26.560 | 8.545 | 1.00 | 42.99 B | O |
| ATOM | 828 | C | SER | B | 22 | 54.822 | −25.007 | 10.699 | 1.00 | 40.70 B | C |
| ATOM | 829 | O | SER | B | 22 | 55.787 | −24.714 | 9.998 | 1.00 | 40.64 B | O |
| ATOM | 830 | N | GLU | B | 23 | 54.091 | −24.106 | 11.348 | 1.00 | 38.86 B | N |
| ATOM | 831 | CA | GLU | B | 23 | 54.364 | −22.676 | 11.264 | 1.00 | 37.00 B | C |
| ATOM | 832 | CB | GLU | B | 23 | 53.078 | −21.892 | 11.557 | 1.00 | 37.30 B | C |
| ATOM | 833 | CG | GLU | B | 23 | 53.240 | −20.380 | 11.631 | 1.00 | 38.01 B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 834 | CD | GLU | B | 23 | 51.911 | −19.648 | 11.519 | 1.00 | 38.73 | B | C |
|---|---|---|---|---|---|---|---|---|---|---|---|---|
| ATOM | 835 | OE1 | GLU | B | 23 | 50.882 | −20.207 | 11.961 | 1.00 | 38.07 | B | O |
| ATOM | 836 | OE2 | GLU | B | 23 | 51.896 | −18.511 | 10.996 | 1.00 | 38.22 | B | O |
| ATOM | 837 | C | GLU | B | 23 | 55.494 | −22.211 | 12.185 | 1.00 | 35.56 | B | C |
| ATOM | 838 | O | GLU | B | 23 | 56.199 | −21.260 | 11.860 | 1.00 | 35.70 | B | O |
| ATOM | 839 | N | GLN | B | 24 | 55.667 | −22.875 | 13.326 | 1.00 | 34.12 | B | N |
| ATOM | 840 | CA | GLN | B | 24 | 56.727 | −22.514 | 14.272 | 1.00 | 32.95 | B | C |
| ATOM | 841 | CB | GLN | B | 24 | 56.644 | −23.344 | 15.540 | 1.00 | 33.15 | B | C |
| ATOM | 842 | CG | GLN | B | 24 | 55.371 | −23.272 | 16.311 | 1.00 | 35.12 | B | C |
| ATOM | 843 | CD | GLN | B | 24 | 55.483 | −24.101 | 17.563 | 1.00 | 37.66 | B | C |
| ATOM | 844 | OE1 | GLN | B | 24 | 55.813 | −25.287 | 17.505 | 1.00 | 40.52 | B | O |
| ATOM | 845 | NE2 | GLN | B | 24 | 55.229 | −23.488 | 18.706 | 1.00 | 38.27 | B | N |
| ATOM | 846 | C | GLN | B | 24 | 58.110 | −22.766 | 13.693 | 1.00 | 32.72 | B | C |
| ATOM | 847 | O | GLN | B | 24 | 59.076 | −22.083 | 14.045 | 1.00 | 31.93 | B | O |
| ATOM | 848 | N | GLU | B | 25 | 58.202 | −23.771 | 12.826 | 1.00 | 32.31 | B | N |
| ATOM | 849 | CA | GLU | B | 25 | 59.470 | −24.143 | 12.216 | 1.00 | 31.68 | B | C |
| ATOM | 850 | CB | GLU | B | 25 | 59.485 | −25.656 | 11.931 | 1.00 | 32.59 | B | C |
| ATOM | 851 | CG | GLU | B | 25 | 59.233 | −26.531 | 13.173 | 1.00 | 34.22 | B | C |
| ATOM | 852 | CD | GLU | B | 25 | 60.296 | −26.368 | 14.262 | 1.00 | 34.77 | B | C |
| ATOM | 853 | OE1 | GLU | B | 25 | 59.978 | −26.561 | 15.454 | 1.00 | 36.34 | B | O |
| ATOM | 854 | OE2 | GLU | B | 25 | 61.456 | −26.059 | 13.935 | 1.00 | 36.40 | B | O |
| ATOM | 855 | C | GLU | B | 25 | 59.804 | −23.353 | 10.949 | 1.00 | 30.50 | B | C |
| ATOM | 856 | O | GLU | B | 25 | 60.852 | −23.565 | 10.340 | 1.00 | 29.64 | B | O |
| ATOM | 857 | N | THR | B | 26 | 58.922 | −22.439 | 10.557 | 1.00 | 29.23 | B | N |
| ATOM | 858 | CA | THR | B | 26 | 59.166 | −21.624 | 9.373 | 1.00 | 30.19 | B | C |
| ATOM | 859 | CB | THR | B | 26 | 58.142 | −20.489 | 9.259 | 1.00 | 31.00 | B | C |
| ATOM | 860 | OG1 | THR | B | 26 | 56.822 | −21.038 | 9.227 | 1.00 | 33.70 | B | O |
| ATOM | 861 | CG2 | THR | B | 26 | 58.382 | −19.684 | 7.997 | 1.00 | 31.13 | B | C |
| ATOM | 862 | C | THR | B | 26 | 60.560 | −21.001 | 9.468 | 1.00 | 30.70 | B | C |
| ATOM | 863 | O | THR | B | 26 | 60.975 | −20.554 | 10.539 | 1.00 | 31.04 | B | O |
| ATOM | 864 | N | LEU | B | 27 | 61.277 | −20.965 | 8.347 | 1.00 | 30.93 | B | N |
| ATOM | 865 | CA | LEU | B | 27 | 62.622 | −20.402 | 8.328 | 1.00 | 29.18 | B | C |
| ATOM | 866 | CB | LEU | B | 27 | 63.471 | −21.120 | 7.284 | 1.00 | 31.12 | B | C |
| ATOM | 867 | CG | LEU | B | 27 | 64.970 | −21.070 | 7.576 | 1.00 | 33.61 | B | C |
| ATOM | 868 | CD1 | LEU | B | 27 | 65.243 | −21.802 | 8.889 | 1.00 | 32.80 | B | C |
| ATOM | 869 | CD2 | LEU | B | 27 | 65.753 | −21.706 | 6.433 | 1.00 | 34.54 | B | C |
| ATOM | 870 | C | LEU | B | 27 | 62.559 | −18.913 | 8.013 | 1.00 | 27.91 | B | C |
| ATOM | 871 | O | LEU | B | 27 | 61.866 | −18.493 | 7.089 | 1.00 | 27.36 | B | O |
| ATOM | 872 | N | VAL | B | 28 | 63.288 | −18.109 | 8.775 | 1.00 | 26.63 | B | N |
| ATOM | 873 | CA | VAL | B | 28 | 63.256 | −16.670 | 8.561 | 1.00 | 25.38 | B | C |
| ATOM | 874 | CB | VAL | B | 28 | 62.249 | −16.018 | 9.530 | 1.00 | 25.06 | B | C |
| ATOM | 875 | CG1 | VAL | B | 28 | 60.848 | −16.521 | 9.245 | 1.00 | 22.93 | B | C |
| ATOM | 876 | CG2 | VAL | B | 28 | 62.626 | −16.347 | 10.967 | 1.00 | 25.37 | B | C |
| ATOM | 877 | C | VAL | B | 28 | 64.606 | −15.968 | 8.714 | 1.00 | 25.60 | B | C |
| ATOM | 878 | O | VAL | B | 28 | 65.554 | −16.523 | 9.266 | 1.00 | 24.51 | B | O |
| ATOM | 879 | N | ARG | B | 29 | 64.671 | −14.740 | 8.202 | 1.00 | 26.32 | B | N |
| ATOM | 880 | CA | ARG | B | 29 | 65.862 | −13.893 | 8.265 | 1.00 | 26.36 | B | C |
| ATOM | 881 | CB | ARG | B | 29 | 66.417 | −13.640 | 6.865 | 1.00 | 29.44 | B | C |
| ATOM | 882 | CG | ARG | B | 29 | 67.420 | −14.653 | 6.377 | 1.00 | 35.76 | B | C |
| ATOM | 883 | CD | ARG | B | 29 | 67.752 | −14.431 | 4.895 | 1.00 | 40.93 | B | C |
| ATOM | 884 | NE | ARG | B | 29 | 68.922 | −15.209 | 4.488 | 1.00 | 44.00 | B | N |
| ATOM | 885 | CZ | ARG | B | 29 | 70.157 | −14.969 | 4.923 | 1.00 | 45.03 | B | C |
| ATOM | 886 | NH1 | ARG | B | 29 | 70.377 | −13.970 | 5.773 | 1.00 | 44.48 | B | N |
| ATOM | 887 | NH2 | ARG | B | 29 | 71.169 | −15.730 | 4.521 | 1.00 | 46.18 | B | N |
| ATOM | 888 | C | ARG | B | 29 | 65.458 | −12.550 | 8.868 | 1.00 | 25.24 | B | C |
| ATOM | 889 | O | ARG | B | 29 | 64.973 | −11.672 | 8.152 | 1.00 | 26.08 | B | O |
| ATOM | 890 | N | PRO | B | 30 | 65.642 | −12.372 | 10.191 | 1.00 | 22.82 | B | N |
| ATOM | 891 | CD | PRO | B | 30 | 66.109 | −13.336 | 11.200 | 1.00 | 21.19 | B | C |
| ATOM | 892 | CA | PRO | B | 30 | 65.275 | −11.108 | 10.830 | 1.00 | 21.09 | B | C |
| ATOM | 893 | CB | PRO | B | 30 | 65.777 | −11.295 | 12.256 | 1.00 | 18.84 | B | C |
| ATOM | 894 | CG | PRO | B | 30 | 65.582 | −12.732 | 12.478 | 1.00 | 19.25 | B | C |
| ATOM | 895 | C | PRO | B | 30 | 65.920 | −9.905 | 10.148 | 1.00 | 21.41 | B | C |
| ATOM | 896 | O | PRO | B | 30 | 67.023 | −10.002 | 9.613 | 1.00 | 21.85 | B | O |
| ATOM | 897 | N | LYS | B | 31 | 65.224 | −8.774 | 10.163 | 1.00 | 20.86 | B | N |
| ATOM | 898 | CA | LYS | B | 31 | 65.754 | −7.561 | 9.572 | 1.00 | 20.51 | B | C |
| ATOM | 899 | CB | LYS | B | 31 | 64.627 | −6.584 | 9.271 | 1.00 | 20.10 | B | C |
| ATOM | 900 | CG | LYS | B | 31 | 63.744 | −7.089 | 8.159 | 1.00 | 21.08 | B | C |
| ATOM | 901 | CD | LYS | B | 31 | 62.678 | −6.107 | 7.802 | 1.00 | 22.40 | B | C |
| ATOM | 902 | CE | LYS | B | 31 | 61.801 | −6.685 | 6.728 | 1.00 | 24.64 | B | C |
| ATOM | 903 | NZ | LYS | B | 31 | 60.672 | −5.777 | 6.428 | 1.00 | 28.16 | B | N |
| ATOM | 904 | C | LYS | B | 31 | 66.755 | −6.969 | 10.542 | 1.00 | 20.98 | B | C |
| ATOM | 905 | O | LYS | B | 31 | 66.823 | −7.376 | 11.691 | 1.00 | 22.03 | B | O |
| ATOM | 906 | N | PRO | B | 32 | 67.543 | −5.993 | 10.094 | 1.00 | 21.99 | B | N |
| ATOM | 907 | CD | PRO | B | 32 | 67.505 | −5.349 | 8.769 | 1.00 | 20.88 | B | C |
| ATOM | 908 | CA | PRO | B | 32 | 68.552 | −5.367 | 10.949 | 1.00 | 22.11 | B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | | |
|---|---|---|---|---|---|---|---|---|---|---|---|
| ATOM | 909 | CB | PRO | B | 32 | 68.893 | −4.093 | 10.190 | 1.00 | 23.23 B | C |
| ATOM | 910 | CG | PRO | B | 32 | 68.806 | −4.569 | 8.758 | 1.00 | 22.91 B | C |
| ATOM | 911 | C | PRO | B | 32 | 68.231 | −5.114 | 12.416 | 1.00 | 22.72 B | C |
| ATOM | 912 | O | PRO | B | 32 | 69.026 | −5.485 | 13.282 | 1.00 | 23.53 B | O |
| ATOM | 913 | N | LEU | B | 33 | 67.090 | −4.500 | 12.719 | 1.00 | 22.94 B | N |
| ATOM | 914 | CA | LEU | B | 33 | 66.772 | −4.221 | 14.123 | 1.00 | 22.90 B | C |
| ATOM | 915 | CB | LEU | B | 33 | 65.696 | −3.143 | 14.235 | 1.00 | 24.77 B | C |
| ATOM | 916 | CG | LEU | B | 33 | 66.288 | −1.756 | 14.535 | 1.00 | 28.92 B | C |
| ATOM | 917 | CD1 | LEU | B | 33 | 67.420 | −1.399 | 13.547 | 1.00 | 26.95 B | C |
| ATOM | 918 | CD2 | LEU | B | 33 | 65.170 | −0.724 | 14.473 | 1.00 | 31.12 B | C |
| ATOM | 919 | C | LEU | B | 33 | 66.393 | −5.424 | 14.966 | 1.00 | 21.68 B | C |
| ATOM | 920 | O | LEU | B | 33 | 66.896 | −5.577 | 16.075 | 1.00 | 21.88 B | O |
| ATOM | 921 | N | LEU | B | 34 | 65.506 | −6.274 | 14.462 | 1.00 | 20.94 B | N |
| ATOM | 922 | CA | LEU | B | 34 | 65.133 | −7.468 | 15.209 | 1.00 | 19.68 B | C |
| ATOM | 923 | CB | LEU | B | 34 | 64.048 | −8.250 | 14.473 | 1.00 | 18.05 B | C |
| ATOM | 924 | CG | LEU | B | 34 | 63.758 | −9.664 | 14.981 | 1.00 | 15.31 B | C |
| ATOM | 925 | CD1 | LEU | B | 34 | 63.339 | −9.643 | 16.437 | 1.00 | 13.94 B | C |
| ATOM | 926 | CD2 | LEU | B | 34 | 62.678 | −10.274 | 14.128 | 1.00 | 13.57 B | C |
| ATOM | 927 | C | LEU | B | 34 | 66.381 | −8.340 | 15.363 | 1.00 | 20.89 B | C |
| ATOM | 928 | O | LEU | B | 34 | 66.583 | −8.968 | 16.402 | 1.00 | 20.95 B | O |
| ATOM | 929 | N | LEU | B | 35 | 67.218 | −8.363 | 14.327 | 1.00 | 20.45 B | N |
| ATOM | 930 | CA | LEU | B | 35 | 68.447 | −9.149 | 14.347 | 1.00 | 22.34 B | C |
| ATOM | 931 | CB | LEU | B | 35 | 69.182 | −9.022 | 13.003 | 1.00 | 22.21 B | C |
| ATOM | 932 | CG | LEU | B | 35 | 70.410 | −9.892 | 12.701 | 1.00 | 21.01 B | C |
| ATOM | 933 | CD1 | LEU | B | 35 | 71.607 | −9.401 | 13.484 | 1.00 | 23.40 B | C |
| ATOM | 934 | CD2 | LEU | B | 35 | 70.104 | −11.338 | 13.026 | 1.00 | 20.20 B | C |
| ATOM | 935 | C | LEU | B | 35 | 69.342 | −8.687 | 15.492 | 1.00 | 23.56 B | C |
| ATOM | 936 | O | LEU | B | 35 | 69.819 | −9.506 | 16.282 | 1.00 | 25.34 B | O |
| ATOM | 937 | N | LYS | B | 36 | 69.567 | −7.380 | 15.590 | 1.00 | 24.88 B | N |
| ATOM | 938 | CA | LYS | B | 36 | 70.400 | −6.841 | 16.665 | 1.00 | 26.33 B | C |
| ATOM | 939 | CB | LYS | B | 36 | 70.529 | −5.318 | 16.553 | 1.00 | 28.76 B | C |
| ATOM | 940 | CG | LYS | B | 36 | 71.228 | −4.689 | 17.758 | 1.00 | 33.99 B | C |
| ATOM | 941 | CD | LYS | B | 36 | 71.153 | −3.159 | 17.762 | 1.00 | 38.12 B | C |
| ATOM | 942 | CE | LYS | B | 36 | 72.023 | −2.540 | 16.661 | 1.00 | 39.99 B | C |
| ATOM | 943 | NZ | LYS | B | 36 | 71.900 | −1.052 | 16.616 | 1.00 | 40.20 B | N |
| ATOM | 944 | C | LYS | B | 36 | 69.757 | −7.187 | 18.001 | 1.00 | 25.07 B | C |
| ATOM | 945 | O | LYS | B | 36 | 70.433 | −7.541 | 18.964 | 1.00 | 25.56 B | O |
| ATOM | 946 | N | LEU | B | 37 | 68.438 | −7.071 | 18.039 | 1.00 | 23.72 B | N |
| ATOM | 947 | CA | LEU | B | 37 | 67.659 | −7.362 | 19.228 | 1.00 | 23.05 B | C |
| ATOM | 948 | CB | LEU | B | 37 | 66.179 | −7.198 | 18.894 | 1.00 | 23.27 B | C |
| ATOM | 949 | CG | LEU | B | 37 | 65.156 | −6.988 | 20.002 | 1.00 | 22.39 B | C |
| ATOM | 950 | CD1 | LEU | B | 37 | 65.148 | −8.176 | 20.938 | 1.00 | 22.88 B | C |
| ATOM | 951 | CD2 | LEU | B | 37 | 65.485 | −5.712 | 20.724 | 1.00 | 21.97 B | C |
| ATOM | 952 | C | LEU | B | 37 | 67.941 | −8.798 | 19.679 | 1.00 | 23.41 B | C |
| ATOM | 953 | O | LEU | B | 37 | 68.180 | −9.066 | 20.860 | 1.00 | 22.57 B | O |
| ATOM | 954 | N | LEU | B | 38 | 67.921 | −9.721 | 18.724 | 1.00 | 22.64 B | N |
| ATOM | 955 | CA | LEU | B | 38 | 68.158 | −11.121 | 19.032 | 1.00 | 21.31 B | C |
| ATOM | 956 | CB | LEU | B | 38 | 67.838 | −11.988 | 17.808 | 1.00 | 18.85 B | C |
| ATOM | 957 | CG | LEU | B | 38 | 66.368 | −11.934 | 17.379 | 1.00 | 17.25 B | C |
| ATOM | 958 | CD1 | LEU | B | 38 | 66.178 | −12.760 | 16.123 | 1.00 | 16.90 B | C |
| ATOM | 959 | CD2 | LEU | B | 38 | 65.462 | −12.430 | 18.509 | 1.00 | 12.89 B | C |
| ATOM | 960 | C | LEU | B | 38 | 69.588 | −11.349 | 19.496 | 1.00 | 22.29 B | C |
| ATOM | 961 | O | LEU | B | 38 | 69.815 | −11.935 | 20.555 | 1.00 | 21.71 B | O |
| ATOM | 962 | N | LYS | B | 39 | 70.554 | −10.878 | 18.713 | 1.00 | 22.57 B | N |
| ATOM | 963 | CA | LYS | B | 39 | 71.952 | −11.053 | 19.082 | 1.00 | 22.22 B | C |
| ATOM | 964 | CB | LYS | B | 39 | 72.871 | −10.518 | 17.978 | 1.00 | 21.13 B | C |
| ATOM | 965 | CG | LYS | B | 39 | 72.856 | −11.376 | 16.731 | 1.00 | 21.02 B | C |
| ATOM | 966 | CD | LYS | B | 39 | 73.951 | −10.999 | 15.757 | 1.00 | 20.77 B | C |
| ATOM | 967 | CE | LYS | B | 39 | 73.888 | −11.897 | 14.531 | 1.00 | 22.57 B | C |
| ATOM | 968 | NZ | LYS | B | 39 | 74.967 | −11.621 | 13.550 | 1.00 | 24.14 B | N |
| ATOM | 969 | C | LYS | B | 39 | 72.292 | −10.390 | 20.410 | 1.00 | 22.10 B | C |
| ATOM | 970 | O | LYS | B | 39 | 73.286 | −10.739 | 21.046 | 1.00 | 23.45 B | O |
| ATOM | 971 | N | SER | B | 40 | 71.462 | −9.445 | 20.840 | 1.00 | 21.94 B | N |
| ATOM | 972 | CA | SER | B | 40 | 71.711 | −8.748 | 22.093 | 1.00 | 21.68 B | C |
| ATOM | 973 | CB | SER | B | 40 | 70.809 | −7.526 | 22.206 | 1.00 | 22.53 B | C |
| ATOM | 974 | OG | SER | B | 40 | 69.479 | −7.917 | 22.486 | 1.00 | 27.18 B | O |
| ATOM | 975 | C | SER | B | 40 | 71.486 | −9.645 | 23.305 | 1.00 | 21.15 B | C |
| ATOM | 976 | O | SER | B | 40 | 71.920 | −9.319 | 24.401 | 1.00 | 20.79 B | O |
| ATOM | 977 | N | VAL | B | 41 | 70.789 | −10.762 | 23.116 | 1.00 | 20.81 B | N |
| ATOM | 978 | CA | VAL | B | 41 | 70.533 | −11.690 | 24.213 | 1.00 | 20.10 B | C |
| ATOM | 979 | CB | VAL | B | 41 | 69.012 | −11.875 | 24.469 | 1.00 | 20.10 B | C |
| ATOM | 980 | CG1 | VAL | B | 41 | 68.448 | −10.651 | 25.163 | 1.00 | 20.00 B | C |
| ATOM | 981 | CG2 | VAL | B | 41 | 68.285 | −12.117 | 23.159 | 1.00 | 20.21 B | C |
| ATOM | 982 | C | VAL | B | 41 | 71.165 | −13.067 | 23.999 | 1.00 | 19.56 B | C |
| ATOM | 983 | O | VAL | B | 41 | 70.695 | −14.069 | 24.539 | 1.00 | 18.39 B | O |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 984 | N | GLY | B | 42 | 72.224 | −13.120 | 23.198 | 1.00 | 19.73 | B | N |
|------|-----|-----|-----|---|----|--------|---------|--------|------|-------|---|---|
| ATOM | 985 | CA | GLY | B | 42 | 72.898 | −14.385 | 22.981 | 1.00 | 20.77 | B | C |
| ATOM | 986 | C | GLY | B | 42 | 72.691 | −15.090 | 21.658 | 1.00 | 22.17 | B | C |
| ATOM | 987 | O | GLY | B | 42 | 73.391 | −16.062 | 21.379 | 1.00 | 24.42 | B | O |
| ATOM | 988 | N | ALA | B | 43 | 71.738 | −14.645 | 20.847 | 1.00 | 22.24 | B | N |
| ATOM | 989 | CA | ALA | B | 43 | 71.522 | −15.287 | 19.554 | 1.00 | 22.66 | B | C |
| ATOM | 990 | CB | ALA | B | 43 | 70.320 | −14.680 | 18.849 | 1.00 | 20.93 | B | C |
| ATOM | 991 | C | ALA | B | 43 | 72.769 | −15.073 | 18.715 | 1.00 | 23.43 | B | C |
| ATOM | 992 | O | ALA | B | 43 | 73.501 | −14.103 | 18.925 | 1.00 | 23.42 | B | O |
| ATOM | 993 | N | GLN | B | 44 | 73.020 | −15.976 | 17.772 | 1.00 | 25.27 | B | N |
| ATOM | 994 | CA | GLN | B | 44 | 74.184 | −15.839 | 16.907 | 1.00 | 27.42 | B | C |
| ATOM | 995 | CB | GLN | B | 44 | 75.422 | −16.377 | 17.613 | 1.00 | 29.51 | B | C |
| ATOM | 996 | CG | GLN | B | 44 | 75.181 | −17.618 | 18.411 | 1.00 | 31.44 | B | C |
| ATOM | 997 | CD | GLN | B | 44 | 76.005 | −17.618 | 19.673 | 1.00 | 35.21 | B | C |
| ATOM | 998 | OE1 | GLN | B | 44 | 76.221 | −18.664 | 20.286 | 1.00 | 38.33 | B | O |
| ATOM | 999 | NE2 | GLN | B | 44 | 76.468 | −16.436 | 20.078 | 1.00 | 33.71 | B | N |
| ATOM | 1000 | C | GLN | B | 44 | 74.060 | −16.454 | 15.519 | 1.00 | 27.16 | B | C |
| ATOM | 1001 | O | GLN | B | 44 | 74.969 | −17.126 | 15.036 | 1.00 | 28.13 | B | O |
| ATOM | 1002 | N | LYS | B | 45 | 72.926 | −16.205 | 14.879 | 1.00 | 26.81 | B | N |
| ATOM | 1003 | CA | LYS | B | 45 | 72.670 | −16.683 | 13.534 | 1.00 | 25.44 | B | C |
| ATOM | 1004 | CB | LYS | B | 45 | 71.723 | −17.884 | 13.555 | 1.00 | 24.61 | B | C |
| ATOM | 1005 | CG | LYS | B | 45 | 72.275 | −19.113 | 14.259 | 1.00 | 23.83 | B | C |
| ATOM | 1006 | CD | LYS | B | 45 | 71.387 | −20.345 | 14.042 | 1.00 | 21.51 | B | C |
| ATOM | 1007 | CE | LYS | B | 45 | 70.025 | −20.201 | 14.700 | 1.00 | 21.68 | B | C |
| ATOM | 1008 | NZ | LYS | B | 45 | 69.171 | −21.397 | 14.466 | 1.00 | 21.07 | B | N |
| ATOM | 1009 | C | LYS | B | 45 | 72.022 | −15.526 | 12.786 | 1.00 | 25.54 | B | C |
| ATOM | 1010 | O | LYS | B | 45 | 71.616 | −14.538 | 13.387 | 1.00 | 23.91 | B | O |
| ATOM | 1011 | N | ASP | B | 46 | 71.944 | −15.637 | 11.470 | 1.00 | 26.59 | B | N |
| ATOM | 1012 | CA | ASP | B | 46 | 71.323 | −14.595 | 10.681 | 1.00 | 28.75 | B | C |
| ATOM | 1013 | CB | ASP | B | 46 | 72.216 | −14.197 | 9.503 | 1.00 | 31.00 | B | C |
| ATOM | 1014 | CG | ASP | B | 46 | 73.525 | −13.573 | 9.952 | 1.00 | 34.10 | B | C |
| ATOM | 1015 | OD1 | ASP | B | 46 | 73.573 | −13.029 | 11.081 | 1.00 | 34.46 | B | O |
| ATOM | 1016 | OD2 | ASP | B | 46 | 74.506 | −13.614 | 9.174 | 1.00 | 37.45 | B | O |
| ATOM | 1017 | C | ASP | B | 46 | 69.989 | −15.121 | 10.182 | 1.00 | 29.00 | B | C |
| ATOM | 1018 | O | ASP | B | 46 | 69.178 | −14.374 | 9.634 | 1.00 | 29.94 | B | O |
| ATOM | 1019 | N | THR | B | 47 | 69.768 | −16.418 | 10.370 | 1.00 | 27.35 | B | N |
| ATOM | 1020 | CA | THR | B | 47 | 68.519 | −17.036 | 9.961 | 1.00 | 25.63 | B | C |
| ATOM | 1021 | CB | THR | B | 47 | 68.686 | −17.806 | 8.641 | 1.00 | 25.07 | B | C |
| ATOM | 1022 | OG1 | THR | B | 47 | 69.360 | −19.038 | 8.886 | 1.00 | 28.76 | B | O |
| ATOM | 1023 | CG2 | THR | B | 47 | 69.517 | −16.990 | 7.661 | 1.00 | 24.39 | B | C |
| ATOM | 1024 | C | THR | B | 47 | 68.045 | −17.964 | 11.085 | 1.00 | 25.43 | B | C |
| ATOM | 1025 | O | THR | B | 47 | 68.833 | −18.722 | 11.666 | 1.00 | 23.76 | B | O |
| ATOM | 1026 | N | TYR | B | 48 | 66.754 | −17.873 | 11.401 | 1.00 | 24.10 | B | N |
| ATOM | 1027 | CA | TYR | B | 48 | 66.151 | −18.659 | 12.469 | 1.00 | 21.15 | B | C |
| ATOM | 1028 | CB | TYR | B | 48 | 65.873 | −17.779 | 13.689 | 1.00 | 17.82 | B | C |
| ATOM | 1029 | CG | TYR | B | 48 | 67.053 | −16.997 | 14.195 | 1.00 | 16.59 | B | C |
| ATOM | 1030 | CD1 | TYR | B | 48 | 67.538 | −15.899 | 13.490 | 1.00 | 13.77 | B | C |
| ATOM | 1031 | CE1 | TYR | B | 48 | 68.644 | −15.183 | 13.950 | 1.00 | 14.25 | B | C |
| ATOM | 1032 | CD2 | TYR | B | 48 | 67.700 | −17.367 | 15.381 | 1.00 | 15.66 | B | C |
| ATOM | 1033 | CE2 | TYR | B | 48 | 68.805 | −16.660 | 15.849 | 1.00 | 13.98 | B | C |
| ATOM | 1034 | CZ | TYR | B | 48 | 69.273 | −15.572 | 15.127 | 1.00 | 13.39 | B | C |
| ATOM | 1035 | OH | TYR | B | 48 | 70.378 | −14.889 | 15.568 | 1.00 | 10.72 | B | O |
| ATOM | 1036 | C | TYR | B | 48 | 64.826 | −19.249 | 12.054 | 1.00 | 21.47 | B | C |
| ATOM | 1037 | O | TYR | B | 48 | 64.346 | −19.036 | 10.942 | 1.00 | 23.23 | B | O |
| ATOM | 1038 | N | THR | B | 49 | 64.241 | −20.002 | 12.973 | 1.00 | 20.15 | B | N |
| ATOM | 1039 | CA | THR | B | 49 | 62.928 | −20.572 | 12.767 | 1.00 | 19.98 | B | C |
| ATOM | 1040 | CB | THR | B | 49 | 62.837 | −22.014 | 13.271 | 1.00 | 20.11 | B | C |
| ATOM | 1041 | OG1 | THR | B | 49 | 63.281 | −22.072 | 14.632 | 1.00 | 19.72 | B | O |
| ATOM | 1042 | CG2 | THR | B | 49 | 63.692 | −22.930 | 12.409 | 1.00 | 19.53 | B | C |
| ATOM | 1043 | C | THR | B | 49 | 62.101 | −19.676 | 13.672 | 1.00 | 20.66 | B | C |
| ATOM | 1044 | O | THR | B | 49 | 62.632 | −19.088 | 14.615 | 1.00 | 20.05 | B | O |
| ATOM | 1045 | N | MET | B | 50 | 60.815 | −19.547 | 13.398 | 1.00 | 21.09 | B | N |
| ATOM | 1046 | CA | MET | B | 50 | 60.002 | −18.694 | 14.238 | 1.00 | 21.27 | B | C |
| ATOM | 1047 | CB | MET | B | 50 | 58.545 | −18.751 | 13.793 | 1.00 | 20.61 | B | C |
| ATOM | 1048 | CG | MET | B | 50 | 58.283 | −18.012 | 12.491 | 1.00 | 19.47 | B | C |
| ATOM | 1049 | SD | MET | B | 50 | 58.635 | −16.258 | 12.644 | 1.00 | 16.90 | B | S |
| ATOM | 1050 | CE | MET | B | 50 | 57.164 | −15.708 | 13.480 | 1.00 | 18.57 | B | C |
| ATOM | 1051 | C | MET | B | 50 | 60.136 | −19.095 | 15.700 | 1.00 | 22.23 | B | C |
| ATOM | 1052 | O | MET | B | 50 | 60.289 | −18.239 | 16.571 | 1.00 | 23.85 | B | O |
| ATOM | 1053 | N | LYS | B | 51 | 60.105 | −20.396 | 15.963 | 1.00 | 22.72 | B | N |
| ATOM | 1054 | CA | LYS | B | 51 | 60.212 | −20.909 | 17.320 | 1.00 | 22.74 | B | C |
| ATOM | 1055 | CB | LYS | B | 51 | 60.233 | −22.430 | 17.274 | 1.00 | 26.32 | B | C |
| ATOM | 1056 | CG | LYS | B | 51 | 60.382 | −23.134 | 18.616 | 1.00 | 32.36 | B | C |
| ATOM | 1057 | CD | LYS | B | 51 | 60.556 | −24.639 | 18.372 | 1.00 | 36.67 | B | C |
| ATOM | 1058 | CE | LYS | B | 51 | 60.845 | −25.426 | 19.641 | 1.00 | 39.04 | B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1059 | NZ | LYS | B | 51 | 61.087 | −26.867 | 19.327 | 1.00 | 39.73 | B | N |
|------|------|-----|-----|---|----|--------|---------|--------|------|-------|---|---|
| ATOM | 1060 | C | LYS | B | 51 | 61.449 | −20.382 | 18.051 | 1.00 | 21.96 | B | C |
| ATOM | 1061 | O | LYS | B | 51 | 61.395 | −20.092 | 19.247 | 1.00 | 20.43 | B | O |
| ATOM | 1062 | N | GLU | B | 52 | 62.559 | −20.247 | 17.331 | 1.00 | 21.19 | B | N |
| ATOM | 1063 | CA | GLU | B | 52 | 63.792 | −19.760 | 17.939 | 1.00 | 21.35 | B | C |
| ATOM | 1064 | CB | GLU | B | 52 | 64.999 | −20.066 | 17.052 | 1.00 | 21.21 | B | C |
| ATOM | 1065 | CG | GLU | B | 52 | 65.197 | −21.531 | 16.758 | 1.00 | 22.21 | B | C |
| ATOM | 1066 | CD | GLU | B | 52 | 66.345 | −21.763 | 15.807 | 1.00 | 23.97 | B | C |
| ATOM | 1067 | OE1 | GLU | B | 52 | 66.385 | −21.063 | 14.777 | 1.00 | 25.44 | B | O |
| ATOM | 1068 | OE2 | GLU | B | 52 | 67.200 | −22.636 | 16.078 | 1.00 | 23.65 | B | O |
| ATOM | 1069 | C | GLU | B | 52 | 63.725 | −18.266 | 18.178 | 1.00 | 21.58 | B | C |
| ATOM | 1070 | O | GLU | B | 52 | 64.227 | −17.779 | 19.186 | 1.00 | 23.46 | B | O |
| ATOM | 1071 | N | VAL | B | 53 | 63.128 | −17.534 | 17.242 | 1.00 | 21.11 | B | N |
| ATOM | 1072 | CA | VAL | B | 53 | 63.004 | −16.092 | 17.398 | 1.00 | 19.95 | B | C |
| ATOM | 1073 | CB | VAL | B | 53 | 62.326 | −15.433 | 16.172 | 1.00 | 19.49 | B | C |
| ATOM | 1074 | CG1 | VAL | B | 53 | 62.038 | −13.960 | 16.454 | 1.00 | 19.40 | B | C |
| ATOM | 1075 | CG2 | VAL | B | 53 | 63.238 | −15.544 | 14.965 | 1.00 | 16.87 | B | C |
| ATOM | 1076 | C | VAL | B | 53 | 62.175 | −15.830 | 18.645 | 1.00 | 19.80 | B | C |
| ATOM | 1077 | O | VAL | B | 53 | 62.524 | −14.980 | 19.466 | 1.00 | 20.88 | B | O |
| ATOM | 1078 | N | LEU | B | 54 | 61.085 | −16.574 | 18.795 | 1.00 | 17.79 | B | N |
| ATOM | 1079 | CA | LEU | B | 54 | 60.230 | −16.418 | 19.962 | 1.00 | 17.35 | B | C |
| ATOM | 1080 | CB | LEU | B | 54 | 59.030 | −17.367 | 19.875 | 1.00 | 15.34 | B | C |
| ATOM | 1081 | CG | LEU | B | 54 | 57.869 | −16.841 | 19.028 | 1.00 | 15.35 | B | C |
| ATOM | 1082 | CD1 | LEU | B | 54 | 56.934 | −17.970 | 18.671 | 1.00 | 16.18 | B | C |
| ATOM | 1083 | CD2 | LEU | B | 54 | 57.139 | −15.747 | 19.795 | 1.00 | 14.28 | B | C |
| ATOM | 1084 | C | LEU | B | 54 | 61.013 | −16.697 | 21.232 | 1.00 | 18.28 | B | C |
| ATOM | 1085 | O | LEU | B | 54 | 60.891 | −15.980 | 22.223 | 1.00 | 20.27 | B | O |
| ATOM | 1086 | N | PHE | B | 55 | 61.833 | −17.739 | 21.202 | 1.00 | 17.82 | B | N |
| ATOM | 1087 | CA | PHE | B | 55 | 62.609 | −18.092 | 22.379 | 1.00 | 16.45 | B | C |
| ATOM | 1088 | CB | PHE | B | 55 | 63.428 | −19.360 | 22.137 | 1.00 | 15.18 | B | C |
| ATOM | 1089 | CG | PHE | B | 55 | 64.192 | −19.814 | 23.342 | 1.00 | 12.26 | B | C |
| ATOM | 1090 | CD1 | PHE | B | 55 | 63.609 | −20.666 | 24.267 | 1.00 | 12.57 | B | C |
| ATOM | 1091 | CD2 | PHE | B | 55 | 65.485 | −19.366 | 23.566 | 1.00 | 12.20 | B | C |
| ATOM | 1092 | CE1 | PHE | B | 55 | 64.307 | −21.071 | 25.406 | 1.00 | 13.48 | B | C |
| ATOM | 1093 | CE2 | PHE | B | 55 | 66.190 | −19.761 | 24.699 | 1.00 | 14.43 | B | C |
| ATOM | 1094 | CZ | PHE | B | 55 | 65.600 | −20.618 | 25.621 | 1.00 | 13.25 | B | C |
| ATOM | 1095 | C | PHE | B | 55 | 63.544 | −16.970 | 22.803 | 1.00 | 15.94 | B | C |
| ATOM | 1096 | O | PHE | B | 55 | 63.599 | −16.625 | 23.983 | 1.00 | 15.63 | B | O |
| ATOM | 1097 | N | TYR | B | 56 | 64.297 | −16.419 | 21.854 | 1.00 | 14.98 | B | N |
| ATOM | 1098 | CA | TYR | B | 56 | 65.223 | −15.338 | 22.179 | 1.00 | 15.81 | B | C |
| ATOM | 1099 | CB | TYR | B | 56 | 66.132 | −15.033 | 20.989 | 1.00 | 13.78 | B | C |
| ATOM | 1100 | CG | TYR | B | 56 | 67.202 | −16.080 | 20.787 | 1.00 | 14.13 | B | C |
| ATOM | 1101 | CD1 | TYR | B | 56 | 68.193 | −16.285 | 21.752 | 1.00 | 12.86 | B | C |
| ATOM | 1102 | CE1 | TYR | B | 56 | 69.174 | −17.252 | 21.576 | 1.00 | 12.44 | B | C |
| ATOM | 1103 | CD2 | TYR | B | 56 | 67.222 | −16.876 | 19.638 | 1.00 | 12.17 | B | C |
| ATOM | 1104 | CE2 | TYR | B | 56 | 68.199 | −17.845 | 19.450 | 1.00 | 10.79 | B | C |
| ATOM | 1105 | CZ | TYR | B | 56 | 69.171 | −18.029 | 20.422 | 1.00 | 13.93 | B | C |
| ATOM | 1106 | OH | TYR | B | 56 | 70.143 | −18.991 | 20.244 | 1.00 | 16.24 | B | O |
| ATOM | 1107 | C | TYR | B | 56 | 64.440 | −14.100 | 22.577 | 1.00 | 16.28 | B | C |
| ATOM | 1108 | O | TYR | B | 56 | 64.821 | −13.365 | 23.497 | 1.00 | 17.43 | B | O |
| ATOM | 1109 | N | LEU | B | 57 | 63.325 | −13.885 | 21.895 | 1.00 | 15.05 | B | N |
| ATOM | 1110 | CA | LEU | B | 57 | 62.491 | −12.742 | 22.191 | 1.00 | 14.33 | B | C |
| ATOM | 1111 | CB | LEU | B | 57 | 61.367 | −12.654 | 21.161 | 1.00 | 9.51 | B | C |
| ATOM | 1112 | CG | LEU | B | 57 | 61.124 | −11.303 | 20.489 | 1.00 | 7.58 | B | C |
| ATOM | 1113 | CD1 | LEU | B | 57 | 62.331 | −10.388 | 20.577 | 1.00 | 3.80 | B | C |
| ATOM | 1114 | CD2 | LEU | B | 57 | 60.759 | −11.572 | 19.048 | 1.00 | 8.90 | B | C |
| ATOM | 1115 | C | LEU | B | 57 | 61.954 | −12.930 | 23.610 | 1.00 | 16.47 | B | C |
| ATOM | 1116 | O | LEU | B | 57 | 61.731 | −11.953 | 24.342 | 1.00 | 18.25 | B | O |
| ATOM | 1117 | N | GLY | B | 58 | 61.772 | −14.191 | 24.004 | 1.00 | 15.84 | B | N |
| ATOM | 1118 | CA | GLY | B | 58 | 61.295 | −14.487 | 25.342 | 1.00 | 15.86 | B | C |
| ATOM | 1119 | C | GLY | B | 58 | 62.346 | −14.152 | 26.381 | 1.00 | 16.79 | B | C |
| ATOM | 1120 | O | GLY | B | 58 | 62.017 | −13.688 | 27.469 | 1.00 | 17.27 | B | O |
| ATOM | 1121 | N | GLN | B | 59 | 63.614 | −14.387 | 26.048 | 1.00 | 18.11 | B | N |
| ATOM | 1122 | CA | GLN | B | 59 | 64.709 | −14.095 | 26.969 | 1.00 | 19.44 | B | C |
| ATOM | 1123 | CB | GLN | B | 59 | 66.039 | −14.681 | 26.476 | 1.00 | 20.58 | B | C |
| ATOM | 1124 | CG | GLN | B | 59 | 66.110 | −16.200 | 26.415 | 1.00 | 21.38 | B | C |
| ATOM | 1125 | CD | GLN | B | 59 | 65.858 | −16.858 | 27.753 | 1.00 | 21.66 | B | C |
| ATOM | 1126 | OE1 | GLN | B | 59 | 66.530 | −16.563 | 28.737 | 1.00 | 22.01 | B | O |
| ATOM | 1127 | NE2 | GLN | B | 59 | 64.886 | −17.765 | 27.794 | 1.00 | 21.89 | B | N |
| ATOM | 1128 | C | GLN | B | 59 | 64.847 | −12.591 | 27.065 | 1.00 | 19.91 | B | C |
| ATOM | 1129 | O | GLN | B | 59 | 65.081 | −12.049 | 28.147 | 1.00 | 20.54 | B | O |
| ATOM | 1130 | N | TYR | B | 60 | 64.712 | −11.918 | 25.925 | 1.00 | 19.05 | B | N |
| ATOM | 1131 | CA | TYR | B | 60 | 64.810 | −10.465 | 25.896 | 1.00 | 19.04 | B | C |
| ATOM | 1132 | CB | TYR | B | 60 | 64.539 | −9.952 | 24.489 | 1.00 | 19.56 | B | C |
| ATOM | 1133 | CG | TYR | B | 60 | 64.745 | −8.469 | 24.334 | 1.00 | 20.31 | B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1134 | CD1 | TYR | B | 60 | 65.989 | −7.955  | 23.976 | 1.00 | 21.40 | B | C |
|------|------|-----|-----|---|----|--------|---------|--------|------|-------|---|---|
| ATOM | 1135 | CE1 | TYR | B | 60 | 66.183 | −6.587  | 23.812 | 1.00 | 21.70 | B | C |
| ATOM | 1136 | CD2 | TYR | B | 60 | 63.694 | −7.575  | 24.535 | 1.00 | 20.38 | B | C |
| ATOM | 1137 | CE2 | TYR | B | 60 | 63.872 | −6.205  | 24.380 | 1.00 | 21.82 | B | C |
| ATOM | 1138 | CZ  | TYR | B | 60 | 65.120 | −5.714  | 24.014 | 1.00 | 22.80 | B | C |
| ATOM | 1139 | OH  | TYR | B | 60 | 65.303 | −4.360  | 23.827 | 1.00 | 20.51 | B | O |
| ATOM | 1140 | C   | TYR | B | 60 | 63.779 | −9.866  | 26.861 | 1.00 | 19.98 | B | C |
| ATOM | 1141 | O   | TYR | B | 60 | 64.126 | −9.128  | 27.791 | 1.00 | 18.48 | B | O |
| ATOM | 1142 | N   | ILE | B | 61 | 62.507 | −10.192 | 26.631 | 1.00 | 19.27 | B | N |
| ATOM | 1143 | CA  | ILE | B | 61 | 61.425 | −9.691  | 27.471 | 1.00 | 18.48 | B | C |
| ATOM | 1144 | CB  | ILE | B | 61 | 60.093 | −10.407 | 27.146 | 1.00 | 15.73 | B | C |
| ATOM | 1145 | CG2 | ILE | B | 61 | 59.081 | −10.185 | 28.269 | 1.00 | 10.18 | B | C |
| ATOM | 1146 | CG1 | ILE | B | 61 | 59.562 | −9.922  | 25.797 | 1.00 | 11.81 | B | C |
| ATOM | 1147 | CD1 | ILE | B | 61 | 58.345 | −10.669 | 25.332 | 1.00 | 8.80  | B | C |
| ATOM | 1148 | C   | ILE | B | 61 | 61.744 | −9.913  | 28.943 | 1.00 | 20.88 | B | C |
| ATOM | 1149 | O   | ILE | B | 61 | 61.638 | −9.002  | 29.763 | 1.00 | 19.97 | B | O |
| ATOM | 1150 | N   | MET | B | 62 | 62.152 | −11.132 | 29.265 | 1.00 | 23.54 | B | N |
| ATOM | 1151 | CA  | MET | B | 62 | 62.448 | −11.486 | 30.640 | 1.00 | 25.72 | B | C |
| ATOM | 1152 | CB  | MET | B | 62 | 62.643 | −12.993 | 30.753 | 1.00 | 26.08 | B | C |
| ATOM | 1153 | CG  | MET | B | 62 | 62.091 | −13.549 | 32.035 | 1.00 | 29.56 | B | C |
| ATOM | 1154 | SD  | MET | B | 62 | 60.293 | −13.384 | 32.054 | 1.00 | 34.09 | B | S |
| ATOM | 1155 | CE  | MET | B | 62 | 59.820 | −15.029 | 31.546 | 1.00 | 35.99 | B | C |
| ATOM | 1156 | C   | MET | B | 62 | 63.668 | −10.773 | 31.202 | 1.00 | 26.75 | B | C |
| ATOM | 1157 | O   | MET | B | 62 | 63.642 | −10.272 | 32.331 | 1.00 | 25.96 | B | O |
| ATOM | 1158 | N   | THR | B | 63 | 64.735 | −10.728 | 30.413 | 1.00 | 27.94 | B | N |
| ATOM | 1159 | CA  | THR | B | 63 | 65.970 | −10.101 | 30.853 | 1.00 | 29.87 | B | C |
| ATOM | 1160 | CB  | THR | B | 63 | 67.103 | −10.310 | 29.814 | 1.00 | 30.48 | B | C |
| ATOM | 1161 | OG1 | THR | B | 63 | 68.312 | −9.735  | 30.311 | 1.00 | 33.04 | B | O |
| ATOM | 1162 | CG2 | THR | B | 63 | 66.773 | −9.641  | 28.499 | 1.00 | 32.87 | B | C |
| ATOM | 1163 | C   | THR | B | 63 | 65.814 | −8.610  | 31.155 | 1.00 | 30.83 | B | C |
| ATOM | 1164 | O   | THR | B | 63 | 66.369 | −8.113  | 32.140 | 1.00 | 30.48 | B | O |
| ATOM | 1165 | N   | LYS | B | 64 | 65.053 | −7.900  | 30.321 | 1.00 | 31.66 | B | N |
| ATOM | 1166 | CA  | LYS | B | 64 | 64.837 | −6.470  | 30.522 | 1.00 | 31.45 | B | C |
| ATOM | 1167 | CB  | LYS | B | 64 | 64.707 | −5.759  | 29.174 | 1.00 | 30.49 | B | C |
| ATOM | 1168 | CG  | LYS | B | 64 | 65.875 | −6.026  | 28.246 | 1.00 | 30.78 | B | C |
| ATOM | 1169 | CD  | LYS | B | 64 | 65.886 | −5.111  | 27.038 | 1.00 | 27.93 | B | C |
| ATOM | 1170 | CE  | LYS | B | 64 | 66.248 | −3.691  | 27.430 | 1.00 | 28.58 | B | C |
| ATOM | 1171 | NZ  | LYS | B | 64 | 66.497 | −2.836  | 26.235 | 1.00 | 28.06 | B | N |
| ATOM | 1172 | C   | LYS | B | 64 | 63.608 | −6.182  | 31.386 | 1.00 | 32.45 | B | C |
| ATOM | 1173 | O   | LYS | B | 64 | 63.177 | −5.039  | 31.502 | 1.00 | 33.33 | B | O |
| ATOM | 1174 | N   | ARG | B | 65 | 63.049 | −7.222  | 31.993 | 1.00 | 33.64 | B | N |
| ATOM | 1175 | CA  | ARG | B | 65 | 61.888 | −7.067  | 32.861 | 1.00 | 34.41 | B | C |
| ATOM | 1176 | CB  | ARG | B | 65 | 62.332 | −6.516  | 34.215 | 1.00 | 36.81 | B | C |
| ATOM | 1177 | CG  | ARG | B | 65 | 63.229 | −7.457  | 34.994 | 1.00 | 41.86 | B | C |
| ATOM | 1178 | CD  | ARG | B | 65 | 63.308 | −7.042  | 36.452 | 1.00 | 47.34 | B | C |
| ATOM | 1179 | NE  | ARG | B | 65 | 63.686 | −8.162  | 37.311 | 1.00 | 52.97 | B | N |
| ATOM | 1180 | CZ  | ARG | B | 65 | 63.593 | −8.153  | 38.640 | 1.00 | 55.54 | B | C |
| ATOM | 1181 | NH1 | ARG | B | 65 | 63.132 | −7.076  | 39.269 | 1.00 | 56.75 | B | N |
| ATOM | 1182 | NH2 | ARG | B | 65 | 63.954 | −9.225  | 39.340 | 1.00 | 55.33 | B | N |
| ATOM | 1183 | C   | ARG | B | 65 | 60.826 | −6.153  | 32.265 | 1.00 | 32.74 | B | C |
| ATOM | 1184 | O   | ARG | B | 65 | 60.469 | −5.140  | 32.862 | 1.00 | 32.38 | B | O |
| ATOM | 1185 | N   | LEU | B | 66 | 60.317 | −6.523  | 31.093 | 1.00 | 31.30 | B | N |
| ATOM | 1186 | CA  | LEU | B | 66 | 59.304 | −5.730  | 30.402 | 1.00 | 28.77 | B | C |
| ATOM | 1187 | CB  | LEU | B | 66 | 59.529 | −5.786  | 28.885 | 1.00 | 27.49 | B | C |
| ATOM | 1188 | CG  | LEU | B | 66 | 60.893 | −5.336  | 28.347 | 1.00 | 26.11 | B | C |
| ATOM | 1189 | CD1 | LEU | B | 66 | 60.878 | −5.401  | 26.831 | 1.00 | 24.34 | B | C |
| ATOM | 1190 | CD2 | LEU | B | 66 | 61.211 | −3.920  | 28.820 | 1.00 | 23.56 | B | C |
| ATOM | 1191 | C   | LEU | B | 66 | 57.884 | −6.176  | 30.709 | 1.00 | 27.69 | B | C |
| ATOM | 1192 | O   | LEU | B | 66 | 56.928 | −5.585  | 30.217 | 1.00 | 27.56 | B | O |
| ATOM | 1193 | N   | TYR | B | 67 | 57.741 | −7.212  | 31.523 | 1.00 | 27.33 | B | N |
| ATOM | 1194 | CA  | TYR | B | 67 | 56.415 | −7.708  | 31.854 | 1.00 | 29.61 | B | C |
| ATOM | 1195 | CB  | TYR | B | 67 | 56.498 | −9.181  | 32.248 | 1.00 | 29.82 | B | C |
| ATOM | 1196 | CG  | TYR | B | 67 | 57.457 | −9.436  | 33.379 | 1.00 | 31.91 | B | C |
| ATOM | 1197 | CD1 | TYR | B | 67 | 57.097 | −9.158  | 34.696 | 1.00 | 31.85 | B | C |
| ATOM | 1198 | CE1 | TYR | B | 67 | 58.000 | −9.322  | 35.735 | 1.00 | 34.03 | B | C |
| ATOM | 1199 | CD2 | TYR | B | 67 | 58.749 | −9.895  | 33.129 | 1.00 | 33.25 | B | C |
| ATOM | 1200 | CE2 | TYR | B | 67 | 59.664 | −10.063 | 34.165 | 1.00 | 34.17 | B | C |
| ATOM | 1201 | CZ  | TYR | B | 67 | 59.282 | −9.770  | 35.463 | 1.00 | 35.02 | B | C |
| ATOM | 1202 | OH  | TYR | B | 67 | 60.190 | −9.884  | 36.488 | 1.00 | 37.50 | B | O |
| ATOM | 1203 | C   | TYR | B | 67 | 55.785 | −6.890  | 32.974 | 1.00 | 31.35 | B | C |
| ATOM | 1204 | O   | TYR | B | 67 | 56.481 | −6.367  | 33.842 | 1.00 | 30.58 | B | O |
| ATOM | 1205 | N   | ASP | B | 68 | 54.461 | −6.775  | 32.940 | 1.00 | 33.62 | B | N |
| ATOM | 1206 | CA  | ASP | B | 68 | 53.721 | −6.020  | 33.944 | 1.00 | 35.75 | B | C |
| ATOM | 1207 | CB  | ASP | B | 68 | 52.294 | −5.755  | 33.457 | 1.00 | 36.70 | B | C |
| ATOM | 1208 | CG  | ASP | B | 68 | 51.532 | −4.804  | 34.366 | 1.00 | 37.77 | B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1209 | OD1 | ASP | B | 68 | 51.592 | −4.975 | 35.606 | 1.00 | 36.47 | B | O |
|---|---|---|---|---|---|---|---|---|---|---|---|---|
| ATOM | 1210 | OD2 | ASP | B | 68 | 50.865 | −3.888 | 33.831 | 1.00 | 39.59 | B | O |
| ATOM | 1211 | C | ASP | B | 68 | 53.675 | −6.795 | 35.254 | 1.00 | 37.04 | B | C |
| ATOM | 1212 | O | ASP | B | 68 | 53.107 | −7.885 | 35.319 | 1.00 | 35.87 | B | O |
| ATOM | 1213 | N | GLU | B | 69 | 54.262 | −6.221 | 36.298 | 1.00 | 39.00 | B | N |
| ATOM | 1214 | CA | GLU | B | 69 | 54.293 | −6.871 | 37.601 | 1.00 | 42.69 | B | C |
| ATOM | 1215 | CB | GLU | B | 69 | 54.897 | −5.931 | 38.649 | 1.00 | 46.78 | B | C |
| ATOM | 1216 | CG | GLU | B | 69 | 56.421 | −5.965 | 38.713 | 1.00 | 52.39 | B | C |
| ATOM | 1217 | CD | GLU | B | 69 | 56.957 | −7.259 | 39.318 | 1.00 | 55.48 | B | C |
| ATOM | 1218 | OE1 | GLU | B | 69 | 56.779 | −7.472 | 40.541 | 1.00 | 56.57 | B | O |
| ATOM | 1219 | OE2 | GLU | B | 69 | 57.552 | −8.063 | 38.566 | 1.00 | 56.69 | B | O |
| ATOM | 1220 | C | GLU | B | 69 | 52.945 | −7.379 | 38.098 | 1.00 | 42.30 | B | C |
| ATOM | 1221 | O | GLU | B | 69 | 52.866 | −8.467 | 38.667 | 1.00 | 42.32 | B | O |
| ATOM | 1222 | N | LYS | B | 70 | 51.884 | −6.608 | 37.888 | 1.00 | 42.26 | B | N |
| ATOM | 1223 | CA | LYS | B | 70 | 50.571 | −7.031 | 38.362 | 1.00 | 42.71 | B | C |
| ATOM | 1224 | CB | LYS | B | 70 | 49.920 | −5.908 | 39.174 | 1.00 | 44.44 | B | C |
| ATOM | 1225 | CG | LYS | B | 70 | 50.148 | −4.517 | 38.629 | 1.00 | 46.51 | B | C |
| ATOM | 1226 | CD | LYS | B | 70 | 49.718 | −3.481 | 39.651 | 1.00 | 48.94 | B | C |
| ATOM | 1227 | CE | LYS | B | 70 | 50.071 | −2.075 | 39.199 | 1.00 | 50.32 | B | C |
| ATOM | 1228 | NZ | LYS | B | 70 | 49.862 | −1.093 | 40.295 | 1.00 | 50.28 | B | N |
| ATOM | 1229 | C | LYS | B | 70 | 49.623 | −7.529 | 37.281 | 1.00 | 41.71 | B | C |
| ATOM | 1230 | O | LYS | B | 70 | 48.455 | −7.808 | 37.541 | 1.00 | 41.35 | B | O |
| ATOM | 1231 | N | GLN | B | 71 | 50.139 | −7.645 | 36.066 | 1.00 | 41.60 | B | N |
| ATOM | 1232 | CA | GLN | B | 71 | 49.370 | −8.142 | 34.933 | 1.00 | 40.95 | B | C |
| ATOM | 1233 | CB | GLN | B | 71 | 48.677 | −6.996 | 34.204 | 1.00 | 42.04 | B | C |
| ATOM | 1234 | CG | GLN | B | 71 | 47.439 | −7.421 | 33.445 | 1.00 | 45.02 | B | C |
| ATOM | 1235 | CD | GLN | B | 71 | 46.287 | −7.799 | 34.365 | 1.00 | 47.37 | B | C |
| ATOM | 1236 | OE1 | GLN | B | 71 | 45.234 | −8.260 | 33.908 | 1.00 | 48.26 | B | O |
| ATOM | 1237 | NE2 | GLN | B | 71 | 46.477 | −7.599 | 35.667 | 1.00 | 47.17 | B | N |
| ATOM | 1238 | C | GLN | B | 71 | 50.452 | −8.753 | 34.065 | 1.00 | 40.06 | B | C |
| ATOM | 1239 | O | GLN | B | 71 | 50.741 | −8.283 | 32.971 | 1.00 | 40.40 | B | O |
| ATOM | 1240 | N | GLN | B | 72 | 51.055 | −9.809 | 34.593 | 1.00 | 39.58 | B | N |
| ATOM | 1241 | CA | GLN | B | 72 | 52.156 | −10.493 | 33.944 | 1.00 | 38.53 | B | C |
| ATOM | 1242 | CB | GLN | B | 72 | 52.618 | −11.645 | 34.838 | 1.00 | 39.47 | B | C |
| ATOM | 1243 | CG | GLN | B | 72 | 53.533 | −11.159 | 35.958 | 1.00 | 42.58 | B | C |
| ATOM | 1244 | CD | GLN | B | 72 | 53.760 | −12.189 | 37.045 | 1.00 | 44.14 | B | C |
| ATOM | 1245 | OE1 | GLN | B | 72 | 53.965 | −13.374 | 36.768 | 1.00 | 44.60 | B | O |
| ATOM | 1246 | NE2 | GLN | B | 72 | 53.740 | −11.737 | 38.294 | 1.00 | 44.27 | B | N |
| ATOM | 1247 | C | GLN | B | 72 | 51.988 | −10.958 | 32.508 | 1.00 | 36.28 | B | C |
| ATOM | 1248 | O | GLN | B | 72 | 52.984 | −11.181 | 31.824 | 1.00 | 36.90 | B | O |
| ATOM | 1249 | N | HIS | B | 73 | 50.753 | −11.090 | 32.036 | 1.00 | 33.40 | B | N |
| ATOM | 1250 | CA | HIS | B | 73 | 50.532 | −11.520 | 30.655 | 1.00 | 31.29 | B | C |
| ATOM | 1251 | CB | HIS | B | 73 | 49.138 | −12.134 | 30.519 | 1.00 | 32.90 | B | C |
| ATOM | 1252 | CG | HIS | B | 73 | 48.030 | −11.173 | 30.794 | 1.00 | 36.49 | B | C |
| ATOM | 1253 | CD2 | HIS | B | 73 | 47.521 | −10.711 | 31.962 | 1.00 | 36.77 | B | C |
| ATOM | 1254 | ND1 | HIS | B | 73 | 47.339 | −10.527 | 29.790 | 1.00 | 38.38 | B | N |
| ATOM | 1255 | CE1 | HIS | B | 73 | 46.454 | −9.706 | 30.328 | 1.00 | 39.39 | B | C |
| ATOM | 1256 | NE2 | HIS | B | 73 | 46.545 | −9.799 | 31.644 | 1.00 | 39.50 | B | N |
| ATOM | 1257 | C | HIS | B | 73 | 50.705 | −10.359 | 29.659 | 1.00 | 28.64 | B | C |
| ATOM | 1258 | O | HIS | B | 73 | 50.638 | −10.550 | 28.444 | 1.00 | 25.66 | B | O |
| ATOM | 1259 | N | ILE | B | 74 | 50.945 | −9.163 | 30.196 | 1.00 | 27.08 | B | N |
| ATOM | 1260 | CA | ILE | B | 74 | 51.131 | −7.953 | 29.398 | 1.00 | 25.27 | B | C |
| ATOM | 1261 | CB | ILE | B | 74 | 50.359 | −6.751 | 29.989 | 1.00 | 24.67 | B | C |
| ATOM | 1262 | CG2 | ILE | B | 74 | 50.705 | −5.491 | 29.219 | 1.00 | 23.79 | B | C |
| ATOM | 1263 | CG1 | ILE | B | 74 | 48.854 | −7.010 | 29.951 | 1.00 | 24.80 | B | C |
| ATOM | 1264 | CD1 | ILE | B | 74 | 48.032 | −5.855 | 30.499 | 1.00 | 24.32 | B | C |
| ATOM | 1265 | C | ILE | B | 74 | 52.596 | −7.535 | 29.322 | 1.00 | 24.48 | B | C |
| ATOM | 1266 | O | ILE | B | 74 | 53.253 | −7.348 | 30.347 | 1.00 | 25.75 | B | O |
| ATOM | 1267 | N | VAL | B | 75 | 53.104 | −7.387 | 28.106 | 1.00 | 22.76 | B | N |
| ATOM | 1268 | CA | VAL | B | 75 | 54.479 | −6.961 | 27.914 | 1.00 | 21.41 | B | C |
| ATOM | 1269 | CB | VAL | B | 75 | 55.142 | −7.727 | 26.751 | 1.00 | 20.53 | B | C |
| ATOM | 1270 | CG1 | VAL | B | 75 | 56.484 | −7.089 | 26.387 | 1.00 | 16.35 | B | C |
| ATOM | 1271 | CG2 | VAL | B | 75 | 55.339 | −9.184 | 27.154 | 1.00 | 18.41 | B | C |
| ATOM | 1272 | C | VAL | B | 75 | 54.441 | −5.470 | 27.607 | 1.00 | 22.75 | B | C |
| ATOM | 1273 | O | VAL | B | 75 | 54.003 | −5.053 | 26.535 | 1.00 | 23.83 | B | O |
| ATOM | 1274 | N | TYR | B | 76 | 54.871 | −4.662 | 28.568 | 1.00 | 23.61 | B | N |
| ATOM | 1275 | CA | TYR | B | 76 | 54.880 | −3.218 | 28.382 | 1.00 | 23.27 | B | C |
| ATOM | 1276 | CB | TYR | B | 76 | 54.705 | −2.508 | 29.730 | 1.00 | 22.31 | B | C |
| ATOM | 1277 | CG | TYR | B | 76 | 54.327 | −1.065 | 29.569 | 1.00 | 22.16 | B | C |
| ATOM | 1278 | CD1 | TYR | B | 76 | 53.049 | −0.703 | 29.142 | 1.00 | 22.65 | B | C |
| ATOM | 1279 | CE1 | TYR | B | 76 | 52.725 | 0.621 | 28.879 | 1.00 | 23.30 | B | C |
| ATOM | 1280 | CD2 | TYR | B | 76 | 55.274 | −0.064 | 29.739 | 1.00 | 23.08 | B | C |
| ATOM | 1281 | CE2 | TYR | B | 76 | 54.968 | 1.264 | 29.477 | 1.00 | 26.22 | B | C |
| ATOM | 1282 | CZ | TYR | B | 76 | 53.694 | 1.602 | 29.044 | 1.00 | 26.37 | B | C |
| ATOM | 1283 | OH | TYR | B | 76 | 53.422 | 2.917 | 28.750 | 1.00 | 27.15 | B | O |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1284 | C   | TYR | B | 76 | 56.212 | −2.842 | 27.733 | 1.00 | 22.74 B | C |
|------|------|-----|-----|---|----|--------|--------|--------|------|---------|---|
| ATOM | 1285 | O   | TYR | B | 76 | 57.232 | −2.714 | 28.408 | 1.00 | 23.63 B | O |
| ATOM | 1286 | N   | CYS | B | 77 | 56.195 | −2.675 | 26.416 | 1.00 | 21.72 B | N |
| ATOM | 1287 | CA  | CYS | B | 77 | 57.404 | −2.361 | 25.668 | 1.00 | 22.93 B | C |
| ATOM | 1288 | CB  | CYS | B | 77 | 57.533 | −3.317 | 24.482 | 1.00 | 22.60 B | C |
| ATOM | 1289 | SG  | CYS | B | 77 | 56.064 | −3.392 | 23.417 | 1.00 | 22.36 B | S |
| ATOM | 1290 | C   | CYS | B | 77 | 57.434 | −0.937 | 25.155 | 1.00 | 23.94 B | C |
| ATOM | 1291 | O   | CYS | B | 77 | 58.189 | −0.612 | 24.240 | 1.00 | 22.38 B | O |
| ATOM | 1292 | N   | SER | B | 78 | 56.624 | −0.084 | 25.763 | 1.00 | 26.48 B | N |
| ATOM | 1293 | CA  | SER | B | 78 | 56.530 | 1.303  | 25.336 | 1.00 | 28.51 B | C |
| ATOM | 1294 | CB  | SER | B | 78 | 55.592 | 2.067  | 26.267 | 1.00 | 29.24 B | C |
| ATOM | 1295 | OG  | SER | B | 78 | 55.163 | 3.260  | 25.642 | 1.00 | 31.92 B | O |
| ATOM | 1296 | C   | SER | B | 78 | 57.857 | 2.050  | 25.221 | 1.00 | 29.04 B | C |
| ATOM | 1297 | O   | SER | B | 78 | 58.106 | 2.703  | 24.213 | 1.00 | 28.79 B | O |
| ATOM | 1298 | N   | ASN | B | 79 | 58.710 | 1.955  | 26.239 | 1.00 | 29.62 B | N |
| ATOM | 1299 | CA  | ASN | B | 79 | 59.988 | 2.668  | 26.207 | 1.00 | 30.17 B | C |
| ATOM | 1300 | CB  | ASN | B | 79 | 60.224 | 3.383  | 27.538 | 1.00 | 32.72 B | C |
| ATOM | 1301 | CG  | ASN | B | 79 | 58.954 | 3.952  | 28.121 | 1.00 | 35.50 B | C |
| ATOM | 1302 | OD1 | ASN | B | 79 | 58.350 | 3.352  | 29.013 | 1.00 | 38.27 B | O |
| ATOM | 1303 | ND2 | ASN | B | 79 | 58.525 | 5.104  | 27.609 | 1.00 | 34.49 B | N |
| ATOM | 1304 | C   | ASN | B | 79 | 61.176 | 1.768  | 25.911 | 1.00 | 29.56 B | C |
| ATOM | 1305 | O   | ASN | B | 79 | 62.276 | 1.996  | 26.407 | 1.00 | 29.57 B | O |
| ATOM | 1306 | N   | ASP | B | 80 | 60.955 | 0.750  | 25.092 | 1.00 | 28.47 B | N |
| ATOM | 1307 | CA  | ASP | B | 80 | 62.008 | −0.185 | 24.746 | 1.00 | 26.85 B | C |
| ATOM | 1308 | CB  | ASP | B | 80 | 61.680 | −1.556 | 25.348 | 1.00 | 26.05 B | C |
| ATOM | 1309 | CG  | ASP | B | 80 | 62.854 | −2.511 | 25.311 | 1.00 | 25.69 B | C |
| ATOM | 1310 | OD1 | ASP | B | 80 | 63.632 | −2.521 | 26.284 | 1.00 | 25.43 B | O |
| ATOM | 1311 | OD2 | ASP | B | 80 | 63.004 | −3.243 | 24.307 | 1.00 | 26.27 B | O |
| ATOM | 1312 | C   | ASP | B | 80 | 62.058 | −0.281 | 23.229 | 1.00 | 26.74 B | C |
| ATOM | 1313 | O   | ASP | B | 80 | 61.064 | 0.002  | 22.560 | 1.00 | 26.42 B | O |
| ATOM | 1314 | N   | LEU | B | 81 | 63.205 | −0.673 | 22.680 | 1.00 | 27.17 B | N |
| ATOM | 1315 | CA  | LEU | B | 81 | 63.319 | −0.811 | 21.229 | 1.00 | 26.44 B | C |
| ATOM | 1316 | CB  | LEU | B | 81 | 64.707 | −1.331 | 20.832 | 1.00 | 26.94 B | C |
| ATOM | 1317 | CG  | LEU | B | 81 | 64.835 | −1.918 | 19.411 | 1.00 | 29.76 B | C |
| ATOM | 1318 | CD1 | LEU | B | 81 | 64.428 | −0.886 | 18.373 | 1.00 | 29.96 B | C |
| ATOM | 1319 | CD2 | LEU | B | 81 | 66.264 | −2.391 | 19.158 | 1.00 | 29.94 B | C |
| ATOM | 1320 | C   | LEU | B | 81 | 62.248 | −1.786 | 20.748 | 1.00 | 25.72 B | C |
| ATOM | 1321 | O   | LEU | B | 81 | 61.798 | −1.716 | 19.597 | 1.00 | 25.96 B | O |
| ATOM | 1322 | N   | LEU | B | 82 | 61.838 | −2.695 | 21.632 | 1.00 | 23.41 B | N |
| ATOM | 1323 | CA  | LEU | B | 82 | 60.818 | −3.670 | 21.268 | 1.00 | 21.59 B | C |
| ATOM | 1324 | CB  | LEU | B | 82 | 60.581 | −4.659 | 22.403 | 1.00 | 19.12 B | C |
| ATOM | 1325 | CG  | LEU | B | 82 | 59.634 | −5.806 | 22.035 | 1.00 | 17.58 B | C |
| ATOM | 1326 | CD1 | LEU | B | 82 | 60.102 | −6.468 | 20.739 | 1.00 | 14.71 B | C |
| ATOM | 1327 | CD2 | LEU | B | 82 | 59.584 | −6.799 | 23.174 | 1.00 | 12.80 B | C |
| ATOM | 1328 | C   | LEU | B | 82 | 59.521 | −2.958 | 20.929 | 1.00 | 20.92 B | C |
| ATOM | 1329 | O   | LEU | B | 82 | 58.707 | −3.463 | 20.156 | 1.00 | 21.23 B | O |
| ATOM | 1330 | N   | GLY | B | 83 | 59.343 | −1.773 | 21.506 | 1.00 | 19.85 B | N |
| ATOM | 1331 | CA  | GLY | B | 83 | 58.149 | −0.998 | 21.243 | 1.00 | 20.09 B | C |
| ATOM | 1332 | C   | GLY | B | 83 | 58.145 | −0.476 | 19.823 | 1.00 | 19.56 B | C |
| ATOM | 1333 | O   | GLY | B | 83 | 57.116 | −0.492 | 19.148 | 1.00 | 17.01 B | O |
| ATOM | 1334 | N   | ASP | B | 84 | 59.307 | −0.024 | 19.366 | 1.00 | 21.15 B | N |
| ATOM | 1335 | CA  | ASP | B | 84 | 59.440 | 0.508  | 18.016 | 1.00 | 24.31 B | C |
| ATOM | 1336 | CB  | ASP | B | 84 | 60.818 | 1.172  | 17.841 | 1.00 | 25.48 B | C |
| ATOM | 1337 | CG  | ASP | B | 84 | 60.995 | 2.415  | 18.713 | 1.00 | 27.23 B | C |
| ATOM | 1338 | OD1 | ASP | B | 84 | 60.111 | 3.297  | 18.665 | 1.00 | 26.20 B | O |
| ATOM | 1339 | OD2 | ASP | B | 84 | 62.018 | 2.520  | 19.434 | 1.00 | 26.96 B | O |
| ATOM | 1340 | C   | ASP | B | 84 | 59.240 | −0.561 | 16.935 | 1.00 | 25.88 B | C |
| ATOM | 1341 | O   | ASP | B | 84 | 58.595 | −0.310 | 15.909 | 1.00 | 25.90 B | O |
| ATOM | 1342 | N   | LEU | B | 85 | 59.790 | −1.753 | 17.164 | 1.00 | 27.13 B | N |
| ATOM | 1343 | CA  | LEU | B | 85 | 59.677 | −2.837 | 16.189 | 1.00 | 27.46 B | C |
| ATOM | 1344 | CB  | LEU | B | 85 | 60.688 | −3.948 | 16.504 | 1.00 | 30.69 B | C |
| ATOM | 1345 | CG  | LEU | B | 85 | 62.168 | −3.543 | 16.434 | 1.00 | 34.05 B | C |
| ATOM | 1346 | CD1 | LEU | B | 85 | 63.041 | −4.711 | 16.850 | 1.00 | 34.94 B | C |
| ATOM | 1347 | CD2 | LEU | B | 85 | 62.523 | −3.097 | 15.020 | 1.00 | 34.47 B | C |
| ATOM | 1348 | C   | LEU | B | 85 | 58.275 | −3.426 | 16.105 | 1.00 | 26.06 B | C |
| ATOM | 1349 | O   | LEU | B | 85 | 57.812 | −3.771 | 15.018 | 1.00 | 25.20 B | O |
| ATOM | 1350 | N   | PHE | B | 86 | 57.600 | −3.545 | 17.248 | 1.00 | 24.87 B | N |
| ATOM | 1351 | CA  | PHE | B | 86 | 56.246 | −4.099 | 17.272 | 1.00 | 23.58 B | C |
| ATOM | 1352 | CB  | PHE | B | 86 | 55.992 | −4.819 | 18.602 | 1.00 | 21.60 B | C |
| ATOM | 1353 | CG  | PHE | B | 86 | 56.485 | −6.245 | 18.634 | 1.00 | 20.28 B | C |
| ATOM | 1354 | CD1 | PHE | B | 86 | 57.418 | −6.704 | 17.705 | 1.00 | 18.78 B | C |
| ATOM | 1355 | CD2 | PHE | B | 86 | 56.018 | −7.129 | 19.612 | 1.00 | 19.50 B | C |
| ATOM | 1356 | CE1 | PHE | B | 86 | 57.877 | −8.015 | 17.749 | 1.00 | 19.74 B | C |
| ATOM | 1357 | CE2 | PHE | B | 86 | 56.470 | −8.449 | 19.671 | 1.00 | 17.87 B | C |
| ATOM | 1358 | CZ  | PHE | B | 86 | 57.400 | −8.896 | 18.739 | 1.00 | 20.02 B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1359 | C   | PHE | B | 86 | 55.170 | −3.036  | 17.029 | 1.00 | 23.30 | B | C |
|------|------|-----|-----|---|----|--------|---------|--------|------|-------|---|---|
| ATOM | 1360 | O   | PHE | B | 86 | 54.005 | −3.358  | 16.789 | 1.00 | 23.27 | B | O |
| ATOM | 1361 | N   | GLY | B | 87 | 55.566 | −1.770  | 17.097 | 1.00 | 22.81 | B | N |
| ATOM | 1362 | CA  | GLY | B | 87 | 54.632 | −0.684  | 16.854 | 1.00 | 23.05 | B | C |
| ATOM | 1363 | C   | GLY | B | 87 | 53.544 | −0.487  | 17.889 | 1.00 | 22.49 | B | C |
| ATOM | 1364 | O   | GLY | B | 87 | 52.536 | 0.171   | 17.626 | 1.00 | 23.12 | B | O |
| ATOM | 1365 | N   | VAL | B | 88 | 53.737 | −1.054  | 19.069 | 1.00 | 21.70 | B | N |
| ATOM | 1366 | CA  | VAL | B | 88 | 52.752 | −0.905  | 20.125 | 1.00 | 20.61 | B | C |
| ATOM | 1367 | CB  | VAL | B | 88 | 51.906 | −2.186  | 20.282 | 1.00 | 21.23 | B | C |
| ATOM | 1368 | CG1 | VAL | B | 88 | 51.039 | −2.373  | 19.045 | 1.00 | 19.66 | B | C |
| ATOM | 1369 | CG2 | VAL | B | 88 | 52.806 | −3.398  | 20.503 | 1.00 | 18.17 | B | C |
| ATOM | 1370 | C   | VAL | B | 88 | 53.375 | −0.552  | 21.465 | 1.00 | 19.81 | B | C |
| ATOM | 1371 | O   | VAL | B | 88 | 54.529 | −0.873  | 21.745 | 1.00 | 21.01 | B | O |
| ATOM | 1372 | N   | PRO | B | 89 | 52.624 | 0.149   | 22.309 | 1.00 | 18.83 | B | N |
| ATOM | 1373 | CD  | PRO | B | 89 | 51.277 | 0.723   | 22.155 | 1.00 | 18.07 | B | C |
| ATOM | 1374 | CA  | PRO | B | 89 | 53.197 | 0.494   | 23.604 | 1.00 | 18.34 | B | C |
| ATOM | 1375 | CB  | PRO | B | 89 | 52.271 | 1.605   | 24.083 | 1.00 | 17.37 | B | C |
| ATOM | 1376 | CG  | PRO | B | 89 | 50.948 | 1.154   | 23.568 | 1.00 | 16.24 | B | C |
| ATOM | 1377 | C   | PRO | B | 89 | 53.168 | −0.759  | 24.504 | 1.00 | 18.24 | B | C |
| ATOM | 1378 | O   | PRO | B | 89 | 53.833 | −0.823  | 25.544 | 1.00 | 18.86 | B | O |
| ATOM | 1379 | N   | SER | B | 90 | 52.399 | −1.760  | 24.087 | 1.00 | 16.38 | B | N |
| ATOM | 1380 | CA  | SER | B | 90 | 52.290 | −2.989  | 24.855 | 1.00 | 16.34 | B | C |
| ATOM | 1381 | CB  | SER | B | 90 | 51.553 | −2.723  | 26.170 | 1.00 | 15.92 | B | C |
| ATOM | 1382 | OG  | SER | B | 90 | 50.163 | −2.503  | 25.954 | 1.00 | 13.70 | B | O |
| ATOM | 1383 | C   | SER | B | 90 | 51.529 | −4.038  | 24.058 | 1.00 | 17.83 | B | C |
| ATOM | 1384 | O   | SER | B | 90 | 50.968 | −3.737  | 22.998 | 1.00 | 19.24 | B | O |
| ATOM | 1385 | N   | PHE | B | 91 | 51.516 | −5.268  | 24.568 | 1.00 | 17.29 | B | N |
| ATOM | 1386 | CA  | PHE | B | 91 | 50.799 | −6.365  | 23.922 | 1.00 | 18.18 | B | C |
| ATOM | 1387 | CB  | PHE | B | 91 | 51.543 | −6.839  | 22.653 | 1.00 | 19.29 | B | C |
| ATOM | 1388 | CG  | PHE | B | 91 | 52.875 | −7.496  | 22.918 | 1.00 | 18.47 | B | C |
| ATOM | 1389 | CD1 | PHE | B | 91 | 52.946 | −8.818  | 23.347 | 1.00 | 19.20 | B | C |
| ATOM | 1390 | CD2 | PHE | B | 91 | 54.058 | −6.788  | 22.746 | 1.00 | 18.75 | B | C |
| ATOM | 1391 | CE1 | PHE | B | 91 | 54.180 | −9.425  | 23.603 | 1.00 | 18.97 | B | C |
| ATOM | 1392 | CE2 | PHE | B | 91 | 55.298 | −7.384  | 23.000 | 1.00 | 18.74 | B | C |
| ATOM | 1393 | CZ  | PHE | B | 91 | 55.358 | −8.702  | 23.429 | 1.00 | 18.69 | B | C |
| ATOM | 1394 | C   | PHE | B | 91 | 50.638 | −7.504  | 24.911 | 1.00 | 17.40 | B | C |
| ATOM | 1395 | O   | PHE | B | 91 | 51.350 | −7.565  | 25.899 | 1.00 | 17.57 | B | O |
| ATOM | 1396 | N   | SER | B | 92 | 49.693 | −8.397  | 24.652 | 1.00 | 19.56 | B | N |
| ATOM | 1397 | CA  | SER | B | 92 | 49.454 | −9.539  | 25.536 | 1.00 | 21.79 | B | C |
| ATOM | 1398 | CB  | SER | B | 92 | 47.942 | −9.736  | 25.737 | 1.00 | 21.20 | B | C |
| ATOM | 1399 | OG  | SER | B | 92 | 47.662 | −10.770 | 26.676 | 1.00 | 21.59 | B | O |
| ATOM | 1400 | C   | SER | B | 92 | 50.075 | −10.820 | 24.952 | 1.00 | 22.70 | B | C |
| ATOM | 1401 | O   | SER | B | 92 | 49.967 | −11.074 | 23.748 | 1.00 | 22.64 | B | O |
| ATOM | 1402 | N   | VAL | B | 93 | 50.722 | −11.626 | 25.795 | 1.00 | 23.39 | B | N |
| ATOM | 1403 | CA  | VAL | B | 93 | 51.332 | −12.866 | 25.318 | 1.00 | 23.01 | B | C |
| ATOM | 1404 | CB  | VAL | B | 93 | 52.384 | −13.398 | 26.293 | 1.00 | 21.98 | B | C |
| ATOM | 1405 | CG1 | VAL | B | 93 | 53.500 | −12.374 | 26.422 | 1.00 | 20.97 | B | C |
| ATOM | 1406 | CG2 | VAL | B | 93 | 51.743 | −13.724 | 27.649 | 1.00 | 20.03 | B | C |
| ATOM | 1407 | C   | VAL | B | 93 | 50.294 | −13.951 | 25.071 | 1.00 | 23.92 | B | C |
| ATOM | 1408 | O   | VAL | B | 93 | 50.627 | −15.108 | 24.845 | 1.00 | 24.02 | B | O |
| ATOM | 1409 | N   | LYS | B | 94 | 49.029 | −13.562 | 25.116 | 1.00 | 25.51 | B | N |
| ATOM | 1410 | CA  | LYS | B | 94 | 47.938 | −14.486 | 24.857 | 1.00 | 26.63 | B | C |
| ATOM | 1411 | CB  | LYS | B | 94 | 46.795 | −14.228 | 25.835 | 1.00 | 27.11 | B | C |
| ATOM | 1412 | CG  | LYS | B | 94 | 47.160 | −14.514 | 27.278 | 1.00 | 28.58 | B | C |
| ATOM | 1413 | CD  | LYS | B | 94 | 45.969 | −14.285 | 28.187 | 1.00 | 30.27 | B | C |
| ATOM | 1414 | CE  | LYS | B | 94 | 46.280 | −14.710 | 29.607 | 1.00 | 33.38 | B | C |
| ATOM | 1415 | NZ  | LYS | B | 94 | 45.116 | −14.468 | 30.507 | 1.00 | 34.90 | B | N |
| ATOM | 1416 | C   | LYS | B | 94 | 47.469 | −14.286 | 23.410 | 1.00 | 26.79 | B | C |
| ATOM | 1417 | O   | LYS | B | 94 | 46.834 | −15.162 | 22.824 | 1.00 | 26.60 | B | O |
| ATOM | 1418 | N   | GLU | B | 95 | 47.800 | −13.125 | 22.848 | 1.00 | 27.48 | B | N |
| ATOM | 1419 | CA  | GLU | B | 95 | 47.457 | −12.777 | 21.469 | 1.00 | 28.49 | B | C |
| ATOM | 1420 | CB  | GLU | B | 95 | 47.538 | −11.265 | 21.265 | 1.00 | 30.15 | B | C |
| ATOM | 1421 | CG  | GLU | B | 95 | 46.813 | −10.455 | 22.298 | 1.00 | 34.01 | B | C |
| ATOM | 1422 | CD  | GLU | B | 95 | 45.337 | −10.472 | 22.077 | 1.00 | 35.09 | B | C |
| ATOM | 1423 | OE1 | GLU | B | 95 | 44.876 | −9.780  | 21.143 | 1.00 | 36.48 | B | O |
| ATOM | 1424 | OE2 | GLU | B | 95 | 44.644 | −11.187 | 22.829 | 1.00 | 37.63 | B | O |
| ATOM | 1425 | C   | GLU | B | 95 | 48.520 | −13.419 | 20.595 | 1.00 | 27.44 | B | C |
| ATOM | 1426 | O   | GLU | B | 95 | 49.365 | −12.723 | 20.043 | 1.00 | 28.88 | B | O |
| ATOM | 1427 | N   | HIS | B | 96 | 48.486 | −14.736 | 20.457 | 1.00 | 26.64 | B | N |
| ATOM | 1428 | CA  | HIS | B | 96 | 49.510 | −15.404 | 19.668 | 1.00 | 25.78 | B | C |
| ATOM | 1429 | CB  | HIS | B | 96 | 49.359 | −16.925 | 19.785 | 1.00 | 26.67 | B | C |
| ATOM | 1430 | CG  | HIS | B | 96 | 49.608 | −17.439 | 21.173 | 1.00 | 28.50 | B | C |
| ATOM | 1431 | CD2 | HIS | B | 96 | 49.587 | −16.809 | 22.371 | 1.00 | 29.42 | B | C |
| ATOM | 1432 | ND1 | HIS | B | 96 | 49.939 | −18.750 | 21.442 | 1.00 | 29.54 | B | N |
| ATOM | 1433 | CE1 | HIS | B | 96 | 50.115 | −18.904 | 22.741 | 1.00 | 27.62 | B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| | | | | | | | | | | |
|---|---|---|---|---|---|---|---|---|---|---|
| ATOM | 1434 | NE2 | HIS | B | 96 | 49.907 | −17.741 | 23.329 | 1.00 | 29.39 B | N |
| ATOM | 1435 | C | HIS | B | 96 | 49.597 | −14.968 | 18.215 | 1.00 | 24.28 B | C |
| ATOM | 1436 | O | HIS | B | 96 | 50.686 | −14.616 | 17.746 | 1.00 | 23.29 B | O |
| ATOM | 1437 | N | ARG | B | 97 | 48.466 | −14.956 | 17.510 | 1.00 | 22.65 B | N |
| ATOM | 1438 | CA | ARG | B | 97 | 48.468 | −14.558 | 16.106 | 1.00 | 21.17 B | C |
| ATOM | 1439 | CB | ARG | B | 97 | 47.078 | −14.744 | 15.489 | 1.00 | 20.89 B | C |
| ATOM | 1440 | CG | ARG | B | 97 | 46.978 | −14.295 | 14.033 | 1.00 | 20.94 B | C |
| ATOM | 1441 | CD | ARG | B | 97 | 48.087 | −14.896 | 13.193 | 1.00 | 20.01 B | C |
| ATOM | 1442 | NE | ARG | B | 97 | 47.927 | −16.334 | 13.019 | 1.00 | 21.31 B | N |
| ATOM | 1443 | CZ | ARG | B | 97 | 48.882 | −17.142 | 12.561 | 1.00 | 21.37 B | C |
| ATOM | 1444 | NH1 | ARG | B | 97 | 50.071 | −16.654 | 12.235 | 1.00 | 18.20 B | N |
| ATOM | 1445 | NH2 | ARG | B | 97 | 48.645 | −18.440 | 12.420 | 1.00 | 20.87 B | N |
| ATOM | 1446 | C | ARG | B | 97 | 48.950 | −13.125 | 15.904 | 1.00 | 20.86 B | C |
| ATOM | 1447 | O | ARG | B | 97 | 49.616 | −12.830 | 14.916 | 1.00 | 19.69 B | O |
| ATOM | 1448 | N | LYS | B | 98 | 48.628 | −12.232 | 16.837 | 1.00 | 21.99 B | N |
| ATOM | 1449 | CA | LYS | B | 98 | 49.078 | −10.841 | 16.718 | 1.00 | 23.04 B | C |
| ATOM | 1450 | CB | LYS | B | 98 | 48.389 | −9.940 | 17.756 | 1.00 | 26.28 B | C |
| ATOM | 1451 | CG | LYS | B | 98 | 46.886 | −9.739 | 17.532 | 1.00 | 31.67 B | C |
| ATOM | 1452 | CD | LYS | B | 98 | 46.057 | −10.965 | 17.958 | 1.00 | 35.98 B | C |
| ATOM | 1453 | CE | LYS | B | 98 | 44.555 | −10.651 | 17.958 | 1.00 | 36.14 B | C |
| ATOM | 1454 | NZ | LYS | B | 98 | 43.773 | −11.582 | 18.832 | 1.00 | 37.04 B | N |
| ATOM | 1455 | C | LYS | B | 98 | 50.601 | −10.737 | 16.876 | 1.00 | 20.53 B | C |
| ATOM | 1456 | O | LYS | B | 98 | 51.261 | −9.956 | 16.185 | 1.00 | 20.06 B | O |
| ATOM | 1457 | N | ILE | B | 99 | 51.157 | −11.526 | 17.789 | 1.00 | 18.42 B | N |
| ATOM | 1458 | CA | ILE | B | 99 | 52.597 | −11.520 | 18.001 | 1.00 | 15.84 B | C |
| ATOM | 1459 | CB | ILE | B | 99 | 52.958 | −12.351 | 19.241 | 1.00 | 13.76 B | C |
| ATOM | 1460 | CG2 | ILE | B | 99 | 54.458 | −12.421 | 19.410 | 1.00 | 11.35 B | C |
| ATOM | 1461 | CG1 | ILE | B | 99 | 52.328 | −11.694 | 20.472 | 1.00 | 11.87 B | C |
| ATOM | 1462 | CD1 | ILE | B | 99 | 52.544 | −12.440 | 21.748 | 1.00 | 12.22 B | C |
| ATOM | 1463 | C | ILE | B | 99 | 53.308 | −12.044 | 16.748 | 1.00 | 16.09 B | C |
| ATOM | 1464 | O | ILE | B | 99 | 54.308 | −11.475 | 16.312 | 1.00 | 15.12 B | O |
| ATOM | 1465 | N | TYR | B | 100 | 52.784 | −13.112 | 16.150 | 1.00 | 16.07 B | N |
| ATOM | 1466 | CA | TYR | B | 100 | 53.388 | −13.640 | 14.935 | 1.00 | 16.12 B | C |
| ATOM | 1467 | CB | TYR | B | 100 | 52.638 | −14.885 | 14.451 | 1.00 | 16.92 B | C |
| ATOM | 1468 | CG | TYR | B | 100 | 53.290 | −16.161 | 14.930 | 1.00 | 18.29 B | C |
| ATOM | 1469 | CD1 | TYR | B | 100 | 53.464 | −16.401 | 16.296 | 1.00 | 20.11 B | C |
| ATOM | 1470 | CE1 | TYR | B | 100 | 54.145 | −17.529 | 16.753 | 1.00 | 20.56 B | C |
| ATOM | 1471 | CD2 | TYR | B | 100 | 53.806 | −17.088 | 14.026 | 1.00 | 17.96 B | C |
| ATOM | 1472 | CE2 | TYR | B | 100 | 54.492 | −18.222 | 14.469 | 1.00 | 20.61 B | C |
| ATOM | 1473 | CZ | TYR | B | 100 | 54.660 | −18.434 | 15.839 | 1.00 | 21.77 B | C |
| ATOM | 1474 | OH | TYR | B | 100 | 55.352 | −19.532 | 16.302 | 1.00 | 21.77 B | O |
| ATOM | 1475 | C | TYR | B | 100 | 53.398 | −12.566 | 13.853 | 1.00 | 15.97 B | C |
| ATOM | 1476 | O | TYR | B | 100 | 54.403 | −12.368 | 13.157 | 1.00 | 15.84 B | O |
| ATOM | 1477 | N | THR | B | 101 | 52.281 | −11.857 | 13.728 | 1.00 | 15.24 B | N |
| ATOM | 1478 | CA | THR | B | 101 | 52.178 | −10.798 | 12.737 | 1.00 | 12.81 B | C |
| ATOM | 1479 | CB | THR | B | 101 | 50.794 | −10.162 | 12.755 | 1.00 | 10.68 B | C |
| ATOM | 1480 | OG1 | THR | B | 101 | 49.832 | −11.108 | 12.267 | 1.00 | 6.90 B | O |
| ATOM | 1481 | CG2 | THR | B | 101 | 50.777 | −8.914 | 11.897 | 1.00 | 8.15 B | C |
| ATOM | 1482 | C | THR | B | 101 | 53.224 | −9.727 | 12.994 | 1.00 | 14.35 B | C |
| ATOM | 1483 | O | THR | B | 101 | 53.925 | −9.305 | 12.076 | 1.00 | 14.48 B | O |
| ATOM | 1484 | N | MET | B | 102 | 53.346 | −9.289 | 14.241 | 1.00 | 15.04 B | N |
| ATOM | 1485 | CA | MET | B | 102 | 54.335 | −8.263 | 14.548 | 1.00 | 16.55 B | C |
| ATOM | 1486 | CB | MET | B | 102 | 54.252 | −7.858 | 16.020 | 1.00 | 17.06 B | C |
| ATOM | 1487 | CG | MET | B | 102 | 52.938 | −7.190 | 16.387 | 1.00 | 18.59 B | C |
| ATOM | 1488 | SD | MET | B | 102 | 52.887 | −6.559 | 18.084 | 1.00 | 20.90 B | S |
| ATOM | 1489 | CE | MET | B | 102 | 52.530 | −8.045 | 18.993 | 1.00 | 19.21 B | C |
| ATOM | 1490 | C | MET | B | 102 | 55.752 | −8.731 | 14.209 | 1.00 | 16.63 B | C |
| ATOM | 1491 | O | MET | B | 102 | 56.572 | −7.954 | 13.721 | 1.00 | 16.93 B | O |
| ATOM | 1492 | N | ILE | B | 103 | 56.037 | −10.005 | 14.452 | 1.00 | 16.66 B | N |
| ATOM | 1493 | CA | ILE | B | 103 | 57.361 | −10.538 | 14.166 | 1.00 | 15.88 B | C |
| ATOM | 1494 | CB | ILE | B | 103 | 57.552 | −11.920 | 14.824 | 1.00 | 14.19 B | C |
| ATOM | 1495 | CG2 | ILE | B | 103 | 58.936 | −12.470 | 14.497 | 1.00 | 13.58 B | C |
| ATOM | 1496 | CG1 | ILE | B | 103 | 57.382 | −11.789 | 16.338 | 1.00 | 12.02 B | C |
| ATOM | 1497 | CD1 | ILE | B | 103 | 57.347 | −13.103 | 17.063 | 1.00 | 10.93 B | C |
| ATOM | 1498 | C | ILE | B | 103 | 57.606 | −10.642 | 12.659 | 1.00 | 16.51 B | C |
| ATOM | 1499 | O | ILE | B | 103 | 58.693 | −10.308 | 12.176 | 1.00 | 14.91 B | O |
| ATOM | 1500 | N | TYR | B | 104 | 56.586 | −11.092 | 11.930 | 1.00 | 17.76 B | N |
| ATOM | 1501 | CA | TYR | B | 104 | 56.656 | −11.248 | 10.475 | 1.00 | 19.65 B | C |
| ATOM | 1502 | CB | TYR | B | 104 | 55.316 | −11.759 | 9.937 | 1.00 | 20.38 B | C |
| ATOM | 1503 | CG | TYR | B | 104 | 55.101 | −13.245 | 10.084 | 1.00 | 20.01 B | C |
| ATOM | 1504 | CD1 | TYR | B | 104 | 53.824 | −13.765 | 10.316 | 1.00 | 20.42 B | C |
| ATOM | 1505 | CE1 | TYR | B | 104 | 53.611 | −15.146 | 10.433 | 1.00 | 20.60 B | C |
| ATOM | 1506 | CD2 | TYR | B | 104 | 56.168 | −14.139 | 9.969 | 1.00 | 19.63 B | C |
| ATOM | 1507 | CE2 | TYR | B | 104 | 55.968 | −15.524 | 10.082 | 1.00 | 21.70 B | C |
| ATOM | 1508 | CZ | TYR | B | 104 | 54.689 | −16.016 | 10.313 | 1.00 | 21.03 B | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1509 | OH | TYR | B | 104 | 54.491 | −17.369 | 10.414 | 1.00 | 22.28 | B | O |
|---|---|---|---|---|---|---|---|---|---|---|---|---|
| ATOM | 1510 | C | TYR | B | 104 | 57.020 | −9.953 | 9.752 | 1.00 | 21.14 | B | C |
| ATOM | 1511 | O | TYR | B | 104 | 57.773 | −9.972 | 8.774 | 1.00 | 21.46 | B | O |
| ATOM | 1512 | N | ARG | B | 105 | 56.473 | −8.836 | 10.227 | 1.00 | 21.73 | B | N |
| ATOM | 1513 | CA | ARG | B | 105 | 56.750 | −7.530 | 9.639 | 1.00 | 22.79 | B | C |
| ATOM | 1514 | CB | ARG | B | 105 | 55.918 | −6.449 | 10.333 | 1.00 | 23.94 | B | C |
| ATOM | 1515 | CG | ARG | B | 105 | 54.422 | −6.692 | 10.285 | 1.00 | 26.38 | B | C |
| ATOM | 1516 | CD | ARG | B | 105 | 53.657 | −5.644 | 11.080 | 1.00 | 28.24 | B | C |
| ATOM | 1517 | NE | ARG | B | 105 | 53.572 | −4.363 | 10.383 | 1.00 | 31.13 | B | N |
| ATOM | 1518 | CZ | ARG | B | 105 | 52.874 | −3.320 | 10.824 | 1.00 | 32.03 | B | C |
| ATOM | 1519 | NH1 | ARG | B | 105 | 52.202 | −3.404 | 11.966 | 1.00 | 33.02 | B | N |
| ATOM | 1520 | NH2 | ARG | B | 105 | 52.830 | −2.200 | 10.116 | 1.00 | 31.61 | B | N |
| ATOM | 1521 | C | ARG | B | 105 | 58.234 | −7.184 | 9.766 | 1.00 | 23.57 | B | C |
| ATOM | 1522 | O | ARG | B | 105 | 58.760 | −6.377 | 8.999 | 1.00 | 22.90 | B | O |
| ATOM | 1523 | N | ASN | B | 106 | 58.905 | −7.798 | 10.739 | 1.00 | 24.76 | B | N |
| ATOM | 1524 | CA | ASN | B | 106 | 60.327 | −7.555 | 10.964 | 1.00 | 24.10 | B | C |
| ATOM | 1525 | CB | ASN | B | 106 | 60.642 | −7.472 | 12.456 | 1.00 | 24.93 | B | C |
| ATOM | 1526 | CG | ASN | B | 106 | 60.034 | −6.265 | 13.110 | 1.00 | 25.53 | B | C |
| ATOM | 1527 | OD1 | ASN | B | 106 | 58.856 | −6.264 | 13.458 | 1.00 | 26.27 | B | O |
| ATOM | 1528 | ND2 | ASN | B | 106 | 60.834 | −5.217 | 13.277 | 1.00 | 25.70 | B | N |
| ATOM | 1529 | C | ASN | B | 106 | 61.233 | −8.611 | 10.358 | 1.00 | 23.49 | B | C |
| ATOM | 1530 | O | ASN | B | 106 | 62.338 | −8.827 | 10.852 | 1.00 | 22.73 | B | O |
| ATOM | 1531 | N | LEU | B | 107 | 60.789 | −9.282 | 9.304 | 1.00 | 22.79 | B | N |
| ATOM | 1532 | CA | LEU | B | 107 | 61.654 | −10.284 | 8.708 | 1.00 | 24.03 | B | C |
| ATOM | 1533 | CB | LEU | B | 107 | 61.743 | −11.516 | 9.618 | 1.00 | 22.22 | B | C |
| ATOM | 1534 | CG | LEU | B | 107 | 60.453 | −12.292 | 9.894 | 1.00 | 21.52 | B | C |
| ATOM | 1535 | CD1 | LEU | B | 107 | 59.996 | −13.035 | 8.634 | 1.00 | 16.87 | B | C |
| ATOM | 1536 | CD2 | LEU | B | 107 | 60.700 | −13.257 | 11.052 | 1.00 | 17.96 | B | C |
| ATOM | 1537 | C | LEU | B | 107 | 61.273 | −10.717 | 7.313 | 1.00 | 24.68 | B | C |
| ATOM | 1538 | O | LEU | B | 107 | 60.229 | −10.348 | 6.784 | 1.00 | 25.72 | B | O |
| ATOM | 1539 | N | VAL | B | 108 | 62.150 | −11.511 | 6.724 | 1.00 | 25.61 | B | N |
| ATOM | 1540 | CA | VAL | B | 108 | 61.936 | −12.031 | 5.390 | 1.00 | 27.06 | B | C |
| ATOM | 1541 | CB | VAL | B | 108 | 63.058 | −11.586 | 4.444 | 1.00 | 25.47 | B | C |
| ATOM | 1542 | CG1 | VAL | B | 108 | 62.957 | −12.341 | 3.135 | 1.00 | 24.63 | B | C |
| ATOM | 1543 | CG2 | VAL | B | 108 | 62.969 | −10.086 | 4.222 | 1.00 | 22.69 | B | C |
| ATOM | 1544 | C | VAL | B | 108 | 61.933 | −13.545 | 5.497 | 1.00 | 28.76 | B | C |
| ATOM | 1545 | O | VAL | B | 108 | 62.874 | −14.138 | 6.029 | 1.00 | 28.49 | B | O |
| ATOM | 1546 | N | VAL | B | 109 | 60.864 | −14.167 | 5.014 | 1.00 | 30.58 | B | N |
| ATOM | 1547 | CA | VAL | B | 109 | 60.759 | −15.614 | 5.072 | 1.00 | 32.56 | B | C |
| ATOM | 1548 | CB | VAL | B | 109 | 59.313 | −16.078 | 4.832 | 1.00 | 31.31 | B | C |
| ATOM | 1549 | CG1 | VAL | B | 109 | 59.278 | −17.576 | 4.574 | 1.00 | 31.62 | B | C |
| ATOM | 1550 | CG2 | VAL | B | 109 | 58.464 | −15.748 | 6.052 | 1.00 | 30.66 | B | C |
| ATOM | 1551 | C | VAL | B | 109 | 61.677 | −16.244 | 4.044 | 1.00 | 35.10 | B | C |
| ATOM | 1552 | O | VAL | B | 109 | 61.527 | −16.022 | 2.849 | 1.00 | 35.31 | B | O |
| ATOM | 1553 | N | VAL | B | 110 | 62.644 | −17.016 | 4.526 | 1.00 | 39.13 | B | N |
| ATOM | 1554 | CA | VAL | B | 110 | 63.585 | −17.692 | 3.650 | 1.00 | 42.88 | B | C |
| ATOM | 1555 | CB | VAL | B | 110 | 64.704 | −18.382 | 4.456 | 1.00 | 41.38 | B | C |
| ATOM | 1556 | CG1 | VAL | B | 110 | 65.680 | −19.047 | 3.511 | 1.00 | 40.84 | B | C |
| ATOM | 1557 | CG2 | VAL | B | 110 | 65.423 | −17.365 | 5.326 | 1.00 | 40.23 | B | C |
| ATOM | 1558 | C | VAL | B | 110 | 62.807 | −18.743 | 2.871 | 1.00 | 47.10 | B | C |
| ATOM | 1559 | O | VAL | B | 110 | 62.454 | −19.793 | 3.411 | 1.00 | 47.39 | B | O |
| ATOM | 1560 | N | ASN | B | 111 | 62.520 | −18.443 | 1.608 | 1.00 | 51.94 | B | N |
| ATOM | 1561 | CA | ASN | B | 111 | 61.778 | −19.364 | 0.753 | 1.00 | 56.97 | B | C |
| ATOM | 1562 | CB | ASN | B | 111 | 61.176 | −18.631 | −0.459 | 1.00 | 60.23 | B | C |
| ATOM | 1563 | CG | ASN | B | 111 | 59.906 | −17.853 | −0.112 | 1.00 | 63.33 | B | C |
| ATOM | 1564 | OD1 | ASN | B | 111 | 58.976 | −18.393 | 0.498 | 1.00 | 64.57 | B | O |
| ATOM | 1565 | ND2 | ASN | B | 111 | 59.860 | −16.584 | −0.513 | 1.00 | 63.31 | B | N |
| ATOM | 1566 | C | ASN | B | 111 | 62.689 | −20.483 | 0.271 | 1.00 | 58.44 | B | C |
| ATOM | 1567 | O | ASN | B | 111 | 63.054 | −20.463 | −0.929 | 1.00 | 58.94 | B | O |
| ATOM | 1568 | OXT | ASN | B | 111 | 63.031 | −21.352 | 1.109 | 1.00 | 59.32 | B | O |
| ATOM | 1569 | C01 | DCB | A | 1 | 44.995 | 14.553 | 26.771 | 1.00 | 19.45 | INH1 | C |
| ATOM | 1570 | C02 | DCB | A | 1 | 45.473 | 14.089 | 25.525 | 1.00 | 19.40 | INH1 | C |
| ATOM | 1571 | C03 | DCB | A | 1 | 46.459 | 13.078 | 25.479 | 1.00 | 18.81 | INH1 | C |
| ATOM | 1572 | C04 | DCB | A | 1 | 46.993 | 12.532 | 26.669 | 1.00 | 18.15 | INH1 | C |
| ATOM | 1573 | C05 | DCB | A | 1 | 46.522 | 12.992 | 27.934 | 1.00 | 18.26 | INH1 | C |
| ATOM | 1574 | C06 | DCB | A | 1 | 45.507 | 14.004 | 28.010 | 1.00 | 19.06 | INH1 | C |
| ATOM | 1575 | C07 | DCB | A | 1 | 44.960 | 14.431 | 29.387 | 1.00 | 18.98 | INH1 | C |
| ATOM | 1576 | C08 | DCB | A | 1 | 44.482 | 15.900 | 29.479 | 1.00 | 18.21 | INH1 | C |
| ATOM | 1577 | O09 | DCB | A | 1 | 45.128 | 16.883 | 29.170 | 1.00 | 18.92 | INH1 | O |
| ATOM | 1578 | O10 | DCB | A | 1 | 43.224 | 16.042 | 29.950 | 1.00 | 18.35 | INH1 | O |
| ATOM | 1579 | N11 | DCB | A | 1 | 43.871 | 13.399 | 29.794 | 1.00 | 19.31 | INH1 | N |
| ATOM | 1580 | C12 | DCB | A | 1 | 42.739 | 13.151 | 28.806 | 1.00 | 20.29 | INH1 | C |
| ATOM | 1581 | C13 | DCB | A | 1 | 42.714 | 11.792 | 28.013 | 1.00 | 21.02 | INH1 | C |
| ATOM | 1582 | C14 | DCB | A | 1 | 41.502 | 11.204 | 27.521 | 1.00 | 22.07 | INH1 | C |
| ATOM | 1583 | C15 | DCB | A | 1 | 41.529 | 9.989 | 26.772 | 1.00 | 21.64 | INH1 | C |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1584 | C16 | DCB | A | 1 | 42.766 | 9.364 | 26.518 | 1.00 | 19.81 | INH1 | C |
|------|------|-----|-----|---|---|--------|-------|--------|------|-------|------|---|
| ATOM | 1585 | CL7 | DCB | A | 1 | 42.851 | 7.955 | 25.617 | 1.00 | 21.03 | INH1 | CL |
| ATOM | 1586 | C18 | DCB | A | 1 | 43.944 | 9.900 | 26.994 | 1.00 | 21.69 | INH1 | C |
| ATOM | 1587 | C19 | DCB | A | 1 | 43.911 | 11.091 | 27.724 | 1.00 | 21.17 | INH1 | C |
| ATOM | 1588 | C20 | DCB | A | 1 | 41.375 | 13.473 | 29.512 | 1.00 | 20.86 | INH1 | C |
| ATOM | 1589 | O21 | DCB | A | 1 | 40.624 | 14.335 | 29.051 | 1.00 | 23.97 | INH1 | O |
| ATOM | 1590 | N22 | DCB | A | 1 | 40.986 | 12.802 | 30.650 | 1.00 | 19.65 | INH1 | N |
| ATOM | 1591 | C23 | DCB | A | 1 | 41.675 | 11.792 | 31.325 | 1.00 | 20.23 | INH1 | C |
| ATOM | 1592 | C24 | DCB | A | 1 | 43.086 | 11.753 | 31.524 | 1.00 | 19.69 | INH1 | C |
| ATOM | 1593 | C25 | DCB | A | 1 | 44.037 | 12.771 | 31.037 | 1.00 | 19.00 | INH1 | C |
| ATOM | 1594 | O26 | DCB | A | 1 | 44.998 | 13.033 | 31.782 | 1.00 | 17.63 | INH1 | O |
| ATOM | 1595 | C27 | DCB | A | 1 | 43.671 | 10.672 | 32.209 | 1.00 | 20.56 | INH1 | C |
| ATOM | 1596 | C28 | DCB | A | 1 | 42.884 | 9.636 | 32.703 | 1.00 | 21.72 | INH1 | C |
| ATOM | 1597 | I29 | DCB | A | 1 | 43.831 | 8.120 | 33.679 | 1.00 | 27.66 | INH1 | I |
| ATOM | 1598 | C30 | DCB | A | 1 | 41.486 | 9.633 | 32.527 | 1.00 | 20.49 | INH1 | C |
| ATOM | 1599 | C31 | DCB | A | 1 | 40.878 | 10.720 | 31.834 | 1.00 | 20.28 | INH1 | C |
| ATOM | 1600 | CL4 | DCB | A | 1 | 46.990 | 12.507 | 23.963 | 1.00 | 22.77 | INH1 | CL |
| ATOM | 1601 | C01 | DCB | B | 1 | 55.033 | −18.308 | 22.747 | 1.00 | 19.12 | INH2 | C |
| ATOM | 1602 | C02 | DCB | B | 1 | 54.627 | −17.796 | 21.500 | 1.00 | 20.84 | INH2 | C |
| ATOM | 1603 | C03 | DCB | B | 1 | 53.586 | −16.858 | 21.435 | 1.00 | 19.81 | INH2 | C |
| ATOM | 1604 | C04 | DCB | B | 1 | 52.928 | −16.427 | 22.609 | 1.00 | 19.80 | INH2 | C |
| ATOM | 1605 | C05 | DCB | B | 1 | 53.324 | −16.933 | 23.869 | 1.00 | 17.07 | INH2 | C |
| ATOM | 1606 | C06 | DCB | B | 1 | 54.391 | −17.878 | 23.966 | 1.00 | 19.91 | INH2 | C |
| ATOM | 1607 | C07 | DCB | B | 1 | 54.852 | −18.369 | 25.359 | 1.00 | 20.82 | INH2 | C |
| ATOM | 1608 | C08 | DCB | B | 1 | 55.351 | −19.841 | 25.402 | 1.00 | 22.94 | INH2 | C |
| ATOM | 1609 | O09 | DCB | B | 1 | 54.794 | −20.807 | 24.886 | 1.00 | 25.59 | INH2 | O |
| ATOM | 1610 | O10 | DCB | B | 1 | 56.509 | −20.014 | 26.080 | 1.00 | 23.06 | INH2 | O |
| ATOM | 1611 | N11 | DCB | B | 1 | 55.878 | −17.334 | 25.899 | 1.00 | 19.57 | INH2 | N |
| ATOM | 1612 | C12 | DCB | B | 1 | 57.080 | −17.004 | 25.022 | 1.00 | 20.13 | INH2 | C |
| ATOM | 1613 | C13 | DCB | B | 1 | 57.132 | −15.603 | 24.277 | 1.00 | 18.49 | INH2 | C |
| ATOM | 1614 | C14 | DCB | B | 1 | 58.375 | −14.960 | 23.931 | 1.00 | 18.55 | INH2 | C |
| ATOM | 1615 | C15 | DCB | B | 1 | 58.397 | −13.717 | 23.229 | 1.00 | 17.27 | INH2 | C |
| ATOM | 1616 | C16 | DCB | B | 1 | 57.174 | −13.094 | 22.866 | 1.00 | 17.55 | INH2 | C |
| ATOM | 1617 | CL7 | DCB | B | 1 | 57.162 | −11.622 | 22.002 | 1.00 | 15.37 | INH2 | CL |
| ATOM | 1618 | C18 | DCB | B | 1 | 55.956 | −13.690 | 23.201 | 1.00 | 18.48 | INH2 | C |
| ATOM | 1619 | C19 | DCB | B | 1 | 55.943 | −14.920 | 23.892 | 1.00 | 16.55 | INH2 | C |
| ATOM | 1620 | C20 | DCB | B | 1 | 58.392 | −17.329 | 25.826 | 1.00 | 20.23 | INH2 | C |
| ATOM | 1621 | O21 | DCB | B | 1 | 59.185 | −18.162 | 25.394 | 1.00 | 25.59 | INH2 | O |
| ATOM | 1622 | N22 | DCB | B | 1 | 58.683 | −16.699 | 27.020 | 1.00 | 19.93 | INH2 | N |
| ATOM | 1623 | C23 | DCB | B | 1 | 57.918 | −15.728 | 27.690 | 1.00 | 20.26 | INH2 | C |
| ATOM | 1624 | C24 | DCB | B | 1 | 56.490 | −15.740 | 27.776 | 1.00 | 20.17 | INH2 | C |
| ATOM | 1625 | C25 | DCB | B | 1 | 55.600 | −16.767 | 27.159 | 1.00 | 20.53 | INH2 | C |
| ATOM | 1626 | O26 | DCB | B | 1 | 54.590 | −17.088 | 27.811 | 1.00 | 21.53 | INH2 | O |
| ATOM | 1627 | C27 | DCB | B | 1 | 55.819 | −14.708 | 28.470 | 1.00 | 21.53 | INH2 | C |
| ATOM | 1628 | C28 | DCB | B | 1 | 56.530 | −13.674 | 29.077 | 1.00 | 21.73 | INH2 | C |
| ATOM | 1629 | I29 | DCB | B | 1 | 55.453 | −12.232 | 30.059 | 1.00 | 25.57 | INH2 | I |
| ATOM | 1630 | C30 | DCB | B | 1 | 57.947 | −13.629 | 29.011 | 1.00 | 19.97 | INH2 | C |
| ATOM | 1631 | C31 | DCB | B | 1 | 58.640 | −14.661 | 28.313 | 1.00 | 19.37 | INH2 | C |
| ATOM | 1632 | CL4 | DCB | B | 1 | 53.130 | −16.225 | 19.915 | 1.00 | 26.49 | INH2 | CL |
| ATOM | 1633 | O | HOH | W | 1 | 50.080 | 10.720 | 15.348 | 1.00 | 7.59 | W | O |
| ATOM | 1634 | O | HOH | W | 2 | 38.444 | 13.118 | 31.386 | 1.00 | 5.35 | W | O |
| ATOM | 1635 | O | HOH | W | 3 | 47.443 | −10.725 | 13.437 | 1.00 | 14.91 | W | O |
| ATOM | 1636 | O | HOH | W | 4 | 29.146 | 13.552 | 26.964 | 1.00 | 15.71 | W | O |
| ATOM | 1637 | O | HOH | W | 5 | 70.995 | −16.794 | 24.450 | 1.00 | 16.59 | W | O |
| ATOM | 1638 | O | HOH | W | 6 | 50.735 | 13.798 | 13.410 | 1.00 | 13.16 | W | O |
| ATOM | 1639 | O | HOH | W | 7 | 49.418 | −5.142 | 21.249 | 1.00 | 15.76 | W | O |
| ATOM | 1640 | O | HOH | W | 8 | 46.736 | −6.924 | 18.802 | 1.00 | 29.90 | W | O |
| ATOM | 1641 | O | HOH | W | 9 | 46.333 | 18.271 | 10.887 | 1.00 | 21.24 | W | O |
| ATOM | 1642 | O | HOH | W | 10 | 44.953 | 1.508 | 16.559 | 1.00 | 16.86 | W | O |
| ATOM | 1643 | O | HOH | W | 11 | 50.119 | 1.302 | 17.902 | 1.00 | 10.56 | W | O |
| ATOM | 1644 | O | HOH | W | 12 | 51.688 | −2.161 | 31.579 | 1.00 | 16.65 | W | O |
| ATOM | 1645 | O | HOH | W | 13 | 42.377 | −8.932 | 17.709 | 1.00 | 34.03 | W | O |
| ATOM | 1646 | O | HOH | W | 14 | 37.372 | 14.678 | 29.417 | 1.00 | 16.58 | W | O |
| ATOM | 1647 | O | HOH | W | 15 | 36.788 | 2.596 | 14.963 | 1.00 | 19.58 | W | O |
| ATOM | 1648 | O | HOH | W | 16 | 55.277 | 13.766 | 18.294 | 1.00 | 13.87 | W | O |
| ATOM | 1649 | O | HOH | W | 17 | 54.375 | 11.978 | 22.811 | 1.00 | 27.18 | W | O |
| ATOM | 1650 | O | HOH | W | 18 | 31.627 | 5.760 | 10.477 | 1.00 | 26.87 | W | O |
| ATOM | 1651 | O | HOH | W | 19 | 73.374 | −18.273 | 9.466 | 1.00 | 13.88 | W | O |
| ATOM | 1652 | O | HOH | W | 20 | 69.316 | −11.815 | 9.399 | 1.00 | 15.93 | W | O |
| ATOM | 1653 | O | HOH | W | 21 | 39.407 | 16.870 | 29.919 | 1.00 | 27.45 | W | O |
| ATOM | 1654 | O | HOH | W | 22 | 26.437 | 13.074 | 9.218 | 1.00 | 27.45 | W | O |
| ATOM | 1655 | O | HOH | W | 23 | 48.241 | −7.611 | 22.677 | 1.00 | 27.74 | W | O |
| ATOM | 1656 | O | HOH | W | 24 | 62.618 | −18.064 | 25.960 | 1.00 | 14.87 | W | O |
| ATOM | 1657 | O | HOH | W | 25 | 41.190 | −7.082 | 20.138 | 1.00 | 33.52 | W | O |
| ATOM | 1658 | O | HOH | W | 26 | 68.699 | −15.754 | 29.529 | 1.00 | 30.32 | W | O |

TABLE 1-continued

HDM2 protein (SEQ ID NO: 2) complexed with
compound 338437 ((4-Chloro-phenyl)-[3-(4-chloro-phenyl)-7-
iodo-2,5-dioxo-1,2,3,5-tetrahydro-benzo[e][1,4]diazepin-4-yl]-acetic
acid

| ATOM | 1659 | O | HOH | W | 27 | 31.174 | 12.013 | 32.184 | 1.00 | 23.09 | W | O |
|---|---|---|---|---|---|---|---|---|---|---|---|---|
| ATOM | 1660 | O | HOH | W | 28 | 59.516 | −20.585 | 21.234 | 1.00 | 23.18 | W | O |
| ATOM | 1661 | O | HOH | W | 29 | 63.647 | −5.623 | 12.316 | 1.00 | 24.20 | W | O |
| ATOM | 1662 | O | HOH | W | 30 | 46.038 | −15.942 | 18.815 | 1.00 | 20.52 | W | O |
| ATOM | 1663 | O | HOH | W | 31 | 29.060 | 3.628 | 15.693 | 1.00 | 24.99 | W | O |
| ATOM | 1664 | O | HOH | W | 32 | 64.750 | −2.147 | 9.054 | 1.00 | 18.00 | W | O |
| ATOM | 1665 | O | HOH | W | 33 | 60.948 | −20.101 | 26.368 | 1.00 | 21.11 | W | O |
| ATOM | 1666 | O | HOH | W | 34 | 33.523 | −2.988 | 26.616 | 1.00 | 26.29 | W | O |
| ATOM | 1667 | O | HOH | W | 35 | 52.195 | 4.178 | 26.652 | 1.00 | 19.95 | W | O |
| ATOM | 1668 | O | HOH | W | 36 | 58.440 | −12.039 | 3.658 | 1.00 | 18.21 | W | O |
| ATOM | 1669 | O | HOH | W | 37 | 55.725 | −4.051 | 36.348 | 1.00 | 24.18 | W | O |
| ATOM | 1670 | O | HOH | W | 38 | 50.596 | −17.942 | 26.802 | 1.00 | 25.64 | W | O |
| ATOM | 1671 | O | HOH | W | 39 | 71.444 | −18.646 | 17.806 | 1.00 | 21.69 | W | O |
| ATOM | 1672 | O | HOH | W | 40 | 27.895 | 16.214 | 12.305 | 1.00 | 17.52 | W | O |
| ATOM | 1673 | O | HOH | W | 41 | 63.206 | −0.871 | 28.592 | 1.00 | 33.36 | W | O |
| ATOM | 1674 | O | HOH | W | 42 | 44.097 | −6.181 | 23.040 | 1.00 | 26.08 | W | O |
| ATOM | 1675 | O | HOH | W | 43 | 60.959 | −16.823 | 28.199 | 1.00 | 22.71 | W | O |
| ATOM | 1676 | O | HOH | W | 44 | 41.993 | 0.362 | 10.843 | 1.00 | 25.21 | W | O |
| ATOM | 1677 | O | HOH | W | 45 | 53.471 | 14.144 | 25.683 | 1.00 | 15.46 | W | O |
| ATOM | 1678 | O | HOH | W | 46 | 77.169 | −14.015 | 22.972 | 1.00 | 30.41 | W | O |
| ATOM | 1679 | O | HOH | W | 47 | 51.042 | 0.090 | 12.306 | 1.00 | 25.87 | W | O |
| ATOM | 1680 | O | HOH | W | 48 | 53.856 | 2.794 | 19.440 | 1.00 | 15.61 | W | O |
| ATOM | 1681 | O | HOH | W | 49 | 51.232 | 3.940 | 19.368 | 1.00 | 15.09 | W | O |
| ATOM | 1682 | O | HOH | W | 50 | 54.070 | 9.295 | 22.941 | 1.00 | 24.70 | W | O |

END

TABLE 2

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

```
REMARK   coordinates from restrained individual B-factor refinement
REMARK   refinement resolution: 25-2.6 A
REMARK   starting   r= 0.2563 free_r = 0.2787
REMARK   final      r= 0.2553 free_r = 0.2761
REMARK   B rmsd for bonded mainchain atoms= 1.483    target= 1.5
REMARK   B rmsd for bonded sidechain atoms= 1.740    target= 2.0
REMARK   B rmsd for angle mainchain atoms= 2.593     target= 2.0
REMARK   B rmsd for angle sidechain atoms= 2.780     target= 2.5
REMARK   rweight=   0.1000 (with wa= 3.71696)
REMARK   target = mlf    steps = 30
REMARK   sg= P4(3)2(1)2 a= 54.3 b= 54.3 c= 83.3 alpha= 90 beta= 90
gamma= 90
REMARK   parameter file 1   : MSI_CNX_TOPPAR: protein_rep.param
REMARK   parameter file 2   : ../cid.par
REMARK   molecular structure file: recycle.psf
REMARK   input coordinates: anneal_9.pdb
REMARK   reflection file= ../M876273_2_P43212.cv
REMARK   ncs= none
REMARK   B-correction resolution: 6.0-2.6
REMARK   initial B-factor correction applied to fobs :
REMARK      B11=  −1.189 B22=  −1.189 B33=   2.379
REMARK      B12=   0.000 B13=   0.000 B23=   0.000
REMARK   B-factor correction applied to coordinate array B:  −0.119
REMARK   bulk solvent: (Mask) density level = 0.341945 e/A^3, B-factor=
22.3925 A^2
REMARK   reflections with |Fobs|/sigma_F < 0.0 rejected
REMARK   reflections with |Fobs| > 10000 * rms(Fobs) rejected
REMARK   theoretical total number of refl. in resol. range:   4173
(100.0%)
REMARK   number of unobserved reflections (no entry or |F|=0):   9
(0.2%)
REMARK   number of reflections rejected:   0 (0.0%)
REMARK   total number of reflections used:   4164 (99.8%)
REMARK   number of reflections in working set:   3737 (89.6%)
REMARK   number of reflections in test set:   427 (10.2%)
CRYST1    54.300   54.300   83.300  90.00   90.00   90.00 P 43 21 2
```

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| REMARK | FILENAME="bindividual.pdb" | | | | | | | | | |
|---|---|---|---|---|---|---|---|---|---|---|
| REMARK | Written by CNX VERSION: 2000.12 | | | | | | | | | |
| ATOM | 1 | C | GLY | A | 16 | 50.842 | 45.566 | 39.472 | 1.00 | 68.15 A | C |
| ATOM | 2 | O | GLY | A | 16 | 49.884 | 45.429 | 40.244 | 1.00 | 68.22 A | O |
| ATOM | 3 | N | GLY | A | 16 | 51.272 | 44.956 | 37.085 | 1.00 | 67.11 A | N |
| ATOM | 4 | CA | GLY | A | 16 | 51.225 | 44.463 | 38.498 | 1.00 | 67.90 A | C |
| ATOM | 5 | N | SER | A | 17 | 51.601 | 46.662 | 39.435 | 1.00 | 67.05 A | N |
| ATOM | 6 | CA | SER | A | 17 | 51.358 | 47.819 | 40.296 | 1.00 | 64.73 A | C |
| ATOM | 7 | CB | SER | A | 17 | 52.359 | 47.851 | 41.458 | 1.00 | 65.01 A | C |
| ATOM | 8 | OG | SER | A | 17 | 52.175 | 46.743 | 42.330 | 1.00 | 63.84 A | O |
| ATOM | 9 | C | SER | A | 17 | 51.495 | 49.080 | 39.449 | 1.00 | 62.82 A | C |
| ATOM | 10 | O | SER | A | 17 | 51.039 | 50.157 | 39.837 | 1.00 | 62.75 A | O |
| ATOM | 11 | N | GLN | A | 18 | 52.130 | 48.925 | 38.289 | 1.00 | 60.52 A | N |
| ATOM | 12 | CA | GLN | A | 18 | 52.323 | 50.023 | 37.346 | 1.00 | 57.89 A | C |
| ATOM | 13 | CB | GLN | A | 18 | 53.377 | 49.652 | 36.306 | 1.00 | 57.50 A | C |
| ATOM | 14 | CG | GLN | A | 18 | 54.800 | 49.725 | 36.791 | 1.00 | 57.38 A | C |
| ATOM | 15 | CD | GLN | A | 18 | 55.786 | 49.390 | 35.687 | 1.00 | 58.16 A | C |
| ATOM | 16 | OE1 | GLN | A | 18 | 55.675 | 49.892 | 34.565 | 1.00 | 56.84 A | O |
| ATOM | 17 | NE2 | GLN | A | 18 | 56.761 | 48.543 | 36.002 | 1.00 | 58.44 A | N |
| ATOM | 18 | C | GLN | A | 18 | 51.013 | 50.299 | 36.620 | 1.00 | 55.87 A | C |
| ATOM | 19 | O | GLN | A | 18 | 50.763 | 51.414 | 36.157 | 1.00 | 55.83 A | O |
| ATOM | 20 | N | ILE | A | 19 | 50.187 | 49.261 | 36.524 | 1.00 | 52.87 A | N |
| ATOM | 21 | CA | ILE | A | 19 | 48.898 | 49.337 | 35.850 | 1.00 | 50.05 A | C |
| ATOM | 22 | CB | ILE | A | 19 | 48.721 | 48.131 | 34.883 | 1.00 | 48.06 A | C |
| ATOM | 23 | CG2 | ILE | A | 19 | 47.404 | 48.239 | 34.138 | 1.00 | 48.17 A | C |
| ATOM | 24 | CG1 | ILE | A | 19 | 49.885 | 48.069 | 33.889 | 1.00 | 45.44 A | C |
| ATOM | 25 | CD1 | ILE | A | 19 | 49.939 | 49.218 | 32.921 | 1.00 | 43.26 A | C |
| ATOM | 26 | C | ILE | A | 19 | 47.769 | 49.319 | 36.884 | 1.00 | 49.72 A | C |
| ATOM | 27 | O | ILE | A | 19 | 47.863 | 48.631 | 37.902 | 1.00 | 49.03 A | O |
| ATOM | 28 | N | PRO | A | 20 | 46.694 | 50.095 | 36.643 | 1.00 | 49.57 A | N |
| ATOM | 29 | CD | PRO | A | 20 | 46.609 | 51.167 | 35.636 | 1.00 | 49.58 A | C |
| ATOM | 30 | CA | PRO | A | 20 | 45.546 | 50.162 | 37.553 | 1.00 | 49.39 A | C |
| ATOM | 31 | CB | PRO | A | 20 | 44.693 | 51.271 | 36.949 | 1.00 | 48.67 A | C |
| ATOM | 32 | CG | PRO | A | 20 | 45.704 | 52.159 | 36.318 | 1.00 | 48.94 A | C |
| ATOM | 33 | C | PRO | A | 20 | 44.784 | 48.836 | 37.628 | 1.00 | 49.97 A | C |
| ATOM | 34 | O | PRO | A | 20 | 44.551 | 48.184 | 36.606 | 1.00 | 50.18 A | O |
| ATOM | 35 | N | ALA | A | 21 | 44.399 | 48.446 | 38.840 | 1.00 | 49.45 A | N |
| ATOM | 36 | CA | ALA | A | 21 | 43.660 | 47.207 | 39.057 | 1.00 | 49.81 A | C |
| ATOM | 37 | CB | ALA | A | 21 | 43.252 | 47.094 | 40.528 | 1.00 | 49.85 A | C |
| ATOM | 38 | C | ALA | A | 21 | 42.419 | 47.133 | 38.160 | 1.00 | 49.65 A | C |
| ATOM | 39 | O | ALA | A | 21 | 42.160 | 46.112 | 37.517 | 1.00 | 49.33 A | O |
| ATOM | 40 | N | SER | A | 22 | 41.650 | 48.217 | 38.125 | 1.00 | 48.76 A | N |
| ATOM | 41 | CA | SER | A | 22 | 40.451 | 48.260 | 37.302 | 1.00 | 47.75 A | C |
| ATOM | 42 | CB | SER | A | 22 | 39.873 | 49.678 | 37.296 | 1.00 | 47.15 A | C |
| ATOM | 43 | OG | SER | A | 22 | 40.857 | 50.625 | 36.915 | 1.00 | 48.43 A | O |
| ATOM | 44 | C | SER | A | 22 | 40.792 | 47.816 | 35.877 | 1.00 | 46.34 A | C |
| ATOM | 45 | O | SER | A | 22 | 40.029 | 47.083 | 35.242 | 1.00 | 45.89 A | O |
| ATOM | 46 | N | GLU | A | 23 | 41.947 | 48.251 | 35.384 | 1.00 | 44.68 A | N |
| ATOM | 47 | CA | GLU | A | 23 | 42.375 | 47.887 | 34.040 | 1.00 | 43.25 A | C |
| ATOM | 48 | CB | GLU | A | 23 | 43.526 | 48.771 | 33.588 | 1.00 | 42.16 A | C |
| ATOM | 49 | CG | GLU | A | 23 | 43.939 | 48.525 | 32.164 | 1.00 | 40.86 A | C |
| ATOM | 50 | CD | GLU | A | 23 | 44.747 | 49.671 | 31.612 | 1.00 | 40.82 A | C |
| ATOM | 51 | OE1 | GLU | A | 23 | 45.613 | 50.189 | 32.344 | 1.00 | 41.52 A | O |
| ATOM | 52 | OE2 | GLU | A | 23 | 44.523 | 50.054 | 30.448 | 1.00 | 41.56 A | O |
| ATOM | 53 | C | GLU | A | 23 | 42.790 | 46.428 | 33.991 | 1.00 | 42.01 A | C |
| ATOM | 54 | O | GLU | A | 23 | 42.419 | 45.701 | 33.076 | 1.00 | 42.32 A | O |
| ATOM | 55 | N | GLN | A | 24 | 43.561 | 45.998 | 34.977 | 1.00 | 41.29 A | N |
| ATOM | 56 | CA | GLN | A | 24 | 43.973 | 44.610 | 35.027 | 1.00 | 42.07 A | C |
| ATOM | 57 | CB | GLN | A | 24 | 44.762 | 44.334 | 36.314 | 1.00 | 41.13 A | C |
| ATOM | 58 | CG | GLN | A | 24 | 46.206 | 44.813 | 36.250 | 1.00 | 42.57 A | C |
| ATOM | 59 | CD | GLN | A | 24 | 46.978 | 44.602 | 37.546 | 1.00 | 43.91 A | C |
| ATOM | 60 | OE1 | GLN | A | 24 | 46.823 | 43.580 | 38.225 | 1.00 | 44.84 A | O |
| ATOM | 61 | NE2 | GLN | A | 24 | 47.831 | 45.564 | 37.884 | 1.00 | 43.17 A | N |
| ATOM | 62 | C | GLN | A | 24 | 42.714 | 43.747 | 34.984 | 1.00 | 43.32 A | C |
| ATOM | 63 | O | GLN | A | 24 | 42.750 | 42.596 | 34.541 | 1.00 | 43.40 A | O |
| ATOM | 64 | N | GLU | A | 25 | 41.596 | 44.326 | 35.423 | 1.00 | 44.62 A | N |
| ATOM | 65 | CA | GLU | A | 25 | 40.314 | 43.618 | 35.464 | 1.00 | 44.92 A | C |
| ATOM | 66 | CB | GLU | A | 25 | 39.471 | 44.123 | 36.642 | 1.00 | 48.33 A | C |
| ATOM | 67 | CG | GLU | A | 25 | 40.216 | 44.254 | 37.972 | 1.00 | 53.04 A | C |
| ATOM | 68 | CD | GLU | A | 25 | 40.899 | 42.969 | 38.423 | 1.00 | 55.79 A | C |
| ATOM | 69 | OE1 | GLU | A | 25 | 41.474 | 42.972 | 39.533 | 1.00 | 57.11 A | O |
| ATOM | 70 | OE2 | GLU | A | 25 | 40.869 | 41.961 | 37.681 | 1.00 | 57.84 A | O |
| ATOM | 71 | C | GLU | A | 25 | 39.472 | 43.697 | 34.184 | 1.00 | 42.75 A | C |
| ATOM | 72 | O | GLU | A | 25 | 38.563 | 42.887 | 33.992 | 1.00 | 42.62 A | O |
| ATOM | 73 | N | THR | A | 26 | 39.760 | 44.666 | 33.319 | 1.00 | 40.18 A | N |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 74 | CA | THR | A | 26 | 39.013 | 44.813 | 32.067 | 1.00 | 38.13 | A | C |
|------|-----|-----|-----|---|----|--------|--------|--------|------|-------|---|---|
| ATOM | 75 | CB | THR | A | 26 | 39.714 | 45.803 | 31.100 | 1.00 | 37.92 | A | C |
| ATOM | 76 | OG1 | THR | A | 26 | 40.061 | 47.002 | 31.803 | 1.00 | 37.02 | A | O |
| ATOM | 77 | CG2 | THR | A | 26 | 38.798 | 46.161 | 29.945 | 1.00 | 36.76 | A | C |
| ATOM | 78 | C | THR | A | 26 | 38.897 | 43.456 | 31.367 | 1.00 | 36.79 | A | C |
| ATOM | 79 | O | THR | A | 26 | 39.859 | 42.693 | 31.321 | 1.00 | 36.47 | A | O |
| ATOM | 80 | N | LEU | A | 27 | 37.715 | 43.152 | 30.841 | 1.00 | 36.63 | A | N |
| ATOM | 81 | CA | LEU | A | 27 | 37.490 | 41.887 | 30.138 | 1.00 | 35.77 | A | C |
| ATOM | 82 | CB | LEU | A | 27 | 36.035 | 41.429 | 30.291 | 1.00 | 36.16 | A | C |
| ATOM | 83 | CG | LEU | A | 27 | 35.799 | 39.909 | 30.293 | 1.00 | 38.05 | A | C |
| ATOM | 84 | CD1 | LEU | A | 27 | 36.293 | 39.313 | 31.617 | 1.00 | 36.12 | A | C |
| ATOM | 85 | CD2 | LEU | A | 27 | 34.305 | 39.610 | 30.112 | 1.00 | 38.41 | A | C |
| ATOM | 86 | C | LEU | A | 27 | 37.808 | 42.130 | 28.665 | 1.00 | 34.52 | A | C |
| ATOM | 87 | O | LEU | A | 27 | 37.395 | 43.139 | 28.090 | 1.00 | 33.72 | A | O |
| ATOM | 88 | N | VAL | A | 28 | 38.540 | 41.204 | 28.054 | 1.00 | 33.53 | A | N |
| ATOM | 89 | CA | VAL | A | 28 | 38.941 | 41.364 | 26.662 | 1.00 | 32.88 | A | C |
| ATOM | 90 | CB | VAL | A | 28 | 40.420 | 41.848 | 26.589 | 1.00 | 32.86 | A | C |
| ATOM | 91 | CG1 | VAL | A | 28 | 40.570 | 43.182 | 27.302 | 1.00 | 31.21 | A | C |
| ATOM | 92 | CG2 | VAL | A | 28 | 41.340 | 40.821 | 27.242 | 1.00 | 33.40 | A | C |
| ATOM | 93 | C | VAL | A | 28 | 38.792 | 40.107 | 25.802 | 1.00 | 31.29 | A | C |
| ATOM | 94 | O | VAL | A | 28 | 38.708 | 38.992 | 26.314 | 1.00 | 30.99 | A | O |
| ATOM | 95 | N | ARG | A | 29 | 38.754 | 40.312 | 24.489 | 1.00 | 29.80 | A | N |
| ATOM | 96 | CA | ARG | A | 29 | 38.641 | 39.224 | 23.528 | 1.00 | 28.94 | A | C |
| ATOM | 97 | CB | ARG | A | 29 | 37.379 | 39.371 | 22.685 | 1.00 | 33.14 | A | C |
| ATOM | 98 | CG | ARG | A | 29 | 36.132 | 38.818 | 23.326 | 1.00 | 38.54 | A | C |
| ATOM | 99 | CD | ARG | A | 29 | 34.905 | 39.188 | 22.511 | 1.00 | 43.39 | A | C |
| ATOM | 100 | NE | ARG | A | 29 | 33.712 | 38.549 | 23.051 | 1.00 | 47.28 | A | N |
| ATOM | 101 | CZ | ARG | A | 29 | 33.397 | 37.276 | 22.843 | 1.00 | 49.30 | A | C |
| ATOM | 102 | NH1 | ARG | A | 29 | 34.185 | 36.511 | 22.093 | 1.00 | 49.75 | A | N |
| ATOM | 103 | NH2 | ARG | A | 29 | 32.309 | 36.763 | 23.405 | 1.00 | 50.29 | A | N |
| ATOM | 104 | C | ARG | A | 29 | 39.842 | 39.254 | 22.602 | 1.00 | 26.43 | A | C |
| ATOM | 105 | O | ARG | A | 29 | 39.935 | 40.121 | 21.727 | 1.00 | 25.41 | A | O |
| ATOM | 106 | N | PRO | A | 30 | 40.785 | 38.315 | 22.789 | 1.00 | 24.69 | A | N |
| ATOM | 107 | CD | PRO | A | 30 | 40.798 | 37.274 | 23.830 | 1.00 | 23.43 | A | C |
| ATOM | 108 | CA | PRO | A | 30 | 41.995 | 38.234 | 21.958 | 1.00 | 23.00 | A | C |
| ATOM | 109 | CB | PRO | A | 30 | 42.826 | 37.151 | 22.643 | 1.00 | 21.72 | A | C |
| ATOM | 110 | CG | PRO | A | 30 | 42.261 | 37.064 | 24.025 | 1.00 | 22.48 | A | C |
| ATOM | 111 | C | PRO | A | 30 | 41.620 | 37.801 | 20.544 | 1.00 | 22.20 | A | C |
| ATOM | 112 | O | PRO | A | 30 | 40.663 | 37.050 | 20.360 | 1.00 | 22.27 | A | O |
| ATOM | 113 | N | LYS | A | 31 | 42.365 | 38.273 | 19.551 | 1.00 | 21.65 | A | N |
| ATOM | 114 | CA | LYS | A | 31 | 42.118 | 37.880 | 18.166 | 1.00 | 19.51 | A | C |
| ATOM | 115 | CB | LYS | A | 31 | 42.825 | 38.839 | 17.210 | 1.00 | 19.68 | A | C |
| ATOM | 116 | CG | LYS | A | 31 | 42.364 | 40.279 | 17.348 | 1.00 | 20.82 | A | C |
| ATOM | 117 | CD | LYS | A | 31 | 43.115 | 41.174 | 16.376 | 1.00 | 22.74 | A | C |
| ATOM | 118 | CE | LYS | A | 31 | 42.641 | 42.630 | 16.435 | 1.00 | 20.68 | A | C |
| ATOM | 119 | NZ | LYS | A | 31 | 43.356 | 43.433 | 15.396 | 1.00 | 21.75 | A | N |
| ATOM | 120 | C | LYS | A | 31 | 42.666 | 36.454 | 18.011 | 1.00 | 18.36 | A | C |
| ATOM | 121 | O | LYS | A | 31 | 43.441 | 35.983 | 18.847 | 1.00 | 17.38 | A | O |
| ATOM | 122 | N | PRO | A | 32 | 42.291 | 35.760 | 16.930 | 1.00 | 17.15 | A | N |
| ATOM | 123 | CD | PRO | A | 32 | 41.612 | 36.293 | 15.736 | 1.00 | 16.30 | A | C |
| ATOM | 124 | CA | PRO | A | 32 | 42.737 | 34.387 | 16.684 | 1.00 | 16.70 | A | C |
| ATOM | 125 | CB | PRO | A | 32 | 42.392 | 34.182 | 15.213 | 1.00 | 16.53 | A | C |
| ATOM | 126 | CG | PRO | A | 32 | 41.180 | 35.032 | 15.044 | 1.00 | 16.35 | A | C |
| ATOM | 127 | C | PRO | A | 32 | 44.198 | 34.043 | 16.997 | 1.00 | 16.73 | A | C |
| ATOM | 128 | O | PRO | A | 32 | 44.470 | 33.062 | 17.695 | 1.00 | 17.12 | A | O |
| ATOM | 129 | N | LEU | A | 33 | 45.137 | 34.830 | 16.483 | 1.00 | 14.62 | A | N |
| ATOM | 130 | CA | LEU | A | 33 | 46.540 | 34.538 | 16.724 | 1.00 | 13.59 | A | C |
| ATOM | 131 | CB | LEU | A | 33 | 47.425 | 35.427 | 15.843 | 1.00 | 15.36 | A | C |
| ATOM | 132 | CG | LEU | A | 33 | 48.097 | 34.759 | 14.626 | 1.00 | 13.91 | A | C |
| ATOM | 133 | CD1 | LEU | A | 33 | 47.597 | 33.319 | 14.406 | 1.00 | 13.51 | A | C |
| ATOM | 134 | CD2 | LEU | A | 33 | 47.838 | 35.609 | 13.411 | 1.00 | 8.87 | A | C |
| ATOM | 135 | C | LEU | A | 33 | 46.936 | 34.641 | 18.189 | 1.00 | 13.14 | A | C |
| ATOM | 136 | O | LEU | A | 33 | 47.545 | 33.724 | 18.715 | 1.00 | 12.37 | A | O |
| ATOM | 137 | N | LEU | A | 34 | 46.610 | 35.744 | 18.856 | 1.00 | 14.58 | A | N |
| ATOM | 138 | CA | LEU | A | 34 | 46.930 | 35.859 | 20.279 | 1.00 | 13.84 | A | C |
| ATOM | 139 | CB | LEU | A | 34 | 46.540 | 37.236 | 20.826 | 1.00 | 13.73 | A | C |
| ATOM | 140 | CG | LEU | A | 34 | 46.613 | 37.449 | 22.347 | 1.00 | 10.65 | A | C |
| ATOM | 141 | CD1 | LEU | A | 34 | 48.041 | 37.367 | 22.818 | 1.00 | 9.38 | A | C |
| ATOM | 142 | CD2 | LEU | A | 34 | 46.029 | 38.795 | 22.701 | 1.00 | 11.47 | A | C |
| ATOM | 143 | C | LEU | A | 34 | 46.158 | 34.771 | 21.039 | 1.00 | 15.75 | A | C |
| ATOM | 144 | O | LEU | A | 34 | 46.678 | 34.176 | 21.975 | 1.00 | 16.50 | A | O |
| ATOM | 145 | N | LEU | A | 35 | 44.917 | 34.506 | 20.635 | 1.00 | 17.07 | A | N |
| ATOM | 146 | CA | LEU | A | 35 | 44.125 | 33.469 | 21.295 | 1.00 | 18.94 | A | C |
| ATOM | 147 | CB | LEU | A | 35 | 42.720 | 33.381 | 20.686 | 1.00 | 16.70 | A | C |
| ATOM | 148 | CG | LEU | A | 35 | 41.753 | 32.424 | 21.391 | 1.00 | 14.51 | A | C |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 149 | CD1 | LEU | A | 35 | 41.542 | 32.888 | 22.825 | 1.00 | 13.73 | A | C |
|------|-----|-----|-----|---|----|--------|--------|--------|------|-------|---|---|
| ATOM | 150 | CD2 | LEU | A | 35 | 40.425 | 32.379 | 20.653 | 1.00 | 13.01 | A | C |
| ATOM | 151 | C   | LEU | A | 35 | 44.815 | 32.094 | 21.218 | 1.00 | 20.66 | A | C |
| ATOM | 152 | O   | LEU | A | 35 | 44.668 | 31.276 | 22.133 | 1.00 | 21.36 | A | O |
| ATOM | 153 | N   | LYS | A | 36 | 45.563 | 31.845 | 20.140 | 1.00 | 20.77 | A | N |
| ATOM | 154 | CA  | LYS | A | 36 | 46.279 | 30.581 | 19.979 | 1.00 | 22.28 | A | C |
| ATOM | 155 | CB  | LYS | A | 36 | 46.792 | 30.398 | 18.547 | 1.00 | 23.62 | A | C |
| ATOM | 156 | CG  | LYS | A | 36 | 45.782 | 29.781 | 17.586 | 1.00 | 28.23 | A | C |
| ATOM | 157 | CD  | LYS | A | 36 | 46.444 | 28.754 | 16.647 | 1.00 | 30.56 | A | C |
| ATOM | 158 | CE  | LYS | A | 36 | 47.556 | 29.366 | 15.789 | 1.00 | 32.43 | A | C |
| ATOM | 159 | NZ  | LYS | A | 36 | 48.108 | 28.414 | 14.778 | 1.00 | 31.16 | A | N |
| ATOM | 160 | C   | LYS | A | 36 | 47.461 | 30.504 | 20.937 | 1.00 | 23.86 | A | C |
| ATOM | 161 | O   | LYS | A | 36 | 47.716 | 29.451 | 21.537 | 1.00 | 26.24 | A | O |
| ATOM | 162 | N   | LEU | A | 37 | 48.196 | 31.603 | 21.076 | 1.00 | 23.16 | A | N |
| ATOM | 163 | CA  | LEU | A | 37 | 49.332 | 31.612 | 21.994 | 1.00 | 24.32 | A | C |
| ATOM | 164 | CB  | LEU | A | 37 | 49.920 | 33.019 | 22.134 | 1.00 | 25.18 | A | C |
| ATOM | 165 | CG  | LEU | A | 37 | 50.647 | 33.606 | 20.934 | 1.00 | 27.89 | A | C |
| ATOM | 166 | CD1 | LEU | A | 37 | 51.343 | 34.901 | 21.343 | 1.00 | 28.24 | A | C |
| ATOM | 167 | CD2 | LEU | A | 37 | 51.659 | 32.597 | 20.431 | 1.00 | 28.07 | A | C |
| ATOM | 168 | C   | LEU | A | 37 | 48.884 | 31.144 | 23.377 | 1.00 | 23.05 | A | C |
| ATOM | 169 | O   | LEU | A | 37 | 49.526 | 30.304 | 24.003 | 1.00 | 20.34 | A | O |
| ATOM | 170 | N   | LEU | A | 38 | 47.770 | 31.706 | 23.834 | 1.00 | 23.36 | A | N |
| ATOM | 171 | CA  | LEU | A | 38 | 47.218 | 31.399 | 25.139 | 1.00 | 24.58 | A | C |
| ATOM | 172 | CB  | LEU | A | 38 | 46.036 | 32.322 | 25.447 | 1.00 | 21.20 | A | C |
| ATOM | 173 | CG  | LEU | A | 38 | 46.216 | 33.821 | 25.189 | 1.00 | 19.16 | A | C |
| ATOM | 174 | CD1 | LEU | A | 38 | 44.954 | 34.538 | 25.619 | 1.00 | 16.77 | A | C |
| ATOM | 175 | CD2 | LEU | A | 38 | 47.420 | 34.370 | 25.950 | 1.00 | 18.04 | A | C |
| ATOM | 176 | C   | LEU | A | 38 | 46.772 | 29.950 | 25.241 | 1.00 | 27.20 | A | C |
| ATOM | 177 | O   | LEU | A | 38 | 46.970 | 29.309 | 26.273 | 1.00 | 29.33 | A | O |
| ATOM | 178 | N   | LYS | A | 39 | 46.175 | 29.419 | 24.182 | 1.00 | 28.13 | A | N |
| ATOM | 179 | CA  | LYS | A | 39 | 45.720 | 28.041 | 24.241 | 1.00 | 29.30 | A | C |
| ATOM | 180 | CB  | LYS | A | 39 | 44.782 | 27.741 | 23.071 | 1.00 | 28.63 | A | C |
| ATOM | 181 | CG  | LYS | A | 39 | 43.532 | 28.596 | 23.123 | 1.00 | 28.78 | A | C |
| ATOM | 182 | CD  | LYS | A | 39 | 42.451 | 28.113 | 22.184 | 1.00 | 27.98 | A | C |
| ATOM | 183 | CE  | LYS | A | 39 | 41.239 | 29.021 | 22.270 | 1.00 | 26.89 | A | C |
| ATOM | 184 | NZ  | LYS | A | 39 | 40.089 | 28.444 | 21.537 | 1.00 | 27.11 | A | N |
| ATOM | 185 | C   | LYS | A | 39 | 46.884 | 27.062 | 24.270 | 1.00 | 30.33 | A | C |
| ATOM | 186 | O   | LYS | A | 39 | 46.787 | 25.998 | 24.883 | 1.00 | 31.74 | A | O |
| ATOM | 187 | N   | SER | A | 40 | 47.993 | 27.428 | 23.633 | 1.00 | 30.27 | A | N |
| ATOM | 188 | CA  | SER | A | 40 | 49.169 | 26.559 | 23.607 | 1.00 | 29.62 | A | C |
| ATOM | 189 | CB  | SER | A | 40 | 50.280 | 27.175 | 22.735 | 1.00 | 28.81 | A | C |
| ATOM | 190 | OG  | SER | A | 40 | 50.904 | 28.292 | 23.357 | 1.00 | 26.68 | A | O |
| ATOM | 191 | C   | SER | A | 40 | 49.701 | 26.301 | 25.020 | 1.00 | 29.48 | A | C |
| ATOM | 192 | O   | SER | A | 40 | 50.396 | 25.316 | 25.254 | 1.00 | 29.59 | A | O |
| ATOM | 193 | N   | VAL | A | 41 | 49.374 | 27.186 | 25.958 | 1.00 | 30.35 | A | N |
| ATOM | 194 | CA  | VAL | A | 41 | 49.827 | 27.044 | 27.345 | 1.00 | 30.76 | A | C |
| ATOM | 195 | CB  | VAL | A | 41 | 50.717 | 28.252 | 27.799 | 1.00 | 30.64 | A | C |
| ATOM | 196 | CG1 | VAL | A | 41 | 52.087 | 28.184 | 27.125 | 1.00 | 29.00 | A | C |
| ATOM | 197 | CG2 | VAL | A | 41 | 50.030 | 29.574 | 27.470 | 1.00 | 28.32 | A | C |
| ATOM | 198 | C   | VAL | A | 41 | 48.678 | 26.891 | 28.345 | 1.00 | 32.02 | A | C |
| ATOM | 199 | O   | VAL | A | 41 | 48.691 | 27.500 | 29.419 | 1.00 | 31.05 | A | O |
| ATOM | 200 | N   | GLY | A | 42 | 47.675 | 26.092 | 27.983 | 1.00 | 33.77 | A | N |
| ATOM | 201 | CA  | GLY | A | 42 | 46.563 | 25.862 | 28.889 | 1.00 | 36.14 | A | C |
| ATOM | 202 | C   | GLY | A | 42 | 45.260 | 26.597 | 28.641 | 1.00 | 38.10 | A | C |
| ATOM | 203 | O   | GLY | A | 42 | 44.201 | 25.971 | 28.653 | 1.00 | 40.02 | A | O |
| ATOM | 204 | N   | ALA | A | 43 | 45.317 | 27.912 | 28.432 | 1.00 | 38.97 | A | N |
| ATOM | 205 | CA  | ALA | A | 43 | 44.107 | 28.703 | 28.203 | 1.00 | 39.16 | A | C |
| ATOM | 206 | CB  | ALA | A | 43 | 44.459 | 30.022 | 27.518 | 1.00 | 38.86 | A | C |
| ATOM | 207 | C   | ALA | A | 43 | 43.080 | 27.938 | 27.375 | 1.00 | 39.94 | A | C |
| ATOM | 208 | O   | ALA | A | 43 | 43.437 | 27.164 | 26.485 | 1.00 | 40.04 | A | O |
| ATOM | 209 | N   | GLN | A | 44 | 41.802 | 28.155 | 27.675 | 1.00 | 41.54 | A | N |
| ATOM | 210 | CA  | GLN | A | 44 | 40.733 | 27.475 | 26.955 | 1.00 | 42.78 | A | C |
| ATOM | 211 | CB  | GLN | A | 44 | 40.609 | 26.037 | 27.466 | 1.00 | 45.11 | A | C |
| ATOM | 212 | CG  | GLN | A | 44 | 40.573 | 25.913 | 28.984 | 1.00 | 47.61 | A | C |
| ATOM | 213 | CD  | GLN | A | 44 | 40.868 | 24.493 | 29.456 | 1.00 | 49.56 | A | C |
| ATOM | 214 | OE1 | GLN | A | 44 | 40.913 | 24.221 | 30.662 | 1.00 | 49.35 | A | O |
| ATOM | 215 | NE2 | GLN | A | 44 | 41.075 | 23.581 | 28.506 | 1.00 | 49.08 | A | N |
| ATOM | 216 | C   | GLN | A | 44 | 39.379 | 28.183 | 27.030 | 1.00 | 42.23 | A | C |
| ATOM | 217 | O   | GLN | A | 44 | 38.355 | 27.557 | 27.322 | 1.00 | 42.70 | A | O |
| ATOM | 218 | N   | LYS | A | 45 | 39.391 | 29.488 | 26.763 | 1.00 | 40.15 | A | N |
| ATOM | 219 | CA  | LYS | A | 45 | 38.184 | 30.307 | 26.765 | 1.00 | 37.90 | A | C |
| ATOM | 220 | CB  | LYS | A | 45 | 38.085 | 31.150 | 28.034 | 1.00 | 39.62 | A | C |
| ATOM | 221 | CG  | LYS | A | 45 | 38.193 | 30.392 | 29.341 | 1.00 | 41.18 | A | C |
| ATOM | 222 | CD  | LYS | A | 45 | 37.768 | 31.288 | 30.502 | 1.00 | 42.96 | A | C |
| ATOM | 223 | CE  | LYS | A | 45 | 38.491 | 32.629 | 30.473 | 1.00 | 45.64 | A | C |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 224 | NZ  | LYS | A | 45 | 38.045 | 33.556 | 31.559 | 1.00 | 48.08 | A | N |
| ATOM | 225 | C   | LYS | A | 45 | 38.296 | 31.254 | 25.585 | 1.00 | 36.61 | A | C |
| ATOM | 226 | O   | LYS | A | 45 | 39.258 | 31.183 | 24.822 | 1.00 | 36.82 | A | O |
| ATOM | 227 | N   | ASP | A | 46 | 37.323 | 32.149 | 25.448 | 1.00 | 34.69 | A | N |
| ATOM | 228 | CA  | ASP | A | 46 | 37.332 | 33.128 | 24.368 | 1.00 | 33.64 | A | C |
| ATOM | 229 | CB  | ASP | A | 46 | 36.015 | 33.106 | 23.577 | 1.00 | 35.21 | A | C |
| ATOM | 230 | CG  | ASP | A | 46 | 35.826 | 31.828 | 22.778 | 1.00 | 36.60 | A | C |
| ATOM | 231 | OD1 | ASP | A | 46 | 36.819 | 31.326 | 22.204 | 1.00 | 35.63 | A | O |
| ATOM | 232 | OD2 | ASP | A | 46 | 34.677 | 31.337 | 22.712 | 1.00 | 36.79 | A | O |
| ATOM | 233 | C   | ASP | A | 46 | 37.529 | 34.526 | 24.935 | 1.00 | 32.32 | A | C |
| ATOM | 234 | O   | ASP | A | 46 | 38.032 | 35.419 | 24.249 | 1.00 | 33.06 | A | O |
| ATOM | 235 | N   | THR | A | 47 | 37.118 | 34.715 | 26.186 | 1.00 | 30.30 | A | N |
| ATOM | 236 | CA  | THR | A | 47 | 37.233 | 36.012 | 26.850 | 1.00 | 27.52 | A | C |
| ATOM | 237 | CB  | THR | A | 47 | 35.849 | 36.568 | 27.265 | 1.00 | 28.37 | A | C |
| ATOM | 238 | OG1 | THR | A | 47 | 35.055 | 35.513 | 27.822 | 1.00 | 28.12 | A | O |
| ATOM | 239 | CG2 | THR | A | 47 | 35.130 | 37.169 | 26.071 | 1.00 | 28.11 | A | C |
| ATOM | 240 | C   | THR | A | 47 | 38.097 | 35.897 | 28.088 | 1.00 | 25.47 | A | C |
| ATOM | 241 | O   | THR | A | 47 | 38.111 | 34.862 | 28.759 | 1.00 | 24.25 | A | O |
| ATOM | 242 | N   | TYR | A | 48 | 38.820 | 36.973 | 28.382 | 1.00 | 24.41 | A | N |
| ATOM | 243 | CA  | TYR | A | 48 | 39.716 | 37.010 | 29.526 | 1.00 | 24.02 | A | C |
| ATOM | 244 | CB  | TYR | A | 48 | 41.142 | 36.566 | 29.126 | 1.00 | 23.01 | A | C |
| ATOM | 245 | CG  | TYR | A | 48 | 41.265 | 35.192 | 28.492 | 1.00 | 22.29 | A | C |
| ATOM | 246 | CD1 | TYR | A | 48 | 40.966 | 34.992 | 27.143 | 1.00 | 21.16 | A | C |
| ATOM | 247 | CE1 | TYR | A | 48 | 41.035 | 33.713 | 26.568 | 1.00 | 20.20 | A | C |
| ATOM | 248 | CD2 | TYR | A | 48 | 41.647 | 34.079 | 29.254 | 1.00 | 21.34 | A | C |
| ATOM | 249 | CE2 | TYR | A | 48 | 41.721 | 32.806 | 28.688 | 1.00 | 20.29 | A | C |
| ATOM | 250 | CZ  | TYR | A | 48 | 41.409 | 32.633 | 27.348 | 1.00 | 19.58 | A | C |
| ATOM | 251 | OH  | TYR | A | 48 | 41.436 | 31.378 | 26.795 | 1.00 | 20.11 | A | O |
| ATOM | 252 | C   | TYR | A | 48 | 39.829 | 38.419 | 30.085 | 1.00 | 24.38 | A | C |
| ATOM | 253 | O   | TYR | A | 48 | 39.512 | 39.403 | 29.409 | 1.00 | 22.46 | A | O |
| ATOM | 254 | N   | THR | A | 49 | 40.288 | 38.497 | 31.329 | 1.00 | 24.50 | A | N |
| ATOM | 255 | CA  | THR | A | 49 | 40.554 | 39.774 | 31.974 | 1.00 | 25.25 | A | C |
| ATOM | 256 | CB  | THR | A | 49 | 40.510 | 39.647 | 33.515 | 1.00 | 26.57 | A | C |
| ATOM | 257 | OG1 | THR | A | 49 | 41.215 | 38.459 | 33.914 | 1.00 | 26.24 | A | O |
| ATOM | 258 | CG2 | THR | A | 49 | 39.056 | 39.580 | 34.017 | 1.00 | 24.91 | A | C |
| ATOM | 259 | C   | THR | A | 49 | 42.000 | 40.027 | 31.524 | 1.00 | 25.63 | A | C |
| ATOM | 260 | O   | THR | A | 49 | 42.738 | 39.079 | 31.248 | 1.00 | 24.71 | A | O |
| ATOM | 261 | N   | MET | A | 50 | 42.414 | 41.281 | 31.424 | 1.00 | 26.39 | A | N |
| ATOM | 262 | CA  | MET | A | 50 | 43.776 | 41.545 | 30.986 | 1.00 | 26.62 | A | C |
| ATOM | 263 | CB  | MET | A | 50 | 44.053 | 43.040 | 30.977 | 1.00 | 25.74 | A | C |
| ATOM | 264 | CG  | MET | A | 50 | 43.446 | 43.740 | 29.780 | 1.00 | 25.74 | A | C |
| ATOM | 265 | SD  | MET | A | 50 | 44.280 | 43.286 | 28.239 | 1.00 | 24.59 | A | S |
| ATOM | 266 | CE  | MET | A | 50 | 45.652 | 44.433 | 28.225 | 1.00 | 22.52 | A | C |
| ATOM | 267 | C   | MET | A | 50 | 44.797 | 40.832 | 31.855 | 1.00 | 28.23 | A | C |
| ATOM | 268 | O   | MET | A | 50 | 45.890 | 40.518 | 31.396 | 1.00 | 29.67 | A | O |
| ATOM | 269 | N   | LYS | A | 51 | 44.442 | 40.554 | 33.105 | 1.00 | 28.66 | A | N |
| ATOM | 270 | CA  | LYS | A | 51 | 45.370 | 39.872 | 33.993 | 1.00 | 29.11 | A | C |
| ATOM | 271 | CB  | LYS | A | 51 | 44.878 | 39.943 | 35.439 | 1.00 | 32.66 | A | C |
| ATOM | 272 | CG  | LYS | A | 51 | 45.919 | 39.458 | 36.443 | 1.00 | 37.67 | A | C |
| ATOM | 273 | CD  | LYS | A | 51 | 45.462 | 39.604 | 37.889 | 1.00 | 41.07 | A | C |
| ATOM | 274 | CE  | LYS | A | 51 | 46.527 | 39.071 | 38.855 | 1.00 | 42.73 | A | C |
| ATOM | 275 | NZ  | LYS | A | 51 | 46.109 | 39.129 | 40.295 | 1.00 | 45.66 | A | N |
| ATOM | 276 | C   | LYS | A | 51 | 45.597 | 38.411 | 33.586 | 1.00 | 28.29 | A | C |
| ATOM | 277 | O   | LYS | A | 51 | 46.723 | 37.908 | 33.669 | 1.00 | 28.36 | A | O |
| ATOM | 278 | N   | GLU | A | 52 | 44.537 | 37.729 | 33.152 | 1.00 | 25.71 | A | N |
| ATOM | 279 | CA  | GLU | A | 52 | 44.662 | 36.334 | 32.732 | 1.00 | 23.60 | A | C |
| ATOM | 280 | CB  | GLU | A | 52 | 43.278 | 35.702 | 32.522 | 1.00 | 24.83 | A | C |
| ATOM | 281 | CG  | GLU | A | 52 | 42.420 | 35.589 | 33.777 | 1.00 | 27.15 | A | C |
| ATOM | 282 | CD  | GLU | A | 52 | 40.989 | 35.116 | 33.479 | 1.00 | 29.01 | A | C |
| ATOM | 283 | OE1 | GLU | A | 52 | 40.281 | 35.785 | 32.691 | 1.00 | 29.80 | A | O |
| ATOM | 284 | OE2 | GLU | A | 52 | 40.568 | 34.078 | 34.032 | 1.00 | 29.19 | A | O |
| ATOM | 285 | C   | GLU | A | 52 | 45.476 | 36.230 | 31.432 | 1.00 | 21.67 | A | C |
| ATOM | 286 | O   | GLU | A | 52 | 46.128 | 35.214 | 31.183 | 1.00 | 20.99 | A | O |
| ATOM | 287 | N   | VAL | A | 53 | 45.425 | 37.266 | 30.598 | 1.00 | 18.55 | A | N |
| ATOM | 288 | CA  | VAL | A | 53 | 46.181 | 37.255 | 29.351 | 1.00 | 16.46 | A | C |
| ATOM | 289 | CB  | VAL | A | 53 | 45.807 | 38.454 | 28.423 | 1.00 | 17.02 | A | C |
| ATOM | 290 | CG1 | VAL | A | 53 | 46.806 | 38.553 | 27.264 | 1.00 | 15.92 | A | C |
| ATOM | 291 | CG2 | VAL | A | 53 | 44.402 | 38.261 | 27.853 | 1.00 | 14.61 | A | C |
| ATOM | 292 | C   | VAL | A | 53 | 47.650 | 37.331 | 29.742 | 1.00 | 15.15 | A | C |
| ATOM | 293 | O   | VAL | A | 53 | 48.436 | 36.443 | 29.403 | 1.00 | 13.10 | A | O |
| ATOM | 294 | N   | LEU | A | 54 | 48.010 | 38.394 | 30.463 | 1.00 | 15.42 | A | N |
| ATOM | 295 | CA  | LEU | A | 54 | 49.375 | 38.570 | 30.952 | 1.00 | 14.74 | A | C |
| ATOM | 296 | CB  | LEU | A | 54 | 49.454 | 39.698 | 31.982 | 1.00 | 12.86 | A | C |
| ATOM | 297 | CG  | LEU | A | 54 | 49.718 | 41.124 | 31.497 | 1.00 | 13.00 | A | C |
| ATOM | 298 | CD1 | LEU | A | 54 | 50.874 | 41.100 | 30.500 | 1.00 | 14.60 | A | C |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 299 | CD2 | LEU | A | 54 | 48.494 | 41.706 | 30.859 | 1.00 | 11.73 | A | C |
|------|-----|-----|-----|---|----|--------|--------|--------|------|-------|---|---|
| ATOM | 300 | C   | LEU | A | 54 | 49.846 | 37.281 | 31.619 | 1.00 | 15.13 | A | C |
| ATOM | 301 | O   | LEU | A | 54 | 51.009 | 36.897 | 31.502 | 1.00 | 16.88 | A | O |
| ATOM | 302 | N   | PHE | A | 55 | 48.942 | 36.605 | 32.312 | 1.00 | 14.69 | A | N |
| ATOM | 303 | CA  | PHE | A | 55 | 49.305 | 35.371 | 32.991 | 1.00 | 16.41 | A | C |
| ATOM | 304 | CB  | PHE | A | 55 | 48.137 | 34.831 | 33.819 | 1.00 | 18.34 | A | C |
| ATOM | 305 | CG  | PHE | A | 55 | 48.428 | 33.500 | 34.429 | 1.00 | 20.72 | A | C |
| ATOM | 306 | CD1 | PHE | A | 55 | 49.136 | 33.411 | 35.626 | 1.00 | 20.24 | A | C |
| ATOM | 307 | CD2 | PHE | A | 55 | 48.101 | 32.324 | 33.749 | 1.00 | 20.52 | A | C |
| ATOM | 308 | CE1 | PHE | A | 55 | 49.524 | 32.170 | 36.135 | 1.00 | 20.60 | A | C |
| ATOM | 309 | CE2 | PHE | A | 55 | 48.485 | 31.079 | 34.248 | 1.00 | 21.73 | A | C |
| ATOM | 310 | CZ  | PHE | A | 55 | 49.199 | 31.001 | 35.444 | 1.00 | 20.59 | A | C |
| ATOM | 311 | C   | PHE | A | 55 | 49.779 | 34.268 | 32.058 | 1.00 | 16.04 | A | C |
| ATOM | 312 | O   | PHE | A | 55 | 50.853 | 33.698 | 32.259 | 1.00 | 17.31 | A | O |
| ATOM | 313 | N   | TYR | A | 56 | 48.960 | 33.949 | 31.060 | 1.00 | 16.71 | A | N |
| ATOM | 314 | CA  | TYR | A | 56 | 49.283 | 32.904 | 30.087 | 1.00 | 17.61 | A | C |
| ATOM | 315 | CB  | TYR | A | 56 | 48.079 | 32.620 | 29.189 | 1.00 | 18.45 | A | C |
| ATOM | 316 | CG  | TYR | A | 56 | 46.996 | 31.859 | 29.902 | 1.00 | 21.48 | A | C |
| ATOM | 317 | CD1 | TYR | A | 56 | 47.213 | 30.541 | 30.318 | 1.00 | 23.38 | A | C |
| ATOM | 318 | CE1 | TYR | A | 56 | 46.237 | 29.832 | 31.013 | 1.00 | 25.16 | A | C |
| ATOM | 319 | CD2 | TYR | A | 56 | 45.766 | 32.459 | 30.198 | 1.00 | 22.53 | A | C |
| ATOM | 320 | CE2 | TYR | A | 56 | 44.773 | 31.761 | 30.898 | 1.00 | 23.90 | A | C |
| ATOM | 321 | CZ  | TYR | A | 56 | 45.019 | 30.445 | 31.303 | 1.00 | 26.15 | A | C |
| ATOM | 322 | OH  | TYR | A | 56 | 44.065 | 29.738 | 32.003 | 1.00 | 26.91 | A | O |
| ATOM | 323 | C   | TYR | A | 56 | 50.450 | 33.345 | 29.243 | 1.00 | 16.78 | A | C |
| ATOM | 324 | O   | TYR | A | 56 | 51.235 | 32.530 | 28.754 | 1.00 | 18.53 | A | O |
| ATOM | 325 | N   | LEU | A | 57 | 50.543 | 34.656 | 29.065 | 1.00 | 15.78 | A | N |
| ATOM | 326 | CA  | LEU | A | 57 | 51.619 | 35.252 | 28.300 | 1.00 | 13.13 | A | C |
| ATOM | 327 | CB  | LEU | A | 57 | 51.348 | 36.749 | 28.171 | 1.00 | 11.95 | A | C |
| ATOM | 328 | CG  | LEU | A | 57 | 51.232 | 37.364 | 26.771 | 1.00 | 13.21 | A | C |
| ATOM | 329 | CD1 | LEU | A | 57 | 50.535 | 36.422 | 25.805 | 1.00 | 10.11 | A | C |
| ATOM | 330 | CD2 | LEU | A | 57 | 50.491 | 38.694 | 26.888 | 1.00 | 10.01 | A | C |
| ATOM | 331 | C   | LEU | A | 57 | 52.922 | 34.973 | 29.074 | 1.00 | 12.23 | A | C |
| ATOM | 332 | O   | LEU | A | 57 | 53.974 | 34.734 | 28.477 | 1.00 | 9.19  | A | O |
| ATOM | 333 | N   | GLY | A | 58 | 52.824 | 34.984 | 30.404 | 1.00 | 11.88 | A | N |
| ATOM | 334 | CA  | GLY | A | 58 | 53.969 | 34.719 | 31.249 | 1.00 | 14.46 | A | C |
| ATOM | 335 | C   | GLY | A | 58 | 54.403 | 33.278 | 31.089 | 1.00 | 17.50 | A | C |
| ATOM | 336 | O   | GLY | A | 58 | 55.594 | 32.988 | 30.928 | 1.00 | 18.69 | A | O |
| ATOM | 337 | N   | GLN | A | 59 | 53.435 | 32.368 | 31.132 | 1.00 | 18.46 | A | N |
| ATOM | 338 | CA  | GLN | A | 59 | 53.728 | 30.958 | 30.975 | 1.00 | 19.45 | A | C |
| ATOM | 339 | CB  | GLN | A | 59 | 52.463 | 30.128 | 31.161 | 1.00 | 22.28 | A | C |
| ATOM | 340 | CG  | GLN | A | 59 | 51.877 | 30.260 | 32.549 | 1.00 | 24.82 | A | C |
| ATOM | 341 | CD  | GLN | A | 59 | 52.956 | 30.214 | 33.619 | 1.00 | 25.90 | A | C |
| ATOM | 342 | OE1 | GLN | A | 59 | 53.655 | 29.212 | 33.768 | 1.00 | 26.11 | A | O |
| ATOM | 343 | NE2 | GLN | A | 59 | 53.104 | 31.312 | 34.361 | 1.00 | 26.90 | A | N |
| ATOM | 344 | C   | GLN | A | 59 | 54.299 | 30.729 | 29.592 | 1.00 | 19.50 | A | C |
| ATOM | 345 | O   | GLN | A | 59 | 55.218 | 29.927 | 29.410 | 1.00 | 20.93 | A | O |
| ATOM | 346 | N   | TYR | A | 60 | 53.765 | 31.450 | 28.616 | 1.00 | 17.52 | A | N |
| ATOM | 347 | CA  | TYR | A | 60 | 54.239 | 31.315 | 27.252 | 1.00 | 18.33 | A | C |
| ATOM | 348 | CB  | TYR | A | 60 | 53.432 | 32.220 | 26.317 | 1.00 | 14.85 | A | C |
| ATOM | 349 | CG  | TYR | A | 60 | 53.776 | 32.069 | 24.845 | 1.00 | 15.47 | A | C |
| ATOM | 350 | CD1 | TYR | A | 60 | 53.279 | 31.001 | 24.089 | 1.00 | 14.63 | A | C |
| ATOM | 351 | CE1 | TYR | A | 60 | 53.581 | 30.873 | 22.716 | 1.00 | 11.14 | A | C |
| ATOM | 352 | CD2 | TYR | A | 60 | 54.594 | 33.007 | 24.196 | 1.00 | 15.88 | A | C |
| ATOM | 353 | CE2 | TYR | A | 60 | 54.902 | 32.886 | 22.826 | 1.00 | 13.26 | A | C |
| ATOM | 354 | CZ  | TYR | A | 60 | 54.391 | 31.818 | 22.096 | 1.00 | 12.81 | A | C |
| ATOM | 355 | OH  | TYR | A | 60 | 54.678 | 31.716 | 20.748 | 1.00 | 10.53 | A | O |
| ATOM | 356 | C   | TYR | A | 60 | 55.728 | 31.664 | 27.158 | 1.00 | 20.42 | A | C |
| ATOM | 357 | O   | TYR | A | 60 | 56.557 | 30.793 | 26.871 | 1.00 | 19.39 | A | O |
| ATOM | 358 | N   | ILE | A | 61 | 56.069 | 32.928 | 27.418 | 1.00 | 21.45 | A | N |
| ATOM | 359 | CA  | ILE | A | 61 | 57.458 | 33.361 | 27.319 | 1.00 | 23.11 | A | C |
| ATOM | 360 | CB  | ILE | A | 61 | 57.624 | 34.874 | 27.588 | 1.00 | 22.76 | A | C |
| ATOM | 361 | CG2 | ILE | A | 61 | 56.939 | 35.682 | 26.499 | 1.00 | 23.31 | A | C |
| ATOM | 362 | CG1 | ILE | A | 61 | 57.085 | 35.230 | 28.965 | 1.00 | 22.24 | A | C |
| ATOM | 363 | CD1 | ILE | A | 61 | 57.384 | 36.655 | 29.349 | 1.00 | 23.32 | A | C |
| ATOM | 364 | C   | ILE | A | 61 | 58.410 | 32.604 | 28.235 | 1.00 | 25.11 | A | C |
| ATOM | 365 | O   | ILE | A | 61 | 59.573 | 32.396 | 27.899 | 1.00 | 25.25 | A | O |
| ATOM | 366 | N   | MET | A | 62 | 57.931 | 32.186 | 29.393 | 1.00 | 27.56 | A | N |
| ATOM | 367 | CA  | MET | A | 62 | 58.797 | 31.452 | 30.293 | 1.00 | 30.23 | A | C |
| ATOM | 368 | CB  | MET | A | 62 | 58.158 | 31.371 | 31.680 | 1.00 | 32.88 | A | C |
| ATOM | 369 | CG  | MET | A | 62 | 59.042 | 30.734 | 32.738 | 1.00 | 34.56 | A | C |
| ATOM | 370 | SD  | MET | A | 62 | 58.113 | 29.481 | 33.637 | 1.00 | 39.80 | A | S |
| ATOM | 371 | CE  | MET | A | 62 | 58.272 | 28.115 | 32.471 | 1.00 | 35.55 | A | C |
| ATOM | 372 | C   | MET | A | 62 | 59.064 | 30.043 | 29.737 | 1.00 | 31.22 | A | C |
| ATOM | 373 | O   | MET | A | 62 | 60.218 | 29.656 | 29.513 | 1.00 | 30.54 | A | O |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 374 | N | THR | A | 63 | 57.997 | 29.291 | 29.483 | 1.00 | 31.07 | A | N |
|------|-----|-----|-----|---|----|--------|--------|--------|------|-------|---|---|
| ATOM | 375 | CA | THR | A | 63 | 58.150 | 27.931 | 28.976 | 1.00 | 31.77 | A | C |
| ATOM | 376 | CB | THR | A | 63 | 56.775 | 27.264 | 28.687 | 1.00 | 30.74 | A | C |
| ATOM | 377 | OG1 | THR | A | 63 | 56.009 | 28.092 | 27.808 | 1.00 | 31.02 | A | O |
| ATOM | 378 | CG2 | THR | A | 63 | 56.004 | 27.044 | 29.982 | 1.00 | 31.19 | A | C |
| ATOM | 379 | C | THR | A | 63 | 59.023 | 27.823 | 27.724 | 1.00 | 32.00 | A | C |
| ATOM | 380 | O | THR | A | 63 | 59.890 | 26.947 | 27.645 | 1.00 | 33.74 | A | O |
| ATOM | 381 | N | LYS | A | 64 | 58.797 | 28.697 | 26.747 | 1.00 | 30.45 | A | N |
| ATOM | 382 | CA | LYS | A | 64 | 59.578 | 28.655 | 25.522 | 1.00 | 29.14 | A | C |
| ATOM | 383 | CB | LYS | A | 64 | 58.783 | 29.262 | 24.363 | 1.00 | 28.22 | A | C |
| ATOM | 384 | CG | LYS | A | 64 | 57.581 | 28.437 | 23.947 | 1.00 | 26.54 | A | C |
| ATOM | 385 | CD | LYS | A | 64 | 56.870 | 29.029 | 22.738 | 1.00 | 26.08 | A | C |
| ATOM | 386 | CE | LYS | A | 64 | 57.757 | 29.029 | 21.514 | 1.00 | 26.73 | A | C |
| ATOM | 387 | NZ | LYS | A | 64 | 57.043 | 29.526 | 20.308 | 1.00 | 26.87 | A | N |
| ATOM | 388 | C | LYS | A | 64 | 60.926 | 29.358 | 25.674 | 1.00 | 29.64 | A | C |
| ATOM | 389 | O | LYS | A | 64 | 61.640 | 29.574 | 24.695 | 1.00 | 28.68 | A | O |
| ATOM | 390 | N | ARG | A | 65 | 61.264 | 29.716 | 26.909 | 1.00 | 31.08 | A | N |
| ATOM | 391 | CA | ARG | A | 65 | 62.541 | 30.359 | 27.206 | 1.00 | 31.77 | A | C |
| ATOM | 392 | CB | ARG | A | 65 | 63.624 | 29.278 | 27.281 | 1.00 | 32.61 | A | C |
| ATOM | 393 | CG | ARG | A | 65 | 63.422 | 28.319 | 28.456 | 1.00 | 36.27 | A | C |
| ATOM | 394 | CD | ARG | A | 65 | 64.128 | 26.980 | 28.268 | 1.00 | 38.75 | A | C |
| ATOM | 395 | NE | ARG | A | 65 | 63.951 | 26.108 | 29.433 | 1.00 | 41.50 | A | N |
| ATOM | 396 | CZ | ARG | A | 65 | 64.107 | 24.782 | 29.425 | 1.00 | 43.14 | A | C |
| ATOM | 397 | NH1 | ARG | A | 65 | 64.444 | 24.144 | 28.308 | 1.00 | 43.25 | A | N |
| ATOM | 398 | NH2 | ARG | A | 65 | 63.923 | 24.087 | 30.540 | 1.00 | 41.34 | A | N |
| ATOM | 399 | C | ARG | A | 65 | 62.931 | 31.442 | 26.193 | 1.00 | 30.62 | A | C |
| ATOM | 400 | O | ARG | A | 65 | 63.990 | 31.365 | 25.562 | 1.00 | 31.11 | A | O |
| ATOM | 401 | N | LEU | A | 66 | 62.069 | 32.447 | 26.043 | 1.00 | 27.85 | A | N |
| ATOM | 402 | CA | LEU | A | 66 | 62.315 | 33.554 | 25.117 | 1.00 | 24.57 | A | C |
| ATOM | 403 | CB | LEU | A | 66 | 60.996 | 34.080 | 24.535 | 1.00 | 21.73 | A | C |
| ATOM | 404 | CG | LEU | A | 66 | 60.195 | 33.192 | 23.588 | 1.00 | 18.58 | A | C |
| ATOM | 405 | CD1 | LEU | A | 66 | 58.917 | 33.893 | 23.171 | 1.00 | 16.38 | A | C |
| ATOM | 406 | CD2 | LEU | A | 66 | 61.039 | 32.882 | 22.373 | 1.00 | 16.78 | A | C |
| ATOM | 407 | C | LEU | A | 66 | 63.023 | 34.696 | 25.829 | 1.00 | 24.06 | A | C |
| ATOM | 408 | O | LEU | A | 66 | 63.334 | 35.715 | 25.221 | 1.00 | 22.74 | A | O |
| ATOM | 409 | N | TYR | A | 67 | 63.255 | 34.535 | 27.127 | 1.00 | 25.28 | A | N |
| ATOM | 410 | CA | TYR | A | 67 | 63.931 | 35.569 | 27.900 | 1.00 | 26.02 | A | C |
| ATOM | 411 | CB | TYR | A | 67 | 63.406 | 35.580 | 29.344 | 1.00 | 26.69 | A | C |
| ATOM | 412 | CG | TYR | A | 67 | 63.546 | 34.267 | 30.069 | 1.00 | 26.95 | A | C |
| ATOM | 413 | CD1 | TYR | A | 67 | 64.668 | 34.000 | 30.850 | 1.00 | 27.52 | A | C |
| ATOM | 414 | CE1 | TYR | A | 67 | 64.836 | 32.770 | 31.469 | 1.00 | 27.15 | A | C |
| ATOM | 415 | CD2 | TYR | A | 67 | 62.587 | 33.269 | 29.928 | 1.00 | 26.57 | A | C |
| ATOM | 416 | CE2 | TYR | A | 67 | 62.742 | 32.031 | 30.544 | 1.00 | 27.84 | A | C |
| ATOM | 417 | CZ | TYR | A | 67 | 63.875 | 31.787 | 31.312 | 1.00 | 27.23 | A | C |
| ATOM | 418 | OH | TYR | A | 67 | 64.068 | 30.554 | 31.888 | 1.00 | 24.32 | A | O |
| ATOM | 419 | C | TYR | A | 67 | 65.443 | 35.347 | 27.857 | 1.00 | 26.40 | A | C |
| ATOM | 420 | O | TYR | A | 67 | 65.917 | 34.216 | 27.828 | 1.00 | 25.07 | A | O |
| ATOM | 421 | N | ASP | A | 68 | 66.194 | 36.440 | 27.837 | 1.00 | 28.69 | A | N |
| ATOM | 422 | CA | ASP | A | 68 | 67.645 | 36.365 | 27.764 | 1.00 | 31.43 | A | C |
| ATOM | 423 | CB | ASP | A | 68 | 68.222 | 37.737 | 27.411 | 1.00 | 31.86 | A | C |
| ATOM | 424 | CG | ASP | A | 68 | 69.688 | 37.666 | 27.043 | 1.00 | 31.50 | A | C |
| ATOM | 425 | OD1 | ASP | A | 68 | 69.997 | 37.105 | 25.972 | 1.00 | 29.47 | A | O |
| ATOM | 426 | OD2 | ASP | A | 68 | 70.526 | 38.154 | 27.833 | 1.00 | 33.11 | A | O |
| ATOM | 427 | C | ASP | A | 68 | 68.313 | 35.848 | 29.035 | 1.00 | 33.44 | A | C |
| ATOM | 428 | O | ASP | A | 68 | 67.871 | 36.128 | 30.152 | 1.00 | 33.12 | A | O |
| ATOM | 429 | N | GLU | A | 69 | 69.399 | 35.105 | 28.845 | 1.00 | 36.37 | A | N |
| ATOM | 430 | CA | GLU | A | 69 | 70.152 | 34.529 | 29.950 | 1.00 | 39.07 | A | C |
| ATOM | 431 | CB | GLU | A | 69 | 71.214 | 33.558 | 29.420 | 1.00 | 42.56 | A | C |
| ATOM | 432 | CG | GLU | A | 69 | 70.627 | 32.277 | 28.851 | 1.00 | 48.37 | A | C |
| ATOM | 433 | CD | GLU | A | 69 | 69.565 | 31.677 | 29.766 | 1.00 | 51.95 | A | C |
| ATOM | 434 | OE1 | GLU | A | 69 | 69.848 | 31.514 | 30.974 | 1.00 | 54.24 | A | O |
| ATOM | 435 | OE2 | GLU | A | 69 | 68.449 | 31.370 | 29.281 | 1.00 | 54.25 | A | O |
| ATOM | 436 | C | GLU | A | 69 | 70.810 | 35.566 | 30.837 | 1.00 | 38.35 | A | C |
| ATOM | 437 | O | GLU | A | 69 | 70.695 | 35.506 | 32.057 | 1.00 | 38.84 | A | O |
| ATOM | 438 | N | LYS | A | 70 | 71.504 | 36.519 | 30.235 | 1.00 | 38.42 | A | N |
| ATOM | 439 | CA | LYS | A | 70 | 72.162 | 37.542 | 31.030 | 1.00 | 38.82 | A | C |
| ATOM | 440 | CB | LYS | A | 70 | 73.285 | 38.187 | 30.210 | 1.00 | 41.21 | A | C |
| ATOM | 441 | CG | LYS | A | 70 | 74.320 | 37.148 | 29.776 | 1.00 | 43.81 | A | C |
| ATOM | 442 | CD | LYS | A | 70 | 75.539 | 37.743 | 29.092 | 1.00 | 46.99 | A | C |
| ATOM | 443 | CE | LYS | A | 70 | 76.504 | 36.632 | 28.674 | 1.00 | 47.44 | A | C |
| ATOM | 444 | NZ | LYS | A | 70 | 77.794 | 37.156 | 28.143 | 1.00 | 48.71 | A | N |
| ATOM | 445 | C | LYS | A | 70 | 71.121 | 38.554 | 31.494 | 1.00 | 37.27 | A | C |
| ATOM | 446 | O | LYS | A | 70 | 70.854 | 38.673 | 32.690 | 1.00 | 36.92 | A | O |
| ATOM | 447 | N | GLN | A | 71 | 70.512 | 39.262 | 30.551 | 1.00 | 35.72 | A | N |
| ATOM | 448 | CA | GLN | A | 71 | 69.476 | 40.228 | 30.893 | 1.00 | 33.41 | A | C |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 449 | CB  | GLN | A | 71 | 69.478 | 41.365 | 29.878 | 1.00 | 34.05 | A | C |
|------|-----|-----|-----|---|----|--------|--------|--------|------|-------|---|---|
| ATOM | 450 | CG  | GLN | A | 71 | 70.781 | 42.116 | 29.818 | 1.00 | 35.15 | A | C |
| ATOM | 451 | CD  | GLN | A | 71 | 70.728 | 43.264 | 28.839 | 1.00 | 36.85 | A | C |
| ATOM | 452 | OE1 | GLN | A | 71 | 70.697 | 43.062 | 27.621 | 1.00 | 37.63 | A | O |
| ATOM | 453 | NE2 | GLN | A | 71 | 70.701 | 44.482 | 29.364 | 1.00 | 38.20 | A | N |
| ATOM | 454 | C   | GLN | A | 71 | 68.115 | 39.512 | 30.898 | 1.00 | 31.00 | A | C |
| ATOM | 455 | O   | GLN | A | 71 | 67.412 | 39.466 | 29.883 | 1.00 | 31.06 | A | O |
| ATOM | 456 | N   | GLN | A | 72 | 67.754 | 38.957 | 32.051 | 1.00 | 27.04 | A | N |
| ATOM | 457 | CA  | GLN | A | 72 | 66.505 | 38.216 | 32.200 | 1.00 | 23.77 | A | C |
| ATOM | 458 | CB  | GLN | A | 72 | 66.437 | 37.583 | 33.592 | 1.00 | 21.94 | A | C |
| ATOM | 459 | CG  | GLN | A | 72 | 65.172 | 36.783 | 33.877 | 1.00 | 19.04 | A | C |
| ATOM | 460 | CD  | GLN | A | 72 | 65.343 | 35.849 | 35.066 | 1.00 | 18.27 | A | C |
| ATOM | 461 | OE1 | GLN | A | 72 | 66.141 | 34.917 | 35.018 | 1.00 | 16.43 | A | O |
| ATOM | 462 | NE2 | GLN | A | 72 | 64.600 | 36.098 | 36.137 | 1.00 | 19.03 | A | N |
| ATOM | 463 | C   | GLN | A | 72 | 65.231 | 39.003 | 31.936 | 1.00 | 21.79 | A | C |
| ATOM | 464 | O   | GLN | A | 72 | 64.255 | 38.438 | 31.464 | 1.00 | 20.39 | A | O |
| ATOM | 465 | N   | HIS | A | 73 | 65.234 | 40.300 | 32.226 | 1.00 | 21.17 | A | N |
| ATOM | 466 | CA  | HIS | A | 73 | 64.039 | 41.103 | 32.004 | 1.00 | 19.46 | A | C |
| ATOM | 467 | CB  | HIS | A | 73 | 64.143 | 42.440 | 32.738 | 1.00 | 19.40 | A | C |
| ATOM | 468 | CG  | HIS | A | 73 | 65.242 | 43.328 | 32.244 | 1.00 | 21.41 | A | C |
| ATOM | 469 | CD2 | HIS | A | 73 | 66.560 | 43.376 | 32.556 | 1.00 | 21.24 | A | C |
| ATOM | 470 | ND1 | HIS | A | 73 | 65.029 | 44.339 | 31.331 | 1.00 | 22.42 | A | N |
| ATOM | 471 | CE1 | HIS | A | 73 | 66.167 | 44.972 | 31.104 | 1.00 | 21.05 | A | C |
| ATOM | 472 | NE2 | HIS | A | 73 | 67.111 | 44.406 | 31.836 | 1.00 | 21.25 | A | N |
| ATOM | 473 | C   | HIS | A | 73 | 63.772 | 41.338 | 30.526 | 1.00 | 20.37 | A | C |
| ATOM | 474 | O   | HIS | A | 73 | 62.667 | 41.747 | 30.156 | 1.00 | 19.89 | A | O |
| ATOM | 475 | N   | ILE | A | 74 | 64.774 | 41.083 | 29.681 | 1.00 | 19.94 | A | N |
| ATOM | 476 | CA  | ILE | A | 74 | 64.607 | 41.259 | 28.239 | 1.00 | 19.76 | A | C |
| ATOM | 477 | CB  | ILE | A | 74 | 65.942 | 41.605 | 27.523 | 1.00 | 20.27 | A | C |
| ATOM | 478 | CG2 | ILE | A | 74 | 65.699 | 41.745 | 26.022 | 1.00 | 18.27 | A | C |
| ATOM | 479 | CG1 | ILE | A | 74 | 66.536 | 42.906 | 28.072 | 1.00 | 22.09 | A | C |
| ATOM | 480 | CD1 | ILE | A | 74 | 65.704 | 44.127 | 27.810 | 1.00 | 22.98 | A | C |
| ATOM | 481 | C   | ILE | A | 74 | 64.060 | 39.970 | 27.611 | 1.00 | 19.56 | A | C |
| ATOM | 482 | O   | ILE | A | 74 | 64.555 | 38.875 | 27.885 | 1.00 | 19.09 | A | O |
| ATOM | 483 | N   | VAL | A | 75 | 63.045 | 40.115 | 26.764 | 1.00 | 17.84 | A | N |
| ATOM | 484 | CA  | VAL | A | 75 | 62.429 | 38.982 | 26.087 | 1.00 | 16.49 | A | C |
| ATOM | 485 | CB  | VAL | A | 75 | 60.918 | 38.928 | 26.388 | 1.00 | 14.74 | A | C |
| ATOM | 486 | CG1 | VAL | A | 75 | 60.245 | 37.892 | 25.529 | 1.00 | 13.12 | A | C |
| ATOM | 487 | CG2 | VAL | A | 75 | 60.707 | 38.602 | 27.852 | 1.00 | 15.39 | A | C |
| ATOM | 488 | C   | VAL | A | 75 | 62.650 | 39.136 | 24.588 | 1.00 | 17.78 | A | C |
| ATOM | 489 | O   | VAL | A | 75 | 62.249 | 40.140 | 23.995 | 1.00 | 17.51 | A | O |
| ATOM | 490 | N   | TYR | A | 76 | 63.302 | 38.150 | 23.977 | 1.00 | 17.97 | A | N |
| ATOM | 491 | CA  | TYR | A | 76 | 63.570 | 38.201 | 22.544 | 1.00 | 18.96 | A | C |
| ATOM | 492 | CB  | TYR | A | 76 | 64.958 | 37.622 | 22.229 | 1.00 | 20.36 | A | C |
| ATOM | 493 | CG  | TYR | A | 76 | 66.085 | 38.507 | 22.713 | 1.00 | 22.91 | A | C |
| ATOM | 494 | CD1 | TYR | A | 76 | 66.677 | 38.306 | 23.966 | 1.00 | 22.46 | A | C |
| ATOM | 495 | CE1 | TYR | A | 76 | 67.685 | 39.168 | 24.438 | 1.00 | 24.23 | A | C |
| ATOM | 496 | CD2 | TYR | A | 76 | 66.525 | 39.587 | 21.942 | 1.00 | 23.56 | A | C |
| ATOM | 497 | CE2 | TYR | A | 76 | 67.532 | 40.457 | 22.408 | 1.00 | 23.98 | A | C |
| ATOM | 498 | CZ  | TYR | A | 76 | 68.102 | 40.242 | 23.653 | 1.00 | 23.95 | A | C |
| ATOM | 499 | OH  | TYR | A | 76 | 69.065 | 41.112 | 24.120 | 1.00 | 24.89 | A | O |
| ATOM | 500 | C   | TYR | A | 76 | 62.499 | 37.438 | 21.801 | 1.00 | 17.43 | A | C |
| ATOM | 501 | O   | TYR | A | 76 | 62.277 | 36.273 | 22.074 | 1.00 | 18.57 | A | O |
| ATOM | 502 | N   | CYS | A | 77 | 61.841 | 38.094 | 20.850 | 1.00 | 19.17 | A | N |
| ATOM | 503 | CA  | CYS | A | 77 | 60.755 | 37.458 | 20.100 | 1.00 | 20.17 | A | C |
| ATOM | 504 | CB  | CYS | A | 77 | 59.410 | 37.978 | 20.628 | 1.00 | 18.05 | A | C |
| ATOM | 505 | SG  | CYS | A | 77 | 59.288 | 39.802 | 20.678 | 1.00 | 17.89 | A | S |
| ATOM | 506 | C   | CYS | A | 77 | 60.792 | 37.612 | 18.575 | 1.00 | 20.92 | A | C |
| ATOM | 507 | O   | CYS | A | 77 | 59.817 | 37.293 | 17.902 | 1.00 | 22.93 | A | O |
| ATOM | 508 | N   | SER | A | 78 | 61.904 | 38.083 | 18.027 | 1.00 | 21.73 | A | N |
| ATOM | 509 | CA  | SER | A | 78 | 62.002 | 38.261 | 16.582 | 1.00 | 23.67 | A | C |
| ATOM | 510 | CB  | SER | A | 78 | 63.369 | 38.828 | 16.209 | 1.00 | 23.31 | A | C |
| ATOM | 511 | OG  | SER | A | 78 | 64.394 | 38.058 | 16.804 | 1.00 | 24.57 | A | O |
| ATOM | 512 | C   | SER | A | 78 | 61.754 | 36.978 | 15.791 | 1.00 | 24.32 | A | C |
| ATOM | 513 | O   | SER | A | 78 | 61.341 | 37.039 | 14.632 | 1.00 | 24.57 | A | O |
| ATOM | 514 | N   | ASN | A | 79 | 62.003 | 35.824 | 16.403 | 1.00 | 23.65 | A | N |
| ATOM | 515 | CA  | ASN | A | 79 | 61.794 | 34.553 | 15.709 | 1.00 | 24.00 | A | C |
| ATOM | 516 | CB  | ASN | A | 79 | 63.081 | 33.709 | 15.694 | 1.00 | 24.75 | A | C |
| ATOM | 517 | CG  | ASN | A | 79 | 64.160 | 34.293 | 14.792 | 1.00 | 25.05 | A | C |
| ATOM | 518 | OD1 | ASN | A | 79 | 65.059 | 34.994 | 15.254 | 1.00 | 25.04 | A | O |
| ATOM | 519 | ND2 | ASN | A | 79 | 64.064 | 34.015 | 13.495 | 1.00 | 25.70 | A | N |
| ATOM | 520 | C   | ASN | A | 79 | 60.668 | 33.742 | 16.343 | 1.00 | 23.53 | A | C |
| ATOM | 521 | O   | ASN | A | 79 | 60.753 | 32.512 | 16.451 | 1.00 | 23.89 | A | O |
| ATOM | 522 | N   | ASP | A | 80 | 59.612 | 34.437 | 16.747 | 1.00 | 21.43 | A | N |
| ATOM | 523 | CA  | ASP | A | 80 | 58.472 | 33.797 | 17.381 | 1.00 | 20.47 | A | C |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 524 | CB  | ASP | A | 80 | 58.658 | 33.789 | 18.907 | 1.00 | 20.36 | A | C |
|------|-----|-----|-----|---|----|--------|--------|--------|------|-------|---|---|
| ATOM | 525 | CG  | ASP | A | 80 | 57.567 | 33.022 | 19.626 | 1.00 | 20.02 | A | C |
| ATOM | 526 | OD1 | ASP | A | 80 | 57.870 | 31.966 | 20.215 | 1.00 | 20.17 | A | O |
| ATOM | 527 | OD2 | ASP | A | 80 | 56.404 | 33.469 | 19.597 | 1.00 | 20.97 | A | O |
| ATOM | 528 | C   | ASP | A | 80 | 57.193 | 34.542 | 17.024 | 1.00 | 20.46 | A | C |
| ATOM | 529 | O   | ASP | A | 80 | 57.218 | 35.752 | 16.742 | 1.00 | 20.32 | A | O |
| ATOM | 530 | N   | LEU | A | 81 | 56.078 | 33.812 | 17.034 | 1.00 | 19.74 | A | N |
| ATOM | 531 | CA  | LEU | A | 81 | 54.766 | 34.379 | 16.725 | 1.00 | 19.05 | A | C |
| ATOM | 532 | CB  | LEU | A | 81 | 53.685 | 33.351 | 17.047 | 1.00 | 20.17 | A | C |
| ATOM | 533 | CG  | LEU | A | 81 | 52.228 | 33.802 | 17.023 | 1.00 | 23.86 | A | C |
| ATOM | 534 | CD1 | LEU | A | 81 | 51.870 | 34.357 | 15.650 | 1.00 | 24.25 | A | C |
| ATOM | 535 | CD2 | LEU | A | 81 | 51.339 | 32.608 | 17.378 | 1.00 | 24.57 | A | C |
| ATOM | 536 | C   | LEU | A | 81 | 54.537 | 35.657 | 17.539 | 1.00 | 17.50 | A | C |
| ATOM | 537 | O   | LEU | A | 81 | 54.022 | 36.656 | 17.027 | 1.00 | 15.88 | A | O |
| ATOM | 538 | N   | LEU | A | 82 | 54.948 | 35.604 | 18.805 | 1.00 | 14.87 | A | N |
| ATOM | 539 | CA  | LEU | A | 82 | 54.821 | 36.718 | 19.734 | 1.00 | 12.91 | A | C |
| ATOM | 540 | CB  | LEU | A | 82 | 55.545 | 36.376 | 21.049 | 1.00 | 11.35 | A | C |
| ATOM | 541 | CG  | LEU | A | 82 | 55.603 | 37.457 | 22.138 | 1.00 | 10.75 | A | C |
| ATOM | 542 | CD1 | LEU | A | 82 | 54.187 | 37.899 | 22.505 | 1.00 | 10.31 | A | C |
| ATOM | 543 | CD2 | LEU | A | 82 | 56.344 | 36.922 | 23.354 | 1.00 | 9.38  | A | C |
| ATOM | 544 | C   | LEU | A | 82 | 55.374 | 38.023 | 19.157 | 1.00 | 12.97 | A | C |
| ATOM | 545 | O   | LEU | A | 82 | 54.738 | 39.083 | 19.263 | 1.00 | 9.83  | A | O |
| ATOM | 546 | N   | GLY | A | 83 | 56.561 | 37.944 | 18.557 | 1.00 | 12.95 | A | N |
| ATOM | 547 | CA  | GLY | A | 83 | 57.163 | 39.129 | 17.980 | 1.00 | 15.06 | A | C |
| ATOM | 548 | C   | GLY | A | 83 | 56.238 | 39.761 | 16.951 | 1.00 | 16.77 | A | C |
| ATOM | 549 | O   | GLY | A | 83 | 56.060 | 40.980 | 16.919 | 1.00 | 15.55 | A | O |
| ATOM | 550 | N   | ASP | A | 84 | 55.635 | 38.924 | 16.112 | 1.00 | 18.65 | A | N |
| ATOM | 551 | CA  | ASP | A | 84 | 54.742 | 39.412 | 15.078 | 1.00 | 21.41 | A | C |
| ATOM | 552 | CB  | ASP | A | 84 | 54.347 | 38.272 | 14.141 | 1.00 | 25.41 | A | C |
| ATOM | 553 | CG  | ASP | A | 84 | 55.547 | 37.604 | 13.507 | 1.00 | 28.55 | A | C |
| ATOM | 554 | OD1 | ASP | A | 84 | 56.489 | 38.335 | 13.100 | 1.00 | 27.94 | A | O |
| ATOM | 555 | OD2 | ASP | A | 84 | 55.539 | 36.354 | 13.412 | 1.00 | 30.30 | A | O |
| ATOM | 556 | C   | ASP | A | 84 | 53.491 | 40.055 | 15.650 | 1.00 | 21.92 | A | C |
| ATOM | 557 | O   | ASP | A | 84 | 53.065 | 41.104 | 15.173 | 1.00 | 22.99 | A | O |
| ATOM | 558 | N   | LEU | A | 85 | 52.906 | 39.428 | 16.666 | 1.00 | 21.04 | A | N |
| ATOM | 559 | CA  | LEU | A | 85 | 51.697 | 39.955 | 17.288 | 1.00 | 22.00 | A | C |
| ATOM | 560 | CB  | LEU | A | 85 | 51.092 | 38.915 | 18.240 | 1.00 | 21.98 | A | C |
| ATOM | 561 | CG  | LEU | A | 85 | 50.821 | 37.544 | 17.609 | 1.00 | 23.19 | A | C |
| ATOM | 562 | CD1 | LEU | A | 85 | 50.177 | 36.593 | 18.628 | 1.00 | 20.96 | A | C |
| ATOM | 563 | CD2 | LEU | A | 85 | 49.923 | 37.734 | 16.390 | 1.00 | 22.60 | A | C |
| ATOM | 564 | C   | LEU | A | 85 | 51.979 | 41.258 | 18.039 | 1.00 | 21.67 | A | C |
| ATOM | 565 | O   | LEU | A | 85 | 51.122 | 42.143 | 18.102 | 1.00 | 20.70 | A | O |
| ATOM | 566 | N   | PHE | A | 86 | 53.182 | 41.376 | 18.597 | 1.00 | 21.86 | A | N |
| ATOM | 567 | CA  | PHE | A | 86 | 53.565 | 42.579 | 19.338 | 1.00 | 20.91 | A | C |
| ATOM | 568 | CB  | PHE | A | 86 | 54.531 | 42.224 | 20.470 | 1.00 | 19.44 | A | C |
| ATOM | 569 | CG  | PHE | A | 86 | 53.852 | 41.763 | 21.741 | 1.00 | 16.86 | A | C |
| ATOM | 570 | CD1 | PHE | A | 86 | 52.508 | 41.381 | 21.742 | 1.00 | 15.83 | A | C |
| ATOM | 571 | CD2 | PHE | A | 86 | 54.564 | 41.710 | 22.936 | 1.00 | 14.83 | A | C |
| ATOM | 572 | CE1 | PHE | A | 86 | 51.878 | 40.952 | 22.914 | 1.00 | 14.04 | A | C |
| ATOM | 573 | CE2 | PHE | A | 86 | 53.949 | 41.281 | 24.119 | 1.00 | 18.00 | A | C |
| ATOM | 574 | CZ  | PHE | A | 86 | 52.596 | 40.902 | 24.105 | 1.00 | 16.08 | A | C |
| ATOM | 575 | C   | PHE | A | 86 | 54.211 | 43.604 | 18.416 | 1.00 | 22.21 | A | C |
| ATOM | 576 | O   | PHE | A | 86 | 54.233 | 44.797 | 18.714 | 1.00 | 23.98 | A | O |
| ATOM | 577 | N   | GLY | A | 87 | 54.728 | 43.140 | 17.284 | 1.00 | 22.25 | A | N |
| ATOM | 578 | CA  | GLY | A | 87 | 55.360 | 44.055 | 16.356 | 1.00 | 20.93 | A | C |
| ATOM | 579 | C   | GLY | A | 87 | 56.711 | 44.578 | 16.820 | 1.00 | 20.93 | A | C |
| ATOM | 580 | O   | GLY | A | 87 | 57.055 | 45.731 | 16.534 | 1.00 | 22.00 | A | O |
| ATOM | 581 | N   | VAL | A | 88 | 57.471 | 43.752 | 17.542 | 1.00 | 18.42 | A | N |
| ATOM | 582 | CA  | VAL | A | 88 | 58.802 | 44.136 | 18.014 | 1.00 | 16.75 | A | C |
| ATOM | 583 | CB  | VAL | A | 88 | 58.791 | 44.793 | 19.420 | 1.00 | 16.55 | A | C |
| ATOM | 584 | CG1 | VAL | A | 88 | 57.951 | 46.054 | 19.405 | 1.00 | 15.93 | A | C |
| ATOM | 585 | CG2 | VAL | A | 88 | 58.312 | 43.795 | 20.462 | 1.00 | 13.35 | A | C |
| ATOM | 586 | C   | VAL | A | 88 | 59.695 | 42.911 | 18.100 | 1.00 | 16.74 | A | C |
| ATOM | 587 | O   | VAL | A | 88 | 59.215 | 41.792 | 18.273 | 1.00 | 16.22 | A | O |
| ATOM | 588 | N   | PRO | A | 89 | 61.013 | 43.114 | 17.978 | 1.00 | 16.36 | A | N |
| ATOM | 589 | CD  | PRO | A | 89 | 61.636 | 44.398 | 17.606 | 1.00 | 17.10 | A | C |
| ATOM | 590 | CA  | PRO | A | 89 | 62.013 | 42.042 | 18.040 | 1.00 | 16.05 | A | C |
| ATOM | 591 | CB  | PRO | A | 89 | 63.221 | 42.659 | 17.344 | 1.00 | 15.83 | A | C |
| ATOM | 592 | CG  | PRO | A | 89 | 63.124 | 44.096 | 17.747 | 1.00 | 18.07 | A | C |
| ATOM | 593 | C   | PRO | A | 89 | 62.322 | 41.623 | 19.476 | 1.00 | 16.21 | A | C |
| ATOM | 594 | O   | PRO | A | 89 | 62.832 | 40.522 | 19.715 | 1.00 | 15.73 | A | O |
| ATOM | 595 | N   | SER | A | 90 | 62.009 | 42.505 | 20.425 | 1.00 | 15.13 | A | N |
| ATOM | 596 | CA  | SER | A | 90 | 62.243 | 42.232 | 21.843 | 1.00 | 14.02 | A | C |
| ATOM | 597 | CB  | SER | A | 90 | 63.738 | 42.128 | 22.130 | 1.00 | 12.56 | A | C |
| ATOM | 598 | OG  | SER | A | 90 | 64.336 | 43.403 | 21.986 | 1.00 | 13.74 | A | O |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 599 | C   | SER | A | 90 | 61.652 | 43.350 | 22.702 | 1.00 | 12.89 | A | C |
|------|-----|-----|-----|---|----|--------|--------|--------|------|-------|---|---|
| ATOM | 600 | O   | SER | A | 90 | 61.331 | 44.422 | 22.192 | 1.00 | 12.05 | A | O |
| ATOM | 601 | N   | PHE | A | 91 | 61.517 | 43.091 | 24.001 | 1.00 | 11.19 | A | N |
| ATOM | 602 | CA  | PHE | A | 91 | 60.972 | 44.069 | 24.926 | 1.00 | 11.45 | A | C |
| ATOM | 603 | CB  | PHE | A | 91 | 59.439 | 44.173 | 24.759 | 1.00 | 10.33 | A | C |
| ATOM | 604 | CG  | PHE | A | 91 | 58.705 | 42.895 | 25.039 | 1.00 | 8.05  | A | C |
| ATOM | 605 | CD1 | PHE | A | 91 | 58.263 | 42.598 | 26.325 | 1.00 | 7.52  | A | C |
| ATOM | 606 | CD2 | PHE | A | 91 | 58.496 | 41.961 | 24.024 | 1.00 | 7.09  | A | C |
| ATOM | 607 | CE1 | PHE | A | 91 | 57.620 | 41.373 | 26.605 | 1.00 | 7.90  | A | C |
| ATOM | 608 | CE2 | PHE | A | 91 | 57.859 | 40.739 | 24.287 | 1.00 | 7.31  | A | C |
| ATOM | 609 | CZ  | PHE | A | 91 | 57.419 | 40.445 | 25.588 | 1.00 | 7.15  | A | C |
| ATOM | 610 | C   | PHE | A | 91 | 61.327 | 43.737 | 26.373 | 1.00 | 13.35 | A | C |
| ATOM | 611 | O   | PHE | A | 91 | 61.795 | 42.632 | 26.685 | 1.00 | 12.34 | A | O |
| ATOM | 612 | N   | SER | A | 92 | 61.102 | 44.708 | 27.254 | 1.00 | 14.78 | A | N |
| ATOM | 613 | CA  | SER | A | 92 | 61.398 | 44.547 | 28.667 | 1.00 | 16.74 | A | C |
| ATOM | 614 | CB  | SER | A | 92 | 62.086 | 45.809 | 29.203 | 1.00 | 15.00 | A | C |
| ATOM | 615 | OG  | SER | A | 92 | 62.293 | 45.719 | 30.607 | 1.00 | 15.51 | A | O |
| ATOM | 616 | C   | SER | A | 92 | 60.148 | 44.254 | 29.499 | 1.00 | 18.09 | A | C |
| ATOM | 617 | O   | SER | A | 92 | 59.156 | 44.978 | 29.422 | 1.00 | 17.05 | A | O |
| ATOM | 618 | N   | VAL | A | 93 | 60.206 | 43.189 | 30.295 | 1.00 | 19.76 | A | N |
| ATOM | 619 | CA  | VAL | A | 93 | 59.094 | 42.822 | 31.163 | 1.00 | 21.70 | A | C |
| ATOM | 620 | CB  | VAL | A | 93 | 59.322 | 41.442 | 31.866 | 1.00 | 22.34 | A | C |
| ATOM | 621 | CG1 | VAL | A | 93 | 59.380 | 40.329 | 30.828 | 1.00 | 22.82 | A | C |
| ATOM | 622 | CG2 | VAL | A | 93 | 60.606 | 41.462 | 32.683 | 1.00 | 20.47 | A | C |
| ATOM | 623 | C   | VAL | A | 93 | 58.891 | 43.884 | 32.239 | 1.00 | 22.48 | A | C |
| ATOM | 624 | O   | VAL | A | 93 | 58.089 | 43.702 | 33.140 | 1.00 | 24.56 | A | O |
| ATOM | 625 | N   | LYS | A | 94 | 59.618 | 44.991 | 32.146 | 1.00 | 24.37 | A | N |
| ATOM | 626 | CA  | LYS | A | 94 | 59.494 | 46.078 | 33.121 | 1.00 | 26.51 | A | C |
| ATOM | 627 | CB  | LYS | A | 94 | 60.873 | 46.623 | 33.515 | 1.00 | 27.71 | A | C |
| ATOM | 628 | CG  | LYS | A | 94 | 61.581 | 45.888 | 34.659 | 1.00 | 30.96 | A | C |
| ATOM | 629 | CD  | LYS | A | 94 | 62.965 | 46.516 | 34.914 | 1.00 | 33.87 | A | C |
| ATOM | 630 | CE  | LYS | A | 94 | 63.695 | 45.915 | 36.127 | 1.00 | 35.49 | A | C |
| ATOM | 631 | NZ  | LYS | A | 94 | 65.052 | 46.534 | 36.343 | 1.00 | 35.43 | A | N |
| ATOM | 632 | C   | LYS | A | 94 | 58.655 | 47.232 | 32.579 | 1.00 | 26.44 | A | C |
| ATOM | 633 | O   | LYS | A | 94 | 58.156 | 48.054 | 33.342 | 1.00 | 27.30 | A | O |
| ATOM | 634 | N   | GLU | A | 95 | 58.522 | 47.305 | 31.259 | 1.00 | 25.84 | A | N |
| ATOM | 635 | CA  | GLU | A | 95 | 57.747 | 48.361 | 30.620 | 1.00 | 25.31 | A | C |
| ATOM | 636 | CB  | GLU | A | 95 | 58.317 | 48.651 | 29.231 | 1.00 | 26.45 | A | C |
| ATOM | 637 | CG  | GLU | A | 95 | 59.798 | 49.016 | 29.200 | 1.00 | 28.64 | A | C |
| ATOM | 638 | CD  | GLU | A | 95 | 60.081 | 50.452 | 29.615 | 1.00 | 30.17 | A | C |
| ATOM | 639 | OE1 | GLU | A | 95 | 59.138 | 51.277 | 29.622 | 1.00 | 31.51 | A | O |
| ATOM | 640 | OE2 | GLU | A | 95 | 61.257 | 50.759 | 29.917 | 1.00 | 28.42 | A | O |
| ATOM | 641 | C   | GLU | A | 95 | 56.286 | 47.904 | 30.500 | 1.00 | 24.66 | A | C |
| ATOM | 642 | O   | GLU | A | 95 | 55.776 | 47.667 | 29.398 | 1.00 | 22.08 | A | O |
| ATOM | 643 | N   | HIS | A | 96 | 55.619 | 47.799 | 31.647 | 1.00 | 24.62 | A | N |
| ATOM | 644 | CA  | HIS | A | 96 | 54.234 | 47.348 | 31.702 | 1.00 | 26.26 | A | C |
| ATOM | 645 | CB  | HIS | A | 96 | 53.694 | 47.452 | 33.132 | 1.00 | 27.90 | A | C |
| ATOM | 646 | CG  | HIS | A | 96 | 54.457 | 46.635 | 34.128 | 1.00 | 30.90 | A | C |
| ATOM | 647 | CD2 | HIS | A | 96 | 55.784 | 46.395 | 34.257 | 1.00 | 31.52 | A | C |
| ATOM | 648 | ND1 | HIS | A | 96 | 53.844 | 45.963 | 35.164 | 1.00 | 32.30 | A | N |
| ATOM | 649 | CE1 | HIS | A | 96 | 54.761 | 45.345 | 35.887 | 1.00 | 32.43 | A | C |
| ATOM | 650 | NE2 | HIS | A | 96 | 55.947 | 45.591 | 35.358 | 1.00 | 32.16 | A | N |
| ATOM | 651 | C   | HIS | A | 96 | 53.279 | 48.052 | 30.747 | 1.00 | 26.13 | A | C |
| ATOM | 652 | O   | HIS | A | 96 | 52.436 | 47.400 | 30.136 | 1.00 | 26.36 | A | O |
| ATOM | 653 | N   | ARG | A | 97 | 53.403 | 49.370 | 30.618 | 1.00 | 25.66 | A | N |
| ATOM | 654 | CA  | ARG | A | 97 | 52.522 | 50.123 | 29.728 | 1.00 | 25.19 | A | C |
| ATOM | 655 | CB  | ARG | A | 97 | 52.708 | 51.639 | 29.953 | 1.00 | 25.74 | A | C |
| ATOM | 656 | CG  | ARG | A | 97 | 51.909 | 52.562 | 29.031 | 1.00 | 24.90 | A | C |
| ATOM | 657 | CD  | ARG | A | 97 | 50.440 | 52.148 | 28.919 | 1.00 | 27.96 | A | C |
| ATOM | 658 | NE  | ARG | A | 97 | 49.677 | 52.294 | 30.157 | 1.00 | 29.51 | A | N |
| ATOM | 659 | CZ  | ARG | A | 97 | 48.450 | 51.804 | 30.337 | 1.00 | 29.81 | A | C |
| ATOM | 660 | NH1 | ARG | A | 97 | 47.849 | 51.133 | 29.359 | 1.00 | 31.04 | A | N |
| ATOM | 661 | NH2 | ARG | A | 97 | 47.817 | 51.986 | 31.489 | 1.00 | 27.76 | A | N |
| ATOM | 662 | C   | ARG | A | 97 | 52.758 | 49.745 | 28.262 | 1.00 | 24.39 | A | C |
| ATOM | 663 | O   | ARG | A | 97 | 51.805 | 49.623 | 27.497 | 1.00 | 25.23 | A | O |
| ATOM | 664 | N   | LYS | A | 98 | 54.010 | 49.547 | 27.865 | 1.00 | 23.55 | A | N |
| ATOM | 665 | CA  | LYS | A | 98 | 54.288 | 49.166 | 26.480 | 1.00 | 23.84 | A | C |
| ATOM | 666 | CB  | LYS | A | 98 | 55.800 | 49.167 | 26.195 | 1.00 | 25.86 | A | C |
| ATOM | 667 | CG  | LYS | A | 98 | 56.406 | 50.558 | 26.039 | 1.00 | 29.53 | A | C |
| ATOM | 668 | CD  | LYS | A | 98 | 57.892 | 50.512 | 25.693 | 1.00 | 31.47 | A | C |
| ATOM | 669 | CE  | LYS | A | 98 | 58.519 | 51.909 | 25.794 | 1.00 | 33.99 | A | C |
| ATOM | 670 | NZ  | LYS | A | 98 | 59.989 | 51.918 | 25.509 | 1.00 | 34.37 | A | N |
| ATOM | 671 | C   | LYS | A | 98 | 53.708 | 47.779 | 26.170 | 1.00 | 23.22 | A | C |
| ATOM | 672 | O   | LYS | A | 98 | 53.150 | 47.563 | 25.091 | 1.00 | 21.35 | A | O |
| ATOM | 673 | N   | ILE | A | 99 | 53.844 | 46.846 | 27.115 | 1.00 | 21.20 | A | N |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 674 | CA  | ILE | A | 99  | 53.323 | 45.496 | 26.938 | 1.00 | 20.16 A | C |
| ---- | --- | --- | --- | - | --- | ------ | ------ | ------ | ---- | ------- | - |
| ATOM | 675 | CB  | ILE | A | 99  | 53.723 | 44.584 | 28.130 | 1.00 | 18.26 A | C |
| ATOM | 676 | CG2 | ILE | A | 99  | 52.911 | 43.290 | 28.108 | 1.00 | 16.58 A | C |
| ATOM | 677 | CG1 | ILE | A | 99  | 55.227 | 44.283 | 28.063 | 1.00 | 16.19 A | C |
| ATOM | 678 | CD1 | ILE | A | 99  | 55.764 | 43.539 | 29.255 | 1.00 | 12.79 A | C |
| ATOM | 679 | C   | ILE | A | 99  | 51.799 | 45.545 | 26.802 | 1.00 | 21.79 A | C |
| ATOM | 680 | O   | ILE | A | 99  | 51.217 | 44.909 | 25.919 | 1.00 | 21.34 A | O |
| ATOM | 681 | N   | TYR | A | 100 | 51.156 | 46.316 | 27.672 | 1.00 | 23.34 A | N |
| ATOM | 682 | CA  | TYR | A | 100 | 49.706 | 46.457 | 27.639 | 1.00 | 24.14 A | C |
| ATOM | 683 | CB  | TYR | A | 100 | 49.243 | 47.387 | 28.763 | 1.00 | 25.12 A | C |
| ATOM | 684 | CG  | TYR | A | 100 | 48.602 | 46.651 | 29.911 | 1.00 | 28.22 A | C |
| ATOM | 685 | CD1 | TYR | A | 100 | 49.336 | 45.739 | 30.681 | 1.00 | 28.65 A | C |
| ATOM | 686 | CE1 | TYR | A | 100 | 48.734 | 45.008 | 31.700 | 1.00 | 28.51 A | C |
| ATOM | 687 | CD2 | TYR | A | 100 | 47.248 | 46.817 | 30.196 | 1.00 | 28.65 A | C |
| ATOM | 688 | CE2 | TYR | A | 100 | 46.632 | 46.088 | 31.215 | 1.00 | 29.38 A | C |
| ATOM | 689 | CZ  | TYR | A | 100 | 47.380 | 45.187 | 31.957 | 1.00 | 29.62 A | C |
| ATOM | 690 | OH  | TYR | A | 100 | 46.766 | 44.450 | 32.938 | 1.00 | 31.04 A | O |
| ATOM | 691 | C   | TYR | A | 100 | 49.154 | 46.960 | 26.299 | 1.00 | 25.10 A | C |
| ATOM | 692 | O   | TYR | A | 100 | 48.138 | 46.446 | 25.812 | 1.00 | 25.32 A | O |
| ATOM | 693 | N   | THR | A | 101 | 49.798 | 47.956 | 25.693 | 1.00 | 23.58 A | N |
| ATOM | 694 | CA  | THR | A | 101 | 49.269 | 48.447 | 24.434 | 1.00 | 24.54 A | C |
| ATOM | 695 | CB  | THR | A | 101 | 49.683 | 49.926 | 24.162 | 1.00 | 25.48 A | C |
| ATOM | 696 | OG1 | THR | A | 101 | 51.085 | 50.021 | 23.920 | 1.00 | 26.87 A | O |
| ATOM | 697 | CG2 | THR | A | 101 | 49.330 | 50.786 | 25.361 | 1.00 | 27.33 A | C |
| ATOM | 698 | C   | THR | A | 101 | 49.627 | 47.539 | 23.259 | 1.00 | 23.52 A | C |
| ATOM | 699 | O   | THR | A | 101 | 49.034 | 47.642 | 22.188 | 1.00 | 24.28 A | O |
| ATOM | 700 | N   | MET | A | 102 | 50.585 | 46.636 | 23.450 | 1.00 | 22.80 A | N |
| ATOM | 701 | CA  | MET | A | 102 | 50.921 | 45.697 | 22.377 | 1.00 | 20.40 A | C |
| ATOM | 702 | CB  | MET | A | 102 | 52.321 | 45.109 | 22.567 | 1.00 | 15.37 A | C |
| ATOM | 703 | CG  | MET | A | 102 | 53.403 | 46.131 | 22.321 | 1.00 | 14.03 A | C |
| ATOM | 704 | SD  | MET | A | 102 | 55.075 | 45.483 | 22.349 | 1.00 | 11.93 A | S |
| ATOM | 705 | CE  | MET | A | 102 | 55.294 | 45.184 | 24.125 | 1.00 | 10.87 A | C |
| ATOM | 706 | C   | MET | A | 102 | 49.863 | 44.592 | 22.392 | 1.00 | 19.65 A | C |
| ATOM | 707 | O   | MET | A | 102 | 49.528 | 44.017 | 21.356 | 1.00 | 19.47 A | O |
| ATOM | 708 | N   | ILE | A | 103 | 49.338 | 44.319 | 23.580 | 1.00 | 18.90 A | N |
| ATOM | 709 | CA  | ILE | A | 103 | 48.300 | 43.321 | 23.764 | 1.00 | 21.34 A | C |
| ATOM | 710 | CB  | ILE | A | 103 | 48.131 | 42.966 | 25.273 | 1.00 | 20.40 A | C |
| ATOM | 711 | CG2 | ILE | A | 103 | 46.835 | 42.185 | 25.497 | 1.00 | 19.03 A | C |
| ATOM | 712 | CG1 | ILE | A | 103 | 49.339 | 42.156 | 25.750 | 1.00 | 19.84 A | C |
| ATOM | 713 | CD1 | ILE | A | 103 | 49.457 | 42.046 | 27.259 | 1.00 | 18.82 A | C |
| ATOM | 714 | C   | ILE | A | 103 | 46.985 | 43.896 | 23.228 | 1.00 | 24.13 A | C |
| ATOM | 715 | O   | ILE | A | 103 | 46.189 | 43.185 | 22.612 | 1.00 | 24.18 A | O |
| ATOM | 716 | N   | TYR | A | 104 | 46.775 | 45.192 | 23.461 | 1.00 | 27.06 A | N |
| ATOM | 717 | CA  | TYR | A | 104 | 45.566 | 45.886 | 23.016 | 1.00 | 29.10 A | C |
| ATOM | 718 | CB  | TYR | A | 104 | 45.608 | 47.344 | 23.491 | 1.00 | 30.33 A | C |
| ATOM | 719 | CG  | TYR | A | 104 | 45.205 | 47.494 | 24.940 | 1.00 | 30.58 A | C |
| ATOM | 720 | CD1 | TYR | A | 104 | 45.775 | 48.469 | 25.754 | 1.00 | 29.56 A | C |
| ATOM | 721 | CE1 | TYR | A | 104 | 45.415 | 48.584 | 27.095 | 1.00 | 29.30 A | C |
| ATOM | 722 | CD2 | TYR | A | 104 | 44.259 | 46.638 | 25.502 | 1.00 | 31.51 A | C |
| ATOM | 723 | CE2 | TYR | A | 104 | 43.894 | 46.746 | 26.836 | 1.00 | 31.90 A | C |
| ATOM | 724 | CZ  | TYR | A | 104 | 44.476 | 47.718 | 27.625 | 1.00 | 30.22 A | C |
| ATOM | 725 | OH  | TYR | A | 104 | 44.113 | 47.801 | 28.947 | 1.00 | 32.03 A | O |
| ATOM | 726 | C   | TYR | A | 104 | 45.321 | 45.824 | 21.510 | 1.00 | 29.49 A | C |
| ATOM | 727 | O   | TYR | A | 104 | 44.173 | 45.769 | 21.067 | 1.00 | 30.07 A | O |
| ATOM | 728 | N   | ARG | A | 105 | 46.397 | 45.831 | 20.731 | 1.00 | 30.44 A | N |
| ATOM | 729 | CA  | ARG | A | 105 | 46.291 | 45.757 | 19.281 | 1.00 | 31.09 A | C |
| ATOM | 730 | CB  | ARG | A | 105 | 47.561 | 46.288 | 18.614 | 1.00 | 32.59 A | C |
| ATOM | 731 | CG  | ARG | A | 105 | 47.624 | 47.803 | 18.491 | 1.00 | 35.48 A | C |
| ATOM | 732 | CD  | ARG | A | 105 | 48.761 | 48.212 | 17.567 | 1.00 | 38.68 A | C |
| ATOM | 733 | NE  | ARG | A | 105 | 50.069 | 47.877 | 18.129 | 1.00 | 41.14 A | N |
| ATOM | 734 | CZ  | ARG | A | 105 | 50.806 | 48.712 | 18.859 | 1.00 | 42.11 A | C |
| ATOM | 735 | NH1 | ARG | A | 105 | 50.368 | 49.942 | 19.117 | 1.00 | 41.27 A | N |
| ATOM | 736 | NH2 | ARG | A | 105 | 51.984 | 48.317 | 19.333 | 1.00 | 42.61 A | N |
| ATOM | 737 | C   | ARG | A | 105 | 46.059 | 44.317 | 18.845 | 1.00 | 31.15 A | C |
| ATOM | 738 | O   | ARG | A | 105 | 45.919 | 44.040 | 17.649 | 1.00 | 30.58 A | O |
| ATOM | 739 | N   | ASN | A | 106 | 46.029 | 43.403 | 19.814 | 1.00 | 30.35 A | N |
| ATOM | 740 | CA  | ASN | A | 106 | 45.797 | 41.992 | 19.523 | 1.00 | 31.38 A | C |
| ATOM | 741 | CB  | ASN | A | 106 | 46.927 | 41.120 | 20.069 | 1.00 | 30.13 A | C |
| ATOM | 742 | CG  | ASN | A | 106 | 48.164 | 41.186 | 19.219 | 1.00 | 30.74 A | C |
| ATOM | 743 | OD1 | ASN | A | 106 | 48.957 | 42.126 | 19.327 | 1.00 | 30.89 A | O |
| ATOM | 744 | ND2 | ASN | A | 106 | 48.335 | 40.193 | 18.346 | 1.00 | 30.12 A | N |
| ATOM | 745 | C   | ASN | A | 106 | 44.480 | 41.497 | 20.087 | 1.00 | 32.04 A | C |
| ATOM | 746 | O   | ASN | A | 106 | 44.309 | 40.303 | 20.324 | 1.00 | 30.99 A | O |
| ATOM | 747 | N   | LEU | A | 107 | 43.543 | 42.409 | 20.297 | 1.00 | 34.74 A | N |
| ATOM | 748 | CA  | LEU | A | 107 | 42.257 | 42.009 | 20.834 | 1.00 | 39.45 A | C |

TABLE 2-continued

HDM2 protein (SEQ ID NO: 2) complexed with
compound 876273 ([8-Chloro-3-(4-chloro-phenyl)-7-iodo-2,5-
dioxo-1,2,3,5-tetrahydro-benzo[e][1,4]diazepin-4-yl]-(4-chloro-
phenyl)-acetic acid)

| ATOM | 749 | CB | LEU | A | 107 | 42.392 | 41.716 | 22.335 | 1.00 | 39.46 | A | C |
|---|---|---|---|---|---|---|---|---|---|---|---|---|
| ATOM | 750 | CG | LEU | A | 107 | 43.091 | 42.738 | 23.238 | 1.00 | 38.61 | A | C |
| ATOM | 751 | CD1 | LEU | A | 107 | 42.333 | 44.055 | 23.242 | 1.00 | 38.52 | A | C |
| ATOM | 752 | CD2 | LEU | A | 107 | 43.181 | 42.176 | 24.647 | 1.00 | 37.16 | A | C |
| ATOM | 753 | C | LEU | A | 107 | 41.157 | 43.025 | 20.604 | 1.00 | 42.25 | A | C |
| ATOM | 754 | O | LEU | A | 107 | 41.327 | 43.993 | 19.859 | 1.00 | 42.75 | A | O |
| ATOM | 755 | N | VAL | A | 108 | 40.021 | 42.778 | 21.245 | 1.00 | 46.00 | A | N |
| ATOM | 756 | CA | VAL | A | 108 | 38.859 | 43.653 | 21.163 | 1.00 | 49.43 | A | C |
| ATOM | 757 | CB | VAL | A | 108 | 37.823 | 43.129 | 20.149 | 1.00 | 48.08 | A | C |
| ATOM | 758 | CG1 | VAL | A | 108 | 37.030 | 44.290 | 19.594 | 1.00 | 48.02 | A | C |
| ATOM | 759 | CG2 | VAL | A | 108 | 38.509 | 42.343 | 19.040 | 1.00 | 46.78 | A | C |
| ATOM | 760 | C | VAL | A | 108 | 38.216 | 43.671 | 22.555 | 1.00 | 53.19 | A | C |
| ATOM | 761 | O | VAL | A | 108 | 37.589 | 42.690 | 22.966 | 1.00 | 52.78 | A | O |
| ATOM | 762 | N | VAL | A | 109 | 38.386 | 44.778 | 23.280 | 1.00 | 57.34 | A | N |
| ATOM | 763 | CA | VAL | A | 109 | 37.829 | 44.921 | 24.630 | 1.00 | 61.10 | A | C |
| ATOM | 764 | CB | VAL | A | 109 | 38.035 | 46.351 | 25.191 | 1.00 | 61.46 | A | C |
| ATOM | 765 | CG1 | VAL | A | 109 | 37.715 | 46.367 | 26.683 | 1.00 | 61.63 | A | C |
| ATOM | 766 | CG2 | VAL | A | 109 | 39.458 | 46.830 | 24.928 | 1.00 | 62.28 | A | C |
| ATOM | 767 | C | VAL | A | 109 | 36.326 | 44.631 | 24.662 | 1.00 | 63.47 | A | C |
| ATOM | 768 | O | VAL | A | 109 | 35.527 | 45.410 | 24.131 | 1.00 | 63.73 | A | O |
| ATOM | 769 | N | VAL | A | 110 | 35.947 | 43.518 | 25.293 | 1.00 | 65.46 | A | N |
| ATOM | 770 | CA | VAL | A | 110 | 34.542 | 43.127 | 25.392 | 1.00 | 67.21 | A | C |
| ATOM | 771 | CB | VAL | A | 110 | 34.366 | 41.919 | 26.365 | 1.00 | 66.97 | A | C |
| ATOM | 772 | CG1 | VAL | A | 110 | 32.939 | 41.374 | 26.283 | 1.00 | 67.04 | A | C |
| ATOM | 773 | CG2 | VAL | A | 110 | 35.371 | 40.825 | 26.033 | 1.00 | 66.24 | A | C |
| ATOM | 774 | C | VAL | A | 110 | 33.697 | 44.309 | 25.898 | 1.00 | 69.20 | A | C |
| ATOM | 775 | O | VAL | A | 110 | 34.287 | 45.249 | 26.488 | 1.00 | 69.94 | A | O |
| ATOM | 776 | OXT | VAL | A | 110 | 32.456 | 44.284 | 25.705 | 1.00 | 70.58 | A | O |
| ATOM | 777 | C1 | CID | A | 1 | 55.200 | 42.184 | 33.980 | 1.00 | 21.13 | INH1 | C |
| ATOM | 778 | C2 | CID | A | 1 | 54.610 | 43.160 | 33.125 | 1.00 | 21.31 | INH1 | C |
| ATOM | 779 | C3 | CID | A | 1 | 53.194 | 43.197 | 32.974 | 1.00 | 21.72 | INH1 | C |
| ATOM | 780 | C4 | CID | A | 1 | 52.372 | 42.284 | 33.667 | 1.00 | 21.74 | INH1 | C |
| ATOM | 781 | C5 | CID | A | 1 | 52.953 | 41.311 | 34.515 | 1.00 | 21.42 | INH1 | C |
| ATOM | 782 | C6 | CID | A | 1 | 54.387 | 41.238 | 34.692 | 1.00 | 22.49 | INH1 | C |
| ATOM | 783 | C7 | CID | A | 1 | 55.092 | 40.168 | 35.590 | 1.00 | 23.66 | INH1 | C |
| ATOM | 784 | C8 | CID | A | 1 | 54.267 | 39.594 | 36.800 | 1.00 | 25.69 | INH1 | C |
| ATOM | 785 | O1 | CID | A | 1 | 54.677 | 38.706 | 37.544 | 1.00 | 29.01 | INH1 | O |
| ATOM | 786 | O2 | CID | A | 1 | 53.229 | 40.347 | 37.224 | 1.00 | 30.64 | INH1 | O |
| ATOM | 787 | N1 | CID | A | 1 | 55.591 | 39.038 | 34.674 | 1.00 | 19.99 | INH1 | N |
| ATOM | 788 | C9 | CID | A | 1 | 54.593 | 38.352 | 33.801 | 1.00 | 18.95 | INH1 | C |
| ATOM | 789 | C10 | CID | A | 1 | 54.631 | 38.684 | 32.289 | 1.00 | 18.04 | INH1 | C |
| ATOM | 790 | C11 | CID | A | 1 | 55.647 | 39.488 | 31.665 | 1.00 | 17.01 | INH1 | C |
| ATOM | 791 | C12 | CID | A | 1 | 55.614 | 39.775 | 30.286 | 1.00 | 16.97 | INH1 | C |
| ATOM | 792 | C13 | CID | A | 1 | 54.563 | 39.261 | 29.507 | 1.00 | 17.64 | INH1 | C |
| ATOM | 793 | CL1 | CID | A | 1 | 54.498 | 39.606 | 27.865 | 1.00 | 14.96 | INH1 | CL |
| ATOM | 794 | C14 | CID | A | 1 | 53.550 | 38.464 | 30.083 | 1.00 | 18.96 | INH1 | C |
| ATOM | 795 | C15 | CID | A | 1 | 53.586 | 38.180 | 31.458 | 1.00 | 17.55 | INH1 | C |
| ATOM | 796 | C16 | CID | A | 1 | 54.559 | 36.817 | 34.087 | 1.00 | 18.08 | INH1 | C |
| ATOM | 797 | O3 | CID | A | 1 | 53.499 | 36.278 | 34.423 | 1.00 | 18.82 | INH1 | O |
| ATOM | 798 | N2 | CID | A | 1 | 55.695 | 36.036 | 33.977 | 1.00 | 16.78 | INH1 | N |
| ATOM | 799 | C17 | CID | A | 1 | 57.002 | 36.408 | 33.618 | 1.00 | 17.03 | INH1 | C |
| ATOM | 800 | C18 | CID | A | 1 | 57.616 | 37.644 | 33.943 | 1.00 | 16.70 | INH1 | C |
| ATOM | 801 | C19 | CID | A | 1 | 56.972 | 38.734 | 34.754 | 1.00 | 19.45 | INH1 | C |
| ATOM | 802 | O4 | CID | A | 1 | 57.728 | 39.367 | 35.532 | 1.00 | 18.52 | INH1 | O |
| ATOM | 803 | C20 | CID | A | 1 | 58.948 | 37.897 | 33.495 | 1.00 | 17.26 | INH1 | C |
| ATOM | 804 | C21 | CID | A | 1 | 59.660 | 36.940 | 32.750 | 1.00 | 18.91 | INH1 | C |
| ATOM | 805 | I1 | CID | A | 1 | 61.599 | 37.431 | 32.161 | 1.00 | 19.64 | INH1 | I |
| ATOM | 806 | C22 | CID | A | 1 | 59.069 | 35.711 | 32.436 | 1.00 | 17.86 | INH1 | C |
| ATOM | 807 | C23 | CID | A | 1 | 57.742 | 35.435 | 32.859 | 1.00 | 17.23 | INH1 | C |
| ATOM | 808 | CL2 | CID | A | 1 | 52.462 | 44.354 | 31.946 | 1.00 | 20.99 | INH1 | CL |
| ATOM | 809 | CL3 | CID | A | 1 | 59.915 | 34.517 | 31.548 | 1.00 | 20.31 | INH1 | CL |
| END | | | | | | | | | | | | |

TABLE 3

Superimposed: trigonal and tetragonal crystal forms
of HDM2 of SEQ ID NO: 2.

REMARK  Superimposed on/xray1/hmdm2/PDB/M338437.pdb
REMARK  The 19 atoms have an RMS distance of    0.249 A
REMARK  RMS delta B =    6.724 A2
REMARK  Estimated RMSD for 2 random proteins  =    5.398 A TABLE 3-continued Superimposed: trigonal and tetragonal crystal forms of HDM2 of SEQ ID NO: 2.

| | | | | | | | | | |
|---|---|---|---|---|---|---|---|---|---|
| REMARK | Relative RMSD | | | | = | 0.04621 | | | |
| REMARK | Normalised RMSD (100) | | | | = | 1.471 A | | | |
| REMARK | coordinates from restrained individual B-factor refinement | | | | | | | | |
| REMARK | refinement resolution: 25-2.6 A | | | | | | | | |
| REMARK | starting  r= 0.2563 free_r= 0.2787 | | | | | | | | |
| REMARK | final   r= 0.2553 free_r= 0.2761 | | | | | | | | |
| REMARK | B rmsd for bonded mainchain atoms= 1.483   target= 1.5 | | | | | | | | |
| REMARK | B rmsd for bonded sidechain atoms= 1.740   target= 2.0 | | | | | | | | |
| REMARK | B rmsd for angle mainchain atoms= 2.593   target= 2.0 | | | | | | | | |
| REMARK | B rmsd for angle sidechain atoms= 2.780   target= 2.5 | | | | | | | | |
| REMARK | rweight= 0.1000 (with wa= 3.71696) | | | | | | | | |
| REMARK | target= mlf  steps= 30 | | | | | | | | |
| REMARK | sg= P4(3)2(1)2 a= 54.3 b= 54.3 c= 83.3 alpha= 90 beta= 90 gamma =90 | | | | | | | | |
| REMARK | parameter file 1  : MSI_CNX_TOPPAR:protein_rep.param | | | | | | | | |
| REMARK | parameter file 2  : ../cid.par | | | | | | | | |
| REMARK | molecular structure file: recycle.psf | | | | | | | | |
| REMARK | input coordinates: anneal_9.pdb | | | | | | | | |
| REMARK | reflection file= ../M876273_2_P43212.cv | | | | | | | | |
| REMARK | ncs= none | | | | | | | | |
| REMARK | B-correction resolution: 6.0-2.6 | | | | | | | | |
| REMARK | initial B-factor correction applied to fobs : | | | | | | | | |
| REMARK |   B11=   −1.189 B22=   −1.189 B33=   2.379 | | | | | | | | |
| REMARK |   B12=   0.000 B13=   0.000 B23=   0.000 | | | | | | | | |
| REMARK | B-factor correction applied to coordinate array B:   −0.119 | | | | | | | | |
| REMARK | bulk solvent: (Mask) density level = 0.341945 e/A^3, B-factor= 22.3925 A^2 | | | | | | | | |
| REMARK | reflections with |Fobs|/sigma_F < 0.0 rejected | | | | | | | | |
| REMARK | reflections with |Fobs| > 10000 * rms(Fobs) rejected | | | | | | | | |
| REMARK | theoretical total number of refl. in resol. range:   4173 (100.0%) | | | | | | | | |
| REMARK | number of unobserved reflections (no entry or |F| = 0):9 (0.2%) | | | | | | | | |
| REMARK | number of reflections rejected:    0 (0.0%) | | | | | | | | |
| REMARK | total number of reflections used:    4164 (99.8%) | | | | | | | | |
| REMARK | number of reflections in working set: 3737 (89.6%) | | | | | | | | |
| REMARK | number of reflections in test set: 427 (10.2%) | | | | | | | | |
| REMARK | FILENAME="bindividual.pdb" | | | | | | | | |
| REMARK | Written by CNX VERSION: 2000.12 | | | | | | | | |
| ATOM | 1 | C | GLY | A | 16 | 48.607 | 19.990 | 25.187 | 1.00 68.15 A |
| ATOM | 2 | O | GLY | A | 16 | 48.239 | 21.106 | 24.797 | 1.00 68.22 A |
| ATOM | 3 | N | GLY | A | 16 | 47.838 | 17.646 | 24.774 | 1.00 67.11 A |
| ATOM | 4 | CA | GLY | A | 16 | 47.594 | 18.911 | 25.537 | 1.00 67.90 A |
| ATOM | 5 | N | SER | A | 17 | 49.889 | 19.652 | 25.332 | 1.00 67.05 A |
| ATOM | 6 | CA | SER | A | 17 | 50.986 | 20.568 | 25.025 | 1.00 64.73 A |
| ATOM | 7 | CB | SER | A | 17 | 51.581 | 21.155 | 26.312 | 1.00 65.01 A |
| ATOM | 8 | OG | SER | A | 17 | 50.639 | 21.978 | 26.989 | 1.00 63.84 A |
| ATOM | 9 | C | SER | A | 17 | 52.053 | 19.794 | 24.258 | 1.00 62.82 A |
| ATOM | 10 | O | SER | A | 17 | 52.921 | 20.382 | 23.611 | 1.00 62.75 A |
| ATOM | 11 | N | GLN | A | 18 | 51.970 | 18.468 | 24.343 | 1.00 60.52 A |
| ATOM | 12 | CA | GLN | A | 18 | 52.895 | 17.577 | 23.647 | 1.00 57.89 A |
| ATOM | 13 | CB | GLN | A | 18 | 52.794 | 16.161 | 24.210 | 1.00 57.50 A |
| ATOM | 14 | CG | GLN | A | 18 | 53.480 | 15.955 | 25.534 | 1.00 57.38 A |
| ATOM | 15 | CD | GLN | A | 18 | 53.377 | 14.514 | 25.999 | 1.00 58.16 A |
| ATOM | 16 | OE1 | GLN | A | 18 | 53.614 | 13.581 | 25.228 | 1.00 56.84 A |
| ATOM | 17 | NE2 | GLN | A | 18 | 53.027 | 14.327 | 27.268 | 1.00 58.44 A |
| ATOM | 18 | C | GLN | A | 18 | 52.532 | 17.529 | 22.169 | 1.00 55.87 A |
| ATOM | 19 | O | GLN | A | 18 | 53.378 | 17.267 | 21.312 | 1.00 55.83 A |
| ATOM | 20 | N | ILE | A | 19 | 51.256 | 17.781 | 21.889 | 1.00 52.87 A |
| ATOM | 21 | CA | ILE | A | 19 | 50.727 | 17.763 | 20.532 | 1.00 50.05 A |
| ATOM | 22 | CB | ILE | A | 19 | 49.408 | 16.940 | 20.476 | 1.00 48.06 A |
| ATOM | 23 | CG2 | ILE | A | 19 | 48.886 | 16.873 | 19.053 | 1.00 48.17 A |
| ATOM | 24 | CG1 | ILE | A | 19 | 49.638 | 15.526 | 21.020 | 1.00 45.44 A |
| ATOM | 25 | CD1 | ILE | A | 19 | 50.552 | 14.677 | 20.180 | 1.00 43.26 A |
| ATOM | 26 | C | ILE | A | 19 | 50.443 | 19.194 | 20.066 | 1.00 49.72 A |
| ATOM | 27 | O | ILE | A | 19 | 50.014 | 20.036 | 20.856 | 1.00 49.03 A |
| ATOM | 28 | N | PRO | A | 20 | 50.702 | 19.490 | 18.777 | 1.00 49.57 A |
| ATOM | 29 | CD | PRO | A | 20 | 51.486 | 18.667 | 17.841 | 1.00 49.58 A |
| ATOM | 30 | CA | PRO | A | 20 | 50.469 | 20.822 | 18.209 | 1.00 49.39 A |
| ATOM | 31 | CB | PRO | A | 20 | 51.058 | 20.705 | 16.808 | 1.00 48.67 A |
| ATOM | 32 | CG | PRO | A | 20 | 52.153 | 19.717 | 16.991 | 1.00 48.94 A |
| ATOM | 33 | C | PRO | A | 20 | 48.982 | 21.187 | 18.171 | 1.00 49.97 A |
| ATOM | 34 | O | PRO | A | 20 | 48.138 | 20.358 | 17.819 | 1.00 50.18 A |
| ATOM | 35 | N | ALA | A | 21 | 48.672 | 22.429 | 18.534 | 1.00 49.45 A |
| ATOM | 36 | CA | ALA | A | 21 | 47.296 | 22.913 | 18.540 | 1.00 49.81 A |
| ATOM | 37 | CB | ALA | A | 21 | 47.270 | 24.405 | 18.880 | 1.00 49.85 A |
| ATOM | 38 | C | ALA | A | 21 | 46.613 | 22.670 | 17.189 | 1.00 49.65 A |

TABLE 3-continued

Superimposed: trigonal and tetragonal crystal forms of HDM2 of SEQ ID NO: 2.

| ATOM | 39 | O | ALA | A | 21 | 45.483 | 22.179 | 17.128 | 1.00 | 49.33 | A |
|---|---|---|---|---|---|---|---|---|---|---|---|
| ATOM | 40 | N | SER | A | 22 | 47.302 | 23.022 | 16.107 | 1.00 | 48.76 | A |
| ATOM | 41 | CA | SER | A | 22 | 46.753 | 22.830 | 14.774 | 1.00 | 47.75 | A |
| ATOM | 42 | CB | SER | A | 22 | 47.823 | 23.134 | 13.721 | 1.00 | 47.15 | A |
| ATOM | 43 | OG | SER | A | 22 | 49.001 | 22.382 | 13.964 | 1.00 | 48.43 | A |
| ATOM | 44 | C | SER | A | 22 | 46.254 | 21.391 | 14.628 | 1.00 | 46.34 | A |
| ATOM | 45 | O | SER | A | 22 | 45.195 | 21.143 | 14.045 | 1.00 | 45.89 | A |
| ATOM | 46 | N | GLU | A | 23 | 47.012 | 20.445 | 15.172 | 1.00 | 44.68 | A |
| ATOM | 47 | CA | GLU | A | 23 | 46.632 | 19.041 | 15.098 | 1.00 | 43.25 | A |
| ATOM | 48 | CB | GLU | A | 23 | 47.804 | 18.149 | 15.472 | 1.00 | 42.16 | A |
| ATOM | 49 | CG | GLU | A | 23 | 47.513 | 16.684 | 15.303 | 1.00 | 40.86 | A |
| ATOM | 50 | CD | GLU | A | 23 | 48.777 | 15.866 | 15.250 | 1.00 | 40.82 | A |
| ATOM | 51 | OE1 | GLU | A | 23 | 49.695 | 16.146 | 16.045 | 1.00 | 41.52 | A |
| ATOM | 52 | OE2 | GLU | A | 23 | 48.856 | 14.942 | 14.418 | 1.00 | 41.56 | A |
| ATOM | 53 | C | GLU | A | 23 | 45.453 | 18.760 | 16.013 | 1.00 | 42.01 | A |
| ATOM | 54 | O | GLU | A | 23 | 44.505 | 18.087 | 15.625 | 1.00 | 42.32 | A |
| ATOM | 55 | N | GLN | A | 24 | 45.512 | 19.278 | 17.229 | 1.00 | 41.29 | A |
| ATOM | 56 | CA | GLN | A | 24 | 44.413 | 19.089 | 18.154 | 1.00 | 42.07 | A |
| ATOM | 57 | CB | GLN | A | 24 | 44.666 | 19.872 | 19.450 | 1.00 | 41.13 | A |
| ATOM | 58 | CG | GLN | A | 24 | 45.643 | 19.180 | 20.391 | 1.00 | 42.57 | A |
| ATOM | 59 | CD | GLN | A | 24 | 45.950 | 19.981 | 21.650 | 1.00 | 43.91 | A |
| ATOM | 60 | OE1 | GLN | A | 24 | 45.068 | 20.622 | 22.233 | 1.00 | 44.84 | A |
| ATOM | 61 | NE2 | GLN | A | 24 | 47.205 | 19.931 | 22.085 | 1.00 | 43.17 | A |
| ATOM | 62 | C | GLN | A | 24 | 43.140 | 19.589 | 17.475 | 1.00 | 43.32 | A |
| ATOM | 63 | O | GLN | A | 24 | 42.035 | 19.139 | 17.790 | 1.00 | 43.40 | A |
| ATOM | 64 | N | GLU | A | 25 | 43.310 | 20.505 | 16.521 | 1.00 | 44.62 | A |
| ATOM | 65 | CA | GLU | A | 25 | 42.183 | 21.095 | 15.795 | 1.00 | 44.92 | A |
| ATOM | 66 | CB | GLU | A | 25 | 42.507 | 22.543 | 15.406 | 1.00 | 48.33 | A |
| ATOM | 67 | CG | GLU | A | 25 | 43.121 | 23.398 | 16.516 | 1.00 | 53.04 | A |
| ATOM | 68 | CD | GLU | A | 25 | 42.283 | 23.449 | 17.787 | 1.00 | 55.79 | A |
| ATOM | 69 | OE1 | GLU | A | 25 | 42.680 | 24.180 | 18.720 | 1.00 | 57.11 | A |
| ATOM | 70 | OE2 | GLU | A | 25 | 41.236 | 22.766 | 17.864 | 1.00 | 57.84 | A |
| ATOM | 71 | C | GLU | A | 25 | 41.731 | 20.336 | 14.541 | 1.00 | 42.75 | A |
| ATOM | 72 | O | GLU | A | 25 | 40.616 | 20.547 | 14.059 | 1.00 | 42.62 | A |
| ATOM | 73 | N | THR | A | 26 | 42.587 | 19.467 | 14.008 | 1.00 | 40.18 | A |
| ATOM | 74 | CA | THR | A | 26 | 42.237 | 18.692 | 12.814 | 1.00 | 38.13 | A |
| ATOM | 75 | CB | THR | A | 26 | 43.254 | 17.547 | 12.563 | 1.00 | 37.92 | A |
| ATOM | 76 | OG1 | THR | A | 26 | 44.589 | 18.059 | 12.647 | 1.00 | 37.02 | A |
| ATOM | 77 | CG2 | THR | A | 26 | 43.047 | 16.942 | 11.187 | 1.00 | 36.76 | A |
| ATOM | 78 | C | THR | A | 26 | 40.847 | 18.074 | 12.983 | 1.00 | 36.79 | A |
| ATOM | 79 | O | THR | A | 26 | 40.511 | 17.574 | 14.054 | 1.00 | 36.47 | A |
| ATOM | 80 | N | LEU | A | 27 | 40.036 | 18.128 | 11.931 | 1.00 | 36.63 | A |
| ATOM | 81 | CA | LEU | A | 27 | 38.686 | 17.559 | 11.973 | 1.00 | 35.77 | A |
| ATOM | 82 | CB | LEU | A | 27 | 37.739 | 18.336 | 11.052 | 1.00 | 36.16 | A |
| ATOM | 83 | CG | LEU | A | 27 | 36.264 | 18.393 | 11.488 | 1.00 | 38.05 | A |
| ATOM | 84 | CD1 | LEU | A | 27 | 36.120 | 19.331 | 12.692 | 1.00 | 36.12 | A |
| ATOM | 85 | CD2 | LEU | A | 27 | 35.394 | 18.895 | 10.328 | 1.00 | 38.41 | A |
| ATOM | 86 | C | LEU | A | 27 | 38.796 | 16.110 | 11.505 | 1.00 | 34.52 | A |
| ATOM | 87 | O | LEU | A | 27 | 39.467 | 15.818 | 10.513 | 1.00 | 33.72 | A |
| ATOM | 88 | N | VAL | A | 28 | 38.135 | 15.204 | 12.218 | 1.00 | 33.53 | A |
| ATOM | 89 | CA | VAL | A | 28 | 38.214 | 13.787 | 11.886 | 1.00 | 32.88 | A |
| ATOM | 90 | CB | VAL | A | 28 | 39.207 | 13.071 | 12.850 | 1.00 | 32.86 | A |
| ATOM | 91 | CG1 | VAL | A | 28 | 40.592 | 13.685 | 12.724 | 1.00 | 31.21 | A |
| ATOM | 92 | CG2 | VAL | A | 28 | 38.726 | 13.204 | 14.292 | 1.00 | 33.40 | A |
| ATOM | 93 | C | VAL | A | 28 | 36.876 | 13.044 | 11.919 | 1.00 | 31.29 | A |
| ATOM | 94 | O | VAL | A | 28 | 35.910 | 13.501 | 12.527 | 1.00 | 30.99 | A |
| ATOM | 95 | N | ARG | A | 29 | 36.841 | 11.897 | 11.248 | 1.00 | 29.80 | A |
| ATOM | 96 | CA | ARG | A | 29 | 35.655 | 11.054 | 11.198 | 1.00 | 28.94 | A |
| ATOM | 97 | CB | ARG | A | 29 | 35.174 | 10.876 | 9.762 | 1.00 | 33.14 | A |
| ATOM | 98 | CG | ARG | A | 29 | 34.296 | 11.991 | 9.254 | 1.00 | 38.54 | A |
| ATOM | 99 | CD | ARG | A | 29 | 34.036 | 11.830 | 7.767 | 1.00 | 43.39 | A |
| ATOM | 100 | NE | ARG | A | 29 | 33.084 | 12.828 | 7.296 | 1.00 | 47.28 | A |
| ATOM | 101 | CZ | ARG | A | 29 | 31.772 | 12.741 | 7.477 | 1.00 | 49.30 | A |
| ATOM | 102 | NH1 | ARG | A | 29 | 31.257 | 11.691 | 8.110 | 1.00 | 49.75 | A |
| ATOM | 103 | NH2 | ARG | A | 29 | 30.978 | 13.716 | 7.049 | 1.00 | 50.29 | A |
| ATOM | 104 | C | ARG | A | 29 | 35.994 | 9.688 | 11.762 | 1.00 | 26.43 | A |
| ATOM | 105 | O | ARG | A | 29 | 36.680 | 8.895 | 11.110 | 1.00 | 25.41 | A |
| ATOM | 106 | N | PRO | A | 30 | 35.528 | 9.397 | 12.989 | 1.00 | 24.69 | A |
| ATOM | 107 | CD | PRO | A | 30 | 34.749 | 10.285 | 13.869 | 1.00 | 23.43 | A |
| ATOM | 108 | CA | PRO | A | 30 | 35.784 | 8.108 | 13.647 | 1.00 | 23.00 | A |
| ATOM | 109 | CB | PRO | A | 30 | 35.223 | 8.308 | 15.053 | 1.00 | 21.72 | A |
| ATOM | 110 | CG | PRO | A | 30 | 35.147 | 9.792 | 15.218 | 1.00 | 22.48 | A |
| ATOM | 111 | C | PRO | A | 30 | 35.023 | 7.001 | 12.923 | 1.00 | 22.20 | A |
| ATOM | 112 | O | PRO | A | 30 | 33.945 | 7.243 | 12.382 | 1.00 | 22.27 | A |
| ATOM | 113 | N | LYS | A | 31 | 35.580 | 5.796 | 12.910 | 1.00 | 21.65 | A |
| ATOM | 114 | CA | LYS | A | 31 | 34.909 | 4.658 | 12.286 | 1.00 | 19.51 | A |
| ATOM | 115 | CB | LYS | A | 31 | 35.901 | 3.519 | 12.056 | 1.00 | 19.68 | A |

TABLE 3-continued

Superimposed: trigonal and tetragonal crystal forms of HDM2 of SEQ ID NO: 2.

| | | | | | | | | | | | |
|---|---|---|---|---|---|---|---|---|---|---|---|
| ATOM | 116 | CG | LYS | A | 31 | 37.058 | 3.899 | 11.150 | 1.00 | 20.82 | A |
| ATOM | 117 | CD | LYS | A | 31 | 38.006 | 2.724 | 10.976 | 1.00 | 22.74 | A |
| ATOM | 118 | CE | LYS | A | 31 | 39.161 | 3.040 | 10.019 | 1.00 | 20.68 | A |
| ATOM | 119 | NZ | LYS | A | 31 | 40.000 | 1.818 | 9.826 | 1.00 | 21.75 | A |
| ATOM | 120 | C | LYS | A | 31 | 33.795 | 4.225 | 13.249 | 1.00 | 18.36 | A |
| ATOM | 121 | O | LYS | A | 31 | 33.793 | 4.605 | 14.422 | 1.00 | 17.38 | A |
| ATOM | 122 | N | PRO | A | 32 | 32.848 | 3.406 | 12.774 | 1.00 | 17.15 | A |
| ATOM | 123 | CD | PRO | A | 32 | 32.886 | 2.665 | 11.501 | 1.00 | 16.30 | A |
| ATOM | 124 | CA | PRO | A | 32 | 31.729 | 2.939 | 13.595 | 1.00 | 16.70 | A |
| ATOM | 125 | CB | PRO | A | 32 | 31.178 | 1.775 | 12.778 | 1.00 | 16.53 | A |
| ATOM | 126 | CG | PRO | A | 32 | 31.463 | 2.200 | 11.378 | 1.00 | 16.35 | A |
| ATOM | 127 | C | PRO | A | 32 | 32.023 | 2.548 | 15.048 | 1.00 | 16.73 | A |
| ATOM | 128 | O | PRO | A | 32 | 31.343 | 3.014 | 15.967 | 1.00 | 17.12 | A |
| ATOM | 129 | N | LEU | A | 33 | 33.016 | 1.692 | 15.264 | 1.00 | 14.62 | A |
| ATOM | 130 | CA | LEU | A | 33 | 33.324 | 1.265 | 16.619 | 1.00 | 13.59 | A |
| ATOM | 131 | CB | LEU | A | 33 | 34.332 | 0.110 | 16.594 | 1.00 | 15.36 | A |
| ATOM | 132 | CG | LEU | A | 33 | 33.787 | -1.301 | 16.896 | 1.00 | 13.91 | A |
| ATOM | 133 | CD1 | LEU | A | 33 | 32.250 | -1.320 | 16.992 | 1.00 | 13.51 | A |
| ATOM | 134 | CD2 | LEU | A | 33 | 34.270 | -2.239 | 15.822 | 1.00 | 8.87 | A |
| ATOM | 135 | C | LEU | A | 33 | 33.800 | 2.397 | 17.516 | 1.00 | 13.14 | A |
| ATOM | 136 | O | LEU | A | 33 | 33.281 | 2.560 | 18.608 | 1.00 | 12.37 | A |
| ATOM | 137 | N | LEU | A | 34 | 34.786 | 3.176 | 17.082 | 1.00 | 14.58 | A |
| ATOM | 138 | CA | LEU | A | 34 | 35.238 | 4.305 | 17.895 | 1.00 | 13.84 | A |
| ATOM | 139 | CB | LEU | A | 34 | 36.430 | 5.015 | 17.246 | 1.00 | 13.73 | A |
| ATOM | 140 | CG | LEU | A | 34 | 36.892 | 6.346 | 17.861 | 1.00 | 10.65 | A |
| ATOM | 141 | CD1 | LEU | A | 34 | 37.437 | 6.120 | 19.247 | 1.00 | 9.38 | A |
| ATOM | 142 | CD2 | LEU | A | 34 | 37.951 | 6.971 | 16.986 | 1.00 | 11.47 | A |
| ATOM | 143 | C | LEU | A | 34 | 34.073 | 5.294 | 18.042 | 1.00 | 15.75 | A |
| ATOM | 144 | O | LEU | A | 34 | 33.877 | 5.874 | 19.103 | 1.00 | 16.50 | A |
| ATOM | 145 | N | LEU | A | 35 | 33.294 | 5.484 | 16.979 | 1.00 | 17.07 | A |
| ATOM | 146 | CA | LEU | A | 35 | 32.152 | 6.395 | 17.046 | 1.00 | 18.94 | A |
| ATOM | 147 | CB | LEU | A | 35 | 31.440 | 6.482 | 15.690 | 1.00 | 16.70 | A |
| ATOM | 148 | CG | LEU | A | 35 | 30.311 | 7.514 | 15.602 | 1.00 | 14.51 | A |
| ATOM | 149 | CD1 | LEU | A | 35 | 30.880 | 8.904 | 15.849 | 1.00 | 13.73 | A |
| ATOM | 150 | CD2 | LEU | A | 35 | 29.646 | 7.453 | 14.237 | 1.00 | 13.01 | A |
| ATOM | 151 | C | LEU | A | 35 | 31.151 | 5.968 | 18.136 | 1.00 | 20.66 | A |
| ATOM | 152 | O | LEU | A | 35 | 30.494 | 6.823 | 18.742 | 1.00 | 21.36 | A |
| ATOM | 153 | N | LYS | A | 36 | 31.039 | 4.661 | 18.385 | 1.00 | 20.77 | A |
| ATOM | 154 | CA | LYS | A | 36 | 30.135 | 4.152 | 19.415 | 1.00 | 22.28 | A |
| ATOM | 155 | CB | LYS | A | 36 | 29.938 | 2.637 | 19.298 | 1.00 | 23.62 | A |
| ATOM | 156 | CG | LYS | A | 36 | 28.839 | 2.214 | 18.330 | 1.00 | 28.23 | A |
| ATOM | 157 | CD | LYS | A | 36 | 28.007 | 1.043 | 18.889 | 1.00 | 30.56 | A |
| ATOM | 158 | CE | LYS | A | 36 | 28.853 | -0.202 | 19.171 | 1.00 | 32.43 | A |
| ATOM | 159 | NZ | LYS | A | 36 | 28.037 | -1.385 | 19.580 | 1.00 | 31.16 | A |
| ATOM | 160 | C | LYS | A | 36 | 30.668 | 4.471 | 20.807 | 1.00 | 23.86 | A |
| ATOM | 161 | O | LYS | A | 36 | 29.901 | 4.855 | 21.700 | 1.00 | 26.24 | A |
| ATOM | 162 | N | LEU | A | 37 | 31.971 | 4.301 | 21.006 | 1.00 | 23.16 | A |
| ATOM | 163 | CA | LEU | A | 37 | 32.558 | 4.608 | 22.308 | 1.00 | 24.32 | A |
| ATOM | 164 | CB | LEU | A | 37 | 34.085 | 4.515 | 22.263 | 1.00 | 25.18 | A |
| ATOM | 165 | CG | LEU | A | 37 | 34.708 | 3.137 | 22.100 | 1.00 | 27.89 | A |
| ATOM | 166 | CD1 | LEU | A | 37 | 36.217 | 3.232 | 22.302 | 1.00 | 28.24 | A |
| ATOM | 167 | CD2 | LEU | A | 37 | 34.095 | 2.198 | 23.119 | 1.00 | 28.07 | A |
| ATOM | 168 | C | LEU | A | 37 | 32.179 | 6.027 | 22.725 | 1.00 | 23.05 | A |
| ATOM | 169 | O | LEU | A | 37 | 31.758 | 6.268 | 23.854 | 1.00 | 20.34 | A |
| ATOM | 170 | N | LEU | A | 38 | 32.338 | 6.956 | 21.788 | 1.00 | 23.36 | A |
| ATOM | 171 | CA | LEU | A | 38 | 32.055 | 8.359 | 22.022 | 1.00 | 24.58 | A |
| ATOM | 172 | CB | LEU | A | 38 | 32.493 | 9.198 | 20.819 | 1.00 | 21.20 | A |
| ATOM | 173 | CG | LEU | A | 38 | 33.886 | 8.937 | 20.238 | 1.00 | 19.16 | A |
| ATOM | 174 | CD1 | LEU | A | 38 | 34.126 | 9.914 | 19.106 | 1.00 | 16.77 | A |
| ATOM | 175 | CD2 | LEU | A | 38 | 34.966 | 9.092 | 21.306 | 1.00 | 18.04 | A |
| ATOM | 176 | C | LEU | A | 38 | 30.581 | 8.602 | 22.302 | 1.00 | 27.20 | A |
| ATOM | 177 | O | LEU | A | 38 | 30.236 | 9.411 | 23.162 | 1.00 | 29.33 | A |
| ATOM | 178 | N | LYS | A | 39 | 29.702 | 7.908 | 21.590 | 1.00 | 28.13 | A |
| ATOM | 179 | CA | LYS | A | 39 | 28.283 | 8.119 | 21.815 | 1.00 | 29.30 | A |
| ATOM | 180 | CB | LYS | A | 39 | 27.467 | 7.488 | 20.686 | 1.00 | 28.63 | A |
| ATOM | 181 | CG | LYS | A | 39 | 27.777 | 8.127 | 19.347 | 1.00 | 28.78 | A |
| ATOM | 182 | CD | LYS | A | 39 | 26.776 | 7.761 | 18.276 | 1.00 | 27.98 | A |
| ATOM | 183 | CE | LYS | A | 39 | 27.154 | 8.415 | 16.960 | 1.00 | 26.89 | A |
| ATOM | 184 | NZ | LYS | A | 39 | 26.074 | 8.260 | 15.959 | 1.00 | 27.11 | A |
| ATOM | 185 | C | LYS | A | 39 | 27.840 | 7.587 | 23.169 | 1.00 | 30.33 | A |
| ATOM | 186 | O | LYS | A | 39 | 26.931 | 8.141 | 23.789 | 1.00 | 31.74 | A |
| ATOM | 187 | N | SER | A | 40 | 28.495 | 6.531 | 23.644 | 1.00 | 30.27 | A |
| ATOM | 188 | CA | SER | A | 40 | 28.148 | 5.948 | 24.939 | 1.00 | 29.62 | A |
| ATOM | 189 | CB | SER | A | 40 | 28.995 | 4.691 | 25.213 | 1.00 | 28.81 | A |
| ATOM | 190 | OG | SER | A | 40 | 30.349 | 5.002 | 25.520 | 1.00 | 26.68 | A |
| ATOM | 191 | C | SER | A | 40 | 28.340 | 6.960 | 26.073 | 1.00 | 29.48 | A |
| ATOM | 192 | O | SER | A | 40 | 27.745 | 6.822 | 27.139 | 1.00 | 29.59 | A |

TABLE 3-continued

Superimposed: trigonal and tetragonal crystal forms of HDM2 of SEQ ID NO: 2.

| ATOM | 193 | N | VAL | A | 41 | 29.170 | 7.974 | 25.843 | 1.00 | 30.35 | A |
|------|-----|------|-----|---|----|--------|--------|--------|------|-------|---|
| ATOM | 194 | CA | VAL | A | 41 | 29.432 | 9.002 | 26.854 | 1.00 | 30.76 | A |
| ATOM | 195 | CB | VAL | A | 41 | 30.944 | 9.047 | 27.267 | 1.00 | 30.64 | A |
| ATOM | 196 | CG1 | VAL | A | 41 | 31.298 | 7.826 | 28.115 | 1.00 | 29.00 | A |
| ATOM | 197 | CG2 | VAL | A | 41 | 31.834 | 9.108 | 26.030 | 1.00 | 28.32 | A |
| ATOM | 198 | C | VAL | A | 41 | 29.013 | 10.407 | 26.413 | 1.00 | 32.02 | A |
| ATOM | 199 | O | VAL | A | 41 | 29.742 | 11.380 | 26.628 | 1.00 | 31.05 | A |
| ATOM | 200 | N | GLY | A | 42 | 27.845 | 10.509 | 25.779 | 1.00 | 33.77 | A |
| ATOM | 201 | CA | GLY | A | 42 | 27.355 | 11.811 | 25.360 | 1.00 | 36.14 | A |
| ATOM | 202 | C | GLY | A | 42 | 27.488 | 12.202 | 23.901 | 1.00 | 38.10 | A |
| ATOM | 203 | O | GLY | A | 42 | 26.516 | 12.669 | 23.310 | 1.00 | 40.02 | A |
| ATOM | 204 | N | ALA | A | 43 | 28.675 | 12.035 | 23.318 | 1.00 | 38.97 | A |
| ATOM | 205 | CA | ALA | A | 43 | 28.897 | 12.403 | 21.919 | 1.00 | 39.16 | A |
| ATOM | 206 | CB | ALA | A | 43 | 30.124 | 11.678 | 21.370 | 1.00 | 38.86 | A |
| ATOM | 207 | C | ALA | A | 43 | 27.678 | 12.101 | 21.054 | 1.00 | 39.94 | A |
| ATOM | 208 | O | ALA | A | 43 | 26.968 | 11.120 | 21.284 | 1.00 | 40.04 | A |
| ATOM | 209 | N | GLN | A | 44 | 27.435 | 12.952 | 20.061 | 1.00 | 41.54 | A |
| ATOM | 210 | CA | GLN | A | 44 | 26.294 | 12.769 | 19.173 | 1.00 | 42.78 | A |
| ATOM | 211 | CB | GLN | A | 44 | 25.018 | 13.232 | 19.881 | 1.00 | 45.11 | A |
| ATOM | 212 | CG | GLN | A | 44 | 25.132 | 14.598 | 20.546 | 1.00 | 47.61 | A |
| ATOM | 213 | CD | GLN | A | 44 | 24.026 | 14.838 | 21.568 | 1.00 | 49.56 | A |
| ATOM | 214 | OE1 | GLN | A | 44 | 23.986 | 15.884 | 22.227 | 1.00 | 49.35 | A |
| ATOM | 215 | NE2 | GLN | A | 44 | 23.124 | 13.866 | 21.708 | 1.00 | 49.08 | A |
| ATOM | 216 | C | GLN | A | 44 | 26.434 | 13.470 | 17.821 | 1.00 | 42.23 | A |
| ATOM | 217 | O | GLN | A | 44 | 25.520 | 14.171 | 17.375 | 1.00 | 42.70 | A |
| ATOM | 218 | N | LYS | A | 45 | 27.585 | 13.271 | 17.180 | 1.00 | 40.15 | A |
| ATOM | 219 | CA | LYS | A | 45 | 27.871 | 13.845 | 15.870 | 1.00 | 37.90 | A |
| ATOM | 220 | CB | LYS | A | 45 | 28.802 | 15.050 | 15.980 | 1.00 | 39.62 | A |
| ATOM | 221 | CG | LYS | A | 45 | 28.359 | 16.141 | 16.933 | 1.00 | 41.18 | A |
| ATOM | 222 | CD | LYS | A | 45 | 29.197 | 17.399 | 16.713 | 1.00 | 42.96 | A |
| ATOM | 223 | CE | LYS | A | 45 | 30.690 | 17.093 | 16.732 | 1.00 | 45.64 | A |
| ATOM | 224 | NZ | LYS | A | 45 | 31.535 | 18.294 | 16.451 | 1.00 | 48.08 | A |
| ATOM | 225 | C | LYS | A | 45 | 28.590 | 12.774 | 15.071 | 1.00 | 36.61 | A |
| ATOM | 226 | O | LYS | A | 45 | 28.771 | 11.657 | 15.553 | 1.00 | 36.82 | A |
| ATOM | 227 | N | ASP | A | 46 | 29.012 | 13.121 | 13.859 | 1.00 | 34.69 | A |
| ATOM | 228 | CA | ASP | A | 46 | 29.736 | 12.187 | 13.006 | 1.00 | 33.64 | A |
| ATOM | 229 | CB | ASP | A | 46 | 29.089 | 12.074 | 11.617 | 1.00 | 35.21 | A |
| ATOM | 230 | CG | ASP | A | 46 | 27.726 | 11.403 | 11.652 | 1.00 | 36.60 | A |
| ATOM | 231 | OD1 | ASP | A | 46 | 27.557 | 10.427 | 12.417 | 1.00 | 35.63 | A |
| ATOM | 232 | OD2 | ASP | A | 46 | 26.830 | 11.846 | 10.899 | 1.00 | 36.79 | A |
| ATOM | 233 | C | ASP | A | 46 | 31.174 | 12.651 | 12.830 | 1.00 | 32.32 | A |
| ATOM | 234 | O | ASP | A | 46 | 32.071 | 11.843 | 12.578 | 1.00 | 33.06 | A |
| ATOM | 235 | N | THR | A | 47 | 31.388 | 13.959 | 12.950 | 1.00 | 30.30 | A |
| ATOM | 236 | CA | THR | A | 47 | 32.718 | 14.543 | 12.790 | 1.00 | 27.52 | A |
| ATOM | 237 | CB | THR | A | 47 | 32.762 | 15.556 | 11.620 | 1.00 | 28.37 | A |
| ATOM | 238 | OG1 | THR | A | 47 | 31.586 | 16.375 | 11.650 | 1.00 | 28.12 | A |
| ATOM | 239 | CG2 | THR | A | 47 | 32.846 | 14.836 | 10.287 | 1.00 | 28.11 | A |
| ATOM | 240 | C | THR | A | 47 | 33.138 | 15.254 | 14.059 | 1.00 | 25.47 | A |
| ATOM | 241 | O | THR | A | 47 | 32.307 | 15.811 | 14.781 | 1.00 | 24.25 | A |
| ATOM | 242 | N | TYR | A | 48 | 34.441 | 15.227 | 14.324 | 1.00 | 24.41 | A |
| ATOM | 243 | CA | TYR | A | 48 | 34.997 | 15.844 | 15.517 | 1.00 | 24.02 | A |
| ATOM | 244 | CB | TYR | A | 48 | 35.073 | 14.830 | 16.681 | 1.00 | 23.01 | A |
| ATOM | 245 | CG | TYR | A | 48 | 33.769 | 14.162 | 17.077 | 1.00 | 22.29 | A |
| ATOM | 246 | CD1 | TYR | A | 48 | 33.259 | 13.087 | 16.347 | 1.00 | 21.16 | A |
| ATOM | 247 | CE1 | TYR | A | 48 | 32.030 | 12.499 | 16.685 | 1.00 | 20.20 | A |
| ATOM | 248 | CD2 | TYR | A | 48 | 33.021 | 14.632 | 18.166 | 1.00 | 21.34 | A |
| ATOM | 249 | CE2 | TYR | A | 48 | 31.801 | 14.050 | 18.510 | 1.00 | 20.29 | A |
| ATOM | 250 | CZ | TYR | A | 48 | 31.312 | 12.990 | 17.762 | 1.00 | 19.58 | A |
| ATOM | 251 | OH | TYR | A | 48 | 30.092 | 12.442 | 18.066 | 1.00 | 20.11 | A |
| ATOM | 252 | C | TYR | A | 48 | 36.412 | 16.340 | 15.265 | 1.00 | 24.38 | A |
| ATOM | 253 | O | TYR | A | 48 | 37.080 | 15.913 | 14.318 | 1.00 | 22.46 | A |
| ATOM | 254 | N | THR | A | 49 | 36.855 | 17.245 | 16.130 | 1.00 | 24.50 | A |
| ATOM | 255 | CA | THR | A | 49 | 38.221 | 17.744 | 16.092 | 1.00 | 25.25 | A |
| ATOM | 256 | CB | THR | A | 49 | 38.333 | 19.134 | 16.762 | 1.00 | 26.57 | A |
| ATOM | 257 | OG1 | THR | A | 49 | 37.583 | 19.131 | 17.989 | 1.00 | 26.24 | A |
| ATOM | 258 | CG2 | THR | A | 49 | 37.796 | 20.235 | 15.829 | 1.00 | 24.91 | A |
| ATOM | 259 | C | THR | A | 49 | 38.932 | 16.699 | 16.965 | 1.00 | 25.63 | A |
| ATOM | 260 | O | THR | A | 49 | 38.307 | 16.088 | 17.833 | 1.00 | 24.71 | A |
| ATOM | 261 | N | MET | A | 50 | 40.216 | 16.466 | 16.740 | 1.00 | 26.39 | A |
| ATOM | 262 | CA | MET | A | 50 | 40.907 | 15.470 | 17.545 | 1.00 | 26.62 | A |
| ATOM | 263 | CB | MET | A | 50 | 42.373 | 15.388 | 17.150 | 1.00 | 25.74 | A |
| ATOM | 264 | CG | MET | A | 50 | 42.589 | 14.617 | 15.865 | 1.00 | 25.74 | A |
| ATOM | 265 | SD | MET | A | 50 | 42.250 | 12.852 | 16.072 | 1.00 | 24.59 | A |
| ATOM | 266 | CE | MET | A | 50 | 43.816 | 12.259 | 16.701 | 1.00 | 22.52 | A |
| ATOM | 267 | C | MET | A | 50 | 40.785 | 15.760 | 19.031 | 1.00 | 28.23 | A |
| ATOM | 268 | O | MET | A | 50 | 40.843 | 14.848 | 19.847 | 1.00 | 29.67 | A |
| ATOM | 269 | N | LYS | A | 51 | 40.594 | 17.026 | 19.388 | 1.00 | 28.66 | A |

TABLE 3-continued

Superimposed: trigonal and tetragonal crystal forms of HDM2 of SEQ ID NO: 2.

| ATOM | 270 | CA | LYS | A | 51 | 40.467 | 17.377 | 20.794 | 1.00 | 29.11 | A |
|------|-----|-----|-----|---|----|--------|--------|--------|------|-------|---|
| ATOM | 271 | CB | LYS | A | 51 | 40.573 | 18.891 | 20.980 | 1.00 | 32.66 | A |
| ATOM | 272 | CG | LYS | A | 51 | 40.687 | 19.300 | 22.445 | 1.00 | 37.67 | A |
| ATOM | 273 | CD | LYS | A | 51 | 40.874 | 20.801 | 22.628 | 1.00 | 41.07 | A |
| ATOM | 274 | CE | LYS | A | 51 | 40.948 | 21.164 | 24.116 | 1.00 | 42.73 | A |
| ATOM | 275 | NZ | LYS | A | 51 | 41.069 | 22.639 | 24.365 | 1.00 | 45.66 | A |
| ATOM | 276 | C | LYS | A | 51 | 39.159 | 16.862 | 21.406 | 1.00 | 28.29 | A |
| ATOM | 277 | O | LYS | A | 51 | 39.143 | 16.411 | 22.557 | 1.00 | 28.36 | A |
| ATOM | 278 | N | GLU | A | 52 | 38.064 | 16.929 | 20.647 | 1.00 | 25.71 | A |
| ATOM | 279 | CA | GLU | A | 52 | 36.775 | 16.451 | 21.144 | 1.00 | 23.60 | A |
| ATOM | 280 | CB | GLU | A | 52 | 35.638 | 16.866 | 20.199 | 1.00 | 24.83 | A |
| ATOM | 281 | CG | GLU | A | 52 | 35.407 | 18.369 | 20.084 | 1.00 | 27.15 | A |
| ATOM | 282 | CD | GLU | A | 52 | 34.383 | 18.732 | 18.998 | 1.00 | 29.01 | A |
| ATOM | 283 | OE1 | GLU | A | 52 | 34.598 | 18.371 | 17.818 | 1.00 | 29.80 | A |
| ATOM | 284 | OE2 | GLU | A | 52 | 33.364 | 19.380 | 19.320 | 1.00 | 29.19 | A |
| ATOM | 285 | C | GLU | A | 52 | 36.785 | 14.921 | 21.293 | 1.00 | 21.67 | A |
| ATOM | 286 | O | GLU | A | 52 | 36.069 | 14.370 | 22.132 | 1.00 | 20.99 | A |
| ATOM | 287 | N | VAL | A | 53 | 37.578 | 14.235 | 20.473 | 1.00 | 18.55 | A |
| ATOM | 288 | CA | VAL | A | 53 | 37.659 | 12.782 | 20.559 | 1.00 | 16.46 | A |
| ATOM | 289 | CB | VAL | A | 53 | 38.461 | 12.163 | 19.371 | 1.00 | 17.02 | A |
| ATOM | 290 | CG1 | VAL | A | 53 | 38.749 | 10.682 | 19.645 | 1.00 | 15.92 | A |
| ATOM | 291 | CG2 | VAL | A | 53 | 37.659 | 12.282 | 18.075 | 1.00 | 14.61 | A |
| ATOM | 292 | C | VAL | A | 53 | 38.350 | 12.471 | 21.879 | 1.00 | 15.15 | A |
| ATOM | 293 | O | VAL | A | 53 | 37.788 | 11.784 | 22.735 | 1.00 | 13.10 | A |
| ATOM | 294 | N | LEU | A | 54 | 39.570 | 12.988 | 22.037 | 1.00 | 15.42 | A |
| ATOM | 295 | CA | LEU | A | 54 | 40.328 | 12.814 | 23.273 | 1.00 | 14.74 | A |
| ATOM | 296 | CB | LEU | A | 54 | 41.548 | 13.736 | 23.309 | 1.00 | 12.86 | A |
| ATOM | 297 | CG | LEU | A | 54 | 42.871 | 13.232 | 22.730 | 1.00 | 13.00 | A |
| ATOM | 298 | CD1 | LEU | A | 54 | 43.132 | 11.821 | 23.250 | 1.00 | 14.60 | A |
| ATOM | 299 | CD2 | LEU | A | 54 | 42.833 | 13.235 | 21.232 | 1.00 | 11.73 | A |
| ATOM | 300 | C | LEU | A | 54 | 39.439 | 13.153 | 24.467 | 1.00 | 15.13 | A |
| ATOM | 301 | O | LEU | A | 54 | 39.515 | 12.511 | 25.514 | 1.00 | 16.88 | A |
| ATOM | 302 | N | PHE | A | 55 | 38.588 | 14.156 | 24.309 | 1.00 | 14.69 | A |
| ATOM | 303 | CA | PHE | A | 55 | 37.710 | 14.556 | 25.397 | 1.00 | 16.41 | A |
| ATOM | 304 | CB | PHE | A | 55 | 36.904 | 15.803 | 25.028 | 1.00 | 18.34 | A |
| ATOM | 305 | CG | PHE | A | 55 | 35.899 | 16.171 | 26.069 | 1.00 | 20.72 | A |
| ATOM | 306 | CD1 | PHE | A | 55 | 36.278 | 16.916 | 27.184 | 1.00 | 20.24 | A |
| ATOM | 307 | CD2 | PHE | A | 55 | 34.596 | 15.672 | 26.001 | 1.00 | 20.52 | A |
| ATOM | 308 | CE1 | PHE | A | 55 | 35.376 | 17.153 | 28.223 | 1.00 | 20.60 | A |
| ATOM | 309 | CE2 | PHE | A | 55 | 33.687 | 15.901 | 27.034 | 1.00 | 21.73 | A |
| ATOM | 310 | CZ | PHE | A | 55 | 34.078 | 16.644 | 28.149 | 1.00 | 20.59 | A |
| ATOM | 311 | C | PHE | A | 55 | 36.739 | 13.473 | 25.838 | 1.00 | 16.04 | A |
| ATOM | 312 | O | PHE | A | 55 | 36.661 | 13.148 | 27.025 | 1.00 | 17.31 | A |
| ATOM | 313 | N | TYR | A | 56 | 35.978 | 12.941 | 24.886 | 1.00 | 16.71 | A |
| ATOM | 314 | CA | TYR | A | 56 | 34.996 | 11.892 | 25.165 | 1.00 | 17.61 | A |
| ATOM | 315 | CB | TYR | A | 56 | 34.136 | 11.624 | 23.930 | 1.00 | 18.45 | A |
| ATOM | 316 | CG | TYR | A | 56 | 33.142 | 12.723 | 23.671 | 1.00 | 21.48 | A |
| ATOM | 317 | CD1 | TYR | A | 56 | 32.090 | 12.951 | 24.565 | 1.00 | 23.38 | A |
| ATOM | 318 | CE1 | TYR | A | 56 | 31.182 | 13.987 | 24.363 | 1.00 | 25.16 | A |
| ATOM | 319 | CD2 | TYR | A | 56 | 33.266 | 13.562 | 22.557 | 1.00 | 22.53 | A |
| ATOM | 320 | CE2 | TYR | A | 56 | 32.363 | 14.610 | 22.339 | 1.00 | 23.90 | A |
| ATOM | 321 | CZ | TYR | A | 56 | 31.322 | 14.816 | 23.251 | 1.00 | 26.15 | A |
| ATOM | 322 | OH | TYR | A | 56 | 30.425 | 15.846 | 23.068 | 1.00 | 26.91 | A |
| ATOM | 323 | C | TYR | A | 56 | 35.709 | 10.628 | 25.567 | 1.00 | 16.78 | A |
| ATOM | 324 | O | TYR | A | 56 | 35.189 | 9.810 | 26.329 | 1.00 | 18.53 | A |
| ATOM | 325 | N | LEU | A | 57 | 36.910 | 10.472 | 25.028 | 1.00 | 15.78 | A |
| ATOM | 326 | CA | LEU | A | 57 | 37.743 | 9.325 | 25.327 | 1.00 | 13.13 | A |
| ATOM | 327 | CB | LEU | A | 57 | 38.982 | 9.382 | 24.437 | 1.00 | 11.95 | A |
| ATOM | 328 | CG | LEU | A | 57 | 39.277 | 8.207 | 23.497 | 1.00 | 13.21 | A |
| ATOM | 329 | CD1 | LEU | A | 57 | 38.000 | 7.628 | 22.913 | 1.00 | 10.11 | A |
| ATOM | 330 | CD2 | LEU | A | 57 | 40.224 | 8.690 | 22.402 | 1.00 | 10.01 | A |
| ATOM | 331 | C | LEU | A | 57 | 38.108 | 9.418 | 26.821 | 1.00 | 12.23 | A |
| ATOM | 332 | O | LEU | A | 57 | 38.197 | 8.403 | 27.515 | 1.00 | 9.19 | A |
| ATOM | 333 | N | GLY | A | 58 | 38.291 | 10.649 | 27.300 | 1.00 | 11.88 | A |
| ATOM | 334 | CA | GLY | A | 58 | 38.620 | 10.877 | 28.691 | 1.00 | 14.46 | A |
| ATOM | 335 | C | GLY | A | 58 | 37.448 | 10.490 | 29.567 | 1.00 | 17.50 | A |
| ATOM | 336 | O | GLY | A | 58 | 37.613 | 9.800 | 30.579 | 1.00 | 18.69 | A |
| ATOM | 337 | N | GLN | A | 59 | 36.257 | 10.934 | 29.178 | 1.00 | 18.46 | A |
| ATOM | 338 | CA | GLN | A | 59 | 35.059 | 10.614 | 29.929 | 1.00 | 19.45 | A |
| ATOM | 339 | CB | GLN | A | 59 | 33.850 | 11.322 | 29.328 | 1.00 | 22.28 | A |
| ATOM | 340 | CG | GLN | A | 59 | 33.967 | 12.829 | 29.389 | 1.00 | 24.82 | A |
| ATOM | 341 | CD | GLN | A | 59 | 34.506 | 13.295 | 30.732 | 1.00 | 25.90 | A |
| ATOM | 342 | OE1 | GLN | A | 59 | 33.883 | 13.079 | 31.771 | 1.00 | 26.11 | A |
| ATOM | 343 | NE2 | GLN | A | 59 | 35.679 | 13.928 | 30.714 | 1.00 | 26.90 | A |
| ATOM | 344 | C | GLN | A | 59 | 34.850 | 9.115 | 29.898 | 1.00 | 19.50 | A |
| ATOM | 345 | O | GLN | A | 59 | 34.441 | 8.511 | 30.893 | 1.00 | 20.93 | A |
| ATOM | 346 | N | TYR | A | 60 | 35.148 | 8.510 | 28.757 | 1.00 | 17.52 | A |

TABLE 3-continued

Superimposed: trigonal and tetragonal crystal forms
of HDM2 of SEQ ID NO: 2.

| ATOM | 347 | CA | TYR | A | 60 | 34.991 | 7.075 | 28.617 | 1.00 | 18.33 | A |
|------|-----|-----|-----|---|----|--------|-------|--------|------|-------|---|
| ATOM | 348 | CB | TYR | A | 60 | 35.359 | 6.636 | 27.198 | 1.00 | 14.85 | A |
| ATOM | 349 | CG | TYR | A | 60 | 35.120 | 5.162 | 26.914 | 1.00 | 15.47 | A |
| ATOM | 350 | CD1 | TYR | A | 60 | 33.838 | 4.676 | 26.632 | 1.00 | 14.63 | A |
| ATOM | 351 | CE1 | TYR | A | 60 | 33.620 | 3.311 | 26.347 | 1.00 | 11.14 | A |
| ATOM | 352 | CD2 | TYR | A | 60 | 36.184 | 4.247 | 26.913 | 1.00 | 15.88 | A |
| ATOM | 353 | CE2 | TYR | A | 60 | 35.974 | 2.882 | 26.631 | 1.00 | 13.26 | A |
| ATOM | 354 | CZ | TYR | A | 60 | 34.691 | 2.425 | 26.349 | 1.00 | 12.81 | A |
| ATOM | 355 | OH | TYR | A | 60 | 34.494 | 1.089 | 26.052 | 1.00 | 10.53 | A |
| ATOM | 356 | C | TYR | A | 60 | 35.862 | 6.332 | 29.635 | 1.00 | 20.42 | A |
| ATOM | 357 | O | TYR | A | 60 | 35.339 | 5.672 | 30.541 | 1.00 | 19.39 | A |
| ATOM | 358 | N | ILE | A | 61 | 37.184 | 6.453 | 29.501 | 1.00 | 21.45 | A |
| ATOM | 359 | CA | ILE | A | 61 | 38.092 | 5.753 | 30.401 | 1.00 | 23.11 | A |
| ATOM | 360 | CB | ILE | A | 61 | 39.576 | 5.969 | 30.026 | 1.00 | 22.76 | A |
| ATOM | 361 | CG2 | ILE | A | 61 | 39.879 | 5.334 | 28.680 | 1.00 | 23.31 | A |
| ATOM | 362 | CG1 | ILE | A | 61 | 39.913 | 7.453 | 30.028 | 1.00 | 22.24 | A |
| ATOM | 363 | CD1 | ILE | A | 61 | 41.385 | 7.709 | 29.846 | 1.00 | 23.32 | A |
| ATOM | 364 | C | ILE | A | 61 | 37.911 | 6.115 | 31.869 | 1.00 | 25.11 | A |
| ATOM | 365 | O | ILE | A | 61 | 38.112 | 5.284 | 32.751 | 1.00 | 25.25 | A |
| ATOM | 366 | N | MET | A | 62 | 37.531 | 7.350 | 32.145 | 1.00 | 27.56 | A |
| ATOM | 367 | CA | MET | A | 62 | 37.335 | 7.737 | 33.527 | 1.00 | 30.23 | A |
| ATOM | 368 | CB | MET | A | 62 | 37.237 | 9.260 | 33.632 | 1.00 | 32.88 | A |
| ATOM | 369 | CG | MET | A | 62 | 37.161 | 9.783 | 35.056 | 1.00 | 34.56 | A |
| ATOM | 370 | SD | MET | A | 62 | 35.808 | 10.961 | 35.203 | 1.00 | 39.80 | A |
| ATOM | 371 | CE | MET | A | 62 | 34.440 | 9.803 | 35.399 | 1.00 | 35.55 | A |
| ATOM | 372 | C | MET | A | 62 | 36.066 | 7.073 | 34.087 | 1.00 | 31.22 | A |
| ATOM | 373 | O | MET | A | 62 | 36.118 | 6.340 | 35.083 | 1.00 | 30.54 | A |
| ATOM | 374 | N | THR | A | 63 | 34.934 | 7.302 | 33.428 | 1.00 | 31.07 | A |
| ATOM | 375 | CA | THR | A | 63 | 33.673 | 6.735 | 33.896 | 1.00 | 31.77 | A |
| ATOM | 376 | CB | THR | A | 63 | 32.495 | 7.074 | 32.939 | 1.00 | 30.74 | A |
| ATOM | 377 | OG1 | THR | A | 63 | 32.818 | 6.664 | 31.608 | 1.00 | 31.02 | A |
| ATOM | 378 | CG2 | THR | A | 63 | 32.206 | 8.569 | 32.956 | 1.00 | 31.19 | A |
| ATOM | 379 | C | THR | A | 63 | 33.710 | 5.221 | 34.115 | 1.00 | 32.00 | A |
| ATOM | 380 | O | THR | A | 63 | 33.230 | 4.730 | 35.142 | 1.00 | 33.74 | A |
| ATOM | 381 | N | LYS | A | 64 | 34.265 | 4.481 | 33.159 | 1.00 | 30.45 | A |
| ATOM | 382 | CA | LYS | A | 64 | 34.331 | 3.035 | 33.288 | 1.00 | 29.14 | A |
| ATOM | 383 | CB | LYS | A | 64 | 34.397 | 2.380 | 31.905 | 1.00 | 28.22 | A |
| ATOM | 384 | CG | LYS | A | 64 | 33.121 | 2.523 | 31.099 | 1.00 | 26.54 | A |
| ATOM | 385 | CD | LYS | A | 64 | 33.198 | 1.785 | 29.769 | 1.00 | 26.08 | A |
| ATOM | 386 | CE | LYS | A | 64 | 33.343 | 0.293 | 29.967 | 1.00 | 26.73 | A |
| ATOM | 387 | NZ | LYS | A | 64 | 33.332 | −0.444 | 28.675 | 1.00 | 26.87 | A |
| ATOM | 388 | C | LYS | A | 64 | 35.509 | 2.586 | 34.151 | 1.00 | 29.64 | A |
| ATOM | 389 | O | LYS | A | 64 | 35.824 | 1.398 | 34.223 | 1.00 | 28.68 | A |
| ATOM | 390 | N | ARG | A | 65 | 36.160 | 3.548 | 34.799 | 1.00 | 31.08 | A |
| ATOM | 391 | CA | ARG | A | 65 | 37.279 | 3.259 | 35.691 | 1.00 | 31.77 | A |
| ATOM | 392 | CB | ARG | A | 65 | 36.720 | 2.800 | 37.041 | 1.00 | 32.61 | A |
| ATOM | 393 | CG | ARG | A | 65 | 35.955 | 3.907 | 37.771 | 1.00 | 36.27 | A |
| ATOM | 394 | CD | ARG | A | 65 | 34.975 | 3.376 | 38.812 | 1.00 | 38.75 | A |
| ATOM | 395 | NE | ARG | A | 65 | 34.298 | 4.465 | 39.521 | 1.00 | 41.50 | A |
| ATOM | 396 | CZ | ARG | A | 65 | 33.149 | 4.343 | 40.190 | 1.00 | 43.14 | A |
| ATOM | 397 | NH1 | ARG | A | 65 | 32.519 | 3.173 | 40.251 | 1.00 | 43.25 | A |
| ATOM | 398 | NH2 | ARG | A | 65 | 32.622 | 5.396 | 40.799 | 1.00 | 41.34 | A |
| ATOM | 399 | C | ARG | A | 65 | 38.254 | 2.216 | 35.131 | 1.00 | 30.62 | A |
| ATOM | 400 | O | ARG | A | 65 | 38.488 | 1.173 | 35.750 | 1.00 | 31.11 | A |
| ATOM | 401 | N | LEU | A | 66 | 38.817 | 2.505 | 33.958 | 1.00 | 27.85 | A |
| ATOM | 402 | CA | LEU | A | 66 | 39.773 | 1.606 | 33.309 | 1.00 | 24.57 | A |
| ATOM | 403 | CB | LEU | A | 66 | 39.657 | 1.699 | 31.781 | 1.00 | 21.73 | A |
| ATOM | 404 | CG | LEU | A | 66 | 38.392 | 1.185 | 31.099 | 1.00 | 18.58 | A |
| ATOM | 405 | CD1 | LEU | A | 66 | 38.477 | 1.413 | 29.603 | 1.00 | 16.38 | A |
| ATOM | 406 | CD2 | LEU | A | 66 | 38.240 | −0.289 | 31.393 | 1.00 | 16.78 | A |
| ATOM | 407 | C | LEU | A | 66 | 41.195 | 1.960 | 33.712 | 1.00 | 24.06 | A |
| ATOM | 408 | O | LEU | A | 66 | 42.146 | 1.312 | 33.286 | 1.00 | 22.74 | A |
| ATOM | 409 | N | TYR | A | 67 | 41.343 | 3.008 | 34.515 | 1.00 | 25.28 | A |
| ATOM | 410 | CA | TYR | A | 67 | 42.665 | 3.428 | 34.962 | 1.00 | 26.02 | A |
| ATOM | 411 | CB | TYR | A | 67 | 42.703 | 4.953 | 35.146 | 1.00 | 26.69 | A |
| ATOM | 412 | CG | TYR | A | 67 | 41.675 | 5.492 | 36.106 | 1.00 | 26.95 | A |
| ATOM | 413 | CD1 | TYR | A | 67 | 41.983 | 5.673 | 37.452 | 1.00 | 27.52 | A |
| ATOM | 414 | CE1 | TYR | A | 67 | 41.025 | 6.108 | 38.356 | 1.00 | 27.15 | A |
| ATOM | 415 | CD2 | TYR | A | 67 | 40.378 | 5.764 | 35.683 | 1.00 | 26.57 | A |
| ATOM | 416 | CE2 | TYR | A | 67 | 39.407 | 6.202 | 36.579 | 1.00 | 27.84 | A |
| ATOM | 417 | CZ | TYR | A | 67 | 39.738 | 6.368 | 37.919 | 1.00 | 27.23 | A |
| ATOM | 418 | OH | TYR | A | 67 | 38.780 | 6.753 | 38.826 | 1.00 | 24.32 | A |
| ATOM | 419 | C | TYR | A | 67 | 43.032 | 2.700 | 36.256 | 1.00 | 26.40 | A |
| ATOM | 420 | O | TYR | A | 67 | 42.178 | 2.422 | 37.091 | 1.00 | 25.07 | A |
| ATOM | 421 | N | ASP | A | 68 | 44.311 | 2.381 | 36.403 | 1.00 | 28.69 | A |
| ATOM | 422 | CA | ASP | A | 68 | 44.785 | 1.659 | 37.574 | 1.00 | 31.43 | A |
| ATOM | 423 | CB | ASP | A | 68 | 46.199 | 1.130 | 37.326 | 1.00 | 31.86 | A |

TABLE 3-continued

Superimposed: trigonal and tetragonal crystal forms of HDM2 of SEQ ID NO: 2.

| ATOM | 424 | CG | ASP | A | 68 | 46.635 | 0.139 | 38.382 | 1.00 | 31.50 | A |
|---|---|---|---|---|---|---|---|---|---|---|---|
| ATOM | 425 | OD1 | ASP | A | 68 | 46.072 | −0.975 | 38.409 | 1.00 | 29.47 | A |
| ATOM | 426 | OD2 | ASP | A | 68 | 47.524 | 0.482 | 39.192 | 1.00 | 33.11 | A |
| ATOM | 427 | C | ASP | A | 68 | 44.770 | 2.474 | 38.864 | 1.00 | 33.44 | A |
| ATOM | 428 | O | ASP | A | 68 | 45.033 | 3.679 | 38.866 | 1.00 | 33.12 | A |
| ATOM | 429 | N | GLU | A | 69 | 44.477 | 1.789 | 39.966 | 1.00 | 36.37 | A |
| ATOM | 430 | CA | GLU | A | 69 | 44.415 | 2.416 | 41.279 | 1.00 | 39.07 | A |
| ATOM | 431 | CB | GLU | A | 69 | 43.852 | 1.432 | 42.311 | 1.00 | 42.56 | A |
| ATOM | 432 | CG | GLU | A | 69 | 42.371 | 1.145 | 42.123 | 1.00 | 48.37 | A |
| ATOM | 433 | CD | GLU | A | 69 | 41.564 | 2.420 | 41.901 | 1.00 | 51.95 | A |
| ATOM | 434 | OE1 | GLU | A | 69 | 41.715 | 3.364 | 42.708 | 1.00 | 54.24 | A |
| ATOM | 435 | OE2 | GLU | A | 69 | 40.782 | 2.480 | 40.921 | 1.00 | 54.25 | A |
| ATOM | 436 | C | GLU | A | 69 | 45.750 | 2.946 | 41.759 | 1.00 | 38.35 | A |
| ATOM | 437 | O | GLU | A | 69 | 45.845 | 4.084 | 42.207 | 1.00 | 38.84 | A |
| ATOM | 438 | N | LYS | A | 70 | 46.788 | 2.128 | 41.672 | 1.00 | 38.42 | A |
| ATOM | 439 | CA | LYS | A | 70 | 48.096 | 2.575 | 42.118 | 1.00 | 38.82 | A |
| ATOM | 440 | CB | LYS | A | 70 | 48.982 | 1.360 | 42.412 | 1.00 | 41.21 | A |
| ATOM | 441 | CG | LYS | A | 70 | 48.362 | 0.471 | 43.491 | 1.00 | 43.81 | A |
| ATOM | 442 | CD | LYS | A | 70 | 49.261 | −0.669 | 43.940 | 1.00 | 46.99 | A |
| ATOM | 443 | CE | LYS | A | 70 | 48.551 | −1.515 | 44.999 | 1.00 | 47.44 | A |
| ATOM | 444 | NZ | LYS | A | 70 | 49.436 | −2.552 | 45.599 | 1.00 | 48.71 | A |
| ATOM | 445 | C | LYS | A | 70 | 48.694 | 3.493 | 41.058 | 1.00 | 37.27 | A |
| ATOM | 446 | O | LYS | A | 70 | 48.890 | 4.684 | 41.300 | 1.00 | 36.92 | A |
| ATOM | 447 | N | GLN | A | 71 | 48.958 | 2.950 | 39.876 | 1.00 | 35.72 | A |
| ATOM | 448 | CA | GLN | A | 71 | 49.496 | 3.755 | 38.787 | 1.00 | 33.41 | A |
| ATOM | 449 | CB | GLN | A | 71 | 50.372 | 2.888 | 37.891 | 1.00 | 34.05 | A |
| ATOM | 450 | CG | GLN | A | 71 | 51.544 | 2.272 | 38.608 | 1.00 | 35.15 | A |
| ATOM | 451 | CD | GLN | A | 71 | 52.414 | 1.462 | 37.678 | 1.00 | 36.85 | A |
| ATOM | 452 | OE1 | GLN | A | 71 | 52.026 | 0.382 | 37.220 | 1.00 | 37.63 | A |
| ATOM | 453 | NE2 | GLN | A | 71 | 53.596 | 1.983 | 37.377 | 1.00 | 38.20 | A |
| ATOM | 454 | C | GLN | A | 71 | 48.326 | 4.349 | 37.986 | 1.00 | 31.00 | A |
| ATOM | 455 | O | GLN | A | 71 | 47.855 | 3.759 | 37.007 | 1.00 | 31.06 | A |
| ATOM | 456 | N | GLN | A | 72 | 47.865 | 5.521 | 38.411 | 1.00 | 27.04 | A |
| ATOM | 457 | CA | GLN | A | 72 | 46.737 | 6.192 | 37.771 | 1.00 | 23.77 | A |
| ATOM | 458 | CB | GLN | A | 72 | 46.355 | 7.443 | 38.567 | 1.00 | 21.94 | A |
| ATOM | 459 | CG | GLN | A | 72 | 45.189 | 8.240 | 37.996 | 1.00 | 19.04 | A |
| ATOM | 460 | CD | GLN | A | 72 | 44.592 | 9.192 | 39.022 | 1.00 | 18.27 | A |
| ATOM | 461 | OE1 | GLN | A | 72 | 44.040 | 8.758 | 40.029 | 1.00 | 16.43 | A |
| ATOM | 462 | NE2 | GLN | A | 72 | 44.704 | 10.491 | 38.773 | 1.00 | 19.03 | A |
| ATOM | 463 | C | GLN | A | 72 | 46.926 | 6.558 | 36.307 | 1.00 | 21.79 | A |
| ATOM | 464 | O | GLN | A | 72 | 45.965 | 6.558 | 35.552 | 1.00 | 20.39 | A |
| ATOM | 465 | N | HIS | A | 73 | 48.155 | 6.859 | 35.899 | 1.00 | 21.17 | A |
| ATOM | 466 | CA | HIS | A | 73 | 48.395 | 7.227 | 34.510 | 1.00 | 19.46 | A |
| ATOM | 467 | CB | HIS | A | 73 | 49.768 | 7.880 | 34.355 | 1.00 | 19.40 | A |
| ATOM | 468 | CG | HIS | A | 73 | 50.918 | 6.974 | 34.667 | 1.00 | 21.41 | A |
| ATOM | 469 | CD2 | HIS | A | 73 | 51.514 | 6.660 | 35.843 | 1.00 | 21.24 | A |
| ATOM | 470 | ND1 | HIS | A | 73 | 51.613 | 6.290 | 33.692 | 1.00 | 22.42 | A |
| ATOM | 471 | CE1 | HIS | A | 73 | 52.588 | 5.596 | 34.254 | 1.00 | 21.05 | A |
| ATOM | 472 | NE2 | HIS | A | 73 | 52.548 | 5.804 | 35.559 | 1.00 | 21.25 | A |
| ATOM | 473 | C | HIS | A | 73 | 48.273 | 6.037 | 33.572 | 1.00 | 20.37 | A |
| ATOM | 474 | O | HIS | A | 73 | 48.166 | 6.219 | 32.355 | 1.00 | 19.89 | A |
| ATOM | 475 | N | ILE | A | 74 | 48.290 | 4.823 | 34.128 | 1.00 | 19.94 | A |
| ATOM | 476 | CA | ILE | A | 74 | 48.158 | 3.618 | 33.310 | 1.00 | 19.76 | A |
| ATOM | 477 | CB | ILE | A | 74 | 48.869 | 2.389 | 33.941 | 1.00 | 20.27 | A |
| ATOM | 478 | CG2 | ILE | A | 74 | 48.667 | 1.165 | 33.052 | 1.00 | 18.27 | A |
| ATOM | 479 | CG1 | ILE | A | 74 | 50.368 | 2.655 | 34.118 | 1.00 | 22.09 | A |
| ATOM | 480 | CD1 | ILE | A | 74 | 51.121 | 2.838 | 32.833 | 1.00 | 22.98 | A |
| ATOM | 481 | C | ILE | A | 74 | 46.676 | 3.261 | 33.133 | 1.00 | 19.56 | A |
| ATOM | 482 | O | ILE | A | 74 | 45.911 | 3.245 | 34.099 | 1.00 | 19.09 | A |
| ATOM | 483 | N | VAL | A | 75 | 46.287 | 2.968 | 31.895 | 1.00 | 17.84 | A |
| ATOM | 484 | CA | VAL | A | 75 | 44.913 | 2.603 | 31.578 | 1.00 | 16.49 | A |
| ATOM | 485 | CB | VAL | A | 75 | 44.335 | 3.551 | 30.508 | 1.00 | 14.74 | A |
| ATOM | 486 | CG1 | VAL | A | 75 | 42.999 | 3.053 | 30.027 | 1.00 | 13.12 | A |
| ATOM | 487 | CG2 | VAL | A | 75 | 44.189 | 4.941 | 31.092 | 1.00 | 15.39 | A |
| ATOM | 488 | C | VAL | A | 75 | 44.901 | 1.172 | 31.058 | 1.00 | 17.78 | A |
| ATOM | 489 | O | VAL | A | 75 | 45.568 | 0.858 | 30.070 | 1.00 | 17.51 | A |
| ATOM | 490 | N | TYR | A | 76 | 44.155 | 0.300 | 31.731 | 1.00 | 17.97 | A |
| ATOM | 491 | CA | TYR | A | 76 | 44.077 | −1.098 | 31.319 | 1.00 | 18.96 | A |
| ATOM | 492 | CB | TYR | A | 76 | 44.029 | −2.024 | 32.544 | 1.00 | 20.36 | A |
| ATOM | 493 | CG | TYR | A | 76 | 45.341 | −2.070 | 33.294 | 1.00 | 22.91 | A |
| ATOM | 494 | CD1 | TYR | A | 76 | 45.582 | −1.227 | 34.385 | 1.00 | 22.46 | A |
| ATOM | 495 | CE1 | TYR | A | 76 | 46.827 | −1.231 | 35.044 | 1.00 | 24.23 | A |
| ATOM | 496 | CD2 | TYR | A | 76 | 46.371 | −2.920 | 32.878 | 1.00 | 23.56 | A |
| ATOM | 497 | CE2 | TYR | A | 76 | 47.621 | −2.929 | 33.530 | 1.00 | 23.98 | A |
| ATOM | 498 | CZ | TYR | A | 76 | 47.840 | −2.083 | 34.606 | 1.00 | 23.95 | A |
| ATOM | 499 | OH | TYR | A | 76 | 49.073 | −2.071 | 35.223 | 1.00 | 24.89 | A |
| ATOM | 500 | C | TYR | A | 76 | 42.856 | −1.303 | 30.454 | 1.00 | 17.43 | A |

TABLE 3-continued

Superimposed: trigonal and tetragonal crystal forms of HDM2 of SEQ ID NO: 2.

| ATOM | 501 | O | TYR | A | 76 | 41.753 | −0.999 | 30.870 | 1.00 | 18.57 | A |
|---|---|---|---|---|---|---|---|---|---|---|---|
| ATOM | 502 | N | CYS | A | 77 | 43.052 | −1.833 | 29.250 | 1.00 | 19.17 | A |
| ATOM | 503 | CA | CYS | A | 77 | 41.940 | −2.034 | 28.318 | 1.00 | 20.17 | A |
| ATOM | 504 | CB | CYS | A | 77 | 41.984 | −0.939 | 27.242 | 1.00 | 18.05 | A |
| ATOM | 505 | SG | CYS | A | 77 | 43.606 | −0.777 | 26.414 | 1.00 | 17.89 | A |
| ATOM | 506 | C | CYS | A | 77 | 41.853 | −3.405 | 27.639 | 1.00 | 20.92 | A |
| ATOM | 507 | O | CYS | A | 77 | 41.084 | −3.577 | 26.698 | 1.00 | 22.93 | A |
| ATOM | 508 | N | SER | A | 78 | 42.619 | −4.379 | 28.110 | 1.00 | 21.73 | A |
| ATOM | 509 | CA | SER | A | 78 | 42.590 | −5.706 | 27.504 | 1.00 | 23.67 | A |
| ATOM | 510 | CB | SER | A | 78 | 43.569 | −6.636 | 28.216 | 1.00 | 23.31 | A |
| ATOM | 511 | OG | SER | A | 78 | 43.353 | −6.594 | 29.612 | 1.00 | 24.57 | A |
| ATOM | 512 | C | SER | A | 78 | 41.202 | −6.344 | 27.497 | 1.00 | 24.32 | A |
| ATOM | 513 | O | SER | A | 78 | 40.917 | −7.189 | 26.647 | 1.00 | 24.57 | A |
| ATOM | 514 | N | ASN | A | 79 | 40.343 | −5.949 | 28.432 | 1.00 | 23.65 | A |
| ATOM | 515 | CA | ASN | A | 79 | 38.996 | −6.517 | 28.492 | 1.00 | 24.00 | A |
| ATOM | 516 | CB | ASN | A | 79 | 38.716 | −7.139 | 29.872 | 1.00 | 24.75 | A |
| ATOM | 517 | CG | ASN | A | 79 | 39.516 | −8.411 | 30.120 | 1.00 | 25.05 | A |
| ATOM | 518 | OD1 | ASN | A | 79 | 40.571 | −8.380 | 30.753 | 1.00 | 25.04 | A |
| ATOM | 519 | ND2 | ASN | A | 79 | 39.021 | −9.534 | 29.608 | 1.00 | 25.70 | A |
| ATOM | 520 | C | ASN | A | 79 | 37.928 | −5.472 | 28.186 | 1.00 | 23.53 | A |
| ATOM | 521 | O | ASN | A | 79 | 36.857 | −5.455 | 28.806 | 1.00 | 23.89 | A |
| ATOM | 522 | N | ASP | A | 80 | 38.222 | −4.611 | 27.219 | 1.00 | 21.43 | A |
| ATOM | 523 | CA | ASP | A | 80 | 37.304 | −3.554 | 26.831 | 1.00 | 20.47 | A |
| ATOM | 524 | CB | ASP | A | 80 | 37.609 | −2.277 | 27.631 | 1.00 | 20.36 | A |
| ATOM | 525 | CG | ASP | A | 80 | 36.608 | −1.170 | 27.370 | 1.00 | 20.02 | A |
| ATOM | 526 | OD1 | ASP | A | 80 | 35.855 | −0.817 | 28.299 | 1.00 | 20.17 | A |
| ATOM | 527 | OD2 | ASP | A | 80 | 36.567 | −0.656 | 26.236 | 1.00 | 20.97 | A |
| ATOM | 528 | C | ASP | A | 80 | 37.439 | −3.270 | 25.341 | 1.00 | 20.46 | A |
| ATOM | 529 | O | ASP | A | 80 | 38.505 | −3.492 | 24.744 | 1.00 | 20.32 | A |
| ATOM | 530 | N | LEU | A | 81 | 36.350 | −2.783 | 24.746 | 1.00 | 19.74 | A |
| ATOM | 531 | CA | LEU | A | 81 | 36.317 | −2.448 | 23.323 | 1.00 | 19.05 | A |
| ATOM | 532 | CB | LEU | A | 81 | 35.019 | −1.709 | 23.010 | 1.00 | 20.17 | A |
| ATOM | 533 | CG | LEU | A | 81 | 34.870 | −1.058 | 21.638 | 1.00 | 23.86 | A |
| ATOM | 534 | CD1 | LEU | A | 81 | 35.022 | −2.102 | 20.539 | 1.00 | 24.25 | A |
| ATOM | 535 | CD2 | LEU | A | 81 | 33.500 | −0.381 | 21.563 | 1.00 | 24.57 | A |
| ATOM | 536 | C | LEU | A | 81 | 37.522 | −1.576 | 22.957 | 1.00 | 17.50 | A |
| ATOM | 537 | O | LEU | A | 81 | 38.155 | −1.766 | 21.913 | 1.00 | 15.88 | A |
| ATOM | 538 | N | LEU | A | 82 | 37.831 | −0.633 | 23.846 | 1.00 | 14.87 | A |
| ATOM | 539 | CA | LEU | A | 82 | 38.944 | 0.290 | 23.679 | 1.00 | 12.91 | A |
| ATOM | 540 | CB | LEU | A | 82 | 39.117 | 1.125 | 24.961 | 1.00 | 11.35 | A |
| ATOM | 541 | CG | LEU | A | 82 | 40.296 | 2.107 | 25.024 | 1.00 | 10.75 | A |
| ATOM | 542 | CD1 | LEU | A | 82 | 40.216 | 3.088 | 23.855 | 1.00 | 10.31 | A |
| ATOM | 543 | CD2 | LEU | A | 82 | 40.284 | 2.839 | 26.357 | 1.00 | 9.38 | A |
| ATOM | 544 | C | LEU | A | 82 | 40.252 | −0.430 | 23.344 | 1.00 | 12.97 | A |
| ATOM | 545 | O | LEU | A | 82 | 40.992 | −0.012 | 22.439 | 1.00 | 9.83 | A |
| ATOM | 546 | N | GLY | A | 83 | 40.538 | −1.503 | 24.080 | 1.00 | 12.95 | A |
| ATOM | 547 | CA | GLY | A | 83 | 41.756 | −2.248 | 23.834 | 1.00 | 15.06 | A |
| ATOM | 548 | C | GLY | A | 83 | 41.816 | −2.728 | 22.391 | 1.00 | 16.77 | A |
| ATOM | 549 | O | GLY | A | 83 | 42.853 | −2.635 | 21.732 | 1.00 | 15.55 | A |
| ATOM | 550 | N | ASP | A | 84 | 40.691 | −3.233 | 21.894 | 1.00 | 18.65 | A |
| ATOM | 551 | CA | ASP | A | 84 | 40.631 | −3.736 | 20.534 | 1.00 | 21.41 | A |
| ATOM | 552 | CB | ASP | A | 84 | 39.294 | −4.432 | 20.288 | 1.00 | 25.41 | A |
| ATOM | 553 | CG | ASP | A | 84 | 39.043 | −5.561 | 21.263 | 1.00 | 28.55 | A |
| ATOM | 554 | OD1 | ASP | A | 84 | 40.004 | −6.324 | 21.550 | 1.00 | 27.94 | A |
| ATOM | 555 | OD2 | ASP | A | 84 | 37.887 | −5.685 | 21.730 | 1.00 | 30.30 | A |
| ATOM | 556 | C | ASP | A | 84 | 40.830 | −2.640 | 19.503 | 1.00 | 21.92 | A |
| ATOM | 557 | O | ASP | A | 84 | 41.547 | −2.838 | 18.525 | 1.00 | 22.99 | A |
| ATOM | 558 | N | LEU | A | 85 | 40.197 | −1.491 | 19.719 | 1.00 | 21.04 | A |
| ATOM | 559 | CA | LEU | A | 85 | 40.314 | −0.373 | 18.790 | 1.00 | 22.00 | A |
| ATOM | 560 | CB | LEU | A | 85 | 39.286 | 0.713 | 19.133 | 1.00 | 21.98 | A |
| ATOM | 561 | CG | LEU | A | 85 | 37.835 | 0.226 | 19.211 | 1.00 | 23.19 | A |
| ATOM | 562 | CD1 | LEU | A | 85 | 36.884 | 1.393 | 19.514 | 1.00 | 20.96 | A |
| ATOM | 563 | CD2 | LEU | A | 85 | 37.472 | −0.450 | 17.892 | 1.00 | 22.60 | A |
| ATOM | 564 | C | LEU | A | 85 | 41.727 | 0.214 | 18.799 | 1.00 | 21.67 | A |
| ATOM | 565 | O | LEU | A | 85 | 42.216 | 0.686 | 17.770 | 1.00 | 20.70 | A |
| ATOM | 566 | N | PHE | A | 86 | 42.381 | 0.173 | 19.958 | 1.00 | 21.86 | A |
| ATOM | 567 | CA | PHE | A | 86 | 43.740 | 0.702 | 20.086 | 1.00 | 20.91 | A |
| ATOM | 568 | CB | PHE | A | 86 | 43.965 | 1.264 | 21.491 | 1.00 | 19.44 | A |
| ATOM | 569 | CG | PHE | A | 86 | 43.487 | 2.688 | 21.671 | 1.00 | 16.86 | A |
| ATOM | 570 | CD1 | PHE | A | 86 | 42.626 | 3.282 | 20.744 | 1.00 | 15.83 | A |
| ATOM | 571 | CD2 | PHE | A | 86 | 43.899 | 3.431 | 22.773 | 1.00 | 14.83 | A |
| ATOM | 572 | CE1 | PHE | A | 86 | 42.181 | 4.597 | 20.908 | 1.00 | 14.04 | A |
| ATOM | 573 | CE2 | PHE | A | 86 | 43.461 | 4.749 | 22.955 | 1.00 | 18.00 | A |
| ATOM | 574 | CZ | PHE | A | 86 | 42.597 | 5.334 | 22.013 | 1.00 | 16.08 | A |
| ATOM | 575 | C | PHE | A | 86 | 44.774 | −0.377 | 19.794 | 1.00 | 22.21 | A |
| ATOM | 576 | O | PHE | A | 86 | 45.917 | −0.080 | 19.447 | 1.00 | 23.98 | A |
| ATOM | 577 | N | GLY | A | 87 | 44.370 | −1.635 | 19.923 | 1.00 | 22.25 | A |

TABLE 3-continued

Superimposed: trigonal and tetragonal crystal forms of HDM2 of SEQ ID NO: 2.

| ATOM | 578 | CA | GLY | A | 87 | 45.298 | −2.717 | 19.664 | 1.00 | 20.93 | A |
|------|-----|-----|-----|---|----|--------|--------|--------|------|-------|---|
| ATOM | 579 | C | GLY | A | 87 | 46.363 | −2.894 | 20.735 | 1.00 | 20.93 | A |
| ATOM | 580 | O | GLY | A | 87 | 47.499 | −3.266 | 20.417 | 1.00 | 22.00 | A |
| ATOM | 581 | N | VAL | A | 88 | 46.015 | −2.621 | 21.994 | 1.00 | 18.42 | A |
| ATOM | 582 | CA | VAL | A | 88 | 46.947 | −2.787 | 23.110 | 1.00 | 16.75 | A |
| ATOM | 583 | CB | VAL | A | 88 | 47.763 | −1.506 | 23.426 | 1.00 | 16.55 | A |
| ATOM | 584 | CG1 | VAL | A | 88 | 48.589 | −1.098 | 22.223 | 1.00 | 15.93 | A |
| ATOM | 585 | CG2 | VAL | A | 88 | 46.836 | −0.394 | 23.892 | 1.00 | 13.35 | A |
| ATOM | 586 | C | VAL | A | 88 | 46.185 | −3.155 | 24.371 | 1.00 | 16.74 | A |
| ATOM | 587 | O | VAL | A | 88 | 45.010 | −2.822 | 24.518 | 1.00 | 16.22 | A |
| ATOM | 588 | N | PRO | A | 89 | 46.854 | −3.851 | 25.300 | 1.00 | 16.36 | A |
| ATOM | 589 | CD | PRO | A | 89 | 48.202 | −4.420 | 25.116 | 1.00 | 17.10 | A |
| ATOM | 590 | CA | PRO | A | 89 | 46.269 | −4.283 | 26.574 | 1.00 | 16.05 | A |
| ATOM | 591 | CB | PRO | A | 89 | 47.181 | −5.427 | 27.000 | 1.00 | 15.83 | A |
| ATOM | 592 | CG | PRO | A | 89 | 48.517 | −4.975 | 26.501 | 1.00 | 18.07 | A |
| ATOM | 593 | C | PRO | A | 89 | 46.232 | −3.155 | 27.604 | 1.00 | 16.21 | A |
| ATOM | 594 | O | PRO | A | 89 | 45.462 | −3.210 | 28.570 | 1.00 | 15.73 | A |
| ATOM | 595 | N | SER | A | 90 | 47.066 | −2.138 | 27.391 | 1.00 | 15.13 | A |
| ATOM | 596 | CA | SER | A | 90 | 47.131 | −0.988 | 28.292 | 1.00 | 14.02 | A |
| ATOM | 597 | CB | SER | A | 90 | 47.652 | −1.409 | 29.663 | 1.00 | 12.56 | A |
| ATOM | 598 | OG | SER | A | 90 | 49.018 | −1.764 | 29.560 | 1.00 | 13.74 | A |
| ATOM | 599 | C | SER | A | 90 | 48.060 | 0.083 | 27.719 | 1.00 | 12.89 | A |
| ATOM | 600 | O | SER | A | 90 | 48.833 | −0.191 | 26.803 | 1.00 | 12.05 | A |
| ATOM | 601 | N | PHE | A | 91 | 47.978 | 1.293 | 28.267 | 1.00 | 11.19 | A |
| ATOM | 602 | CA | PHE | A | 91 | 48.807 | 2.397 | 27.816 | 1.00 | 11.45 | A |
| ATOM | 603 | CB | PHE | A | 91 | 48.290 | 2.943 | 26.466 | 1.00 | 10.33 | A |
| ATOM | 604 | CG | PHE | A | 91 | 46.891 | 3.480 | 26.518 | 1.00 | 8.05 | A |
| ATOM | 605 | CD1 | PHE | A | 91 | 46.655 | 4.817 | 26.828 | 1.00 | 7.52 | A |
| ATOM | 606 | CD2 | PHE | A | 91 | 45.800 | 2.638 | 26.304 | 1.00 | 7.09 | A |
| ATOM | 607 | CE1 | PHE | A | 91 | 45.338 | 5.315 | 26.932 | 1.00 | 7.90 | A |
| ATOM | 608 | CE2 | PHE | A | 91 | 44.485 | 3.118 | 26.404 | 1.00 | 7.31 | A |
| ATOM | 609 | CZ | PHE | A | 91 | 44.256 | 4.467 | 26.721 | 1.00 | 7.15 | A |
| ATOM | 610 | C | PHE | A | 91 | 48.869 | 3.517 | 28.852 | 1.00 | 13.35 | A |
| ATOM | 611 | O | PHE | A | 91 | 48.090 | 3.547 | 29.817 | 1.00 | 12.34 | A |
| ATOM | 612 | N | SER | A | 92 | 49.807 | 4.437 | 28.644 | 1.00 | 14.78 | A |
| ATOM | 613 | CA | SER | A | 92 | 49.996 | 5.558 | 29.548 | 1.00 | 16.74 | A |
| ATOM | 614 | CB | SER | A | 92 | 51.493 | 5.769 | 29.811 | 1.00 | 15.00 | A |
| ATOM | 615 | OG | SER | A | 92 | 51.712 | 6.925 | 30.610 | 1.00 | 15.51 | A |
| ATOM | 616 | C | SER | A | 92 | 49.384 | 6.854 | 29.012 | 1.00 | 18.09 | A |
| ATOM | 617 | O | SER | A | 92 | 49.653 | 7.257 | 27.881 | 1.00 | 17.05 | A |
| ATOM | 618 | N | VAL | A | 93 | 48.562 | 7.502 | 29.835 | 1.00 | 19.76 | A |
| ATOM | 619 | CA | VAL | A | 93 | 47.941 | 8.765 | 29.456 | 1.00 | 21.70 | A |
| ATOM | 620 | CB | VAL | A | 93 | 46.883 | 9.242 | 30.506 | 1.00 | 22.34 | A |
| ATOM | 621 | CG1 | VAL | A | 93 | 45.727 | 8.253 | 30.571 | 1.00 | 22.82 | A |
| ATOM | 622 | CG2 | VAL | A | 93 | 47.520 | 9.393 | 31.880 | 1.00 | 20.47 | A |
| ATOM | 623 | C | VAL | A | 93 | 49.001 | 9.852 | 29.311 | 1.00 | 22.48 | A |
| ATOM | 624 | O | VAL | A | 93 | 48.672 | 11.011 | 29.120 | 1.00 | 24.56 | A |
| ATOM | 625 | N | LYS | A | 94 | 50.272 | 9.479 | 29.402 | 1.00 | 24.37 | A |
| ATOM | 626 | CA | LYS | A | 94 | 51.369 | 10.441 | 29.268 | 1.00 | 26.51 | A |
| ATOM | 627 | CB | LYS | A | 94 | 52.454 | 10.190 | 30.323 | 1.00 | 27.71 | A |
| ATOM | 628 | CG | LYS | A | 94 | 52.235 | 10.866 | 31.682 | 1.00 | 30.96 | A |
| ATOM | 629 | CD | LYS | A | 94 | 53.375 | 10.491 | 32.648 | 1.00 | 33.87 | A |
| ATOM | 630 | CE | LYS | A | 94 | 53.298 | 11.223 | 33.998 | 1.00 | 35.49 | A |
| ATOM | 631 | NZ | LYS | A | 94 | 54.414 | 10.825 | 34.930 | 1.00 | 35.43 | A |
| ATOM | 632 | C | LYS | A | 94 | 52.014 | 10.375 | 27.886 | 1.00 | 26.44 | A |
| ATOM | 633 | O | LYS | A | 94 | 52.693 | 11.309 | 27.469 | 1.00 | 27.30 | A |
| ATOM | 634 | N | GLU | A | 95 | 51.821 | 9.260 | 27.190 | 1.00 | 25.84 | A |
| ATOM | 635 | CA | GLU | A | 95 | 52.386 | 9.076 | 25.859 | 1.00 | 25.31 | A |
| ATOM | 636 | CB | GLU | A | 95 | 52.648 | 7.590 | 25.612 | 1.00 | 26.45 | A |
| ATOM | 637 | CG | GLU | A | 95 | 53.540 | 6.907 | 26.643 | 1.00 | 28.64 | A |
| ATOM | 638 | CD | GLU | A | 95 | 55.022 | 7.198 | 26.457 | 1.00 | 30.17 | A |
| ATOM | 639 | OE1 | GLU | A | 95 | 55.415 | 7.657 | 25.359 | 1.00 | 31.51 | A |
| ATOM | 640 | OE2 | GLU | A | 95 | 55.798 | 6.948 | 27.407 | 1.00 | 28.42 | A |
| ATOM | 641 | C | GLU | A | 95 | 51.394 | 9.612 | 24.818 | 1.00 | 24.66 | A |
| ATOM | 642 | O | GLU | A | 95 | 50.809 | 8.851 | 24.037 | 1.00 | 22.08 | A |
| ATOM | 643 | N | HIS | A | 96 | 51.225 | 10.932 | 24.808 | 1.00 | 24.62 | A |
| ATOM | 644 | CA | HIS | A | 96 | 50.295 | 11.590 | 23.900 | 1.00 | 26.26 | A |
| ATOM | 645 | CB | HIS | A | 96 | 50.410 | 13.113 | 24.027 | 1.00 | 27.90 | A |
| ATOM | 646 | CG | HIS | A | 96 | 50.114 | 13.629 | 25.400 | 1.00 | 30.90 | A |
| ATOM | 647 | CD2 | HIS | A | 96 | 50.422 | 13.138 | 26.625 | 1.00 | 31.52 | A |
| ATOM | 648 | ND1 | HIS | A | 96 | 49.432 | 14.807 | 25.621 | 1.00 | 32.30 | A |
| ATOM | 649 | CE1 | HIS | A | 96 | 49.333 | 15.018 | 26.922 | 1.00 | 32.43 | A |
| ATOM | 650 | NE2 | HIS | A | 96 | 49.926 | 14.019 | 27.554 | 1.00 | 32.16 | A |
| ATOM | 651 | C | HIS | A | 96 | 50.420 | 11.193 | 22.435 | 1.00 | 26.13 | A |
| ATOM | 652 | O | HIS | A | 96 | 49.408 | 11.006 | 21.764 | 1.00 | 26.36 | A |
| ATOM | 653 | N | ARG | A | 97 | 51.648 | 11.067 | 21.938 | 1.00 | 25.66 | A |
| ATOM | 654 | CA | ARG | A | 97 | 51.857 | 10.696 | 20.540 | 1.00 | 25.19 | A |

TABLE 3-continued

Superimposed: trigonal and tetragonal crystal forms
of HDM2 of SEQ ID NO: 2.

| ATOM | 655 | CB | ARG | A | 97 | 53.344 | 10.864 | 20.161 | 1.00 | 25.74 | A |
|---|---|---|---|---|---|---|---|---|---|---|---|
| ATOM | 656 | CG | ARG | A | 97 | 53.734 | 10.433 | 18.746 | 1.00 | 24.90 | A |
| ATOM | 657 | CD | ARG | A | 97 | 52.779 | 10.981 | 17.684 | 1.00 | 27.96 | A |
| ATOM | 658 | NE | ARG | A | 97 | 52.817 | 12.435 | 17.532 | 1.00 | 29.51 | A |
| ATOM | 659 | CZ | ARG | A | 97 | 51.931 | 13.132 | 16.820 | 1.00 | 29.81 | A |
| ATOM | 660 | NH1 | ARG | A | 97 | 50.936 | 12.508 | 16.197 | 1.00 | 31.04 | A |
| ATOM | 661 | NH2 | ARG | A | 97 | 52.037 | 14.451 | 16.722 | 1.00 | 27.76 | A |
| ATOM | 662 | C | ARG | A | 97 | 51.371 | 9.269 | 20.265 | 1.00 | 24.39 | A |
| ATOM | 663 | O | ARG | A | 97 | 50.775 | 9.012 | 19.222 | 1.00 | 25.23 | A |
| ATOM | 664 | N | LYS | A | 98 | 51.605 | 8.344 | 21.189 | 1.00 | 23.55 | A |
| ATOM | 665 | CA | LYS | A | 98 | 51.145 | 6.970 | 20.983 | 1.00 | 23.84 | A |
| ATOM | 666 | CB | LYS | A | 98 | 51.678 | 6.034 | 22.082 | 1.00 | 25.86 | A |
| ATOM | 667 | CG | LYS | A | 98 | 53.151 | 5.669 | 21.933 | 1.00 | 29.53 | A |
| ATOM | 668 | CD | LYS | A | 98 | 53.621 | 4.689 | 23.004 | 1.00 | 31.47 | A |
| ATOM | 669 | CE | LYS | A | 98 | 55.149 | 4.543 | 22.978 | 1.00 | 33.99 | A |
| ATOM | 670 | NZ | LYS | A | 98 | 55.672 | 3.627 | 24.040 | 1.00 | 34.37 | A |
| ATOM | 671 | C | LYS | A | 98 | 49.611 | 6.908 | 20.955 | 1.00 | 23.22 | A |
| ATOM | 672 | O | LYS | A | 98 | 49.031 | 6.190 | 20.136 | 1.00 | 21.35 | A |
| ATOM | 673 | N | ILE | A | 99 | 48.963 | 7.658 | 21.849 | 1.00 | 21.20 | A |
| ATOM | 674 | CA | ILE | A | 99 | 47.507 | 7.689 | 21.909 | 1.00 | 20.16 | A |
| ATOM | 675 | CB | ILE | A | 99 | 47.017 | 8.541 | 23.112 | 1.00 | 18.26 | A |
| ATOM | 676 | CG2 | ILE | A | 99 | 45.526 | 8.843 | 22.980 | 1.00 | 16.58 | A |
| ATOM | 677 | CG1 | ILE | A | 99 | 47.306 | 7.793 | 24.421 | 1.00 | 16.19 | A |
| ATOM | 678 | CD1 | ILE | A | 99 | 47.022 | 8.589 | 25.665 | 1.00 | 12.79 | A |
| ATOM | 679 | C | ILE | A | 99 | 46.949 | 8.256 | 20.601 | 1.00 | 21.79 | A |
| ATOM | 680 | O | ILE | A | 99 | 46.008 | 7.710 | 20.019 | 1.00 | 21.34 | A |
| ATOM | 681 | N | TYR | A | 100 | 47.543 | 9.348 | 20.133 | 1.00 | 23.34 | A |
| ATOM | 682 | CA | TYR | A | 100 | 47.113 | 9.978 | 18.891 | 1.00 | 24.14 | A |
| ATOM | 683 | CB | TYR | A | 100 | 47.961 | 11.220 | 18.611 | 1.00 | 25.12 | A |
| ATOM | 684 | CG | TYR | A | 100 | 47.228 | 12.508 | 18.883 | 1.00 | 28.22 | A |
| ATOM | 685 | CD1 | TYR | A | 100 | 46.799 | 12.833 | 20.177 | 1.00 | 28.65 | A |
| ATOM | 686 | CE1 | TYR | A | 100 | 46.065 | 13.989 | 20.423 | 1.00 | 28.51 | A |
| ATOM | 687 | CD2 | TYR | A | 100 | 46.908 | 13.379 | 17.843 | 1.00 | 28.65 | A |
| ATOM | 688 | CE2 | TYR | A | 100 | 46.170 | 14.541 | 18.077 | 1.00 | 29.38 | A |
| ATOM | 689 | CZ | TYR | A | 100 | 45.752 | 14.835 | 19.366 | 1.00 | 29.62 | A |
| ATOM | 690 | OH | TYR | A | 100 | 45.002 | 15.961 | 19.589 | 1.00 | 31.04 | A |
| ATOM | 691 | C | TYR | A | 100 | 47.149 | 9.048 | 17.671 | 1.00 | 25.10 | A |
| ATOM | 692 | O | TYR | A | 100 | 46.216 | 9.055 | 16.857 | 1.00 | 25.32 | A |
| ATOM | 693 | N | THR | A | 101 | 48.206 | 8.251 | 17.524 | 1.00 | 23.58 | A |
| ATOM | 694 | CA | THR | A | 101 | 48.252 | 7.383 | 16.362 | 1.00 | 24.54 | A |
| ATOM | 695 | CB | THR | A | 101 | 49.714 | 7.004 | 15.972 | 1.00 | 25.48 | A |
| ATOM | 696 | OG1 | THR | A | 101 | 50.297 | 6.160 | 16.962 | 1.00 | 26.87 | A |
| ATOM | 697 | CG2 | THR | A | 101 | 50.552 | 8.262 | 15.841 | 1.00 | 27.33 | A |
| ATOM | 698 | C | THR | A | 101 | 47.376 | 6.143 | 16.527 | 1.00 | 23.52 | A |
| ATOM | 699 | O | THR | A | 101 | 47.074 | 5.459 | 15.553 | 1.00 | 24.28 | A |
| ATOM | 700 | N | MET | A | 102 | 46.949 | 5.851 | 17.753 | 1.00 | 22.80 | A |
| ATOM | 701 | CA | MET | A | 102 | 46.052 | 4.711 | 17.956 | 1.00 | 20.40 | A |
| ATOM | 702 | CB | MET | A | 102 | 46.081 | 4.229 | 19.408 | 1.00 | 15.37 | A |
| ATOM | 703 | CG | MET | A | 102 | 47.385 | 3.556 | 19.756 | 1.00 | 14.03 | A |
| ATOM | 704 | SD | MET | A | 102 | 47.437 | 2.805 | 21.384 | 1.00 | 11.93 | A |
| ATOM | 705 | CE | MET | A | 102 | 47.530 | 4.281 | 22.436 | 1.00 | 10.87 | A |
| ATOM | 706 | C | MET | A | 102 | 44.645 | 5.163 | 17.563 | 1.00 | 19.65 | A |
| ATOM | 707 | O | MET | A | 102 | 43.829 | 4.371 | 17.091 | 1.00 | 19.47 | A |
| ATOM | 708 | N | ILE | A | 103 | 44.384 | 6.451 | 17.755 | 1.00 | 18.90 | A |
| ATOM | 709 | CA | ILE | A | 103 | 43.108 | 7.049 | 17.406 | 1.00 | 21.34 | A |
| ATOM | 710 | CB | ILE | A | 103 | 42.959 | 8.459 | 18.055 | 1.00 | 20.40 | A |
| ATOM | 711 | CG2 | ILE | A | 103 | 41.789 | 9.217 | 17.425 | 1.00 | 19.03 | A |
| ATOM | 712 | CG1 | ILE | A | 103 | 42.757 | 8.312 | 19.565 | 1.00 | 19.84 | A |
| ATOM | 713 | CD1 | ILE | A | 103 | 42.941 | 9.601 | 20.345 | 1.00 | 18.82 | A |
| ATOM | 714 | C | ILE | A | 103 | 43.045 | 7.183 | 15.881 | 1.00 | 24.13 | A |
| ATOM | 715 | O | ILE | A | 103 | 41.996 | 6.968 | 15.271 | 1.00 | 24.18 | A |
| ATOM | 716 | N | TYR | A | 104 | 44.182 | 7.530 | 15.277 | 1.00 | 27.06 | A |
| ATOM | 717 | CA | TYR | A | 104 | 44.283 | 7.701 | 13.827 | 1.00 | 29.10 | A |
| ATOM | 718 | CB | TYR | A | 104 | 45.702 | 8.155 | 13.462 | 1.00 | 30.33 | A |
| ATOM | 719 | CG | TYR | A | 104 | 45.914 | 9.635 | 13.689 | 1.00 | 30.58 | A |
| ATOM | 720 | CD1 | TYR | A | 104 | 47.148 | 10.137 | 14.093 | 1.00 | 29.56 | A |
| ATOM | 721 | CE1 | TYR | A | 104 | 47.328 | 11.499 | 14.323 | 1.00 | 29.30 | A |
| ATOM | 722 | CD2 | TYR | A | 104 | 44.862 | 10.533 | 13.516 | 1.00 | 31.51 | A |
| ATOM | 723 | CE2 | TYR | A | 104 | 45.032 | 11.892 | 13.742 | 1.00 | 31.90 | A |
| ATOM | 724 | CZ | TYR | A | 104 | 46.264 | 12.366 | 14.146 | 1.00 | 30.22 | A |
| ATOM | 725 | OH | TYR | A | 104 | 46.411 | 13.711 | 14.379 | 1.00 | 32.03 | A |
| ATOM | 726 | C | TYR | A | 104 | 43.895 | 6.466 | 13.017 | 1.00 | 29.49 | A |
| ATOM | 727 | O | TYR | A | 104 | 43.336 | 6.587 | 11.926 | 1.00 | 30.07 | A |
| ATOM | 728 | N | ARG | A | 105 | 44.188 | 5.287 | 13.553 | 1.00 | 30.44 | A |
| ATOM | 729 | CA | ARG | A | 105 | 43.851 | 4.039 | 12.883 | 1.00 | 31.09 | A |
| ATOM | 730 | CB | ARG | A | 105 | 44.714 | 2.889 | 13.407 | 1.00 | 32.59 | A |
| ATOM | 731 | CG | ARG | A | 105 | 46.098 | 2.802 | 12.783 | 1.00 | 35.48 | A |

TABLE 3-continued

Superimposed: trigonal and tetragonal crystal forms of HDM2 of SEQ ID NO: 2.

| | | | | | | | | | | | |
|---|---|---|---|---|---|---|---|---|---|---|---|
| ATOM | 732 | CD | ARG | A | 105 | 46.758 | 1.479 | 13.140 | 1.00 | 38.68 | A |
| ATOM | 733 | NE | ARG | A | 105 | 47.041 | 1.380 | 14.572 | 1.00 | 41.14 | A |
| ATOM | 734 | CZ | ARG | A | 105 | 48.198 | 1.727 | 15.132 | 1.00 | 42.11 | A |
| ATOM | 735 | NH1 | ARG | A | 105 | 49.192 | 2.196 | 14.382 | 1.00 | 41.27 | A |
| ATOM | 736 | NH2 | ARG | A | 105 | 48.362 | 1.605 | 16.446 | 1.00 | 42.61 | A |
| ATOM | 737 | C | ARG | A | 105 | 42.382 | 3.705 | 13.104 | 1.00 | 31.15 | A |
| ATOM | 738 | O | ARG | A | 105 | 41.887 | 2.692 | 12.599 | 1.00 | 30.58 | A |
| ATOM | 739 | N | ASN | A | 106 | 41.691 | 4.552 | 13.867 | 1.00 | 30.35 | A |
| ATOM | 740 | CA | ASN | A | 106 | 40.272 | 4.349 | 14.137 | 1.00 | 31.38 | A |
| ATOM | 741 | CB | ASN | A | 106 | 39.995 | 4.297 | 15.639 | 1.00 | 30.13 | A |
| ATOM | 742 | CG | ASN | A | 106 | 40.393 | 2.984 | 16.250 | 1.00 | 30.74 | A |
| ATOM | 743 | OD1 | ASN | A | 106 | 41.568 | 2.754 | 16.549 | 1.00 | 30.89 | A |
| ATOM | 744 | ND2 | ASN | A | 106 | 39.415 | 2.094 | 16.427 | 1.00 | 30.12 | A |
| ATOM | 745 | C | ASN | A | 106 | 39.408 | 5.429 | 13.517 | 1.00 | 32.04 | A |
| ATOM | 746 | O | ASN | A | 106 | 38.293 | 5.677 | 13.970 | 1.00 | 30.99 | A |
| ATOM | 747 | N | LEU | A | 107 | 39.914 | 6.070 | 12.474 | 1.00 | 34.74 | A |
| ATOM | 748 | CA | LEU | A | 107 | 39.144 | 7.115 | 11.828 | 1.00 | 39.45 | A |
| ATOM | 749 | CB | LEU | A | 107 | 39.166 | 8.383 | 12.694 | 1.00 | 39.46 | A |
| ATOM | 750 | CG | LEU | A | 107 | 40.507 | 8.908 | 13.220 | 1.00 | 38.61 | A |
| ATOM | 751 | CD1 | LEU | A | 107 | 41.418 | 9.298 | 12.068 | 1.00 | 38.52 | A |
| ATOM | 752 | CD2 | LEU | A | 107 | 40.252 | 10.105 | 14.120 | 1.00 | 37.16 | A |
| ATOM | 753 | C | LEU | A | 107 | 39.614 | 7.441 | 10.425 | 1.00 | 42.25 | A |
| ATOM | 754 | O | LEU | A | 107 | 40.442 | 6.732 | 9.848 | 1.00 | 42.75 | A |
| ATOM | 755 | N | VAL | A | 108 | 39.057 | 8.516 | 9.882 | 1.00 | 46.00 | A |
| ATOM | 756 | CA | VAL | A | 108 | 39.397 | 8.997 | 8.549 | 1.00 | 49.43 | A |
| ATOM | 757 | CB | VAL | A | 108 | 38.365 | 8.541 | 7.499 | 1.00 | 48.08 | A |
| ATOM | 758 | CG1 | VAL | A | 108 | 39.032 | 8.443 | 6.146 | 1.00 | 48.02 | A |
| ATOM | 759 | CG2 | VAL | A | 108 | 37.735 | 7.216 | 7.907 | 1.00 | 46.78 | A |
| ATOM | 760 | C | VAL | A | 108 | 39.389 | 10.529 | 8.612 | 1.00 | 53.19 | A |
| ATOM | 761 | O | VAL | A | 108 | 38.321 | 11.145 | 8.684 | 1.00 | 52.78 | A |
| ATOM | 762 | N | VAL | A | 109 | 40.576 | 11.136 | 8.601 | 1.00 | 57.34 | A |
| ATOM | 763 | CA | VAL | A | 109 | 40.708 | 12.596 | 8.664 | 1.00 | 61.10 | A |
| ATOM | 764 | CB | VAL | A | 109 | 42.177 | 13.052 | 8.480 | 1.00 | 61.46 | A |
| ATOM | 765 | CG1 | VAL | A | 109 | 42.306 | 14.528 | 8.847 | 1.00 | 61.63 | A |
| ATOM | 766 | CG2 | VAL | A | 109 | 43.115 | 12.193 | 9.320 | 1.00 | 62.28 | A |
| ATOM | 767 | C | VAL | A | 109 | 39.875 | 13.293 | 7.584 | 1.00 | 63.47 | A |
| ATOM | 768 | O | VAL | A | 109 | 40.196 | 13.206 | 6.394 | 1.00 | 63.73 | A |
| ATOM | 769 | N | VAL | A | 110 | 38.817 | 13.989 | 8.004 | 1.00 | 65.46 | A |
| ATOM | 770 | CA | VAL | A | 110 | 37.941 | 14.697 | 7.073 | 1.00 | 67.21 | A |
| ATOM | 771 | CB | VAL | A | 110 | 36.927 | 15.603 | 7.840 | 1.00 | 66.97 | A |
| ATOM | 772 | CG1 | VAL | A | 110 | 35.873 | 16.155 | 6.878 | 1.00 | 67.04 | A |
| ATOM | 773 | CG2 | VAL | A | 110 | 36.262 | 14.817 | 8.961 | 1.00 | 66.24 | A |
| ATOM | 774 | C | VAL | A | 110 | 38.775 | 15.570 | 6.119 | 1.00 | 69.20 | A |
| ATOM | 775 | O | VAL | A | 110 | 39.949 | 15.862 | 6.458 | 1.00 | 69.94 | A |
| ATOM | 776 | OXT | VAL | A | 110 | 38.248 | 15.956 | 5.046 | 1.00 | 70.58 | A |
| ATOM | 777 | C1 | CID | A | 1 | 46.320 | 13.011 | 27.769 | 1.00 | 21.13 | INH1 |
| ATOM | 778 | C2 | CID | A | 1 | 46.849 | 12.548 | 26.529 | 1.00 | 21.31 | INH1 |
| ATOM | 779 | C3 | CID | A | 1 | 46.319 | 13.053 | 25.307 | 1.00 | 21.72 | INH1 |
| ATOM | 780 | C4 | CID | A | 1 | 45.283 | 14.011 | 25.313 | 1.00 | 21.74 | INH1 |
| ATOM | 781 | C5 | CID | A | 1 | 44.753 | 14.472 | 26.542 | 1.00 | 21.42 | INH1 |
| ATOM | 782 | C6 | CID | A | 1 | 45.261 | 13.981 | 27.804 | 1.00 | 22.49 | INH1 |
| ATOM | 783 | C7 | CID | A | 1 | 44.698 | 14.428 | 29.194 | 1.00 | 23.66 | INH1 |
| ATOM | 784 | C8 | CID | A | 1 | 44.052 | 15.860 | 29.277 | 1.00 | 25.69 | INH1 |
| ATOM | 785 | O1 | CID | A | 1 | 43.517 | 16.308 | 30.288 | 1.00 | 29.01 | INH1 |
| ATOM | 786 | O2 | CID | A | 1 | 44.409 | 16.731 | 28.309 | 1.00 | 30.64 | INH1 |
| ATOM | 787 | N1 | CID | A | 1 | 43.714 | 13.347 | 29.673 | 1.00 | 19.99 | INH1 |
| ATOM | 788 | C9 | CID | A | 1 | 42.570 | 12.996 | 28.781 | 1.00 | 18.95 | INH1 |
| ATOM | 789 | C10 | CID | A | 1 | 42.648 | 11.641 | 28.034 | 1.00 | 18.04 | INH1 |
| ATOM | 790 | C11 | CID | A | 1 | 43.669 | 10.654 | 28.259 | 1.00 | 17.01 | INH1 |
| ATOM | 791 | C12 | CID | A | 1 | 43.700 | 9.448 | 27.530 | 1.00 | 16.97 | INH1 |
| ATOM | 792 | C13 | CID | A | 1 | 42.708 | 9.210 | 26.564 | 1.00 | 17.64 | INH1 |
| ATOM | 793 | CL1 | CID | A | 1 | 42.737 | 7.786 | 25.674 | 1.00 | 14.96 | INH1 |
| ATOM | 794 | C14 | CID | A | 1 | 41.687 | 10.153 | 26.318 | 1.00 | 18.96 | INH1 |
| ATOM | 795 | C15 | CID | A | 1 | 41.659 | 11.354 | 27.046 | 1.00 | 17.55 | INH1 |
| ATOM | 796 | C16 | CID | A | 1 | 41.205 | 13.214 | 29.506 | 1.00 | 18.08 | INH1 |
| ATOM | 797 | O3 | CID | A | 1 | 40.363 | 13.973 | 29.015 | 1.00 | 18.82 | INH1 |
| ATOM | 798 | N2 | CID | A | 1 | 40.909 | 12.577 | 30.698 | 1.00 | 16.78 | INH1 |
| ATOM | 799 | C17 | CID | A | 1 | 41.690 | 11.680 | 31.447 | 1.00 | 17.03 | INH1 |
| ATOM | 800 | C18 | CID | A | 1 | 43.101 | 11.735 | 31.572 | 1.00 | 16.70 | INH1 |
| ATOM | 801 | C19 | CID | A | 1 | 43.977 | 12.786 | 30.947 | 1.00 | 19.45 | INH1 |
| ATOM | 802 | O4 | CID | A | 1 | 44.965 | 13.160 | 31.626 | 1.00 | 18.52 | INH1 |
| ATOM | 803 | C20 | CID | A | 1 | 43.769 | 10.744 | 32.353 | 1.00 | 17.26 | INH1 |
| ATOM | 804 | C21 | CID | A | 1 | 43.051 | 9.726 | 33.006 | 1.00 | 18.91 | INH1 |
| ATOM | 805 | I1 | CID | A | 1 | 44.145 | 8.343 | 34.119 | 1.00 | 19.64 | INH1 |
| ATOM | 806 | C22 | CID | A | 1 | 41.657 | 9.670 | 32.902 | 1.00 | 17.86 | INH1 |
| ATOM | 807 | C23 | CID | A | 1 | 40.966 | 10.637 | 32.123 | 1.00 | 17.23 | INH1 |

TABLE 3-continued

Superimposed: trigonal and tetragonal crystal forms of HDM2 of SEQ ID NO: 2.

| ATOM | 808 | CL2 | CID | A | 1 | 46.930 | 12.505 | 23.805 | 1.00 | 20.99 | INH1 |
|------|-----|-----|-----|---|---|--------|--------|--------|------|-------|------|
| ATOM | 809 | CL3 | CID | A | 1 | 40.751 | 8.456  | 33.699 | 1.00 | 20.31 | INH1 |
| END  |     |     |     |   |   |        |        |        |      |       |      |

We claim:

1. A crystal consisting of HDM2 amino acid residues 17-111 of SEQ ID NO:1, with a ligand, wherein said ligand is a non-peptide small molecule inhibitor of HDM2, wherein said non-peptide small molecule inhibitor prevents HDM2 from interacting with p53, and wherein said crystal has a spacegroup selected from the group consisting of a trigonal spacegroup of $P3_221$ and a tetragonal spacegroup of $P4_32_12$ and said crystal comprises a unit cell selected from the group consisting of: a cell having dimensions of 98.6 Å, 98.6 Å and 74.7 Å, and alpha=90°, beta=90° and gamma=120°; and, a cell having dimensions of 54.3 Å, 54.3 Å, 83.3 Å and alpha=90°, beta=90° and gamma=90°.

2. The crystal of claim 1, wherein the crystal effectively diffracts X-rays for determination of atomic coordinates to a resolution of at least about 3.0 Å.

3. The crystal of claim 1 wherein said ligand is selected from the group consisting of (4-Chloro-phenyl)-[3-(4-chloro-phenyl)-7-iodo-2,5-dioxo-1,2,3,5-tetrahydro-benzo [e][1,4]diazepin-4-yl]-acetic acid; [8-Chloro-3-(4-chloro-phenyl)-7-iodo-2,5-dioxo-1,2,3,5-tetrahydro-benzo[e][1,4] diazepin-4-yl]-(4-chloro-phenyl)-acetic acid); and derivatives thereof.

4. A method for the production of a crystal complex comprising an HDM2 protein consisting of amino acids 17-111 of SEQ ID NO: 1 and a ligand comprising:

(a) contacting the HDM2 protein consisting of amino acids 17-111 of SEQ ID NO: 1 with said ligand in a suitable solution comprising PEG and NaSCN; and, (b) crystallizing said resulting complex of HDM2 protein consisting of amino acids 17-111 of SEQ ID NO: 1 ligand from said solution, wherein said PEG has an average molecular weight of about 400 and is present in solution at about 2% w/v and said NaSCN is present in solution at about 100 mM.

5. A method for the production of a crystal complex comprising:

mixing 1-2 μl of HDM2 protein consisting of amino acids 17-111 of SEQ ID NO: 1 complexed with a small molecule and concentrated to ca. 10 mg/ml in a 1:1 ratio with well solution (1.8-2.4 M $(NH_4)_2SO_4$, 100 mM buffer pH. 6.5-9.0, 2% PEG 400, 100 mM NaSCN);

placing said mixed solution on a glass cover slip;

inverting the glass cover slip and sealing the glass cover slip over a reservoir of 500-1000 μl of well solution;

incubating the glass cover slip at 4° C. for from about 3 to about 7 days to permit formation of crystals; and harvesting the crystals.

\* \* \* \* \*

SEQUENCE LISTING

<160> NUMBER OF SEQ ID NOS: 12

<210> SEQ ID NO 1
<211> LENGTH: 491
<212> TYPE: PRT
<213> ORGANISM: Homo sapiens

<400> SEQUENCE: 1

```
Met Cys Asn Thr Asn Met Ser Val Pro Thr Asp Gly Ala Val Thr Thr
  1               5                  10                  15

Ser Gln Ile Pro Ala Ser Glu Gln Glu Thr Leu Val Arg Pro Lys Pro
             20                  25                  30

Leu Leu Leu Lys Leu Leu Lys Ser Val Gly Ala Gln Lys Asp Thr Tyr
         35                  40                  45

Thr Met Lys Glu Val Leu Phe Tyr Leu Gly Gln Tyr Ile Met Thr Lys
     50                  55                  60

Arg Leu Tyr Asp Glu Lys Gln Gln His Ile Val Tyr Cys Ser Asn Asp
 65                  70                  75                  80

Leu Leu Gly Asp Leu Phe Gly Val Pro Ser Phe Ser Val Lys Glu His
                 85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300
```

```
Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
        355                 360                 365

Asp Ser Arg Glu Ser Cys Val Glu Glu Asn Asp Asp Lys Ile Thr Gln
    370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
                420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 2
<211> LENGTH: 95
<212> TYPE: PRT
<213> ORGANISM: Homo sapiens

<400> SEQUENCE: 2

Ser Gln Ile Pro Ala Ser Glu Gln Glu Thr Leu Val Arg Pro Lys Pro
1               5                   10                  15

Leu Leu Leu Lys Leu Leu Lys Ser Val Gly Ala Gln Lys Asp Thr Tyr
            20                  25                  30

Thr Met Lys Glu Val Leu Phe Tyr Leu Gly Gln Tyr Ile Met Thr Lys
        35                  40                  45

Arg Leu Tyr Asp Glu Lys Gln Gln His Ile Val Tyr Cys Ser Asn Asp
    50                  55                  60

Leu Leu Gly Asp Leu Phe Gly Val Pro Ser Phe Ser Val Lys Glu His
65                  70                  75                  80

Arg Lys Ile Tyr Thr Met Ile Tyr Arg Asn Leu Val Val Val Asn
                85                  90                  95

<210> SEQ ID NO 3
<211> LENGTH: 92
<212> TYPE: PRT
<213> ORGANISM: Homo sapiens

<400> SEQUENCE: 3

Glu Gln Glu Thr Leu Val Arg Pro Lys Pro Leu Leu Leu Lys Leu Leu
1               5                   10                  15

Lys Ser Val Gly Ala Gln Lys Asp Thr Tyr Thr Met Lys Glu Val Leu
            20                  25                  30

Phe Tyr Leu Gly Gln Tyr Ile Met Thr Lys Arg Leu Tyr Asp Glu Lys
        35                  40                  45
```

```
Gln Gln His Ile Val Tyr Cys Ser Asn Asp Leu Leu Gly Asp Leu Phe
        50                  55                  60

Gly Val Pro Ser Phe Ser Val Lys Glu His Arg Lys Ile Tyr Thr Met
 65                  70                  75                  80

Ile Tyr Arg Asn Leu Val Val Val Asn Gln Gln Glu
                85                  90

<210> SEQ ID NO 4
<211> LENGTH: 95
<212> TYPE: PRT
<213> ORGANISM: Homo sapiens

<400> SEQUENCE: 4

Ser Gln Ile Pro Ala Ser Glu Gln Glu Thr Leu Val Arg Pro Lys Gly
 1               5                  10                  15

Leu Leu Leu Lys Leu Leu Lys Ser Val Gly Ala Gln Lys Asp Thr Tyr
                20                  25                  30

Thr Met Lys Glu Val Leu Phe Tyr Leu Gly Gln Tyr Ile Met Thr Lys
            35                  40                  45

Arg Leu Tyr Asp Glu Lys Gln Gln His Ile Val Tyr Cys Ser Asn Asp
        50                  55                  60

Leu Leu Gly Asp Leu Phe Gly Val Pro Ser Phe Ser Val Lys Glu His
 65                  70                  75                  80

Arg Lys Ile Tyr Thr Met Ile Tyr Arg Asn Leu Val Val Val Asn
                85                  90                  95

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctctctcgga tcccagattc cagcttcgga acaagag                              37

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tatatatctc gagtcagttc tcactcacag atgtacctga g                         41

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgacgattgg atccgaacaa agaccctg                                        28

<210> SEQ ID NO 8
<211> LENGTH: 36
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 8
ggctactact ccgagtcatt cctgctgatt gactac                                36

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctctctcgga tcccagattc agcttccgga acaagag                               37

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcagcagct cgagtcaatt gactactacc aagttc                                36

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Pro Arg Phe Met Asp Tyr Trp Glu Gly Leu Asn
  1               5                  10

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Phe Met Asp Tyr Trp Glu Gly Leu
  1               5
```